(12) United States Patent
Bradner et al.

(10) Patent No.: US 9,694,084 B2
(45) Date of Patent: Jul. 4, 2017

(54) METHODS TO INDUCE TARGETED PROTEIN DEGRADATION THROUGH BIFUNCTIONAL MOLECULES

(71) Applicant: Dana-Farber Cancer Institute, Inc., Boston, MA (US)

(72) Inventors: James Bradner, Weston, MA (US); Dennis Buckley, Jamaica Plain, MA (US); Georg Winter, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/707,930

(22) Filed: May 8, 2015

(65) Prior Publication Data
US 2016/0176916 A1    Jun. 23, 2016

Related U.S. Application Data

(60) Provisional application No. 62/096,318, filed on Dec. 23, 2014, provisional application No. 62/128,457, filed on Mar. 4, 2015, provisional application No. 62/149,170, filed on Apr. 17, 2015.

(51) Int. Cl.
| | | |
|---|---|---|
| *C07D 495/14* | (2006.01) | |
| *A61K 47/48* | (2006.01) | |
| *C07J 43/00* | (2006.01) | |
| *C07D 487/04* | (2006.01) | |
| *C07D 471/04* | (2006.01) | |
| *C07D 401/14* | (2006.01) | |
| *A61K 31/454* | (2006.01) | |
| *C07J 3/00* | (2006.01) | |

(52) U.S. Cl.
CPC ...... *A61K 47/48061* (2013.01); *A61K 31/454* (2013.01); *A61K 47/48023* (2013.01); *A61K 47/48038* (2013.01); *A61K 47/48092* (2013.01); *A61K 47/48123* (2013.01); *C07D 401/14* (2013.01); *C07D 471/04* (2013.01); *C07D 487/04* (2013.01); *C07D 495/14* (2013.01); *C07J 43/003* (2013.01); *C07J 3/005* (2013.01)

(58) Field of Classification Search
None
See application file for complete search history.

(56) References Cited

U.S. PATENT DOCUMENTS

| | | | |
|---|---|---|---|
| 6,306,663 B1 | 10/2001 | Kenten et al. | |
| 6,559,280 B2 | 5/2003 | Kenten et al. | |
| 7,041,298 B2 | 5/2006 | Deshaies et al. | |
| 7,074,620 B2 | 7/2006 | Kenten et al. | |
| 7,208,157 B2 | 4/2007 | Dashaies et al. | |
| 7,273,920 B2 | 9/2007 | Kenten et al. | |
| 9,125,915 B2 | 9/2015 | Miyoshi et al. | |
| 9,249,161 B2 | 2/2016 | Albrecht et al. | |
| 2010/0286127 A1 | 11/2010 | Miyoshi et al. | |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0045607 A1 | 2/2015 | Hakansson | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0022642 A1 | 1/2016 | Crews et al. | |
| 2016/0045607 A1 | 2/2016 | Crew et al. | |
| 2016/0046661 A1 | 2/2016 | Gray et al. | |
| 2016/0058872 A1 | 3/2016 | Crew et al. | |

FOREIGN PATENT DOCUMENTS

| | | |
|---|---|---|
| WO | WO 98/11111 | 3/1998 |
| WO | WO 2006/102557 | 9/2006 |
| WO | WO 2008/122038 | 10/2008 |
| WO | WO 2012/003281 A2 | 1/2012 |
| WO | WO 2012/079022 A1 | 6/2012 |
| WO | WO 2012/178208 | 12/2012 |
| WO | WO 2013/106643 | 7/2013 |
| WO | WO 2015/160845 | 10/2015 |
| WO | WO 2016/105518 A1 | 6/2016 |

OTHER PUBLICATIONS

Banaszynski, L. A., et al. (2006). "A rapid, reversible, and tunable method to regulate protein function in living cells using synthetic small molecules." Cell 126(5): 995-1004.
Banaszynski, L. A., et al. (2008). "Chemical control of protein stability and function in living mice." Nat Med 14(10): 1123-1127.
Burkhard, J. A. et al (2013) "Synthesis and Stability of Oxetane Analogs of Thalidomide and Lenalidomide" Org Lett 15(7): 4312-4315.
Filippakopoulos, P. and S. Knapp (2014). "Targeting bromodomains: epigenetic readers of lysine acetylation." Nat Rev Drug Discov 13(5): 337-356.
Lu, G., et al. (2014). "The myeloma drug lenalidomide promotes the cereblon-dependent destruction of Ikaros proteins." Science 343(6168): 305-309.
Hines, J., et al. (2013). "Posttranslational protein knockdown coupled to receptor tyrosine kinase activation with phosphoPROTACs." Proc Natl Acad Sci U S A 110(22): 8942-8947.
Huttlin, E. L., et al. (2010). "A tissue-specific atlas of mouse protein phosphorylation and expression." Cell 143(7): 1174-1189.
Ito, T., et al. (2010). "Identification of a Primary Target of Thalidomide Teratogenicity." Science 327(5971): 1345-1350.
Itoh, Y., et al. (2010). "Protein knockdown using methyl bestatin-ligand hybrid molecules: design and synthesis of inducers of ubiquitination-mediated degradation of cellular retinoic acid-binding proteins." J Am Chem Soc 132(16): 5820-5826.

(Continued)

*Primary Examiner* — Paul V Ward
(74) *Attorney, Agent, or Firm* — Knowles Intellectual Property Strategies, LLC

(57) ABSTRACT

The present application provides bifunctional compounds which act as protein degradation inducing moieties. The present application also relates to methods for the targeted degradation of endogenous proteins through the use of the bifunctional compounds that link a cereblon-binding moiety to a ligand that is capable of binding to the targeted protein which can be utilized in the treatment of proliferative disorders. The present application also provides methods for making compounds of the application and intermediates thereof.

84 Claims, 42 Drawing Sheets

(56) References Cited

OTHER PUBLICATIONS

Bartlett, J. B., et al. (2004). "The evolution of thalidomide and its IMiD derivatives as anticancer agents." Nat Rev Cancer 4(4): 314-322.
Krönke, J., et al. (2014). "Lenalidomide Causes Selective Degradation of IKZF1 and IKZF3 in Multiple Myeloma Cells." Science 343(6168): 301-305.
Liu, K. et al. (2013) "Design and biological characterization of hybrid compounds of curcumin and thalidomide for multiple myeloma." Org. Biomol. Chem., 2013, 11, 4757.
Mertz, J. A., et al. (2011). "Targeting MYC dependence in cancer by inhibiting BET bromodomains." Proceedings of the National Academy of Sciences 108(40): 16669-16674.
Neklesa, T. K., et al. (2011). "Small-molecule hydrophobic tagging-induced degradation of HaloTag fusion proteins." Nat Chem Biol 7(8): 538-543.
Pratt, M. R., et al. (2007). "Small-molecule-mediated rescue of protein function by an inducible proteolytic shunt." Proceedings of the National Academy of Sciences 104(27): 11209-11214.
Sakamoto, K. M., et al. (2001). "Protacs: chimeric molecules that target proteins to the Skpl-Cullin-F box complex for ubiquitination and degradation." Proc Natl Acad Sci U S A 98(15): 8554-8559.
Schneekloth, J. S., et al. (2004). "Chemical Genetic Control of Protein Levels: Selective in Vivo Targeted Degradation." J Am Chem Soc 126(12): 3748-3754.
Soucy, T. A., et al. (2009). "An inhibitor of NEDD8-activating enzyme as a new approach to treat cancer." Nature 458(7239): 732-736.
Sufan, R. I. and M. Ohh (2006). "Role of the NEDD8 modification of Cu12 in the sequential activation of ECV complex." Neoplasia 8(11): 956-963.
Winter, G. E., et al. (2015). "Phthalimide conjugation as a strategy for in vivo target protein degradation." Science 348(6241): 1376-1381.
Wu, Y. L., et al. (2005). "Structural basis for an unexpected mode of SERM-mediated ER antagonism." Mol Cell 18(4): 413-424.
Anand P. et al., "BET bromodomains mediate transcriptional pause release in heart failure," Cell 154, 569-582 (2013).
Anders L. et al., "Genome-wide determination of drug localization," Nature Biotechnology 32, 92-96 (2013).
Brown J.D. et al., "NF-κB directs dynamic super enhancer formation in inflammation and atherogenesis," Mol. Cell 56, 219-231 (2014).
Budin G. et al., "Bioorthogonal Probes for Polo-like Kinase 1 Imaging and Quantification," Angewandte Chemie International Ed. 50, 9378-9381 (2011).
Chang X. and Stewart K. A., "What is the functional role of the thalidomide binding protein cereblon?" Int J Biochem Mol Biol. 2(3), 287-294 (2011).
Chapuy B. et al., "Discovery and characterization of super-enhancer-associated dependencies in diffuse large B cell lymphoma.," Cancer Cell 24, 777-790 (2013).
Crews C.M., "Targeting the undruggable proteome: the small molecules of my dreams.," Chem. Biol. 17(6), 551-555 (2010).
Delmore J.E. et al., "BET bromodomain inhibition as a therapeutic strategy to target c-Myc," Cell 146, 904-917 (2011).
Filippakopoulos P. et al., "Selective inhibition of BET bromodomains," Nature 468, 1067-1073 (2010).
Fischer E.S. et al., "The Molecular Basis of CRL4$^{DDB2/CSA}$ Ubiquitin Ligase Architecture, Targeting, and Activation," Cell 147, 1024-1039 (2011).
Fischer E.S. et al., "Structure of the DDB1-CRBN E3 ubiquitin ligase in complex with thalidomide," Nature 512, 49-53 (2014).
Holt D.A. et al., "Design, synthesis, and kinetic evaluation of high-affinity FKBP ligands and the X-ray crystal structures of their complexes with FKBP12," J. Am. Chem. Soc. 115, 9925-9938 (1993).
Liu J. et al., "Calcineurin is a common target of cyclophilin-cyclosporin A and FKBP-FK506 complexes," Cell 66, 807-15 (1991).
Loven J. et al., "Selective inhibition of tumor oncogenes by disruption of super-enhancers," Cell 153, 320-334 (2013).
Lu G. et al., "The myeloma drug lenalidomide promotes the cereblon-dependent destruction of Ikaros proteins," Science 343, 305-309 (2014).
Mayer D. A. et al., "Multicenter randomized trial comparing tacrolimus (FK506) and cyclosporine in the prevention of renal allograft rejection: a report of the European Tacrolimus Multicenter Renal Study Group," Transplantation 64(3), 436-43 (1997).
McKeown M. R. et al., "Biased multicomponent reactions to develop novel bromodomain inhibitors," J. Med. Chem. 57, 9019-9027 (2014).
Nicodeme E. et al., "Suppression of inflammation by a synthetic histone mimic," Nature 468, 1119-1123 (2010).
Petroski M.E. and Deshaies R. J., "Function and regulation of cullin-ring ubiquitin ligases," Nat. Rev. Mol. Cell. Biol. 6, 9-20 (2005).
Schneekloth J.S. Jr. and Crews C. M., "Chemical approaches to controlling intracellular protein degradation," Chembiochem 6(1), 40-46 (2005).
Siekierka J. J. et al., "A cytosolic binding protein for the immunosuppressant FK506 has peptidyl-prolyl isomerase activity but is distinct from cyclophilin," Nature 341, 755-7 (1989).
Sufan R.I., and Ohh M., "Role of the NEDD8 modification of Cu12 in the sequential activation of ECV complex," Neoplasia 8, 956-963 (2006).
Wang T. et al., "Specific interaction of type I receptors of the TGF-beta family with the immunophilin FKBP-12," Science 265, 674-6 (1994).
Zuber J. et al., "RNAi screen identifies Brd4 as a therapeutic target in acute myeloid leukaemia," Nature 478, 524-528 (2011).
Buckley et al., HaloPROTACS: Use of Small Molecule PROTACs to Induce Degradation of HaloTag Fusion Proteins, ACS Chemical Biology, 2015, 10; 1831-1837.
Buckley et al., Small-Molecule Control of Intracellular Protein Levels through Modulation of the Ubiquitin Proteasome System, Angewandte Reviews, 2014, 53; 2312-2330.
Buckley et al., Small-Molecule Inhibitors of the Interaction between the E3 Ligase VHL and HIF1α, Angewandte Chemie, 2012, 51; 11463-11467.
Chung et al., Discovery and Characterization of Small Molecule Inhibitors of the BET -O97Family Bromodomains, Journal of Medical Chemistry, 2011, 54; 3827-3838.
Corson et al, Design and applications of bifunctional small molecules: Why two heads are better than one, ACS Chemical Biology, 2008, 3(11); 677-692.
Dawson et al., Inhibition of BET recruitment to chromatin as an effective treatment for MLL-fusion leukaemia, Nature, 2011, 478; 529-533.
Faden et al., Generic tools for conditionally altering protein abundance and phenotypes on demand, Biol.Chem., 2014, 395(7-8); 737-762.
Giancotti, Deregulation of cell signaling in cancer, FEBS Letters, 2014, 588; 2558-2570.
Gosink et al., Redirecting the specificity of ubiquitination by modifying ubiquitin-conjugating enzymes, PNAS, 1995, 92; 9117-9121.
Gustafson et al., Small-Molecule-Mediated Degradation of the Androgen Receptor through Hydrophobic Tagging, Angewandte Chemie, 2015, 54; 9659-962.
Hewings et al., 3,5-Dimethylisoxazoles Act As Acetyl-lysine-mimetic Bromodomain2011nds, Journal of Medical Chemistry, 2011, 54; 6761-6770.
Jacques et al., Differentiation of antiinflamatory and antitumorigenic properties of stabilized enantiomers of thalidomide analogs, PNAS, 2015, 112; E1471-E1479.
Lallemand-Breitenbach et al., Role of Promyelocytic Leukemia (PML) Sumolation in Nuclear Body Formation, 11S Proteasome Recruitment, and As2O3-induced PML or PML/Retinoic Acid Receptor α Degradation, j. Exp. Med., 2001, 193; 1361-1371.
Lee et al., Targeted Degradation of the Aryl Hydrocarbon Receptor by the PROTAC Approach: A Useful Chemical Genetic Tool, ChemBioChem, 2007, 8: 2058-2062.

(56) References Cited

OTHER PUBLICATIONS

Nawaz et al., Proteasome-dependent degradation of the human estrogen receptor, PNAS, 1999, 96; 1758-1862.
Raina et al., Chemical Inducers of Targeted Protein Degradation, Journal of Biological Chemistry, 2010, 285; 11057-11060.
Rodriguez-Gonzalez et al., Targeting steroid hormone receptors for ubiquitination and degradation in breast and prostate cancer, Oncogene, 2008, 27; 7201-7211.
Ruchelman et al.,Isosteric analogs of lenalidomide and pomalidomide: Synthesis and biological activity, Bioorganic & Medical Chemistry Letters. 2012, 23; 360-365.
Sakamato et al., Chimeric molecules that target proteins to the Skpl-Cullin-F box complex for ubiquitination and degradation, PNAS, 2001, 98; 8554-8559.
Sakamoto et al., Development of Protacs to Target Cancer-promoting Proteins for Ubiquitination and Degradation, Molecular & Cellular Proteomics, 2003, 2.12; 1350-1357.
Schneekloth et al., Targeted Intracellular protein degradation induced by a small molecule: En route to chemical proteomics, Bioorganic & Medicinal Chemistry Letters, 2008, 18; 5904-5908.
Smith et al., Targeted Intracellular Protein Degradation Induced by a Small Molecule : En Route to Chemical Proteomics, Bioorg.Med. Chem. Lett., 2008, 18(22); 5904-5908.
Zhou et al., Harnessing the Ubiquitination Machinery to Target the Degradation of Specific Cellular Proteins, Molecular Cell, 2000, 6; 751-756.
International Search Report and Written Opinion for PCT/US2015/000274 mailed Mar. 18, 2016.

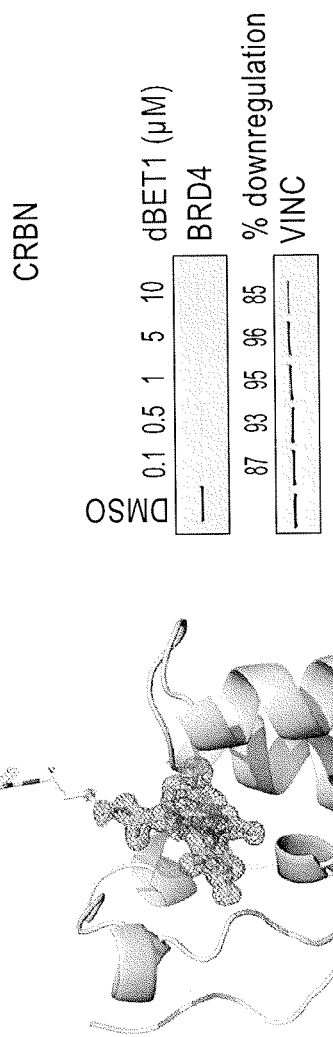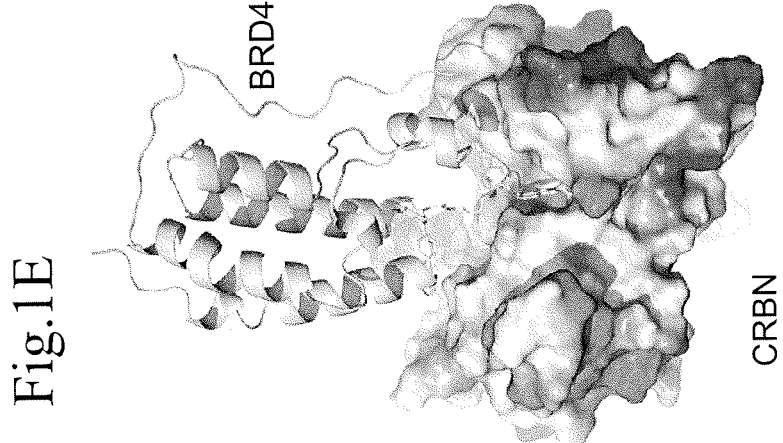

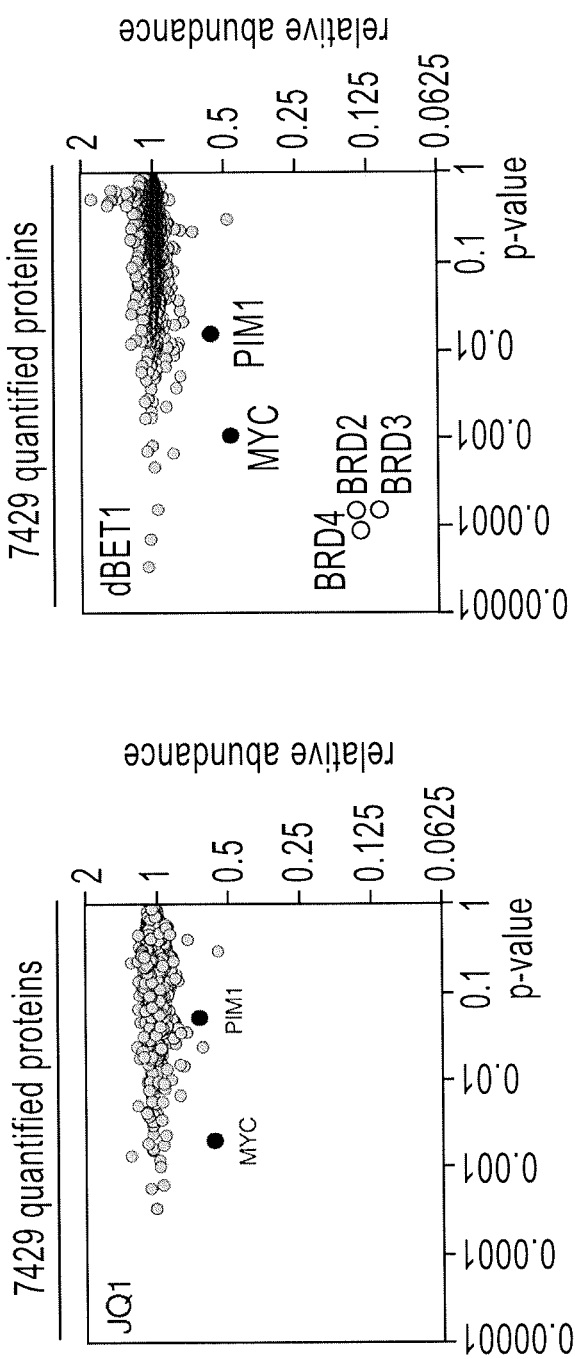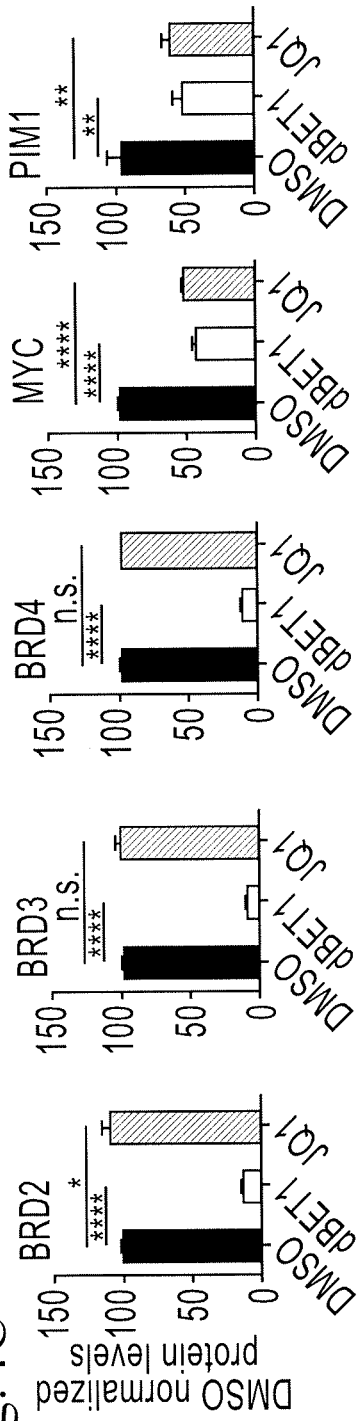
Fig. 4A
Fig. 4B
Fig. 4C

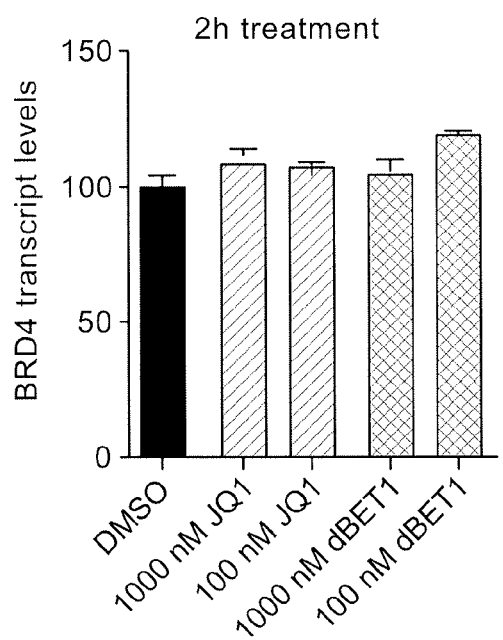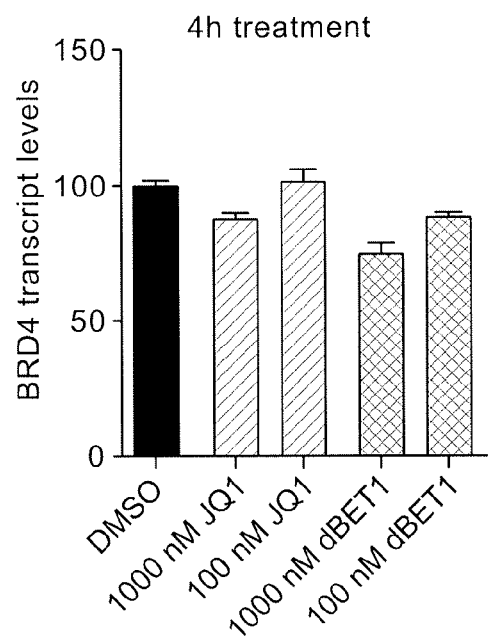
Fig. 6A
Fig. 6B

| PK parameters | Unit | Mean | SD |
|---|---|---|---|
| Tmax | hr | 0.500 | 0.433 |
| Cmax | ng/ml | 308 | 78.5 |
| Terminal $t_{1/2}$ | hr | 6.69 | 1.95 |
| $AUC_{last}$ | hr*ng/ml | 2109 | 528 |
| $AUC_{INF}$ | hr*ng/ml | 2295 | 466 |

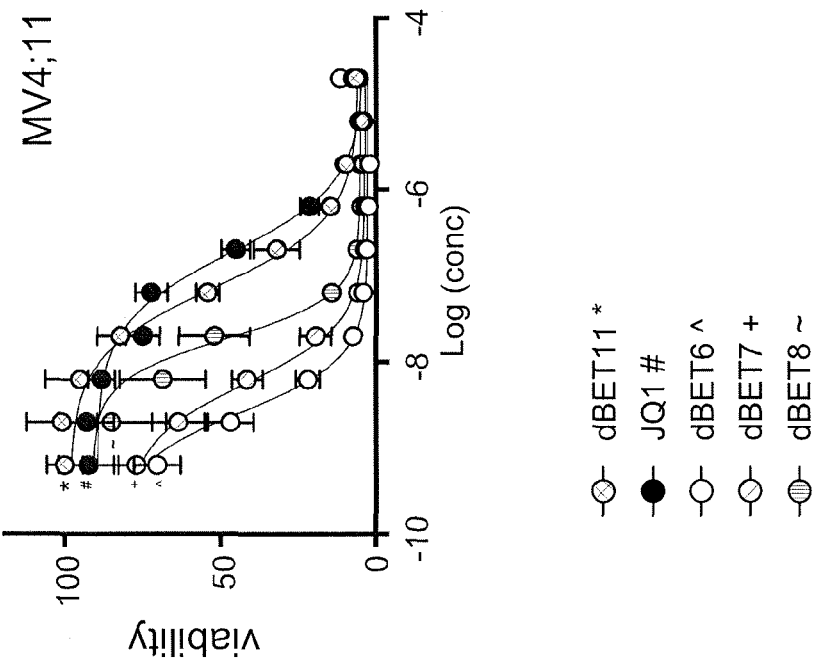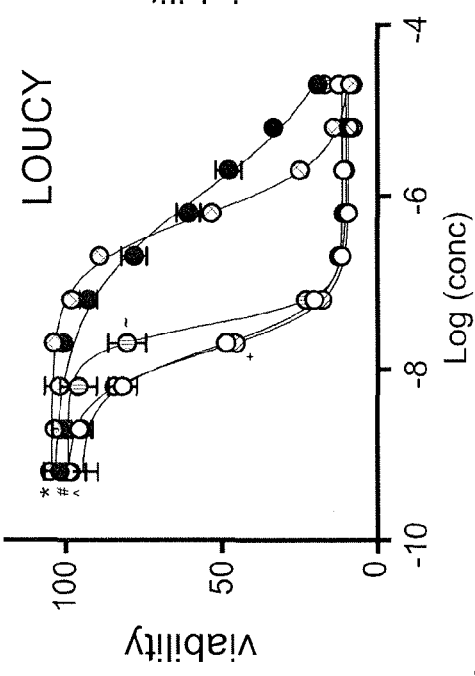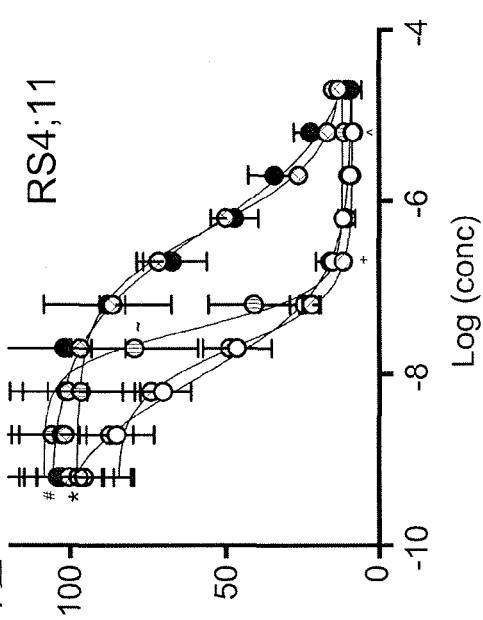

METHODS TO INDUCE TARGETED PROTEIN DEGRADATION THROUGH BIFUNCTIONAL MOLECULES

RELATED APPLICATIONS

This application claims priority to and the benefit of U.S. Ser. No. 62/096,318, filed on Dec. 23, 2014, U.S. Ser. No. 62/128,457, filed on Mar. 4, 2015, and U.S. Ser. No. 62/149,170, filed on Apr. 17, 2015, the contents of each of which are incorporated by reference in their entirety.

BACKGROUND

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity.

Cereblon (CRBN) interacts with damaged DNA binding protein 1 and forms an E3 ubiquitin ligase complex with Cullin 4 where it functions as a substrate receptor in which the proteins recognized by CRBN might be ubiquitinated and degraded by proteasomes. Proteasome-mediated degradation of unneeded or damaged proteins plays a very important role in maintaining regular function of a cell, such as cell survival, proliferation and growth. A new role for CRBN has been identified, i.e., the binding of immunomodulatory drugs (IMiDs), e.g. thalidomide, to CRBN has now been associated with teratogenicity and also the cytotoxicity of IMiDs, including lenalidomide, which are widely used to treat multiple myeloma patients. CRBN is likely a key player in the binding, ubiquitination and degradation of factors involved in maintaining function of myeloma cells. These new findings regarding the role of CRBN in IMiD action stimulated intense investigation of CRBN's downstream factors involved in maintaining regular function of a cell (Chang X. Int J Biochem Mol Biol. 2011; 2(3): 287-294).

The UPP is used to induce selective protein degradation, including use of fusion proteins to artificially ubiquitinate target proteins and synthetic small-molecule probes to induce proteasome-dependent degradation. Proteolysis Targeting Chimeras (PROTACs), heterobifunctional compounds composed of a target protein-binding ligand and an E3 ubiquitin ligase ligand, induced proteasome-mediated degradation of selected proteins via their recruitment to E3 ubiquitin ligase and subsequent ubiquitination. These druglike molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C., Chemistry & Biology, 2010, 17(6):551-555; Schnnekloth J S Jr., Chembiochem, 2005, 6(1):40-46).

Successful treatment of various oncologic and immunologic disorders, such as cancer, is still a highly unmet need. Therefore, continued development of alternative approaches to cure or treat such disorders, including developing therapies involving protein degradation technology, remains of strong interest. Novel methods of more general nature than existing methods with respect to possible targets and different cell lines or different in vivo systems could potentially lead to the development of future therapeutic treatments.

SUMMARY

The present application relates novel bifunctional compounds, which function to recruit targeted proteins to E3 Ubiquitin Ligase for degradation, and methods of preparation and uses thereof.

The present application further relates to targeted degradation of proteins through the use of bifunctional molecules, including bifunctional molecules that link a cereblon-binding moiety to a ligand that binds the targeted protein.

The present application also relates to a bifunctional compound having the following structure:
Degron-Linker-Targeting Ligand,
wherein the Linker is covalently bound to at least one Degron and at least one Targeting Ligand, the Degron is a compound capable of binding to a ubiquitin ligase such as an E3 Ubiquitin Ligase (e.g., cereblon), and the Targeting Ligand is capable of binding to the targeted protein(s).

The present application also relates to a novel degradation inducing moiety, or Degron, which is small in size and highly effective in recruiting targeted proteins for degradation.

The present application further relates to a compound having Formula D, D1, or D3:

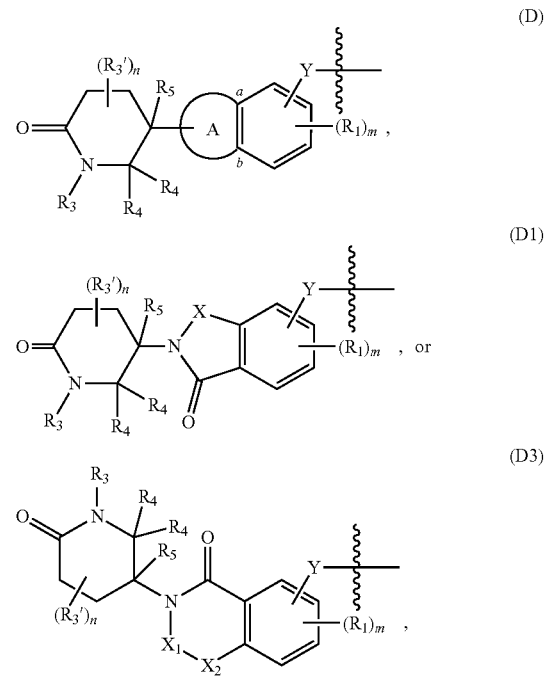

or an enantiomer, diastereomer, or stereoisomer thereof, wherein

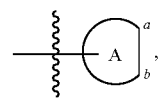

X, $X_1$, $X_2$, Y, $R_1$, $R_2$, $R_2'$, $R_3$, $R_3'$, $R_4$, $R_5$, m and n are each as defined herein.

The present application further relates to a Linker having Formula L0:

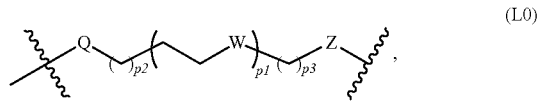

or an enantiomer, diastereomer, or stereoisomer thereof, wherein p1, p2, p3, W, Q, and Z are each as defined herein, the Linker is covalently bonded to the Degron with the ⁓ next to Q, and covalently bonded to the Targeting Ligand with the ⁓ next to Z.

The present application further relates to the Targeting Ligands described herein, including a compound of Formula TL-I to TL-VII.

The present application further relates to a bifunctional compound of Formula X, I, or II:

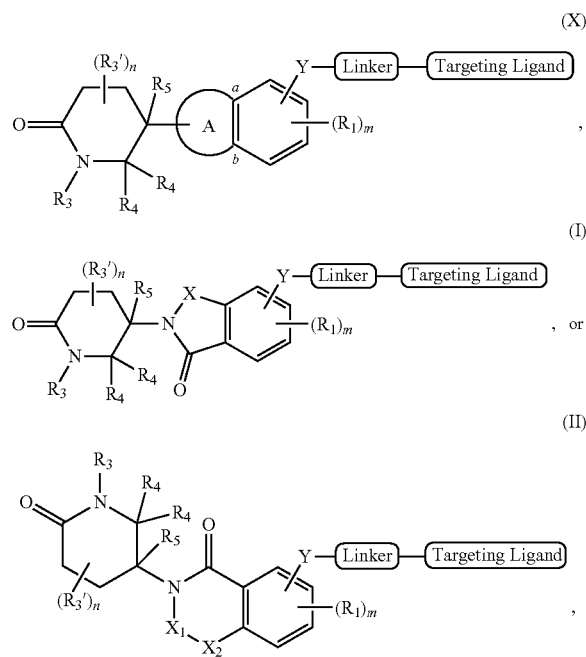

or an enantiomer, diastereomer, stereoisomer, or a pharmaceutically acceptable salt thereof, wherein the Linker is a group that covalently binds to the Targeting Ligand and Y, and the Targeting Ligand is capable of binding to or binds to a targeted protein, and wherein

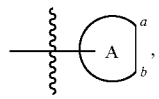

X, $X_1$, $X_2$, Y, $R_1$, $R_2$, $R_2'$, $R_3$, $R_3'$, $R_4$, $R_5$, m and n are each as defined herein.

The present application further relates to a pharmaceutical formulation comprising a therapeutically effective amount of a bifunctional compound of Formula X, I, or II and a pharmaceutically acceptable carrier.

The present application also relates to a method for treating a disease or condition which is modulated by a targeted protein by administering a therapeutically effective amount of a bifunctional compound of Formula X, I, or II to a subject in need thereof.

The present application also relates to use of a bifunctional compound of Formula X, I, or II or a pharmaceutical formulation of the application for treating a disease or condition which is modulated by a targeted protein.

The present application also relates to use of a bifunctional compound of Formula X, I, or II or a pharmaceutical formulation of the application in the manufacture of a medicament for treating a disease or condition which is modulated by a targeted protein.

The present application also relates to methods for treating cancer by administering a therapeutically effective amount of a bifunctional compound of Formula X, I, or II to a subject in need thereof.

The present application also relates to use of a bifunctional compound of Formula X, I, or II or a pharmaceutical formulation of the application for treating cancer.

The present application also relates to use of a bifunctional compound of Formula X, I, or II or a pharmaceutical formulation of the application in the manufacture of a medicament for treating cancer.

The compounds and methods of the present application address unmet needs in the treatment of diseases or disorders in which pathogenic or oncogenic endogenous proteins play a role, such as, for example, cancer.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present application will be apparent from the following detailed description and claims.

BRIEF DESCRIPTION OF THE DRAWINGS

The foregoing summary, as well as the following detailed description of the application, will be better understood when read in conjunction with the appended drawings.

FIGS. 1A-1H (i.e. FIGS. 1A, 1B, 1C, 1D, 1E, 1F, 1G, and 1H): Design and characterization of dBET1. FIG. 1A shows the chemical structure of JQ1(S), JQ1(R) and the phthalimides; FIG. 1B shows the chemical structure of dBET1; FIG. 1C shows DMSO normalized BRD4 binding signal measured by AlphaScreen for the indicated compounds (values represent mean±stdev of triplicate analysis); FIG. 1D shows the crystal structure of dBET1 bound to bromodomain 1 of BRD4; FIG. 1E shows docking of the structure in FIG. 1D into the published DDB1-CRBN structure; FIG. 1F shows immunoblot analysis for BRD4 and Vinculin after 18 h treatment of MV4-11 cells with the indicated concentrations of dBET1; FIG. 1G shows the crystal structure of dBET1 bound to BRD4 overlaid with the structure of JQ1 bound to BRD4; FIG. 1H is a Western blot illustrating the degree of degradation of BRD4 and reduction in c-MYC by treatment of cells with increased concentrations of a bifunctional compound of the application, dBET1.

FIGS. 2A, 2B, 2C, 2D, 2E, 2F, 2G, 2H, 2I, 2J, 2K, 2L, 2M, 2N, 2O, 2P, and 2Q): FIG. 2A shows the immunoblot analysis for BRD4 after treatment of MV4-11 cells with the indicated concentrations of dBET1(R) for 18 h; FIG. 2B shows cell count normalized BRD4 levels as determined by high-content assay in SUM149 cells treated with the indicated concentrations of dBET1 and dBET1(R) for 18 h (values represent mean±stdev of triplicate analysis, normalized to DMSO treated cells and baseline corrected based on immunoblots in FIG. 2C); FIG. 2C shows immunoblot analysis for BRD4 and Vinculin after treatment of SUM149 cells with the indicated concentrations of dBET1 and dBET1(R) for 18 h; FIG. 2D shows immunoblot analysis for BRD4 and Vinculin after treatment of MV4-11 cells with 100 nM dBET1 at the indicated time points; FIG. 2E shows cellular viability dose-response of dBET1 and JQ1 treatment for 24 h in MV4-11 as determined by ATP levels (values represent mean±stdev of quadruplicate analysis); FIG. 2F is a bar graph depiction of fold increase of apoptosis assessed via caspase glo assay relative to DMSO treated controls after 24 h treatment in MV4-11 or DHL4 cells (values represent mean±stdev of quadruplicate analysis); FIG. 2G shows immunoblot analysis for BRD4 and Vinculin after treatment of primary patient cells with the indicated concentrations of dBET1 for 24 hours; FIG. 2H is a bar graph depiction of fraction of Annexin V positive primary patient cells after 24 h treatment with either dBET1 or JQ1 at the indicated concentrations (values represent the average of duplicates and the range as error bars) (representative counter plots shown in FIGS. 2L and 2M); FIGS. 2I and 2J are immunoblot analysis showing BRD4 and Vinculin 18 h after dBET1 treatment with the indicated concentrations in SUM159 and MOLM13, respectively; FIG. 2K shows immunoblot analysis for BRD2, BRD3, and BRD4 and c-Myc at different time points after treatment of cells with the 100 nM of dBET1; FIG. 2L are a series of flow cytometry plots illustrating Annexin V/PI data of primary patient cells treated with the indicated concentrations of JQ1 and dBET1 for 24 h; FIG. 2M is a bar graph depiction of Annexin V positive MV4-11 cells after treatment with dBET1 or JQ1 at the indicated concentrations (data represents mean±stdev of triplicate analysis); FIG. 2N is an immunoblot analysis of cleaved caspase 3, PARP cleavage and vinculin after treatment with dBET1 and JQ1 at the indicated concentrations for 24 h; FIG. 2O are bar graphs illustrating the kinetic advantage of BET degradation on apoptosis (Caspase-GLO) relative to treated controls: MV4-1 cells were treated for 4 or 8 h with JQ1 or dBET1 at the indicated concentrations, followed by drug wash-out before being plated in drug-free media for 24 h; FIG. 2P is a bar graph depiction of fold increase of apoptosis of MV4-11 cells treated for 4 or 8 h with JQ1 or dBET1 at the indicated concentrations, relative to DMSO treated controls assessed via caspase glo assay (drug were washed out with PBS (3×) before being plated in drug-free media for a final treatment duration of 24 h); FIG. 2Q is an immunoblot analysis of cleaved caspase 3, PARP cleavage and vinculin after identical treatment conditions in FIG. 2P.

FIGS. 3A, 3B, 3C, 3D, 3E, and 3F): FIGS. 3A, 3B, 3C and 3D show chemical and genetic rescue of dBET1-mediated degradation of BRD4. FIG. 3A shows immunoblot analysis for BRD4 and Vinculin after treatment of MV4-11 cells with the indicated concentrations of dBET1, JQ1, and thalidomide for 24 h; FIG. 3B shows immunoblot analysis for BRD4 and Vinculin after 4 h pre-treatment with either DMSO, Carfilzomib (0.4 µM), JQ1 (10 µM) or thalidomide (10 µM) followed by 2 h dBET1 treatment at a concentration of 100 nM; FIG. 3C shows immunoblot analysis for BRD4 and Vinculin after a 4 h pre-treatment with 1 µM MLN4924 followed by 2 h dBET1 treatment at the indicated concentrations; FIG. 3D shows immunoblot analysis for BRD4, CRBN and tubulin after treatment of MM1S$^{WT}$ or MM1S$^{CRBN-/-}$ with dBET1 for 18 h at the indicated concentrations; FIG. 3E is an immunoblot analysis comparing the concentration of BRD4 in cells treated with various concentrations of thalidomide, JQ1, and dBET1; FIG. 3F is an immunoblot analysis showing the concentration of BRD4 in cells treated with carfilzomib (400 nM), JQ1 (20 uM), or thalidomide (20 uM) for 4 hours and with dBET1 (100 nM) as indicated for 2 hours.

FIGS. 4A-4F (i.e. FIGS. 4A, 4B, 4C, 4D, 4E, and 4F): FIGS. 4A, 4B, 4C, 4D, and 4E show selective BET bromodomain degradation by expression proteomics: MV4-11 cells were treated for 2 hours with DMSO, 250 nM dBET1 or 250 nM JQ1. FIG. 4A depicts fold change of abundance of 7429 proteins comparing JQ1 to DMSO treatment as well as their respective p-value (T-test) (data from triplicate analysis); FIG. 4B depicts fold change of abundance of 7429 proteins comparing 250 nM dBET1 to DMSO treatment (data from triplicate analysis); FIG. 4C is a bar graph depiction of changes in protein levels of the selected proteins as shown normalized to DMSO (values represent mean±stdev of triplicates); FIG. 4D shows immunoblot analysis of BRD2, BRD3, BRD4, MYC, PIM1 and VINC after 2 h treatment of MV4-11 cells with either DMSO, 250 nM dBET1 or 250 nM JQ1; FIG. 4E is a bar graph depiction of qRT-PCR analysis of transcript levels of BRD2, BRD3, BRD4, MYC and PIM1 after 2 h treatment of MV4-11 cells with either DMSO, 250 nM dBET1 or 250 nM JQ1 (values represent mean+/−stdev of triplicates); FIG. 4F is an immunoblot analysis for IKZF3 and Vinculin after 24 h treatment with thalidomide or the indicated concentrations of dBET1 in MM1S cell line.

FIG. 5A is a Western blot showing the concentration of BRD4 in cells treated with various concentrations of JQ1-Rev, in comparison with 100 nM of a bifunctional compound of the application, dBET1. FIG. 5B is a drawing of the chemical structure of JQ1-Rev (JQI-11-079).

FIGS. 6A and 6B: FIGS. 6A and 6B are a series of graphs that illustrate the transcription levels of BRD4 assayed via qRT-PCR after 2 hrs (FIG. 6A) or 4 hrs (FIG. 6B) from cells treated with various concentrations of JQ1 or dBET.

FIG. 9A is a Western blot illustrating reduction in PLK1 by treatment of cells with increased concentrations of a bifunctional compound of the application, dBET2; FIG. 9B is a bar graph depicting PLK intensity in dBET2 treated cells as percentage of that in DMSO treated cells.

FIGS. 10A, 10B, 10C, and 10D): dFKBP-1 and dFKBP-2 mediated degradation of FKBP12. FIG. 10A depicts chemical structures of dFKBP-1 and dFKBP-2; FIG. 10B illustrates immunoblot analysis for FKBP12 and Vinculin after 18 h treatment with the indicated compounds; FIG. 10C shows immunoblot analysis for FKBP12 and Vinculin after a 4 h pre-treatment with either DMSO, Carfilzomib (400 nM), MLN4924 (1 μM), SLF (20 μM) or thalidomide (10 μM) followed by a 4 h dFKBP-1 treatment at a concentration of 1 μM in MV4-11 cells; FIG. 10D shows immunoblot analysis for FKBP12, CRBN and tubulin after treatment of 293FT$^{WT}$ or 293FT$^{CRBN-/-}$ with dFKBP12 at the indicated concentrations for 18 h.

FIGS. 11A, 11B, and 11C): FIG. 11A is a diagram showing selectivity of dBET1 for binding to BETs over other human bromodomains, as determined by single point screening (BromoScan); FIG. 11B shows results from a dimerization assay measuring dBET1 induced proximity (at 111 nM) between recombinant BRD4 bromodomain and recombinant CRBN-DDB1 (values represent mean±stdev of quadruplicate analysis and are normalized to DMSO); FIG. 11C is a bar graph showing the competition of dBET1 induced proximity in the presence of DMSO (vehicle), JQ1(S), thal-(−), JQ1(R) and thal-(+), all at a final concentration of 1 μM (values represent mean±stdev of quadruplicate analysis and are normalized to DMSO).

FIGS. 12A, 12B, 12C, 12D, and 12E): FIG. 12A is a bar graph showing the tumor volume of vehicle treated mice (n=5) or mice treated with dBET1 at a concentration of 50 mg/kg (n=6) over a treatment period of 14 days; FIG. 12B is a bar graph comparing the tumor weight after termination of the experiment shown in FIG. 12A on day 14; FIG. 12C is an immunoblot analysis for BRD4, MYC and Vinculin using tumor lysates from mice treated either once for 4 h or twice for 22 h and 4 h compared to a vehicle treated control; FIG. 12D shows immunohistochemistry staining for BRD4, MYC and Ki67 of a representative tumor of a dBET1 treated and a control treated mouse; FIG. 12E is a bar graph depicting quantification of the staining in FIG. 12D based on 3 independent areas within that section (data represents mean±stdev of triplicate analysis and is normalized to DMSO).

FIGS. 13A, 13B, 13C, and 13D): Pharmacokinetic studies of dBET1 in CD1 mice. FIG. 13A is a graph showing concentration of dBET1 in CD1 mice following intraperitoneal injection of dBET1 formulated in 0.5% MC in water; FIG. 13B is a table depicting pharmacokinetic parameters in mice from FIG. 13A; FIG. 13C is a graph showing the change in weight of mice treated with 50 mg/kg q.d. of dBET1 or vehicle; FIG. 13D are bar graphs showing changes in HTC, WBC, or PLT in mice from FIG. 13C.

FIGS. 14A, 14B, 14C, 14D, 14E, 14F, 14G, 14H, 14I, 14J, 14K, 14L, 14M, 14N, 14O, 14P, 14Q, 14R, 14S, 14T, 14U, 14V, 14W, 14X, 14Y, 14Z, 14AA, and 14BB): High content assay measuring BRD4 levels in cells (293FT$^{WT}$ or 293FT$^{CRBN-/-}$) after 4 hour treatment with indicated concentrations of the bifunctional compounds of the present application. FIGS. 14A and 14B: BRD4 levels in 293FT$^{WT}$ (FIG. 14A) or 293FT$^{CRBN-/-}$ (FIG. 14B) after 4 hour treatment with indicated concentrations of JQ1; FIGS. 14C and 14D: BRD4 levels in 293FT$^{WT}$ (FIG. 14C) or 293FT$^{CRBN-/-}$ (FIG. 14D) after 4 hour treatment with indicated concentrations of dBET1; FIGS. 14E and 14F: BRD4 levels in 293FT$^{WT}$ (FIG. 14E) or 293FT$^{CRBN-/-}$ (FIG. 14F) after 4 hour treatment with indicated concentrations of dBET2; FIGS. 14G and 14H: BRD4 levels in 293FT$^{WT}$ (FIG. 14G) or 293FT$^{CRBN-/-}$ (FIG. 14H) after 4 hour treatment with indicated concentrations of dBET3; FIGS. 14I and 14J: BRD4 levels in 293FT$^{WT}$ (FIG. 14I) or 293FT$^{CRBN-/-}$ (FIG. 14J) after 4 hour treatment with indicated concentrations of dBET4; FIGS. 14K and 14L: BRD4 levels in 293FT$^{WT}$ (FIG. 14K) or 293FT$^{CRBN-/-}$ (FIG. 14L) after 4 hour treatment with indicated concentrations of dBET5; FIGS. 14M and 14N: BRD4 levels in 293FT$^{WT}$ (FIG. 14M) or 293FT$^{CRBN-/-}$ (FIG. 14N) after 4 hour treatment with indicated concentrations of dBET6; FIGS. 14O and 14P: BRD4 levels in 293FT$^{WT}$ (FIG. 14O) or 293FT$^{CRBN-/-}$ (FIG. 14P) after 4 hour treatment with indicated concentrations of dBET7; FIGS. 14Q and 14R: BRD4 levels in 293FT$^{WT}$ (FIG. 14Q) or 293FT$^{CRBN-/-}$ (FIG. 14R) after 4 hour treatment with indicated concentrations of dBET8; FIGS. 14S and 14T: BRD4 levels in 293FT$^{WT}$ (FIG. 14S) or 293FT$^{CRBN-/-}$ (FIG. 14T) after 4 hour treatment with indicated concentrations of dBET9; FIGS. 14U and 14V: BRD4 levels in 293FT$^{WT}$ (FIG. 14U) or 293FT$^{CRBN-/-}$ (FIG. 14V) after 4 hour treatment with indicated concentrations of dBET10; FIGS. 14W and 14X: BRD4 levels in 293FT$^{WT}$ (FIG. 14W) or 293FT$^{CRBN-/-}$ (FIG. 14X) after 4 hour treatment with indicated concentrations of dBET15; FIGS. 14Y and 14Z: BRD4 levels in 293FT$^{WT}$ (FIG. 14Y) or 293FT$^{CRBN-/-}$ (FIG. 14Z) after 4 hour treatment with indicated concentrations of dBET17; FIGS. 14AA and 14BB: BRD4 levels in 293FT$^{WT}$ (FIG. 14AA) or 293FT$^{CRBN-/-}$ (FIG. 14BB) after 4 hour treatment with indicated concentrations of dBET18.

FIGS. 15A, 15B, 15C, 15D, 15E, and 15F): Immunoblots of BRD levels in cells treated with varying concentrations of the bifunctional compounds of the present application. FIG. 15A is an immunoblot showing BRD4 levels in BAF3_K-RAS cells treated with the indicated concentrations of dBET1 or dBET6 for 16.5 hours; FIG. 15B is an immunoblot showing BRD4 levels in BAF3_K-RAS or SEMK2 cells treated with the indicated concentrations of dBET1 for 16.5 hours; FIG. 15C is an immunoblot showing BRD4 levels in SEMK2 cells treated with the indicated concentrations of dBET1 or dBET6 for 16.5 hours; FIG. 15D is an immunoblot showing BRD4 levels in Monomac1 cells treated with the indicated concentrations of dBET1 or dBET6 for 16 hours; FIG. 15E is an immunoblot showing levels of BRD4, BRD2, and BRD3 at various time points in MV4-11 cells treated with 50 nM of dBET6; FIG. 15F is an immunoblot showing BRD4 levels in MM1S$^{WT}$ or MM1S$^{CRBN-/-}$ cells treated with the indicated concentrations of dBET6 for 16 hours.

FIG. 16A is an immunoblot showing levels of BRD4 and PLK1 in cells (WT or CRBN−/−) treated with 1 μM of dBET2, dBET7, dBET8, or dBET10; FIG. 16B is an immunoblot showing BRD4 levels at the indicated time points after the cells were treated with 100 nM dBET18.

FIGS. 17A-17E (i.e. FIGS. 17A, 17B, 17C, 17D, and 17E): Cell viability after treatment with the bifunctional compounds of the present application. FIGS. 17A and 17B indicate cell viability EC$_{50}$ values of the bifunctional compounds of the present application in various cells lines; FIGS. 17C, 17D and 17E show cell viability after treatment with increasing concentrations of JQ1, dBET1, dBET6, dBET7, or dBET8.

FIGS. 18A, 18B, and 18C) show viability of MOLT4 (FIG. 18A), DND41 (FIG. 18B), and CUTLL1 (FIG. 18C) cells after being treated with increasing concentrations of dBET compounds.

DETAILED DESCRIPTION

Figure 1A:
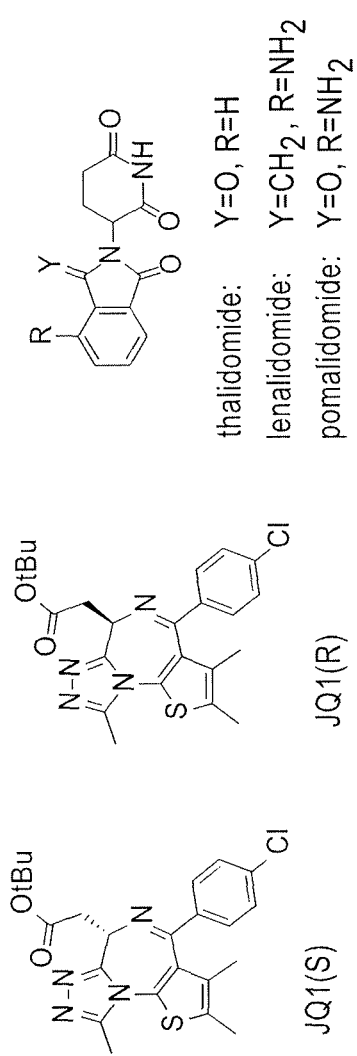
Figure 1B:
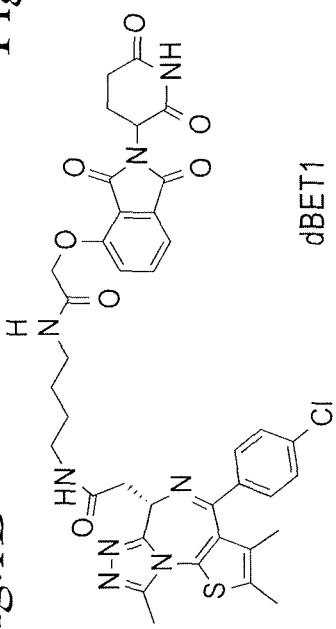

Small-molecule antagonists disable discrete biochemical properties of the protein targets. For multi-domain protein targets, the pharmacologic consequence of drug action is limited by selective disruption of one domain-specific activity. Also, target inhibition is kinetically limited by the durability and degree of the target engagement. These features of traditional drug molecules are challenging to the development of inhibitors targeting transcription factors and chromatin-associated epigenetic proteins, which function as multi-domain biomolecular scaffolds and generally feature rapid association and dissociation kinetics. A chemical strategy was devised to prompt ligand-dependent target protein degradation via chemical conjugation with derivatized phthalimides that hijack the function of the Cereblon E3 ubiquitin ligase complex. Using this approach, an acetyl-lysine competitive antagonist that displaces BET bromodomains from chromatin (JQ1) was converted to a phthalimide-conjugated ligand that prompts immediate Cereblon-dependent BET protein degradation (dBET1). Expression proteomics confirmed high specificity for BET family members BRD2, BRD3 and BRD4 among 7429 proteins detected. Degradation of BET bromodomains is associated with a more rapid and robust apoptotic response compared to bromodomain inhibition in primary human leukemic blasts and in human leukemia xenograft in vivo. Following this approach, additional series of phthalimide-conjugated ligands targeting other proteins for degradation, such as FKBP12, were also developed. A facile new strategy to control the stability of target proteins, including previously intractable protein targets, is described herein.

As discussed above, there remains a need for the development of novel therapies for the treatment of various disorders, including oncologic and immunologic disorders. The present application provides novel compounds of general Formula I, which induce formation of a complex between two proteins to result in a desired biological effect. These compounds can be prepared by using traditional synthetic methods and used by means of addition to a subject as drugs.

The present application provides a novel class of compounds useful for the treatment of cancer and other proliferative conditions.

The present application relates to small molecule E3 ligase ligands (Degrons) which are covalently linked to a targeted protein ligand through a Linker of varying length and functionality, which can be used as therapeutics for treating various diseases including cancer. The present application also relates to a technology platform of bringing targeted proteins to E3 ligases, for example CRBN, for ubiquitination and subsequent proteasomal degradation using the bifunctional small molecules comprising a thalidomide-like Degron and a Targeting Ligand connected to each other via a Linker.

This technology platform provides therapies based upon depression of target protein levels by degradation. The novel technology allows for targeted degradation to occur in a more general nature than existing methods with respect to possible targets and different cell lines or different in vivo systems.

Compounds of the present application may offer important clinical benefits to patients, in particular for the treatment of the disease states and conditions modulated by the proteins of interest.

Compounds of the Application

The present application relates to bifunctional compounds which find utility as modulators of ubiquitination and proteosomal degradation of targeted proteins, especially compounds comprising an inhibitor of a polypeptide or a protein that is degraded and/or otherwise inhibited by the bifunctional compounds of the present application. In particular, the present application is directed to compounds which contain a ligand, e.g., a small molecule ligand (i.e., having a molecular weight of below 2,000, 1,000, 500, or 200 Daltons), such as a thalidomide-like ligand, which is capable of binding to a ubiquitin ligase, such as cereblon, and a moiety that is capable of binding to a target protein, in such a way that the target protein is placed in proximity to the ubiquitin ligase to effect degradation (and/or inhibition) of that protein.

In general, the present application provides compounds having the general structure:

Degron-Linker-Targeting Ligand, wherein the Linker is covalently bound to at least one Degron and at least one Targeting Ligand, the Degron is a compound capable of binding to a ubiquitin ligase such as an E3 Ubiquitin Ligase (e.g., cereblon), and the Targeting Ligand is capable of binding to the targeted protein(s).

In certain embodiments, the present application provides a compound of Formula X:

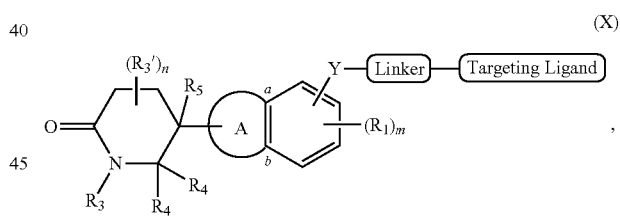

(X)

or an enantiomer, diastereomer, stereoisomer, or a pharmaceutically acceptable salt thereof, wherein:

the Linker is a group that covalently binds to the Targeting Ligand and Y; and the Targeting Ligand is capable of binding to or binds to a targeted protein;

and wherein

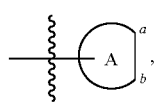

X, $X_1$, $X_2$, Y, $R_1$, $R_2$, $R_2'$, $R_3$, $R_3'$, $R_4$, $R_5$, m and n are each as defined herein.

In certain embodiments, the present application provides a compound of Formula I:

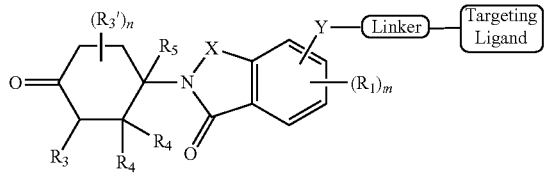
(I)

or an enantiomer, diastereomer, stereoisomer, or pharmaceutically acceptable salt thereof, wherein:

the Linker is a group that covalently binds to the Targeting Ligand and Y; and the Targeting Ligand is capable of binding to or binds to a targeted protein;

and wherein X, XY, $R_1$, $R_2$, $R_2'$, $R_3$, $R_3'$, $R_4$, $R_5$, m and n are each as defined herein.

In certain embodiments, the present application provides a compound of Formula I:

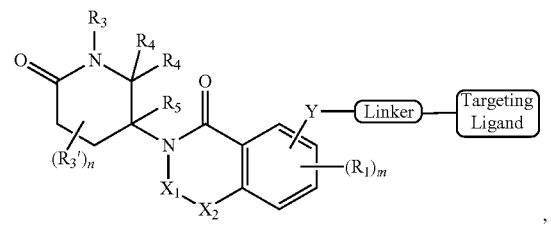
(II)

or an enantiomer, diastereomer, stereoisomer, or pharmaceutically acceptable salt thereof, wherein:

the Linker is a group that covalently binds to the Targeting Ligand and Y; and the Targeting Ligand is capable of binding to or binds to a targeted protein;

and wherein $X_1$, $X_2$, Y, $R_1$, $R_2$, $R_2'$, $R_3$, $R_3'$, $R_4$, $R_5$, m and n are each as defined herein.

Degron

The Degron is a compound that serves to link a targeted protein, through the Linker and Targeting Ligand, to a ubiquitin ligase for proteosomal degradation. In certain embodiments, the Degron is a compound that is capable of binding to or binds to a ubiquitin ligase. In further embodiments, the Degron is a compound that is capable of binding to or binds to a E3 Ubiquitin Ligase. In further embodiments, the Degron is a compound that is capable of binding to or binds to cereblon. In further embodiments, the Degron is a thalidomide or a derivative or analog thereof.

In certain embodiments, the Degron is a compound having Formula D:

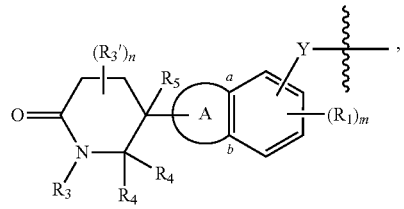
(D)

or an enantiomer, diastereomer, or stereoisomer thereof, wherein:

is

Y is a bond, $(CH_2)_{1-6}$, $(CH_2)_{0-6}$—O, $(CH_2)_{0-6}$—C(O)NR$_2'$, $(CH_2)_{0-6}$—NR$_2'$C(O), $(CH_2)_{0-6}$—NH, or $(CH_2)_{0-6}$—NR$_2$;

X is C(O) or C($R_3$)$_2$;

$X_1$—$X_2$ is C($R_3$)=N or C($R_3$)$_2$—C($R_3$)$_2$;

each $R_1$ is independently halogen, OH, $C_1$-$C_6$ alkyl, or $C_1$-$C_6$ alkoxy;

$R_2$ is $C_1$-$C_6$ alkyl, C(O)—$C_1$-$C_6$ alkyl, or C(O)—$C_3$-$C_6$ cycloalkyl;

$R_2'$ is H or $C_1$-$C_6$ alkyl;

each $R_3$ is independently H or $C_1$-$C_3$ alkyl;

each $R_3'$ is independently $C_1$-$C_3$ alkyl;

each $R_4$ is independently H or $C_1$-$C_3$ alkyl; or two $R_4$, together with the carbon atom to which they are attached, form C(O), a $C_3$-$C_6$ carbocycle, or a 4-, 5-, or 6-membered heterocycle comprising 1 or 2 heteroatoms selected from N and O;

$R_5$ is H, deuterium, $C_1$-$C_3$ alkyl, F, or Cl;

m is 0, 1, 2 or 3; and n is 0, 1 or 2;

wherein the compound is covalently bonded to another moiety (e.g., a compound, or a Linker) via 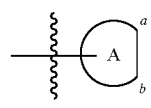

In certain embodiments, the Degron is a compound of Formula D, wherein is

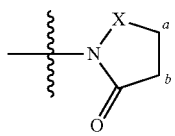

In certain embodiments, the Degron is a compound of Formula D, wherein

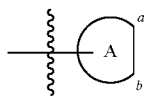

is

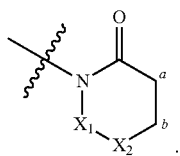

In certain embodiments, the Degron is a compound of Formula D, wherein X is C(O).

In certain embodiments, the Degron is a compound of Formula D, wherein X is $C(R_3)_2$; and each $R_3$ is H. In certain embodiments, X is $C(R_3)_2$; and one of $R_3$ is H, and the other is $C_1$-$C_3$ alkyl selected from methyl, ethyl, and propyl. In certain embodiments, X is $C(R_3)_2$; and each $R_3$ is independently selected from methyl, ethyl, and propyl.

In certain embodiments, the Degron is a compound of Formula D, wherein $X_1$-$X_2$ is $C(R_3)$=N. In certain embodiments, $X_1$-$X_2$ is CH=N. In certain embodiments, $X_1$-$X_2$ is $C(R_3)$=N; and $R_3$ is $C_1$-$C_3$ alkyl selected from methyl, ethyl, and propyl. In certain embodiments, $X_1$-$X_2$ is $C(CH_3)$=N.

In certain embodiments, the Degron is a compound of Formula D, wherein $X_1$-$X_2$ is $C(R_3)_2$—$C(R_3)_2$; and each $R_3$ is H. In certain embodiments, $X_1$-$X_2$ is $C(R_3)_2$—$C(R_3)_2$; and one of $R_3$ is H, and the other three $R_3$ are independently $C_1$-$C_3$ alkyl selected from methyl, ethyl, and propyl. In certain embodiments, $X_1$-$X_2$ is $C(R_3)_2$—$C(R_3)_2$; and two of the $R_3$ are H, and the other two $R_3$ are independently $C_1$-$C_3$ alkyl selected from methyl, ethyl, and propyl. In certain embodiments, $X_1$-$X_2$ is $C(R_3)_2$—$C(R_3)_2$; and three of the $R_3$ are H, and the remaining $R_3$ is $C_1$-$C_3$ alkyl selected from methyl, ethyl, and propyl.

In certain embodiments, the Degron is a compound of Formula D, wherein Y is a bond.

In certain embodiments, the Degron is a compound of Formula D, wherein Y is $(CH_2)_1$, $(CH_2)_2$, $(CH_2)_3$, $(CH_2)_4$, $(CH_2)_5$, or $(CH_2)_6$. In certain embodiments, Y is $(CH_2)_1$, $(CH_2)_2$, or $(CH_2)_3$. In certain embodiments, Y is $(CH_2)_1$ or $(CH_2)_2$.

In certain embodiments, the Degron is a compound of Formula D, wherein Y is O, $CH_2$—O, $(CH_2)_2$—O, $(CH_2)_3$—O, $(CH_2)_4$—O, $(CH_2)_5$—O, or $(CH_2)_6$—O. In certain embodiments, Y is O, $CH_2$—O, $(CH_2)_2$—O, or $(CH_2)_3$—O. In certain embodiments, Y is O or $CH_2$—O. In certain embodiments, Y is O.

In certain embodiments, the Degron is a compound of Formula D, wherein Y is $C(O)NR_2'$, $CH_2$—$C(O)NR_2'$, $(CH_2)_2$—$C(O)NR_2'$, $(CH_2)_3$—$C(O)NR_2'$, $(CH_2)_4$—$C(O)NR_2'$, $(CH_2)_5$—$C(O)NR_2'$, or $(CH_2)_6$—$C(O)NR_2'$. In certain embodiments, Y is $C(O)NR_2'$, $CH_2$—$C(O)NR_2'$, $(CH_2)_2$—$C(O)NR_2'$, or $(CH_2)_3$—$C(O)NR_2'$. In certain embodiments, Y is $C(O)NR_2'$ or $CH_2$—$C(O)NR_2'$. In certain embodiments, Y is $C(O)NR_2'$.

In certain embodiments, the Degron is a compound of Formula D, wherein Y is $NR_2'C(O)$, $CH_2$—$NR_2'C(O)$, $(CH_2)_2$—$NR_2'C(O)$, $(CH_2)_3$—$NR_2'C(O)$, $(CH_2)_4$—$NR_2'C(O)$, $(CH_2)_5$—$NR_2'C(O)$, or $(CH_2)_6$—$NR_2'C(O)$. In certain embodiments, Y is $NR_2'C(O)$, $CH_2$—$NR_2'C(O)$, $(CH_2)_2$—$NR_2'C(O)$, or $(CH_2)_3$—$NR_2'C(O)$. In certain embodiments, Y is $NR_2'C(O)$ or $CH_2$—$NR_2'C(O)$. In certain embodiments, Y is $NR_2'C(O)$.

In certain embodiments, the Degron is a compound of Formula D, wherein $R_2'$ is H. In certain embodiments, the Degron is a compound of Formula D, wherein $R_2'$ is selected from methyl, ethyl, propyl, butyl, i-butyl, t-butyl, pentyl, i-pentyl, and hexyl. In certain embodiments, $R_2'$ is $C_1$-$C_3$ alkyl selected from methyl, ethyl, and propyl.

In certain embodiments, the Degron is a compound of Formula D, wherein Y is NH, $CH_2$—NH, $(CH_2)_2$—NH, $(CH_2)_3$—NH, $(CH_2)_4$—NH, $(CH_2)_5$—NH, or $(CH_2)_6$—NH. In certain embodiments, Y is NH, $CH_2$—NH, $(CH_2)_2$—NH, or $(CH_2)_3$—NH. In certain embodiments, Y is NH or $CH_2$—NH. In certain embodiments, Y is NH.

In certain embodiments, the Degron is a compound of Formula D, wherein Y is $NR_2$, $CH_2$—$NR_2$, $(CH_2)_2$—$NR_2$, $(CH_2)_3$—$NR_2$, $(CH_2)_4$—$NR_2$, $(CH_2)_5$—$NR_2$, or $(CH_2)_6$—$NR_2$. In certain embodiments, Y is $NR_2$, $CH_2$—$NR_2$, $(CH_2)_2$—$NR_2$, or $(CH_2)_3$—$NR_2$. In certain embodiments, Y is $NR_2$ or $CH_2$—$NR_2$. In certain embodiments, Y is $NR_2$.

In certain embodiments, the Degron is a compound of Formula D, wherein $R_2$ is selected from methyl, ethyl, propyl, butyl, i-butyl, t-butyl, pentyl, i-pentyl, and hexyl. In certain embodiments, $R_2$ is $C_1$-$C_3$ alkyl selected from methyl, ethyl, and propyl.

In certain embodiments, the Degron is a compound of Formula D, wherein $R_2$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In certain embodiments, $R_2$ is C(O)—$C_1$-$C_3$ alkyl selected from C(O)-methyl, C(O)-ethyl, and C(O)-propyl.

In certain embodiments, the Degron is a compound of Formula D, wherein $R_2$ is selected from C(O)-cyclopropyl, C(O)-cyclobutyl, C(O)-cyclopentyl, and C(O)-cyclohexyl. In certain embodiments, $R_2$ is C(O)-cyclopropyl.

In certain embodiments, the Degron is a compound of Formula D, wherein $R_3$ is H.

In certain embodiments, the Degron is a compound of Formula D, wherein $R_3$ is $C_1$-$C_3$ alkyl selected from methyl, ethyl, and propyl. In certain embodiments, $R_3$ is methyl.

In certain embodiments, the Degron is a compound of Formula D, wherein n is 0.

In certain embodiments, the Degron is a compound of Formula D, wherein n is 1.

In certain embodiments, the Degron is a compound of Formula D, wherein n is 2.

In certain embodiments, the Degron is a compound of Formula D, wherein each $R_3'$ is independently $C_1$-$C_3$ alkyl selected from methyl, ethyl, and propyl.

In certain embodiments, the Degron is a compound of Formula D, wherein m is 0.

In certain embodiments, the Degron is a compound of Formula D, wherein m is 1.

In certain embodiments, the Degron is a compound of Formula D, wherein m is 2.

In certain embodiments, the Degron is a compound of Formula D, wherein m is 3.

In certain embodiments, the Degron is a compound of Formula D, wherein each $R_1$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In further embodiments, the Degron is a compound of Formula D, wherein each $R_1$ is independently selected from F, Cl, OH, methyl, ethyl, propyl, butyl, i-butyl, t-butyl, methoxy, and ethoxy.

In certain embodiments, the Degron is a compound of Formula D, wherein each $R_4$ is H.

In certain embodiments, the Degron is a compound of Formula D, wherein one of $R_4$ is H, and the other $R_4$ is $C_1$-$C_3$ alkyl selected from methyl, ethyl, and propyl.

In certain embodiments, the Degron is a compound of Formula D, wherein each $R_4$ is independently $C_1$-$C_3$ alkyl selected from methyl, ethyl, and propyl.

In certain embodiments, the Degron is a compound of Formula D, wherein two $R_4$, together with the carbon atom to which they are attached, form C(O).

In certain embodiments, the Degron is a compound of Formula D, wherein two $R_4$, together with the carbon atom to which they are attached, form cyclopropyl, cyclobutyl, cyclopentyl, or cyclohexyl.

In certain embodiments, the Degron is a compound of Formula D, wherein two $R_4$, together with the carbon atom to which they are attached, form a 4-, 5-, or 6-membered heterocycle selected from oxetane, azetidine, tetrahydrofuran, pyrrolidine, piperidine, piperazine, and morpholine. In certain embodiments, two $R_4$, together with the carbon atom to which they are attached, form oxetane.

In certain embodiments, the Degron is a compound of Formula D, wherein $R_5$ is H, deuterium, or $C_1$-$C_3$ alkyl. In further embodiments, $R_5$ is in the (5) or (R) configuration. In further embodiments, $R_5$ is in the (5) configuration. In certain embodiments, the Degron is a compound of Formula D, wherein the compound comprises a racemic mixture of (S)-$R_5$ and (R)-$R_5$.

In certain embodiments, the Degron is a compound of Formula D, wherein $R_5$ is H.

In certain embodiments, the Degron is a compound of Formula D, wherein $R_5$ is deuterium.

In certain embodiments, the Degron is a compound of Formula D, wherein $R_5$ is $C_1$-$C_3$ alkyl selected from methyl, ethyl, and propyl. In certain embodiments, $R_5$ is methyl.

In certain embodiments, the Degron is a compound of Formula D, wherein $R_5$ is F or Cl. In further embodiments, $R_5$ is in the (S) or (R) configuration. In further embodiments, $R_5$ is in the (R) configuration. In certain embodiments, the Degron is a compound of Formula D, wherein the compound comprises a racemic mixture of (S)—$R_5$ and (R)—$R_5$. In certain embodiments, $R_5$ is F.

Each of the moieties defined for one of

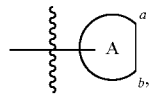

X, $X_1$, $X_2$, Y, $R_1$, $R_2$, $R_2'$, $R_3$, $R_3'$, $R_4$, $R_5$, m, and n, can be combined with any of the moieties defined for the others of

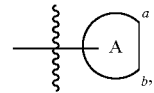

X, $X_1$, $X_2$, Y, $R_1$, $R_2$, $R_2'$, $R_3$, $R_3'$, $R_4$, $R_5$, m, and n.

In certain embodiments, the Degron is a compound having Formula D1:

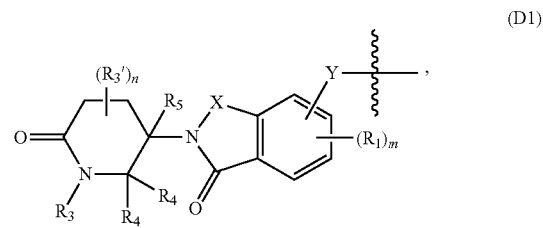

(D1)

or an enantiomer, diastereomer, or stereoisomer thereof, wherein X, Y, $R_1$, $R_2$, $R_2'$, $R_3$, $R_3'$, $R_4$, $R_5$, m, and n are each as defined above in Formula D.

Each of X, Y, $R_1$, $R_2$, $R_2'$, $R_3$, $R_3'$, $R_4$, $R_5$, m, and n can be selected from the moieties described above in Formula D. Each of the moieties defined for one of X, Y, $R_1$, $R_2$, $R_2'$, $R_3$, $R_3'$, $R_4$, $R_5$, m, and n, can be combined with any of the moieties defined for the others of X, Y, $R_1$, $R_2$, $R_2'$, $R_3$, $R_3'$, $R_4$, $R_5$, m, and n, as described above in Formula D.

In certain embodiments, the Degron is a compound of Formula D2:

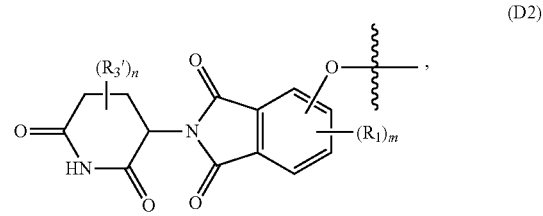

(D2)

or an enantiomer, diastereomer, or stereoisomer thereof, wherein each of $R_1$, $R_3'$, m and n is as defined above and can be selected from any moieties or combinations thereof described above.

In certain embodiments, the Degron is a compound of the following structure:

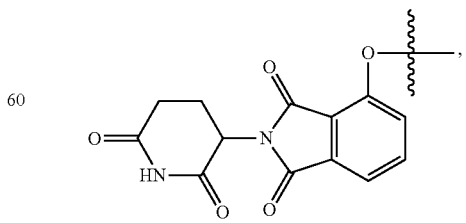

or an enantiomer, diastereomer, or stereoisomer thereof.

In certain embodiments, the Degron is a compound of Formula D3:

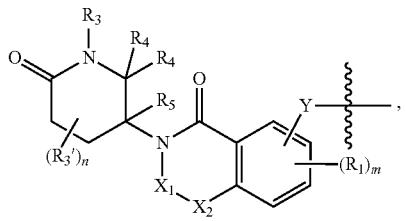

(D3)

or an enantiomer, diastereomer, or stereoisomer thereof, wherein $X_1$, $X_2$, Y, $R_1$, $R_2$, $R_2'$, $R_3$, $R_3'$, $R_4$, $R_5$, m, and n are each as defined above in Formula D.

Each of $X_1$, $X_2$, Y, $R_1$, $R_2$, $R_2'$, $R_3$, $R_3'$, $R_4$, $R_5$, m, and n can be selected from the moieties described above in Formula D. Each of the moieties defined for one of $X_1$, $X_2$, Y, $R_1$, $R_2$, $R_2'$, $R_3$, $R_3'$, $R_4$, $R_5$, m, and n, can be combined with any of the moieties defined for the others of $X_1$, $X_2$, Y, $R_1$, $R_2$, $R_2'$, $R_3$, $R_3'$, $R_4$, $R_5$, m, and n, as described above in Formula D.

In certain embodiments, the Degron is selected from the following, wherein X is H, deuterium, $C_1$-$C_3$ alkyl, or halgen; and R is a Linker:

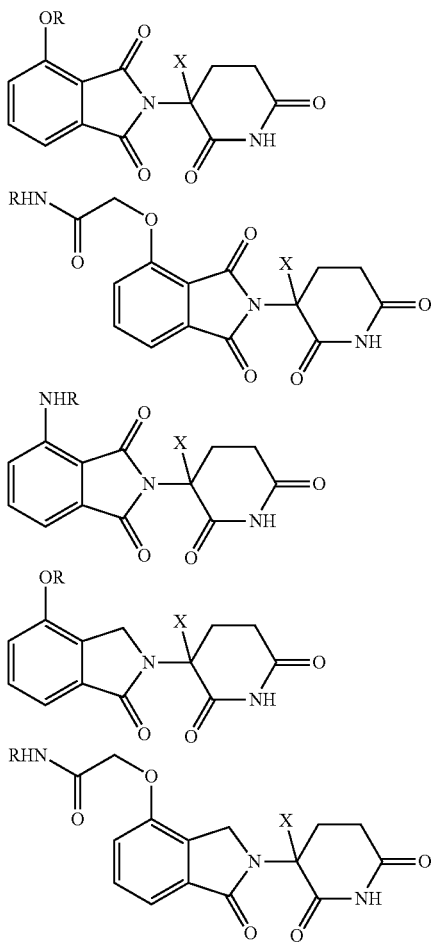

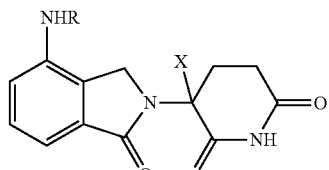

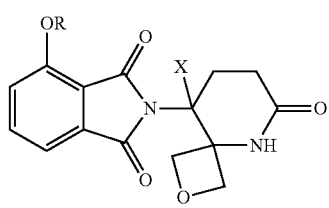

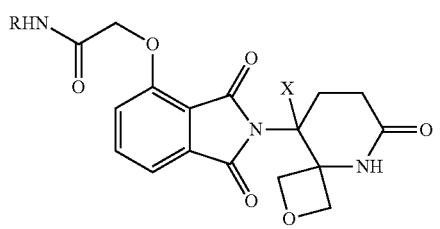

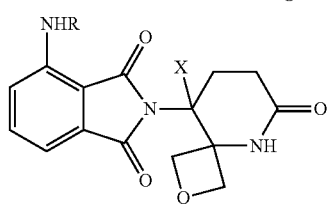

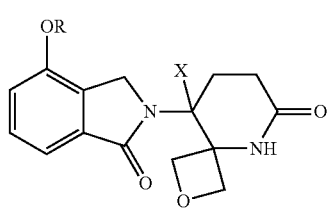

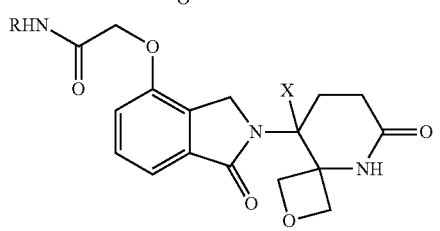

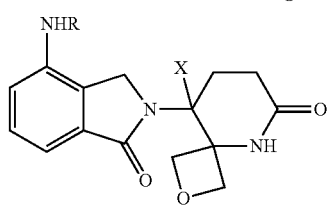

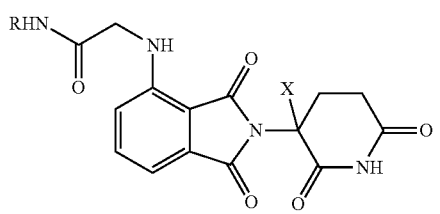

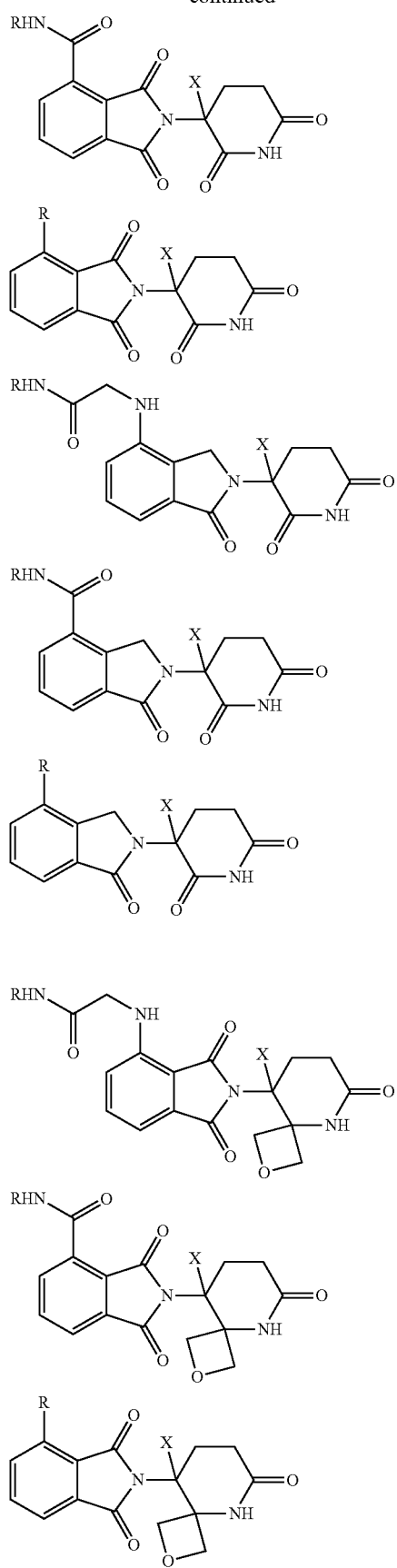
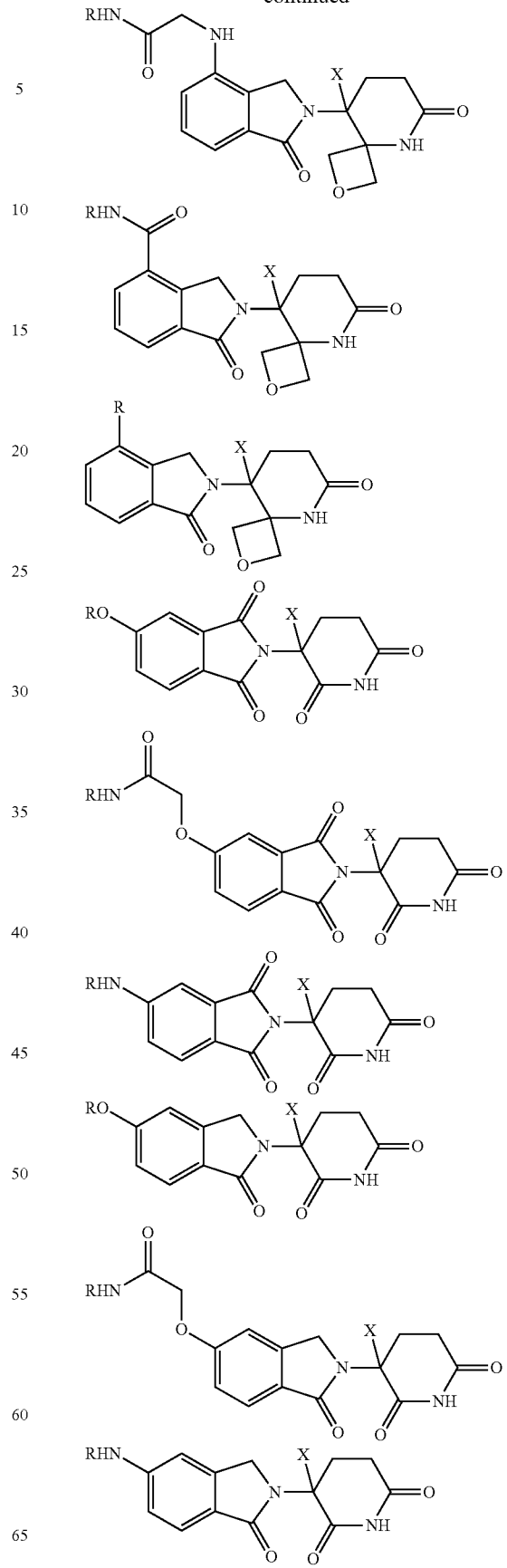

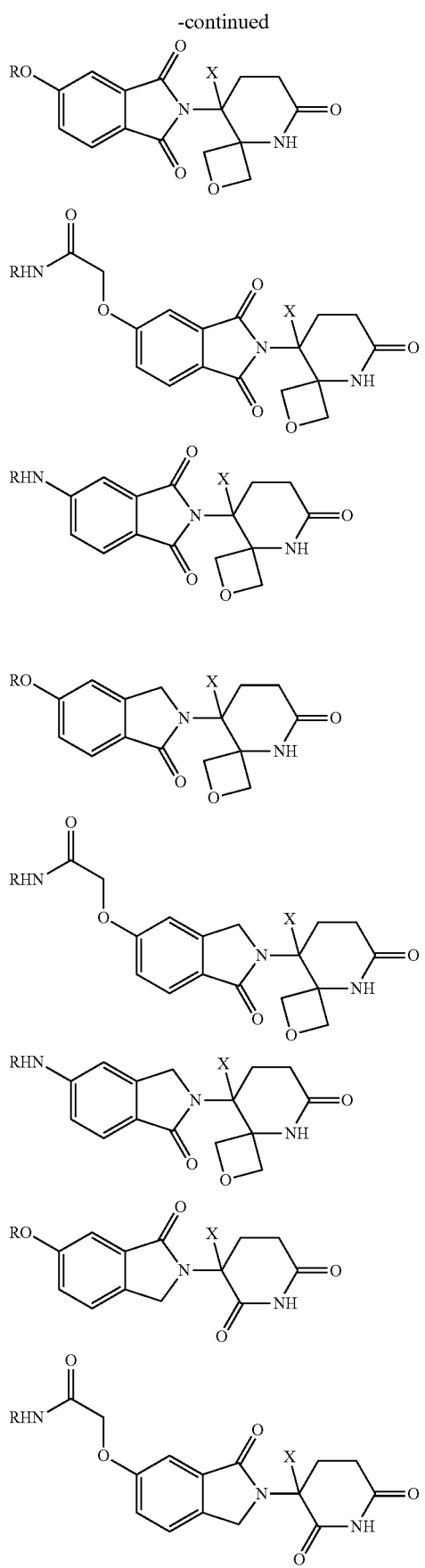
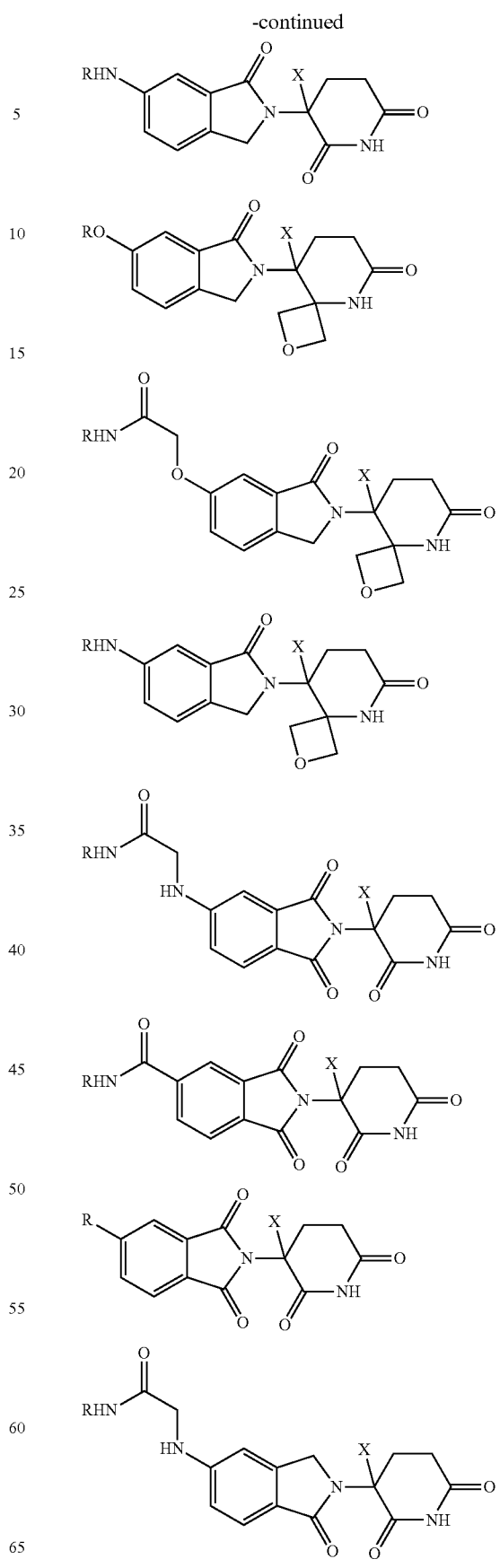

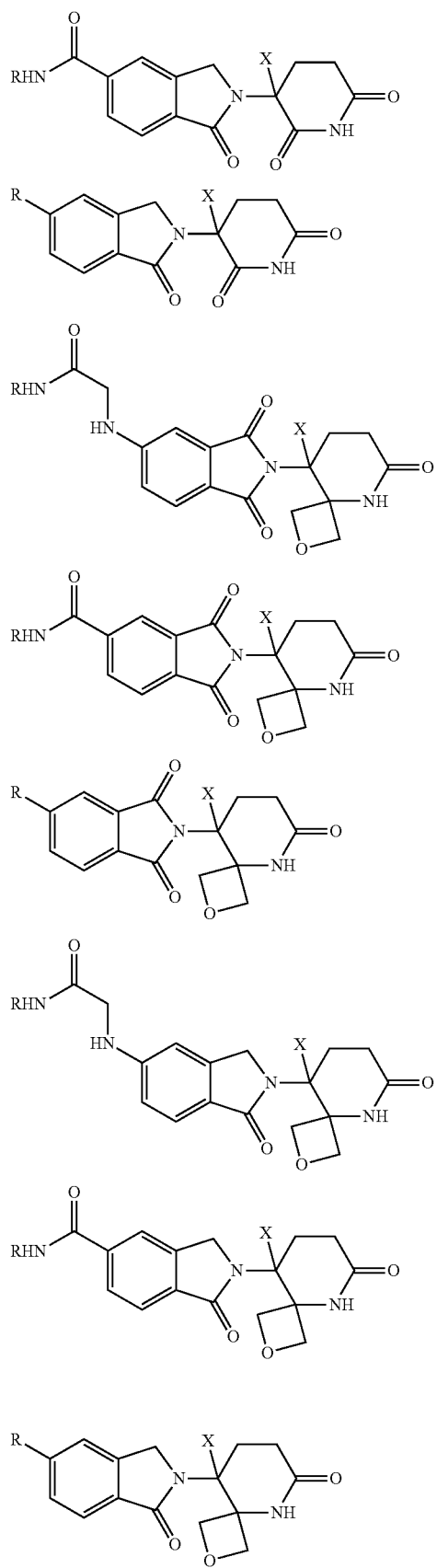
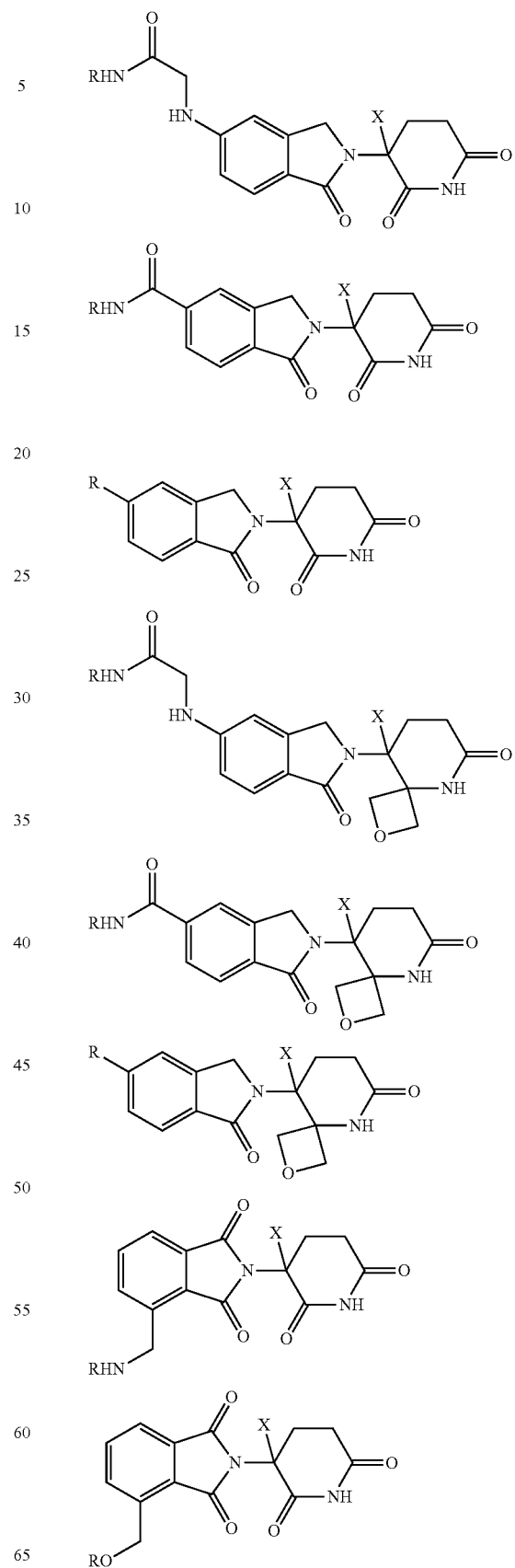

25
-continued
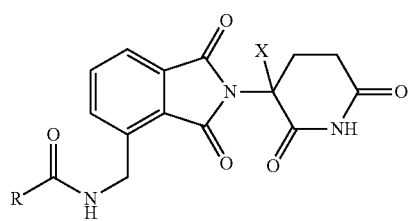
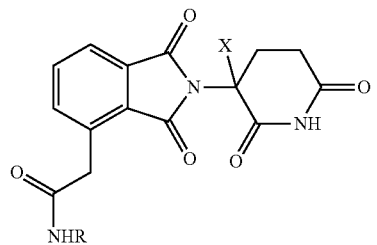
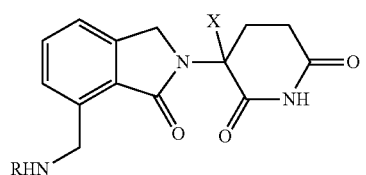
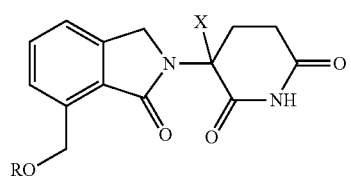
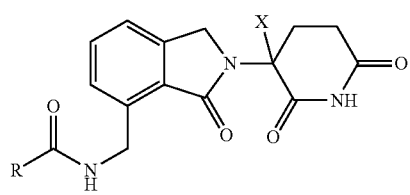
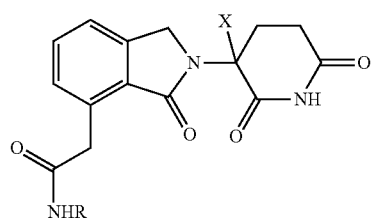
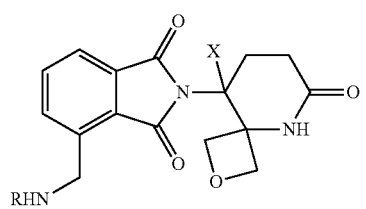
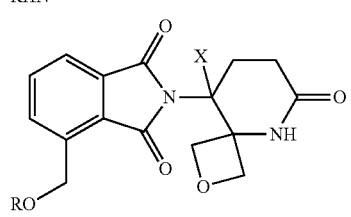
26
-continued
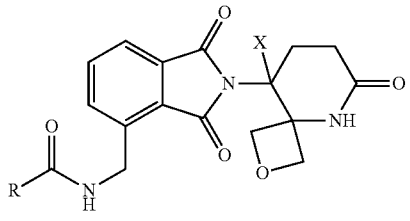
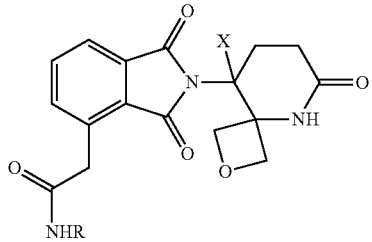
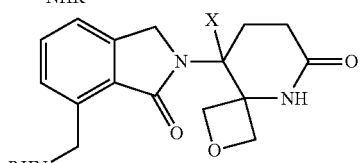
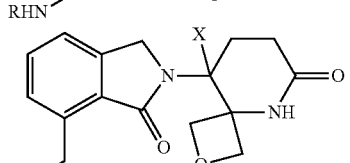
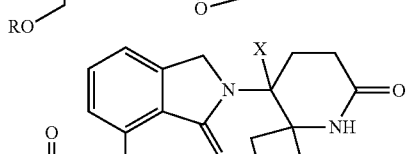
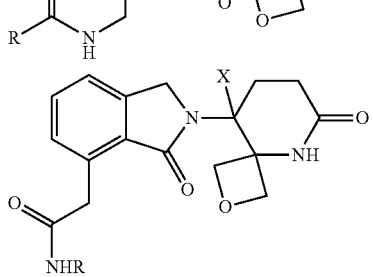
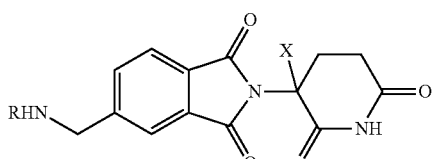
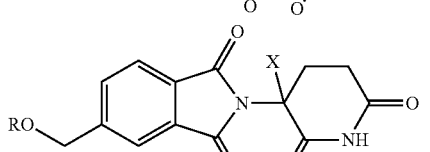
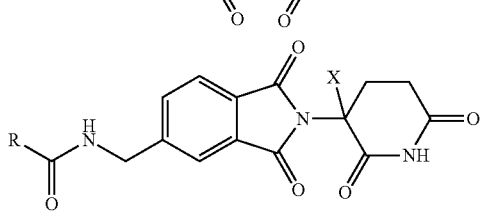

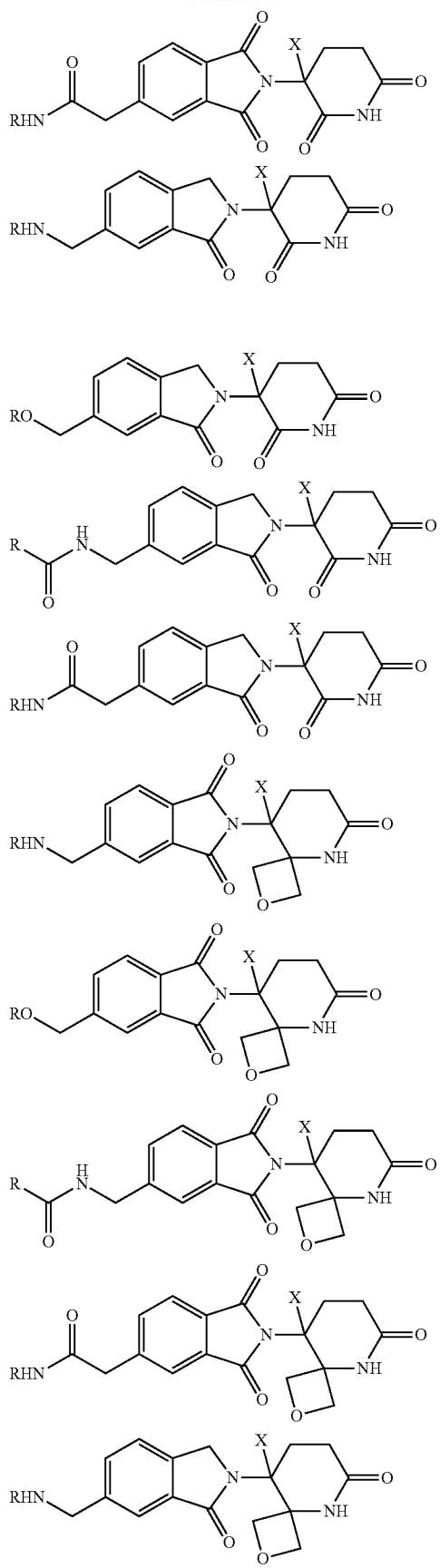
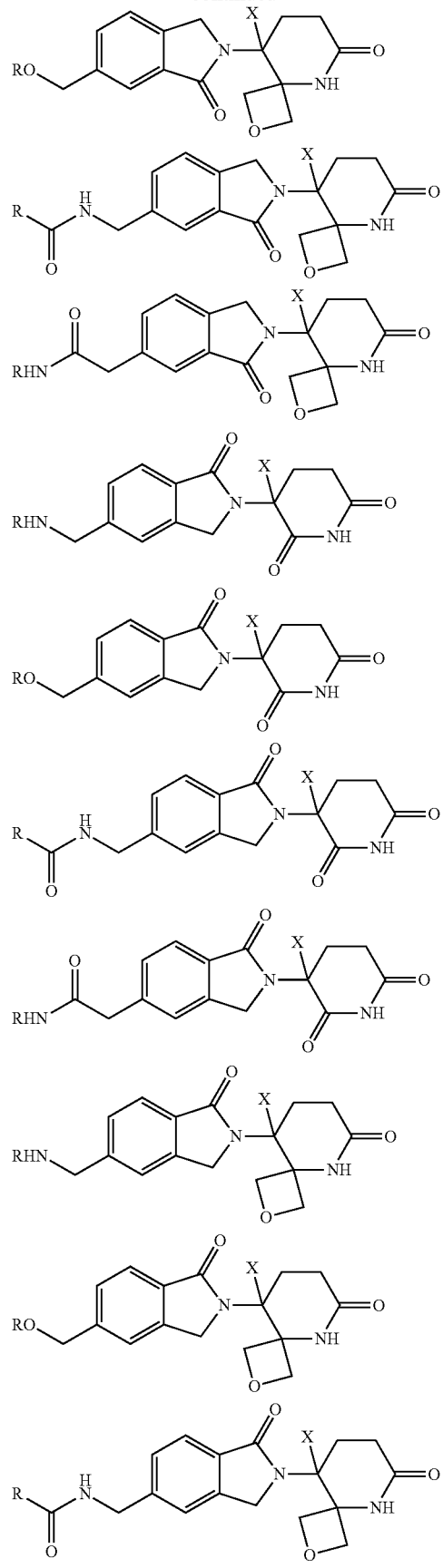

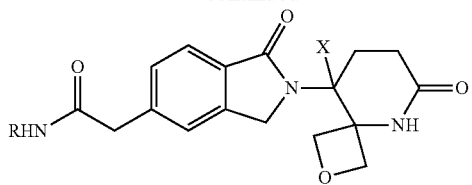
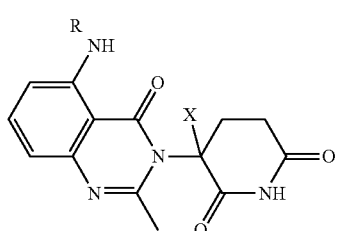
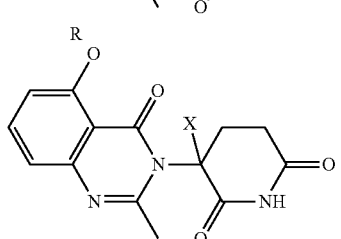
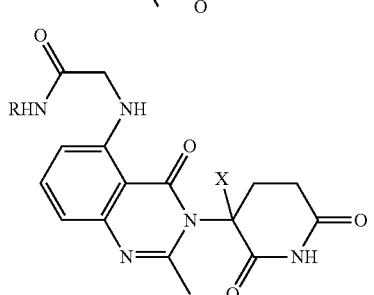
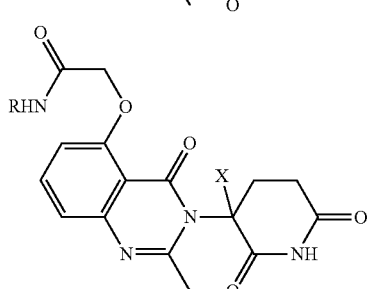
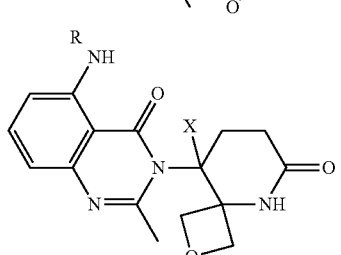
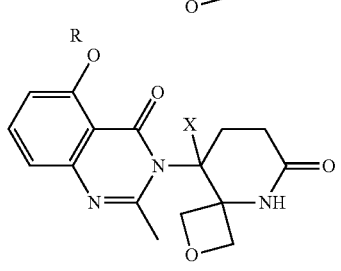
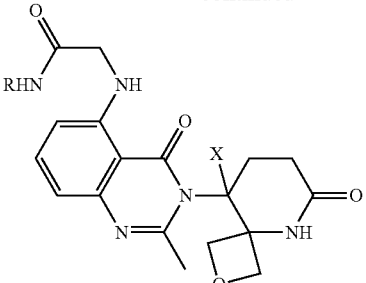
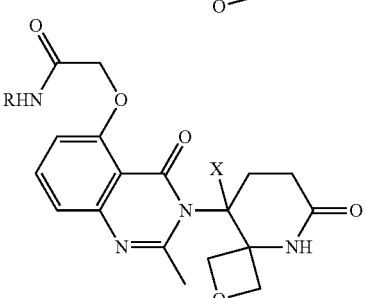
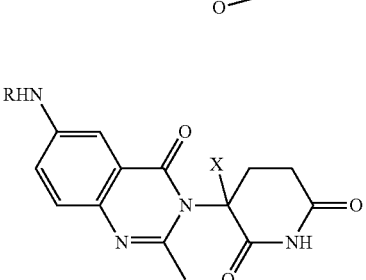
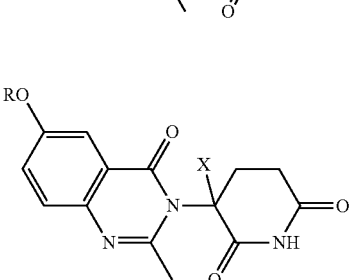
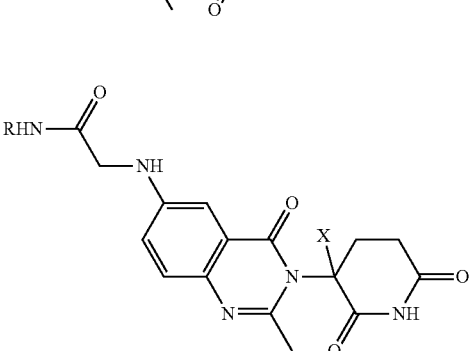
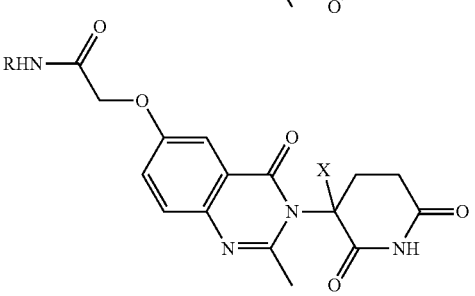

31
-continued
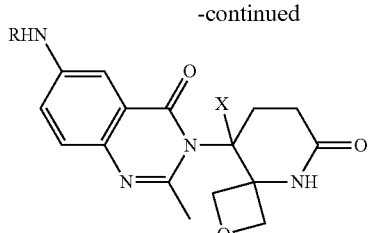
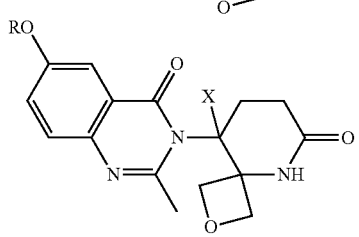
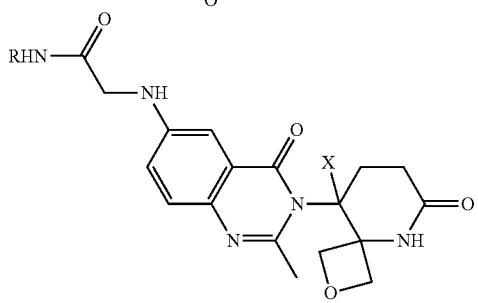
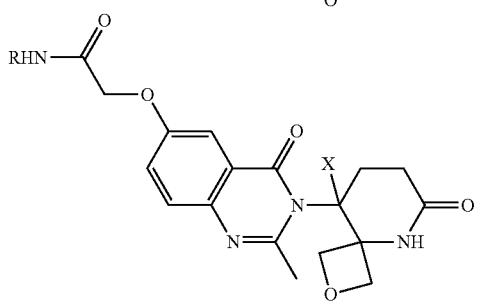
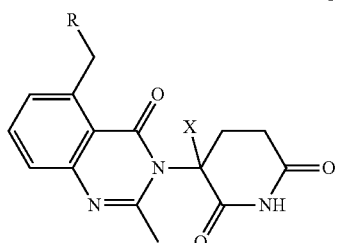
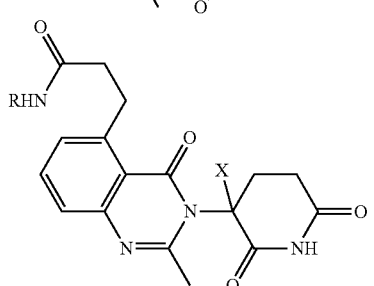
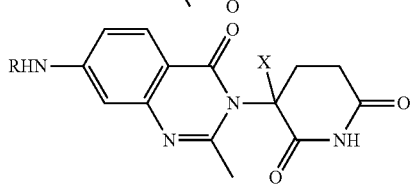
32
-continued
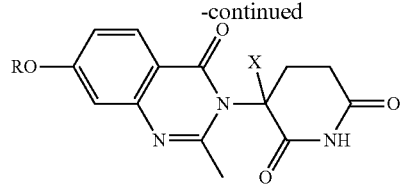
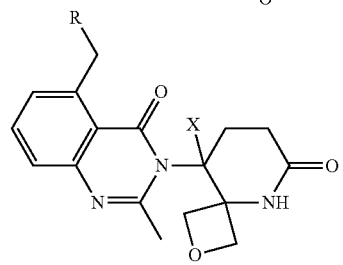
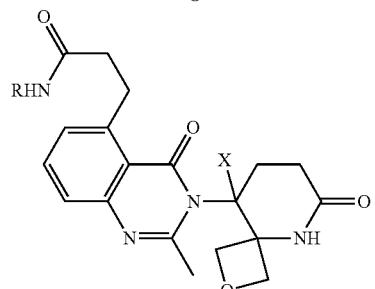
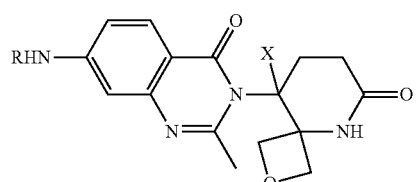
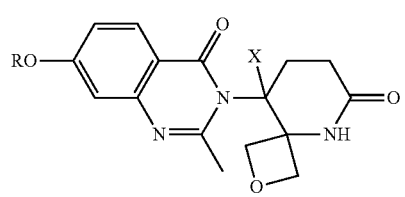
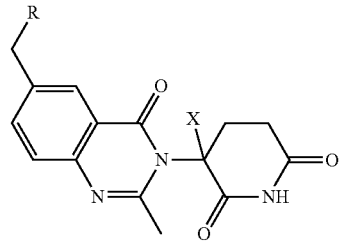
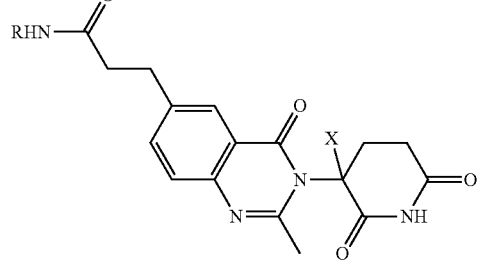

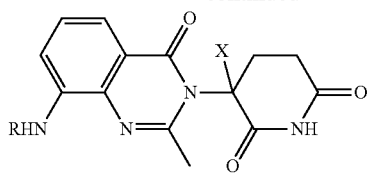
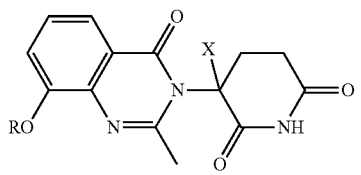
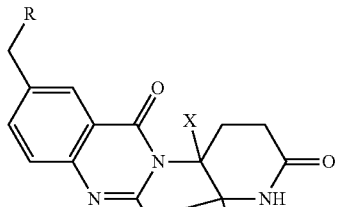
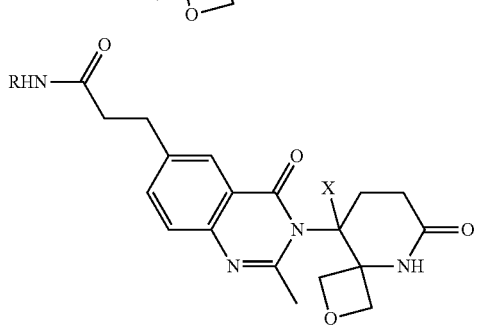
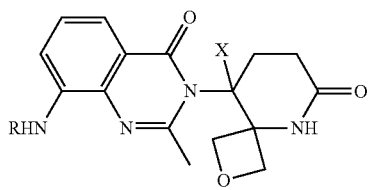
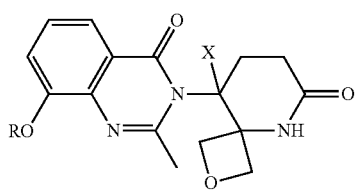
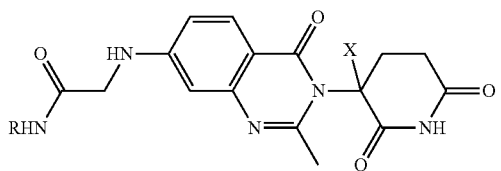
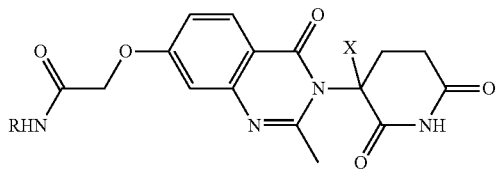
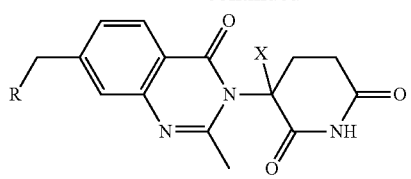
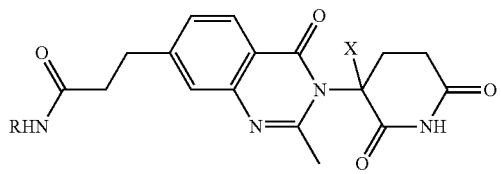
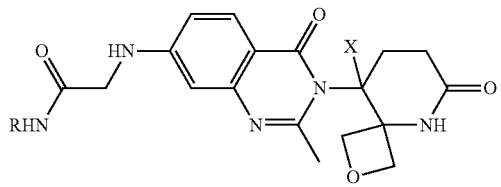
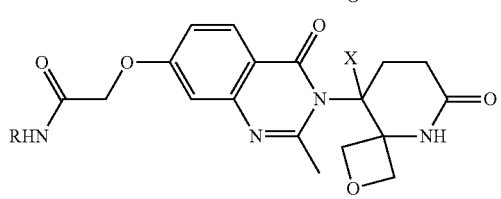
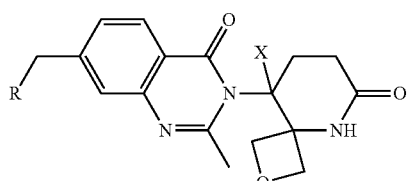
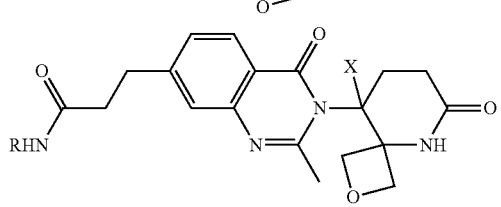
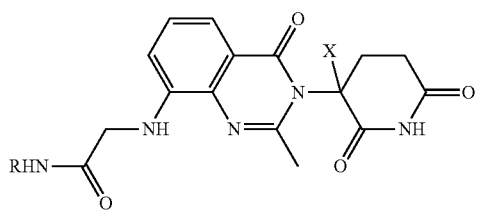
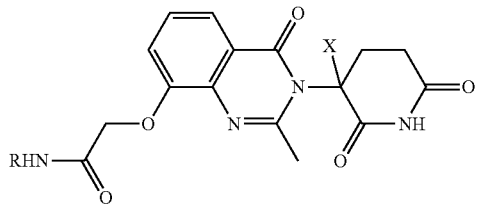
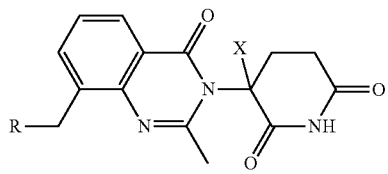

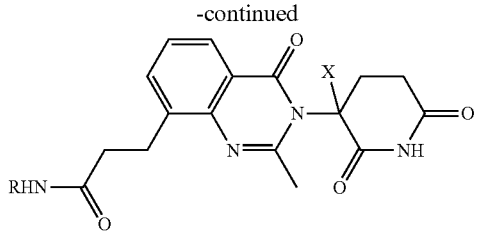
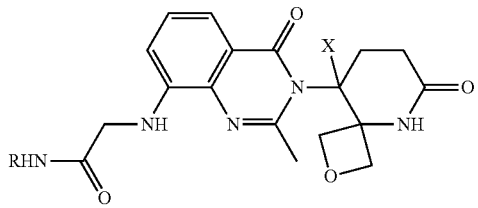
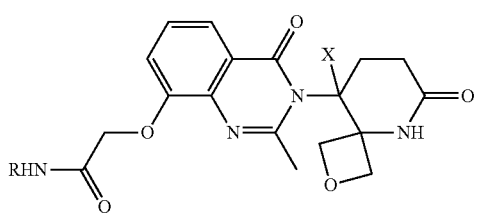
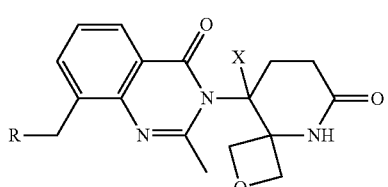
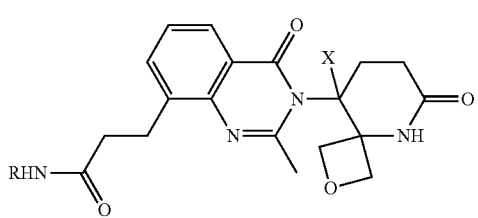
In certain embodiments, the Degron is selected from the following:
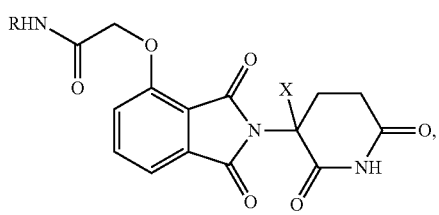
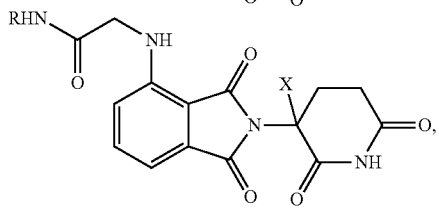
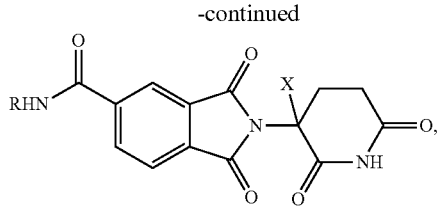
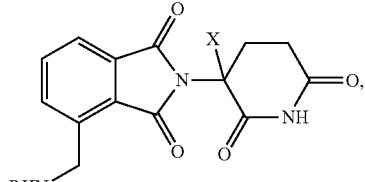
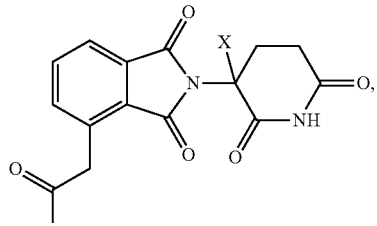
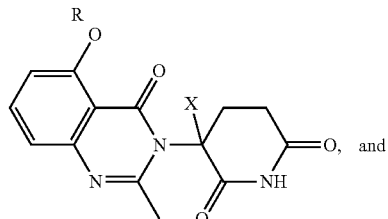
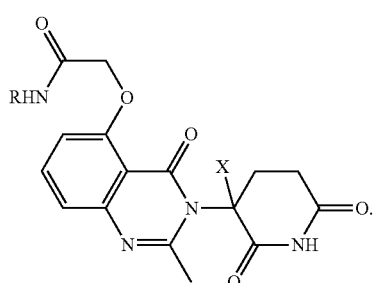
In certain embodiments, the Degron is selected from the following:
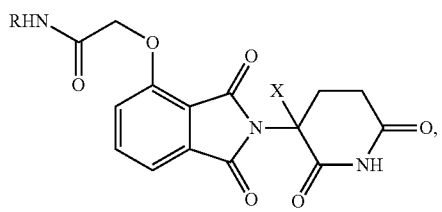
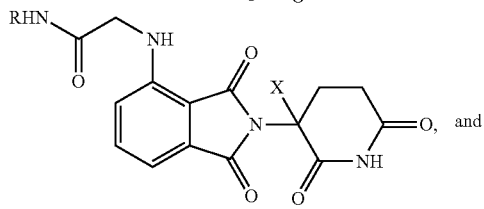

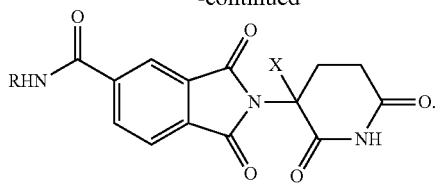

Linker

The Linker is a bond or a carbon chain that serves to link a Targeting Ligand with a Degron. In certain embodiments, the carbon chain optionally comprises one, two, three, or more heteroatoms selected from N, O, and S. In certain embodiments, the carbon chain comprises only saturated chain carbon atoms. In certain embodiments, the carbon chain optionally comprises two or more unsaturated chain carbon atoms (e.g., C=C or C≡C). In certain embodiments, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl).

In certain embodiments, the Linker comprises at least 5 chain atoms (e.g., C, O, N, and S). In certain embodiments, the Linker comprises less than 20 chain atoms (e.g., C, O, N, and S). In certain embodiments, the Linker comprises 5, 6, 7, 8, 9, 10, 11, 12, 13, 14, 15, 16, 17, 18, or 19 chain atoms (e.g., C, O, N, and S). In certain embodiments, the Linker comprises 5, 7, 9, 11, 13, 15, 17, or 19 chain atoms (e.g., C, O, N, and S). In certain embodiments, the Linker comprises 5, 7, 9, or 11 chain atoms (e.g., C, O, N, and S). In certain embodiments, the Linker comprises 6, 8, 10, 12, 14, 16, or 18 chain atoms (e.g., C, O, N, and S). In certain embodiments, the Linker comprises 6, 8, 10, or 12 chain atoms (e.g., C, O, N, and S).

In certain embodiments, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In certain embodiments, the non-bulky substitution is located on the chain carbon atom proximal to the Degron (i.e., the carbon atom is separated from the carbon atom to which the Degron is bonded by at least 3, 4, or 5 chain atoms in the Linker).

In certain embodiments, the Linker is of Formula L0:

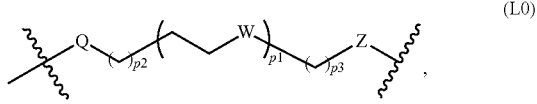

(L0)

or an enantiomer, diastereomer, or stereoisomer thereof, wherein
p1 is an integer selected from 0 to 12;
p2 is an integer selected from 0 to 12;
p3 is an integer selected from 1 to 6;
each W is independently absent, $CH_2$, O, S, NH or $NR_5$;
Z is absent, $CH_2$, O, NH or $NR_5$;
each $R_5$ is independently $C_1$-$C_3$ alkyl; and
Q is absent or —$CH_2C(O)NH$—,
wherein the Linker is covalently bonded to the Degron with the ⊰ next to Q, and covalently bonded to the Targeting Ligand with the ⊰
next to Z, and wherein the total number of chain atoms in the Linker is less than 20.

In certain embodiments, the Linker-Targeting Ligand (TL) has the structure of Formula L1 or L2:

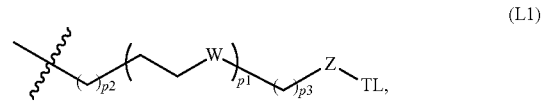

(L1)

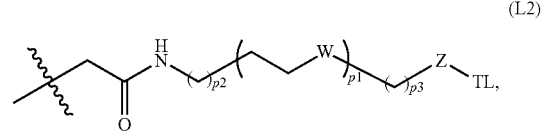

(L2)

or an enantiomer, diastereomer, or stereoisomer thereof, wherein:
p1 is an integer selected from 0 to 12;
p2 is an integer selected from 0 to 12;
p3 is an integer selected from 1 to 6;
each W is independently absent, $CH_2$, O, S, NH or $NR_5$;
Z is absent, $CH_2$, O, NH or $NR_5$;
each $R_5$ is independently $C_1$-$C_3$ alkyl; and
TL is a Targeting Ligand,
wherein the Linker is covalently bonded to the Degron with ⊰

In certain embodiments, p1 is an integer selected from 0 to 10.
In certain embodiments, p1 is an integer selected from 2 to 10.
In certain embodiments, p1 is selected from 1, 2, 3, 4, 5, and 6.
In certain embodiments, p1 is selected from 1, 3, and 5.
In certain embodiments, p1 is selected from 1, 2, and 3.
In certain embodiments, p1 is 3.
In certain embodiments, p2 is an integer selected from 0 to 10.
In certain embodiments, p2 is selected from 0, 1, 2, 3, 4, 5, and 6.
In certain embodiments, p2 is an integer selected from 0 and 1.
In certain embodiments, p3 is an integer selected from 1 to 5.
In certain embodiments, p3 is selected from 2, 3, 4, and 5.
In certain embodiments, p3 is selected from 1, 2, and 3.
In certain embodiments, p3 is selected from 2 and 3.
In certain embodiments, at least one W is $CH_2$.
In certain embodiments, at least one W is O.
In certain embodiments, at least one W is S.
In certain embodiments, at least one W is NH.
In certain embodiments, at least one W is $NR_5$; and $R_5$ is $C_1$-$C_3$ alkyl selected from methyl, ethyl, and propyl.
In certain embodiments, W is O.
In certain embodiments, Z is absent.
In certain embodiments, Z is $CH_2$.
In certain embodiments, Z is O.
In certain embodiments, Z is NH.
In certain embodiments, Z is $NR_5$; and $R_5$ is $C_1$-$C_3$ alkyl selected from methyl, ethyl, and propyl.

In certain embodiments, Z is part of the Targeting Ligand that is bonded to the Linker, namely, Z is formed from reacting a functional group of the Targeting Ligand with the Linker.

In certain embodiments, W is CH$_2$, and Z is CH$_2$.
In certain embodiments, W is O, and Z is CH$_2$.
In certain embodiments, W is CH$_2$, and Z is O.
In certain embodiments, W is O, and Z is O.
In certain embodiments, the Linker-Targeting Ligand has the structure of:

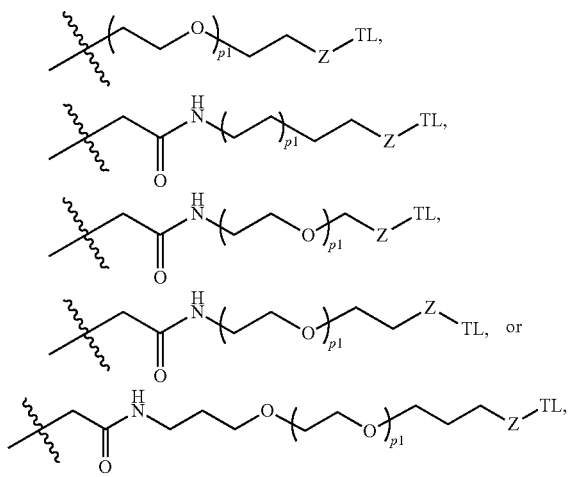

wherein Z, TL, and p1 are each as described above.

Any one of the Degrons described herein can be covalently bound to any one of the Linkers described herein.

In certain embodiments, the present application relates to the Degron-Linker (DL) having the following structure:

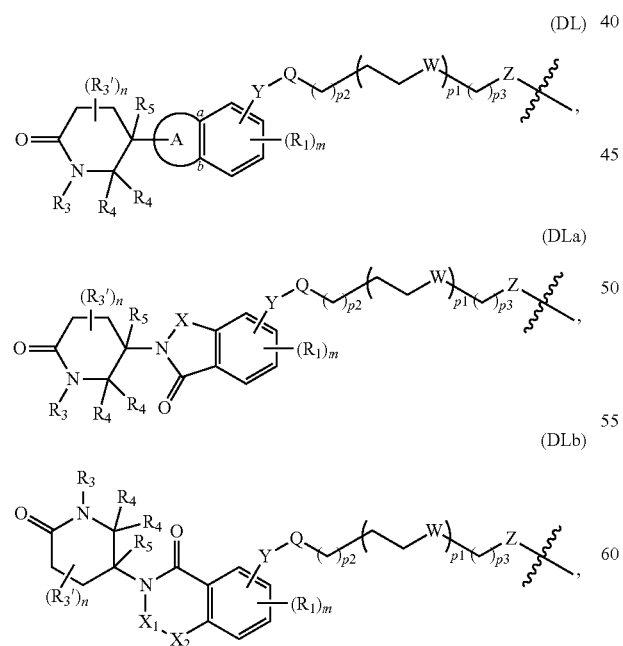

wherein each of the variables is as described above in Formula D and Formula L0, and a Targeting Ligand is covalently bonded to the DL with the $\xi$ next to Z.

In certain embodiments, the present application relates to the Degron-Linker (DL) having the following structure:

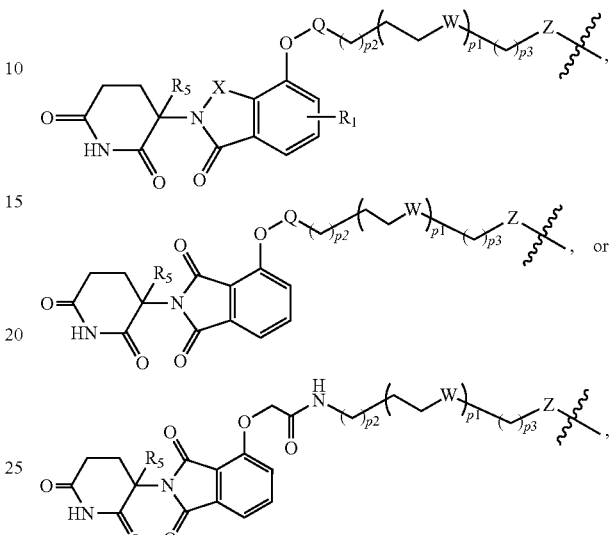

wherein each of the variables is as described above in Formula D and Formula L0, and a Targeting Ligand is covalently bonded to the DL with the $\xi$ next to Z.

In certain embodiments, the present application relates to the Degron-Linker (DL) intermediates having the following structure:

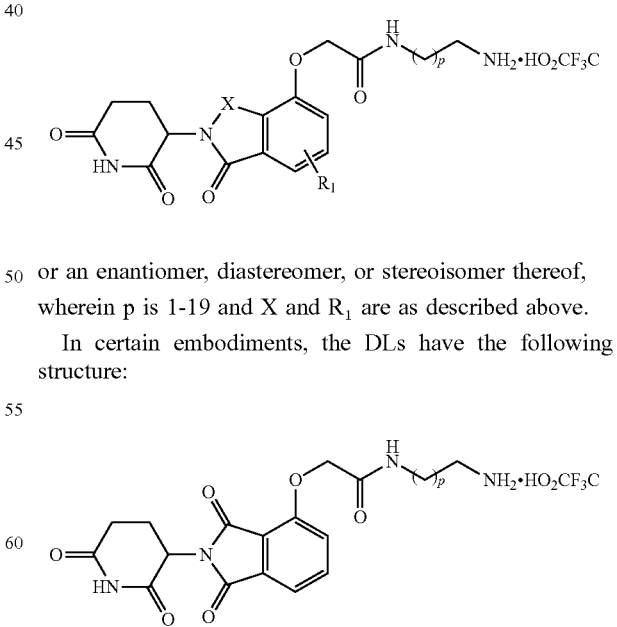

or an enantiomer, diastereomer, or stereoisomer thereof, wherein p is 1-19 and X and R$_1$ are as described above.

In certain embodiments, the DLs have the following structure:

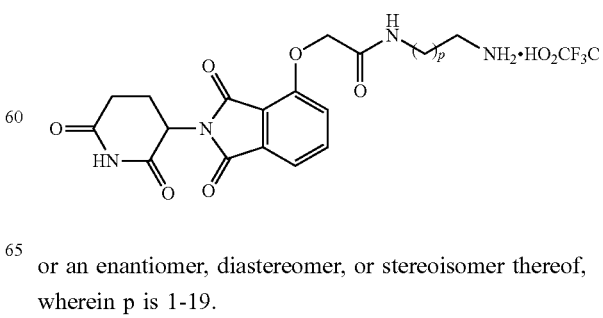

or an enantiomer, diastereomer, or stereoisomer thereof, wherein p is 1-19.

In certain embodiments, the DL intermediate has the following structure:
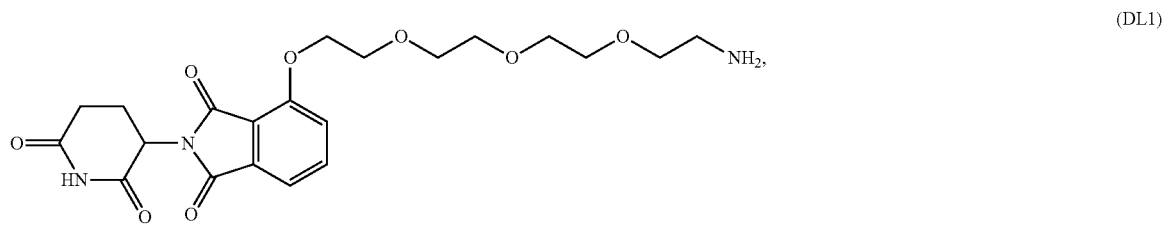
(DL1)
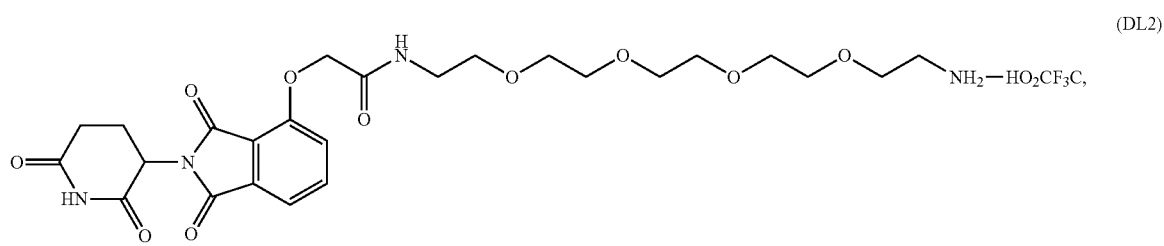
(DL2)
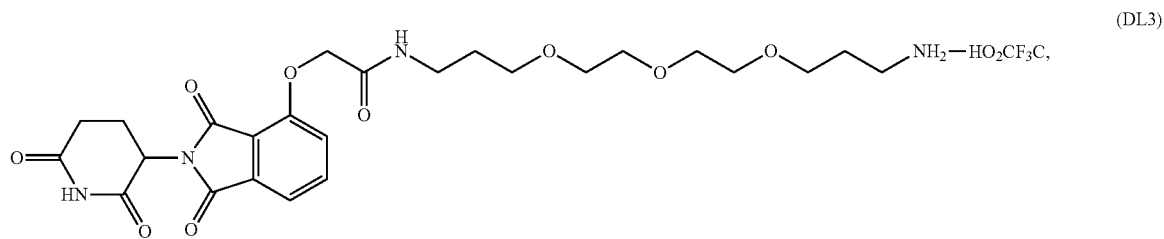
(DL3)
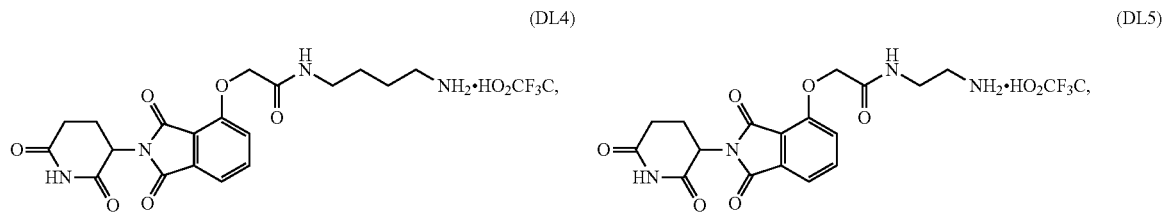
(DL4) (DL5)
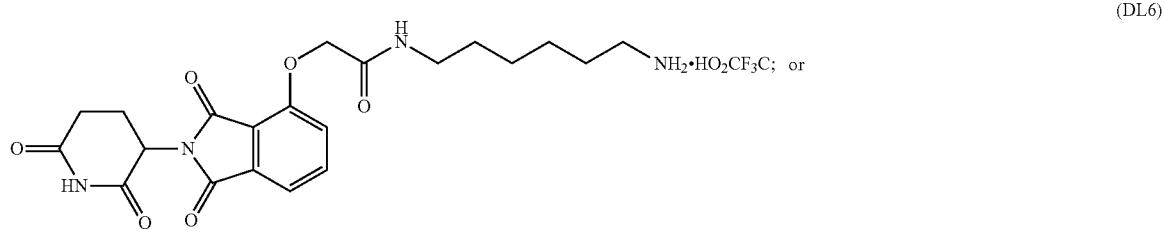
(DL6) or
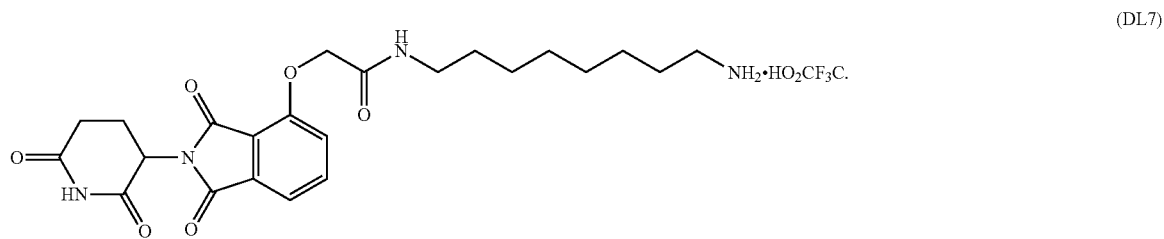
(DL7)

Some embodiments of the present application relate to a bifunctional compound having the following structure:

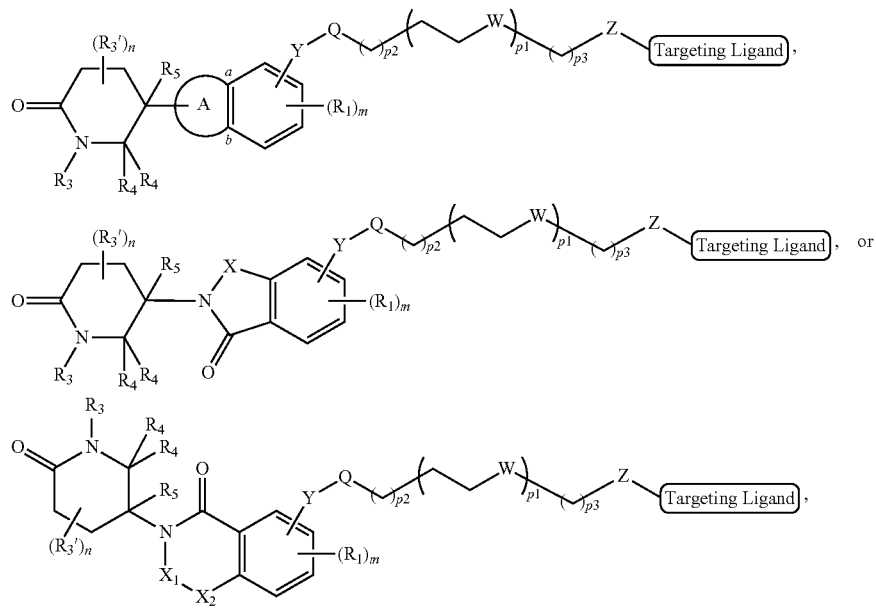

or an enantiomer, diastereomer, or stereoisomer thereof, wherein each of the variables is as described above in Formula D and Formula L0, and the Targeting Ligand is described herein below.

Further embodiments of the present application relate to a bifunctional compound having the following structure:

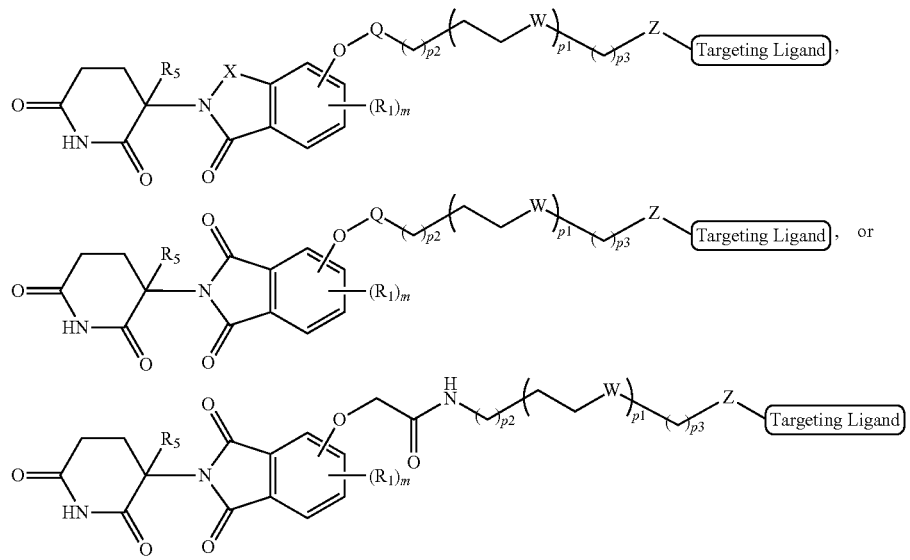

or an enantiomer, diastereomer, or stereoisomer thereof, wherein each of the variables is as described above in Formula D and Formula L0, and the Targeting Ligand is described herein below.

Certain embodiments of the present application relate to bifunctional compounds having one of the following structures:

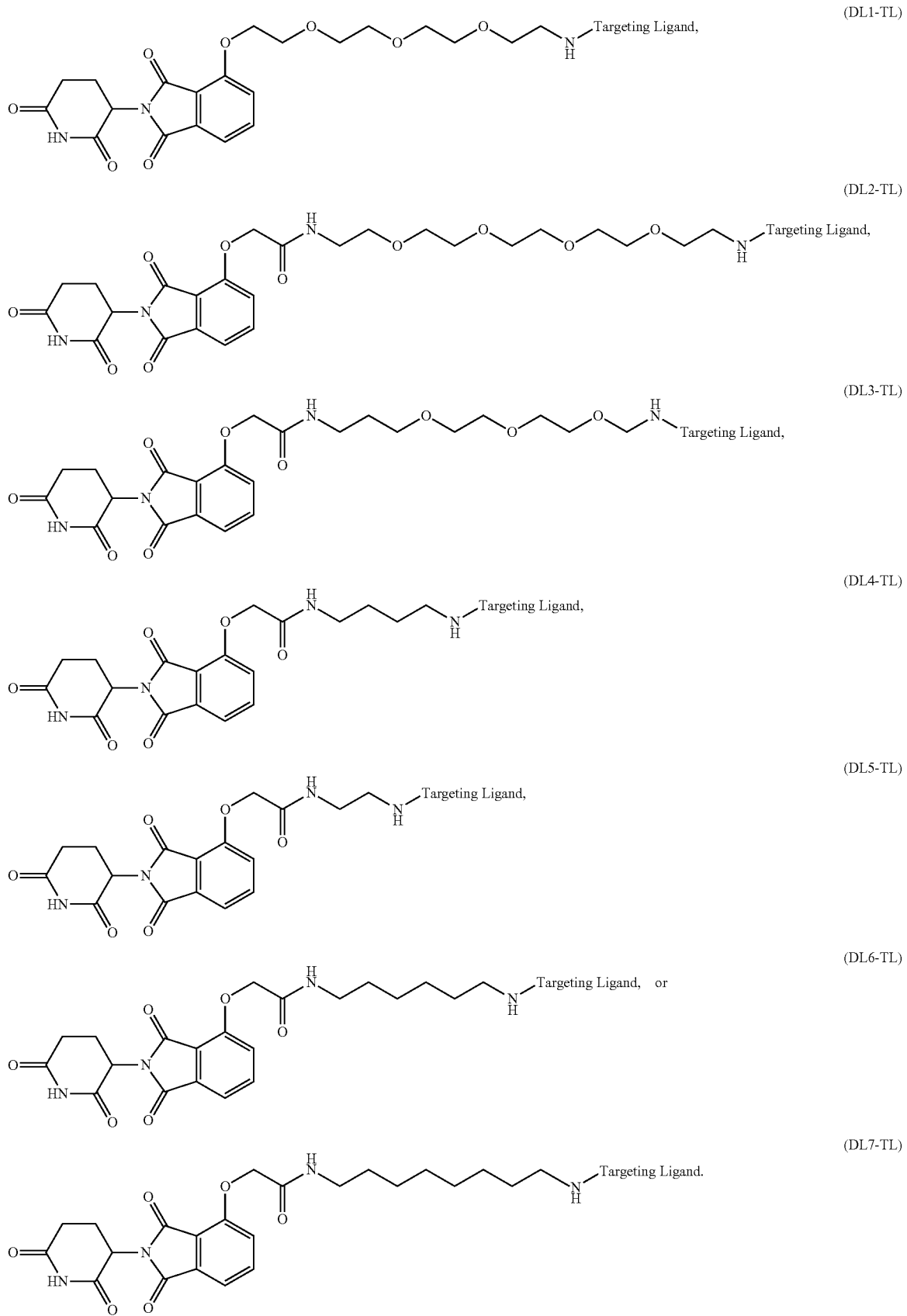

In certain embodiments, the Linker may be a polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In certain embodiments, the Linker is designed and optimized based on SAR (structure-activity relationship) and X-ray crystallography of the Targeting Ligand with regard to the location of attachment for the Linker.

In certain embodiments, the optimal Linker length and composition vary by target and can be estimated based upon X-ray structures of the original Targeting Ligand bound to its target. Linker length and composition can be also modified to modulate metabolic stability and pharmacokinetic (PK) and pharmacodynamics (PD) parameters.

In certain embodiments, where the Target Ligand binds multiple targets, selectivity may be achieved by varying Linker length where the ligand binds some of its targets in different binding pockets, e.g., deeper or shallower binding pockets than others.

Targeting Ligand

Targeting Ligand (TL) (or target protein moiety or target protein ligand or ligand) is a small molecule which is capable of binding to or binds to a target protein of interest.

Some embodiments of the present application relate to TLs which include but are not limited to Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the Targeting Ligand is a compound that is capable of binding to or binds to a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, a kinase to which the Targeting Ligand is capable of binding or binds includes, but is not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, a BET bromodomain-containing protein to which the Targeting Ligand is capable of binding or binds includes, but is not limited to, BRD1, BRD2, BRD3, BRD4, BRD5, BRD6, BRD7, BRD8, BRD9, BRD10, and BRDT. In certain embodiments, a BET bromodomain-containing protein is BRD4.

In certain embodiments, a nuclear protein to which the Targeting Ligand is capable of binding or binds includes, but is not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the Targeting Ligand is selected from a kinase inhibitor, a BET bromodomain-containing protein inhibitor, cytosolic signaling protein FKBP12 ligand, an HDAC inhibitor, a lysine methyltransferase inhibitor, an angiogenesis inhibitor, an immunosuppressive compound, and an aryl hydrocarbon receptor (AHR) inhibitor.

Non-limiting examples of TLs are shown in below and represent Targeting Ligands of certain types of proteins of interest.

BRD Targeting Ligand

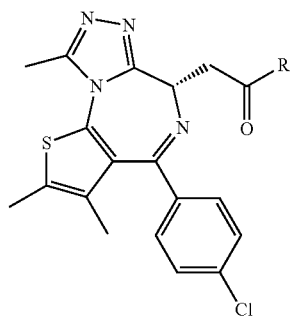

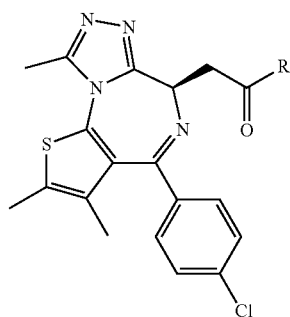

49
-continued
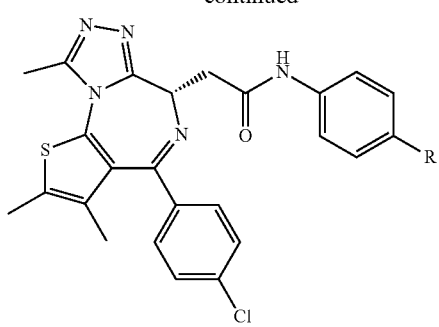
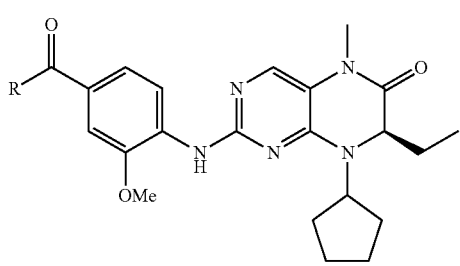
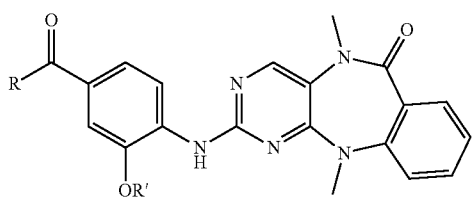
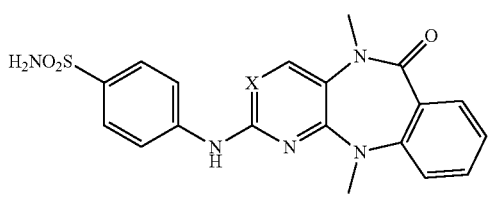
R: Degron-Linker; R′: methyl or ethyl
CREBBP Targeting Ligand
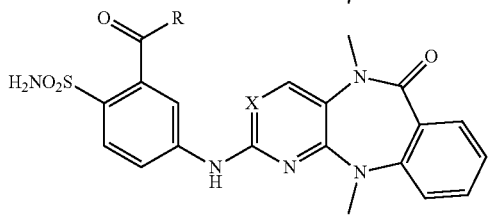
50
-continued
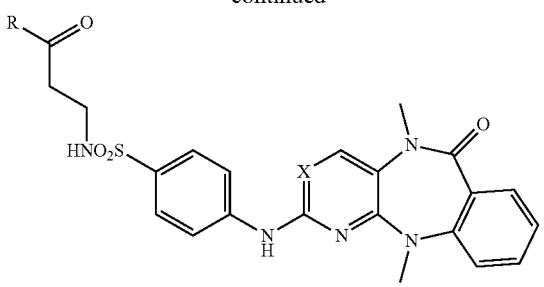
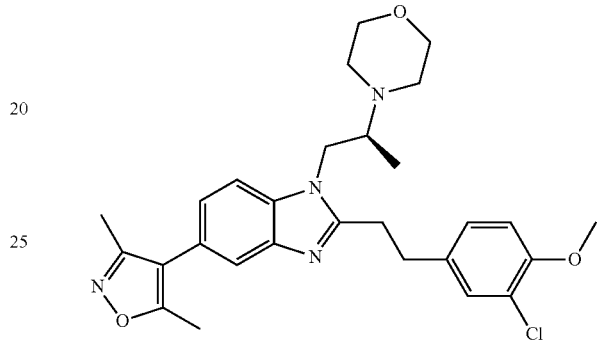
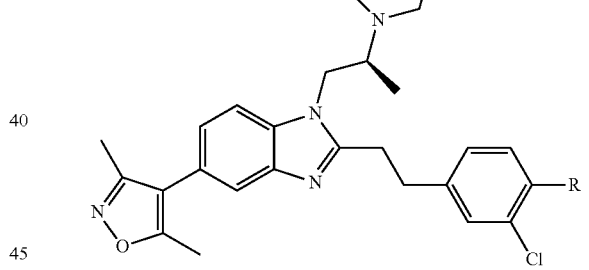
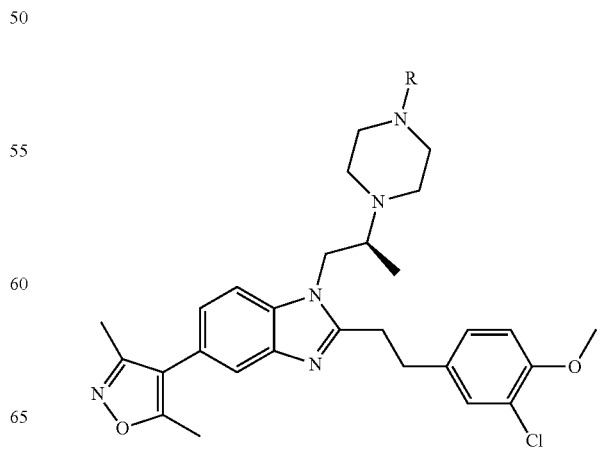

-continued
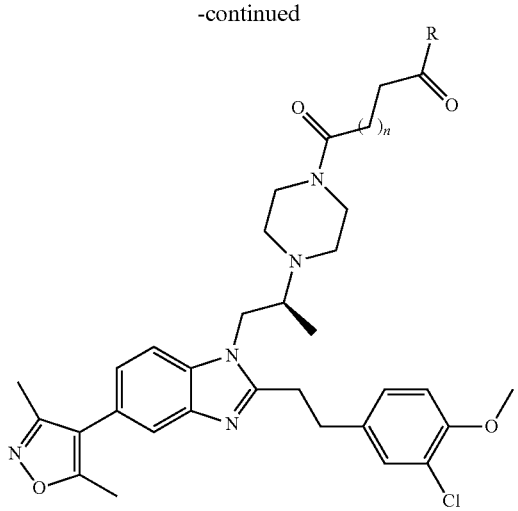
R: Degron-Linker; X: N or CH; n: 0-8
SMARCA4/PB1/SMARCA2 Targeting Ligand
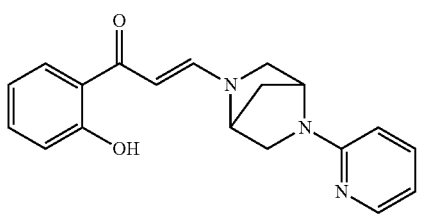
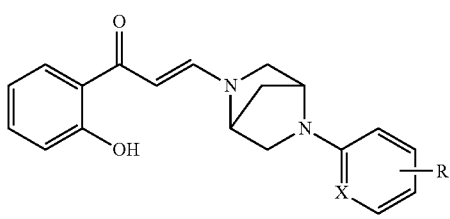
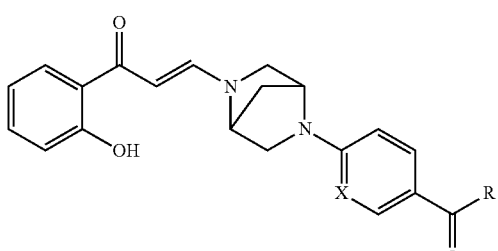
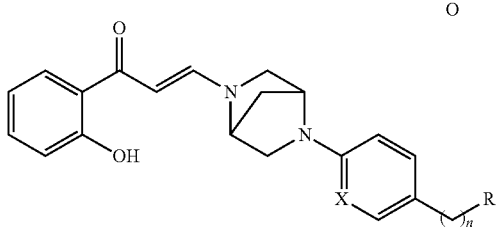
R: Degron-Linker; X: N or CH; n: 0-8
TRIM24/BRPF1 Targeting Ligand
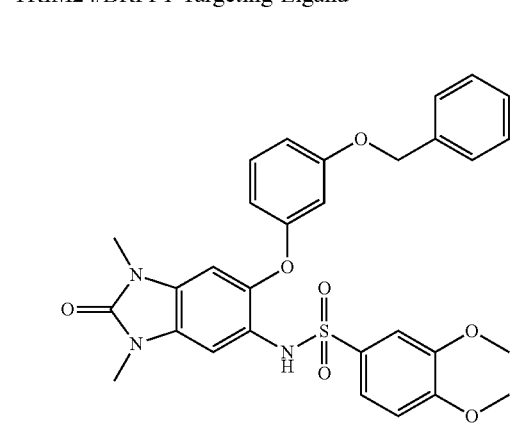
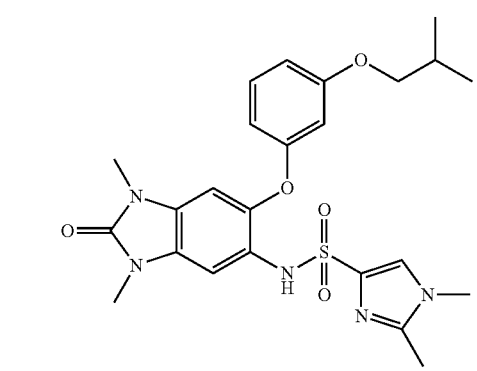
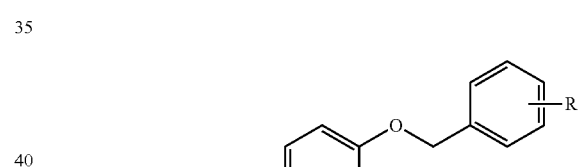
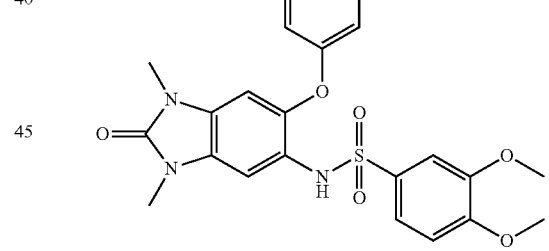
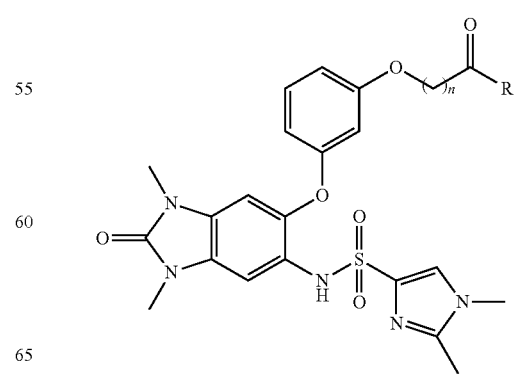

53
-continued
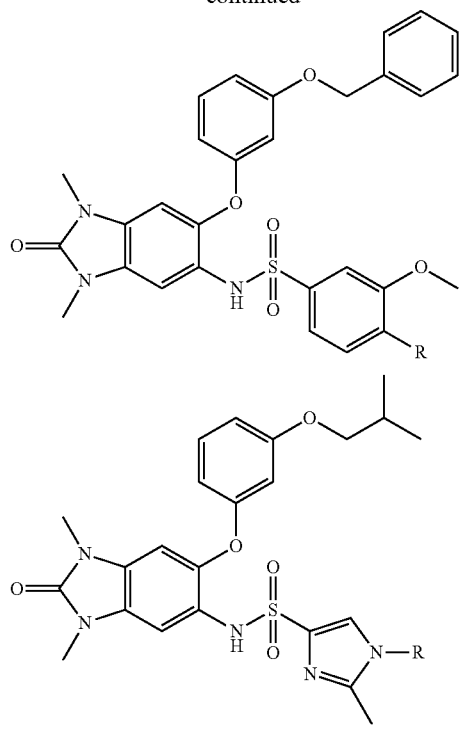
R: Degron-Linker; n: 0-8
Glucocorticoid Receptor Targeting Ligand
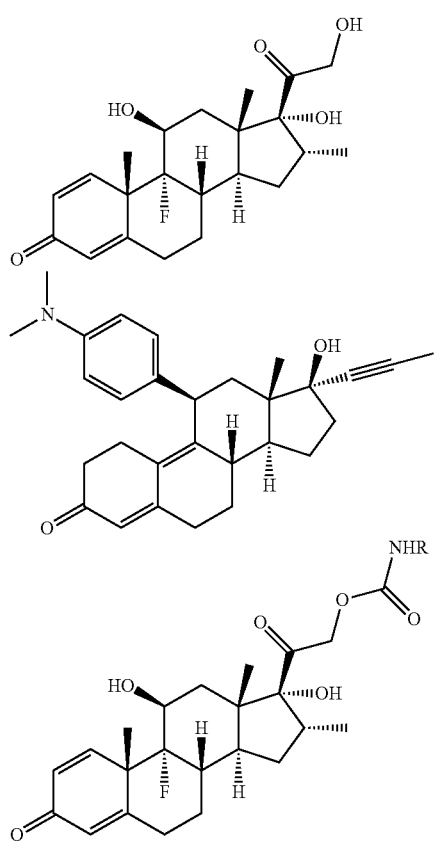
54
-continued
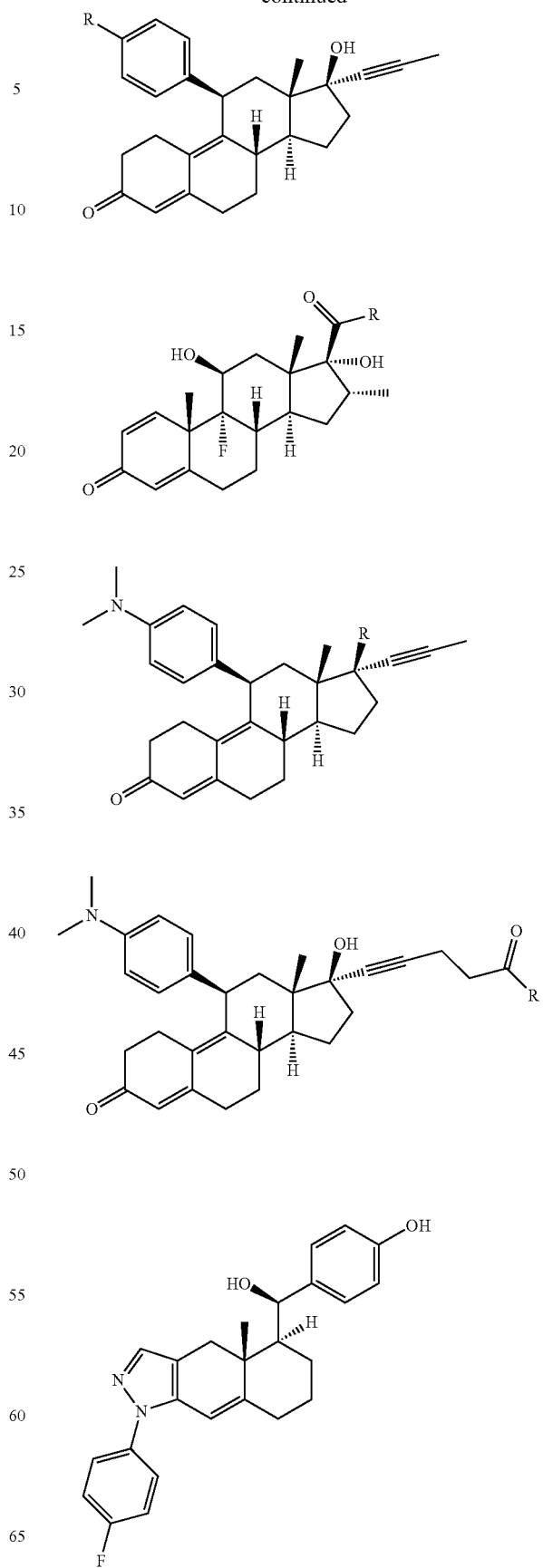

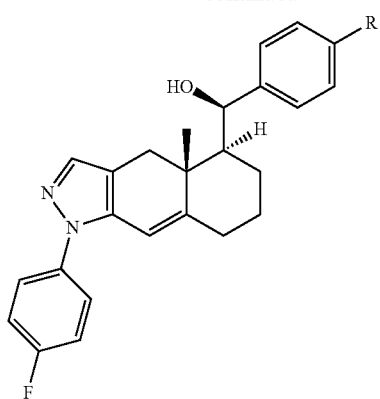
R: Degron-Linker
Estrogen/Androgen Receptor Targeting Ligand
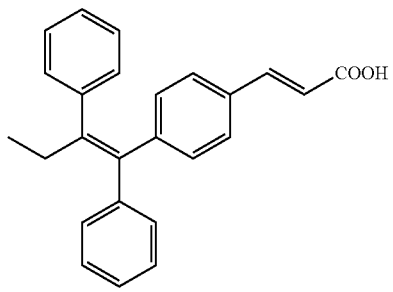
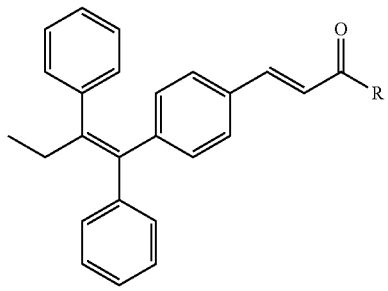
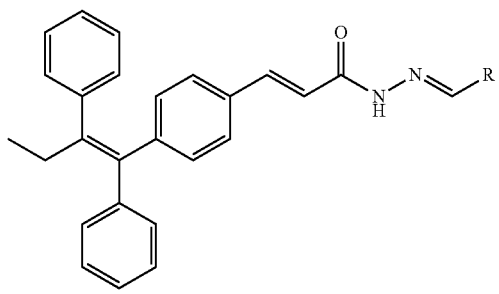
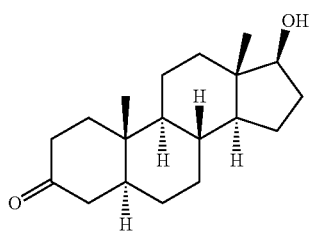
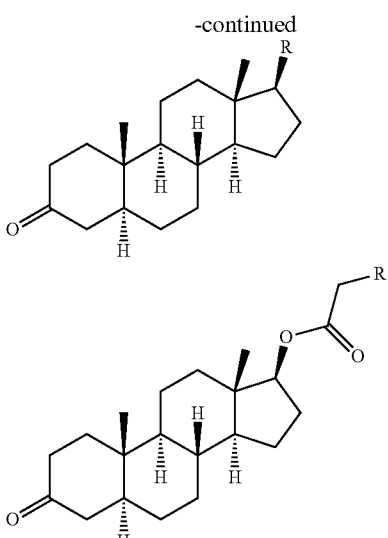
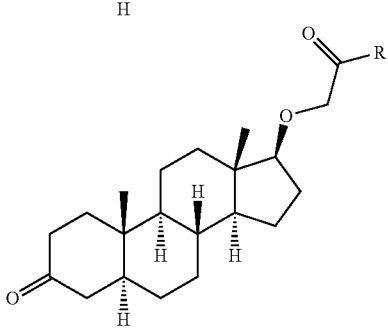
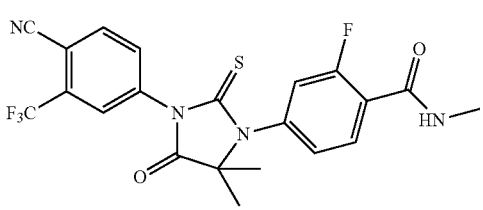
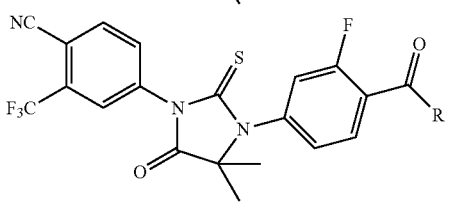
R: Degron-Linker
DOT1L Targeting Ligand
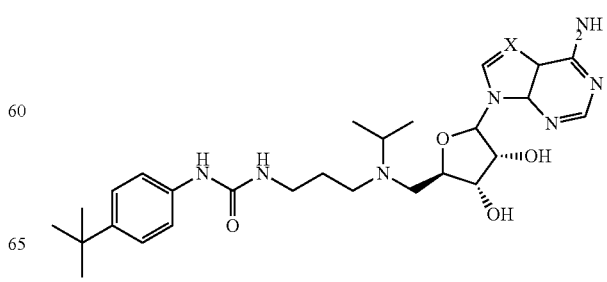

57
-continued
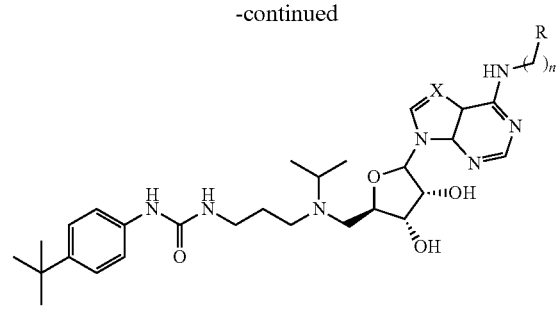
R: Degron-Linker; X: N or CH; n: 0-8
BRAF Targeting Ligand
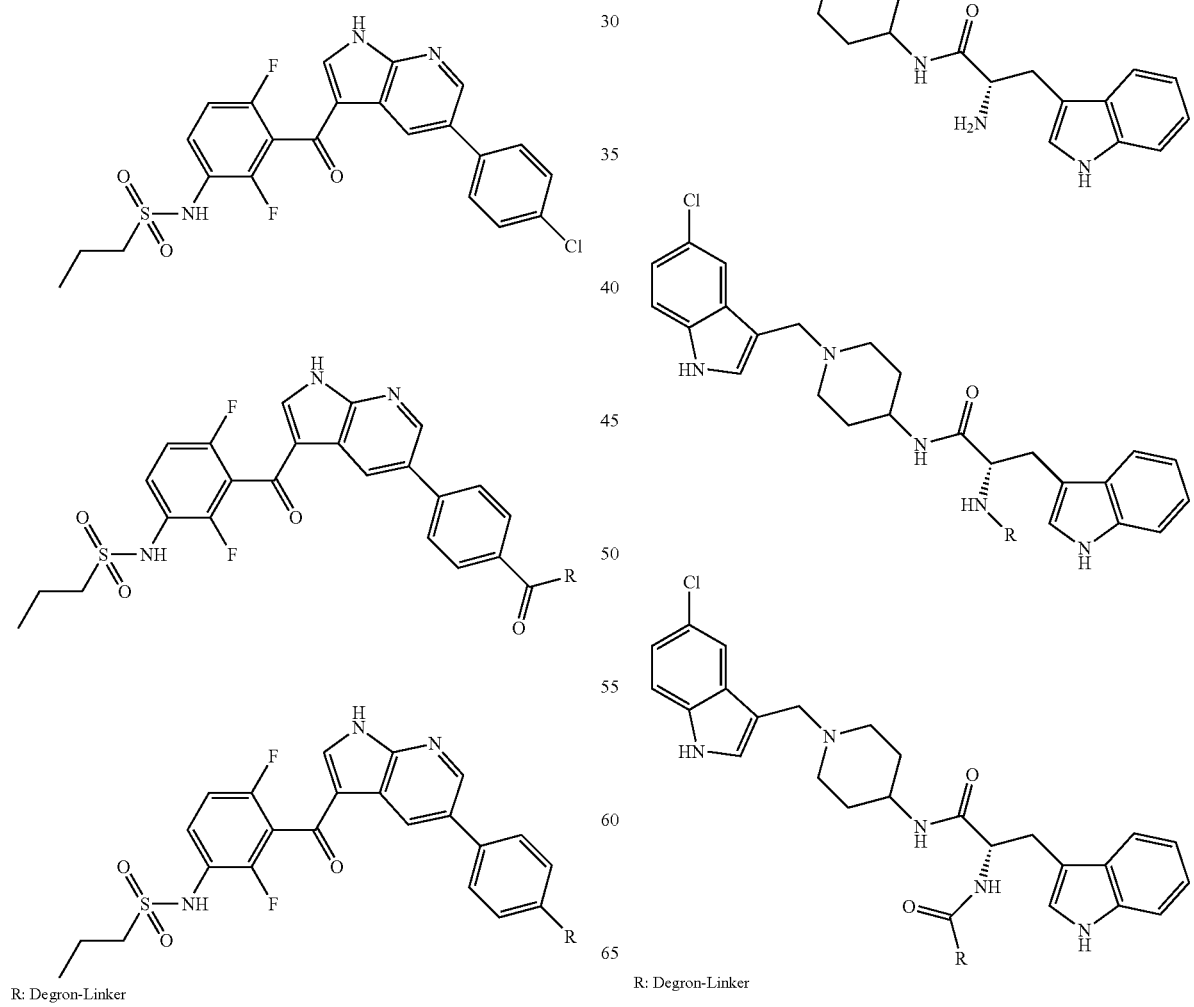
R: Degron-Linker
Ras Targeting Ligand
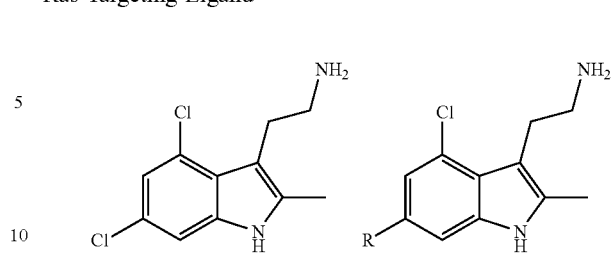
R: Degron-Linker RasG12C Targeting Ligand
Her3 Targeting Ligand
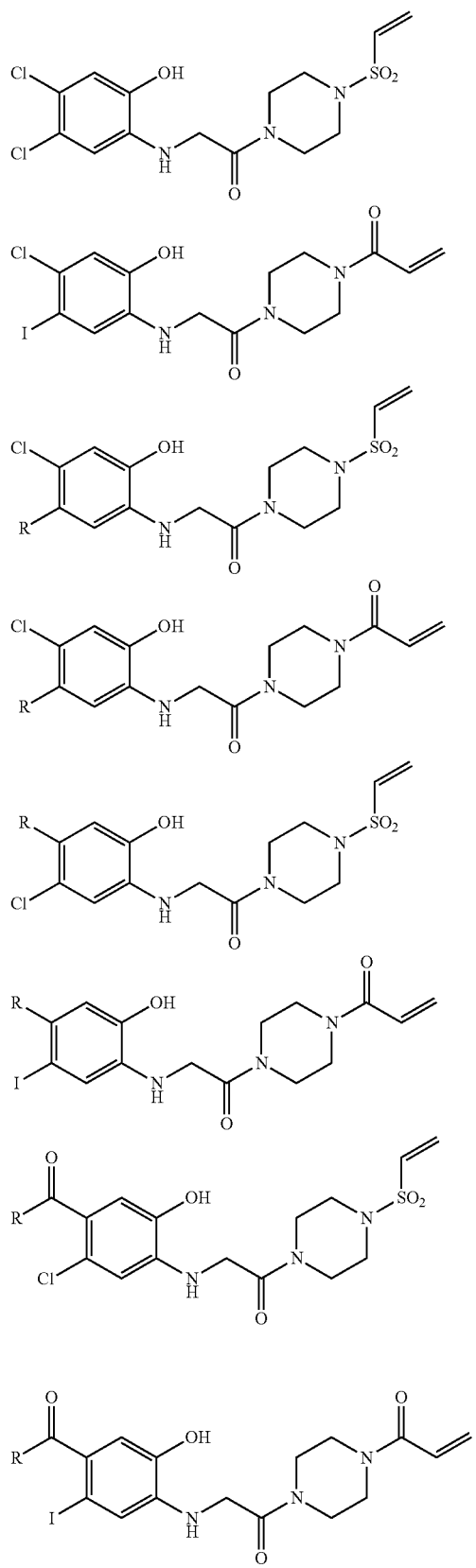
R: Degron-Linker
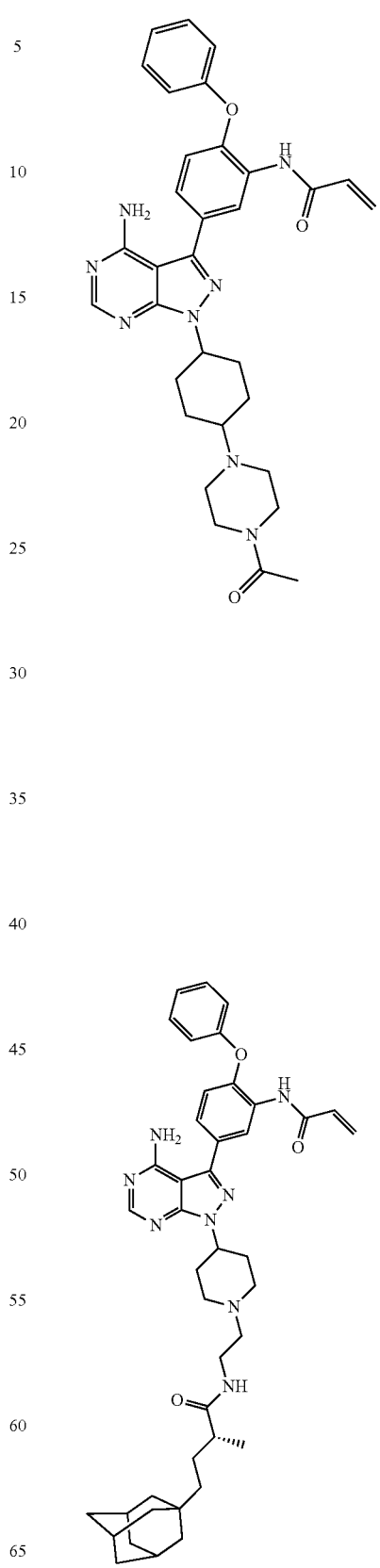

61
-continued
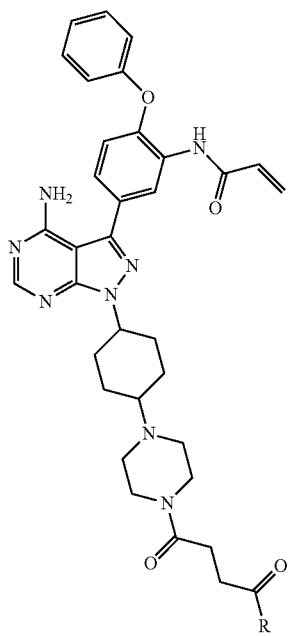
62
-continued
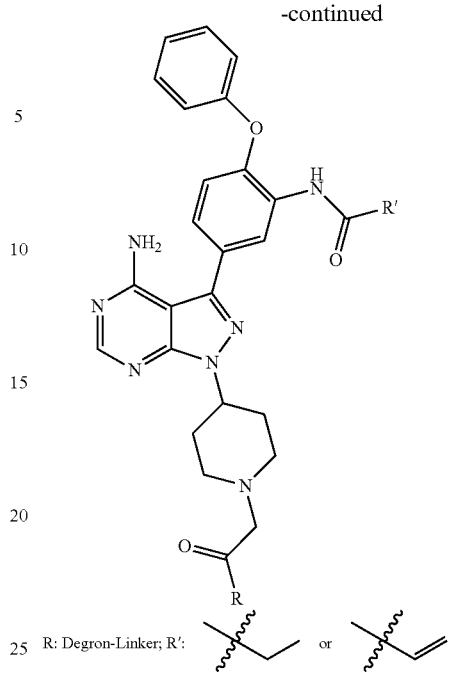
R: Degron-Linker; R': [structures]
Bcl-2/Bcl-XL Targeting Ligand
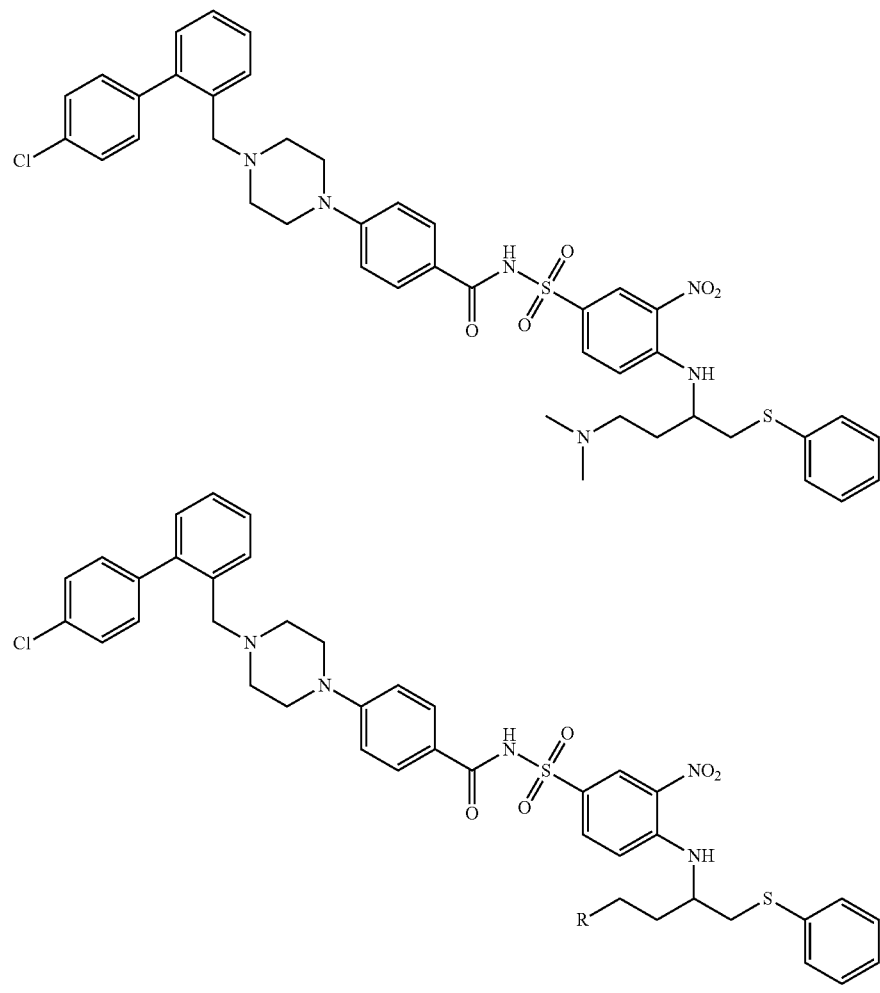
R: Degron-Linker HDAC Targeting Ligand
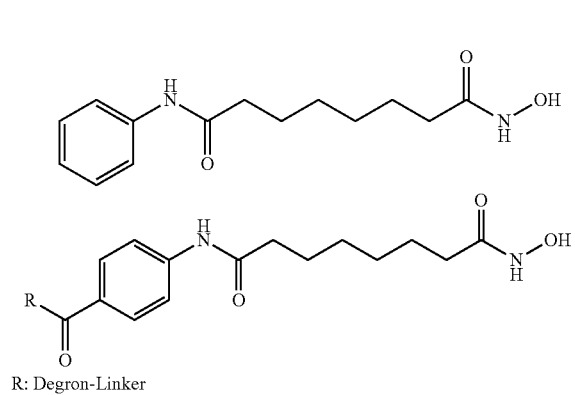
R: Degron-Linker
PPAR-Gamma Targeting Ligand
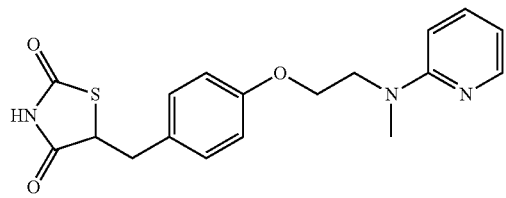
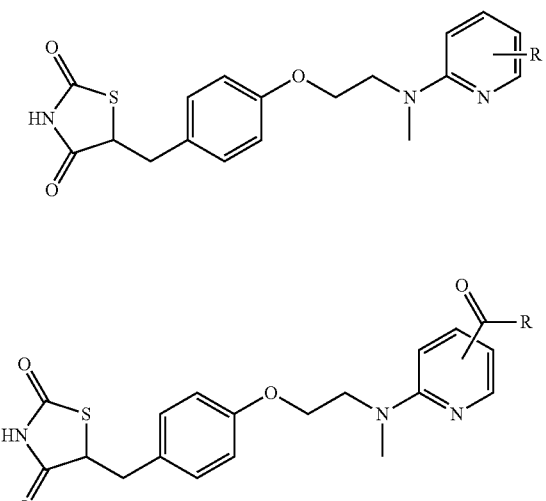
R: Degron-Linker
In certain embodiments, the present application relates to the compounds containing the TL moieties shown in Table 1.
TABLE 1
| Targeting Ligands 1-6 | |
|---|---|
| Compound | Structure |
| TL1 | 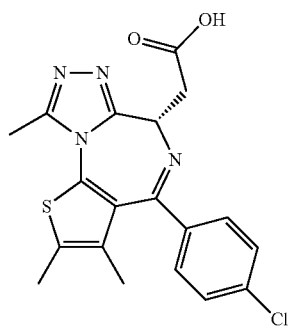 [SMILES: Cc1sc2c(c1C)C(c1ccc(Cl)cc1)=N[C@@H](CC(=O)O)c1nnc(C)n1-2] Ang. Chem. Int'l. Ed. 50, 9378 (2011) |
| TL2 |  |

TABLE 1-continued
Targeting Ligands 1-6
| Compound | Structure |
|---|---|
| TL3 | 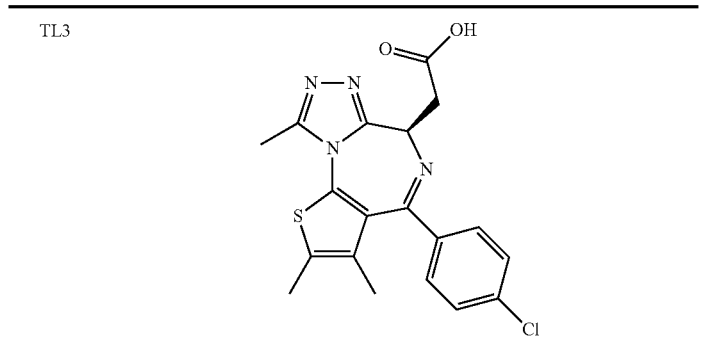 |
| TL4 | 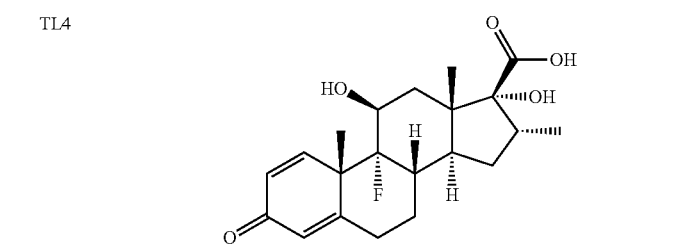 |
| TL5 | 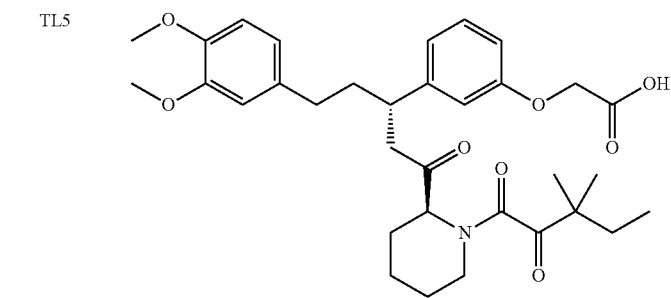
JACS 115, 9925 (1993) |
| TL6 | 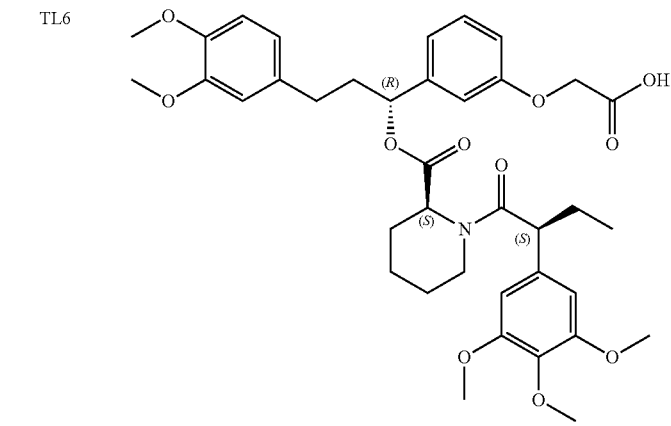 |

TABLE 1-continued

Targeting Ligands 1-6

| Compound | Structure |
|---|---|
| TL7 | 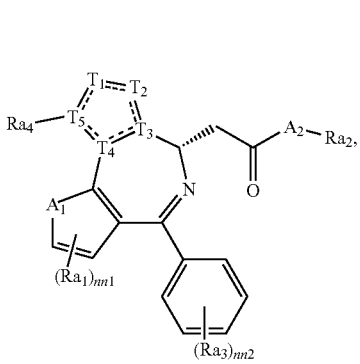 |

In certain embodiments, a Targeting Ligand is a compound of Formula TL-I:

(TL-I)

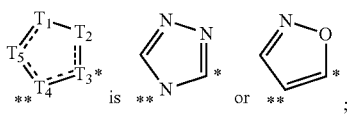

or a pharmaceutically acceptable salt thereof, wherein:

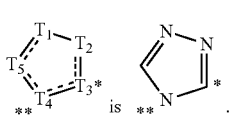

$A_1$ is S or C═C;
$A_2$ is $NRa_5$ or O;
nn1 is 0, 1, or 2;
each $Ra_1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa_5L$, OL, $NRa_5L$, or L;
$Ra_2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;
nn2 is 0, 1, 2, or 3;
each $Ra_3$ is independently $C_1$-$C_3$ alkyl, $(CH_2)_{0-3}$—CN, $(CH_2)_{0-3}$-halogen, L, or $C(O)NRa_5L$;
$Ra_4$ is $C_1$-$C_3$ alkyl;
$Ra_5$ is H or $C_1$-$C_3$ alkyl; and
L is a Linker,
provided that the compound of Formula TL-I is substituted with only one L.

In certain embodiments,

In certain embodiments,

In certain embodiments, $A_1$ is S.
In certain embodiments, $A_1$ is C═C.
In certain embodiments, $A_2$ is $NRa_5$. In further embodiments, $Ra_5$ is H. In other embodiments, $Ra_5$ is $C_1$-$C_3$ alkyl (e.g., methyl, ethyl, propyl, or i-propyl). In further embodiments, $Ra_5$ is methyl.
In certain embodiments, $A_2$ is O.
In certain embodiments, nn1 is 0.
In certain embodiments, nn1 is 1.
In certain embodiments, nn1 is 2.
In certain embodiments, at least one $Ra_1$ is $C_1$-$C_3$ alkyl (e.g., methyl, ethyl, propyl, or i-propyl). In further embodiments, at least one $Ra_1$ is methyl. In further embodiments, two $Ra_1$ are methyl.
In certain embodiments, at least one $Ra_1$ is CN, $(CH_2)$—CN, $(CH_2)_2$—CN, or $(CH_2)_3$—CN. In further embodiments, at least one $Ra_1$ is $(CH_2)$—CN.
In certain embodiments, at least one $Ra_1$ is halogen (e.g., F, Cl, or Br), $(CH_2)$-halogen, $(CH_2)_2$-halogen, or $(CH_2)_3$-halogen. In further embodiments, at least one $Ra_1$ is Cl, $(CH_2)$—Cl, $(CH_2)_2$—Cl, or $(CH_2)_3$—Cl.
In certain embodiments, at least one $Ra_1$ is OH, $(CH_2)$—OH, $(CH_2)_2$—OH, or $(CH_2)_3$—OH.
In certain embodiments, at least one $Ra_1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra_1$ is methoxy.
In certain embodiments, one $Ra_1$ is $C(O)NRa_5L$. In further embodiments, $Ra_5$ is H. In other embodiments, $Ra_5$ is $C_1$-$C_3$ alkyl (e.g., methyl, ethyl, propyl, or i-propyl).
In certain embodiments, one $Ra_1$ is OL.
In certain embodiments, one $Ra_1$ is $NRa_5L$. In further embodiments, $Ra_5$ is H. In other embodiments, $Ra_5$ is $C_1$-$C_3$ alkyl (e.g., methyl, ethyl, propyl, or i-propyl). In other embodiments, $Ra_5$ is methyl.

In certain embodiments, one $Ra_1$ is L.

In certain embodiments, $Ra_2$ is H.

In certain embodiments, $Ra_2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_2$ is methyl, ethyl, or t-butyl.

In certain embodiments, $Ra_2$ is heterocyclyl, (CH$_2$)-heterocyclyl, (CH$_2$)$_2$-heterocyclyl, or (CH$_2$)$_3$-heterocyclyl. In further embodiments, $Ra_2$ is (CH$_2$)$_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, the heterocyclyl is substituted with C(O)L.

In certain embodiments, the heterocyclyl is substituted with L.

In certain embodiments, $Ra_2$ is phenyl, (CH$_2$)-phenyl, (CH$_2$)$_2$-phenyl, or (CH$_2$)$_3$-phenyl. In further embodiments, $Ra_2$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, the phenyl is substituted with L.

In certain embodiments, $Ra_2$ is L.

In certain embodiments, nn2 is 0.
In certain embodiments, nn2 is 1.
In certain embodiments, nn2 is 2.
In certain embodiments, nn2 is 3.

In certain embodiments, at least one $Ra_3$ is $C_1$-$C_3$ alkyl (e.g., methyl, ethyl, propyl, or i-propyl). In further embodiments, at least one $Ra_3$ is methyl.

In certain embodiments, at least one $Ra_3$ is CN, (CH$_2$)—CN, (CH$_2$)$_2$—CN, or (CH$_2$)$_3$—CN. In further embodiments, at least one $Ra_3$ is CN.

In certain embodiments, at least one $Ra_3$ is halogen (e.g., F, Cl, or Br), (CH$_2$)-halogen, (CH$_2$)$_2$-halogen, or (CH$_2$)$_3$-halogen. In further embodiments, at least one $Ra_3$ is Cl, (CH$_2$)—Cl, (CH$_2$)$_2$—Cl, or (CH$_2$)$_3$—Cl. In further embodiments, at least one $Ra_3$ is Cl.

In certain embodiments, one $Ra_3$ is L.

In certain embodiments, one $Ra_3$ is C(O)NRa$_5$L. In further embodiments, $Ra_5$ is H. In other embodiments, $Ra_5$ is $C_1$-$C_3$ alkyl (e.g., methyl, ethyl, propyl, or i-propyl).

In certain embodiments, $Ra_4$ is $C_1$-$C_3$ alkyl (e.g., methyl, ethyl, propyl, or i-propyl). In further embodiments, $Ra_4$ is methyl.

In certain embodiments, $Ra_5$ is H.

In certain embodiments, $Ra_5$ is $C_1$-$C_3$ alkyl (e.g., methyl, ethyl, propyl, or i-propyl). In further embodiments, $Ra_5$ is methyl.

Each of the moieties defined for one of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2 can be combined with any of the moieties defined for the others of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2

In certain embodiments,

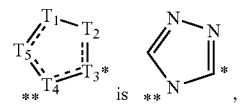

and $A_1$ is S.

In certain embodiments, and $A_1$ is C=C.

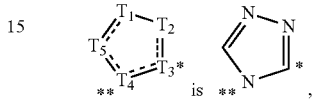

In certain embodiments,

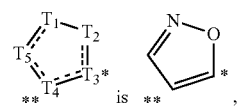

and $A_1$ is C=C.

In certain embodiments, $A_2$ is NH, and $Ra_2$ is (CH$_2$)$_{0-3}$-heterocyclyl. In further embodiments, $Ra_2$ is (CH$_2$)$_3$-heterocyclyl. In further embodiments, the heterocyclyl is piperazinyl. In further embodiments, the heterocyclyl is substituted with $C_1$-$C_3$ alkyl, L, or C(O)L.

In certain embodiments, $A_2$ is NH, and $Ra_2$ is (CH$_2$)$_{0-3}$-phenyl. In further embodiments, $Ra_2$ is phenyl. In further embodiments, the phenyl is substituted with OH or L.

In certain embodiments, $A_2$ is NH, and $Ra_2$ is L.

In certain embodiments, $A_2$ is NH, and $Ra_2$ is H or $C_1$-$C_6$ alkyl. In further embodiments, $Ra_2$ is $C_1$-$C_4$ alkyl.

In certain embodiments, $A_2$ is O, and $Ra_2$ is H or $C_1$-$C_6$ alkyl. In further embodiments, $Ra_2$ is $C_1$-$C_4$ alkyl.

In certain embodiments, a Targeting Ligand is a compound of Formula TL-I1:

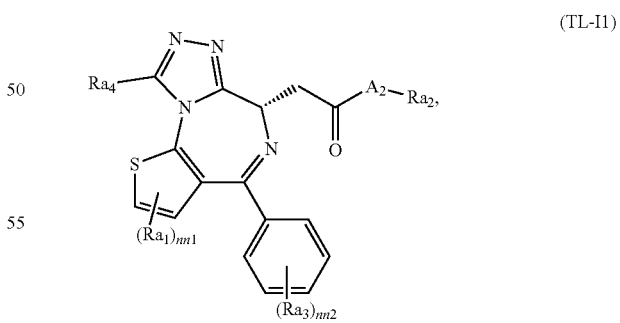

(TL-I1)

or a pharmaceutically acceptable salt thereof, wherein $A_2$, $Ra_1$, $Ra_2$, $Ra_3$, $Ra_4$, $Ra_5$, nn1, and nn2 are each as defined above in Formula TL-I.

Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I1a-TL-I1d:

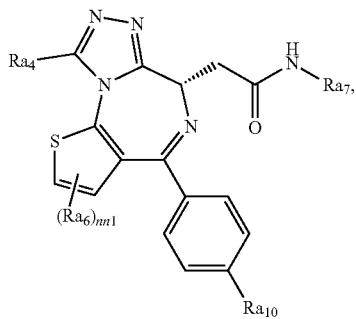
(TL-I1a)

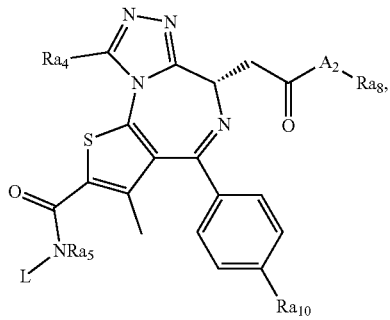
(TL-I1b)

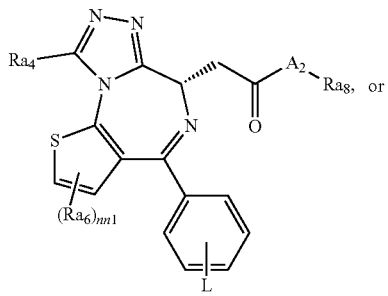
(TL-I1c)

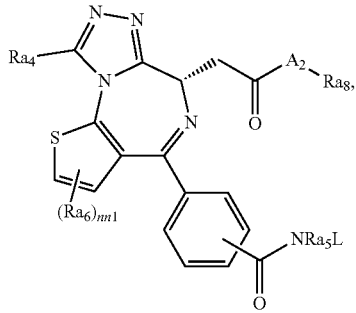
(TL-I1d)

or a pharmaceutically acceptable salt thereof, wherein:

each $Ra_6$ is independently $C_1$-$C_3$ alkyl, $(CH_2)_{0-3}$—CN, $(CH_2)_{0-3}$-halogen, $(CH_2)_{0-3}$—OH, or $(CH_2)_{0-3}$—$C_1$-$C_3$ alkoxy;

$Ra_7$ is $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is substituted with L or C(O)L, and wherein the phenyl is substituted with L;

$Ra_8$ is H, $C_1$-$C_6$ alkyl, $(CH_2)_{0-3}$-heterocyclyl, or $(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, and wherein the phenyl is optionally substituted with $C_1$-$C_3$ alkyl, CN, halogen, OH, or $C_1$-$C_3$ alkoxy;

$Ra_{10}$ is $C_1$-$C_3$ alkyl, $(CH_2)_{0-3}$—CN, or $(CH_2)_{0-3}$-halogen; and $A_2$, $Ra_4$, $Ra_5$, nn1, and L are each as defined above in Formula TL-I.

In certain embodiments, nn1 is 0.
In certain embodiments, nn1 is 1.
In certain embodiments, nn1 is 2.
In certain embodiments, at least one $Ra_6$ is $C_1$-$C_3$ alkyl (e.g., methyl, ethyl, propyl, or i-propyl). In further embodiments, at least one $Ra_6$ is methyl. In further embodiments, two $Ra_6$ are methyl.

In certain embodiments, at least one $Ra_6$ is CN, $(CH_2)$—CN, $(CH_2)_2$—CN, or $(CH_2)_3$—CN. In further embodiments, at least one $Ra_6$ is $(CH_2)$—CN.

In certain embodiments, at least one $Ra_6$ is halogen (e.g., F, Cl, or Br), $(CH_2)$-halogen, $(CH_2)_2$-halogen, or $(CH_2)_3$-halogen. In further embodiments, at least one $Ra_6$ is Cl, $(CH_2)$—Cl, $(CH_2)_2$—Cl, or $(CH_2)_3$—Cl.

In certain embodiments, at least one $Ra_6$ is OH, $(CH_2)$—OH, $(CH_2)_2$—OH, or $(CH_2)_3$—OH.

In certain embodiments, at least one $Ra_6$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra_6$ is methoxy.

In certain embodiments, $Ra_7$ is heterocyclyl, $(CH_2)$-heterocyclyl, $(CH_2)_2$-heterocyclyl, or $(CH_2)_3$-heterocyclyl. In further embodiments, $Ra_7$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with C(O)L.

In certain embodiments, the heterocyclyl is substituted with L.

In certain embodiments, $Ra_7$ is phenyl, $(CH_2)$-phenyl, $(CH_2)_2$-phenyl, or $(CH_2)_3$-phenyl. In further embodiments, $Ra_7$ is phenyl.

In certain embodiments, $Ra_7$ is L.
In certain embodiments, $Ra_8$ is H.
In certain embodiments, $Ra_8$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_8$ is methyl, ethyl, or t-butyl.

In certain embodiments, $Ra_8$ is heterocyclyl, $(CH_2)$-heterocyclyl, $(CH_2)_2$-heterocyclyl, or $(CH_2)_3$-heterocyclyl. In further embodiments, $Ra_8$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, $Ra_8$ is phenyl, $(CH_2)$-phenyl, $(CH_2)_2$-phenyl, or $(CH_2)_3$-phenyl. In further embodiments, $Ra_8$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, $Ra_{10}$ is $C_1$-$C_3$ alkyl (e.g., methyl, ethyl, propyl, or i-propyl).

In certain embodiments, $Ra_{10}$ is CN, $(CH_2)$—CN, $(CH_2)_2$—CN, or $(CH_2)_3$—CN.

In certain embodiments, $Ra_{10}$ is halogen (e.g., F, Cl, or Br), $(CH_2)$-halogen, $(CH_2)_2$-halogen, or $(CH_2)_3$-halogen. In further embodiments, $Ra_{10}$ is Cl, $(CH_2)$—Cl, $(CH_2)_2$—Cl, or $(CH_2)_3$—Cl. In further embodiments, $Ra_{10}$ is Cl.

Each of $A_2$, $Ra_4$, $Ra_5$, and nn1 may be selected from the moieties described above in Formula TL-I. Each of the moieties defined for one of $A_2$, $Ra_4$, $Ra_5$, $Ra_6$, $Ra_7$, $Ra_8$, $Ra_{10}$, and nn1, can be combined with any of the moieties defined for the others of $A_2$, $Ra_4$, $Ra_5$, $Ra_6$, $Ra_7$, $Ra_8$, $Ra_{10}$, and nn1, as described above and in Formula TL-I.

In certain embodiments, a Targeting Ligand is a compound of Formula TL-I2:

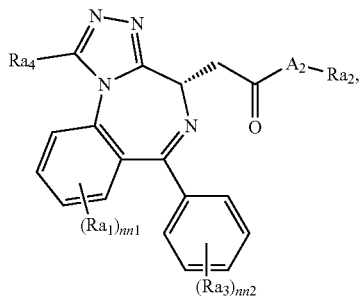

(TL-I2)

or a pharmaceutically acceptable salt thereof, wherein $A_2$, $Ra_1$, $Ra_2$, $Ra_3$, $Ra_4$, $Ra_5$, nn1, and nn2 are each as defined above in Formula TL-I.

Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I2a-TL-I2c:

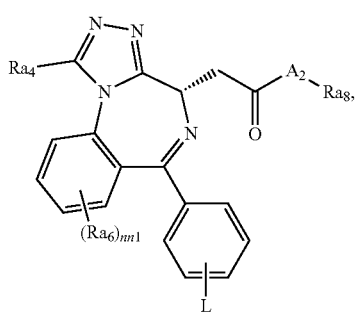

(TL-I2a)

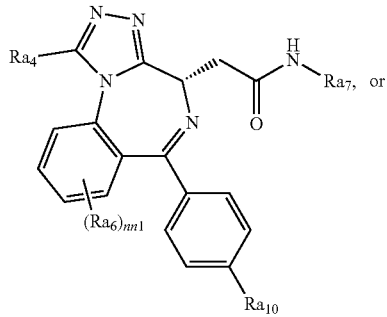

(TL-I2b)

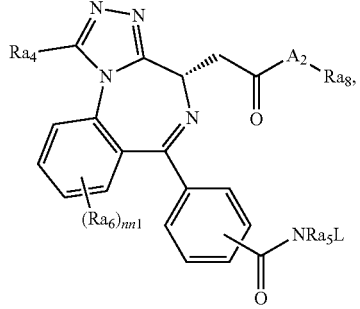

(TL-I2c)

or a pharmaceutically acceptable salt thereof, wherein $A_2$, $Ra_4$, $Ra_5$, nn1, and L are each as defined above in Formula TL-I, and $Ra_6$, $Ra_7$, $Ra_8$, and $Ra_{10}$ are each as defined above in Formula TL-I1a-TL-I1d.

Each of $A_2$, $Ra_4$, $Ra_5$, and nn1 may be selected from the moieties described above in Formula TL-I, and each of $Ra_6$, $Ra_7$, $Ra_8$, and $Ra_{10}$ may be selected from the moieties described above in Formula TL-I1a-TL-I1d. Each of the moieties defined for one of $A_2$, $Ra_4$, $Ra_5$, $Ra_6$, $Ra_7$, $Ra_8$, $Ra_{10}$, and nn1, can be combined with any of the moieties defined for the others of $A_2$, $Ra_4$, $Ra_5$, $Ra_6$, $Ra_7$, $Ra_8$, $Ra_{10}$, and nn1, as described above in Formula TL-I and TL-I1a-TL-I1d.

In certain embodiments, a Targeting Ligand is a compound of Formula TL-I3:

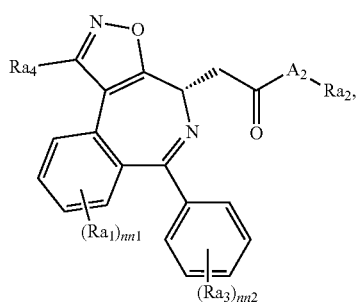

(TL-I3)

or a pharmaceutically acceptable salt thereof.

$A_2$, $Ra_1$, $Ra_2$, $Ra_3$, $Ra_4$, $Ra_5$, nn1, and nn2 are each as defined above in Formula TL-I. Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I3a-TL-I3c:

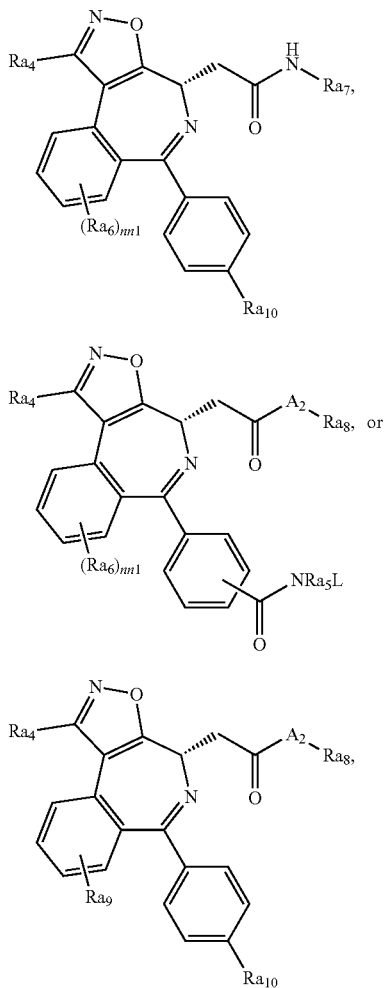

or a pharmaceutically acceptable salt thereof, wherein:
$Ra_9$ is $C(O)NRa_5L$, $OL$, $NRa_5L$, or $L$;
$A_2$, $Ra_4$, $Ra_5$, $nn1$, and $L$ are each as defined above in Formula TL-I; and
$Ra_6$, $Ra_7$, $Ra_8$, and $Ra_m$ are each as defined above in Formula TL-I1a-TL-I1d.

In certain embodiments, $Ra_9$ is $C(O)NRa_5L$. In further embodiments, $Ra_5$ is H. In other embodiments, $Ra_5$ is $C_1$-$C_3$ alkyl (e.g., methyl, ethyl, propyl, or i-propyl).

In certain embodiments, $Ra_9$ is OL.

In certain embodiments, $Ra_9$ is $NRa_5L$. In further embodiments, $Ra_5$ is H. In other embodiments, $Ra_5$ is $C_1$-$C_3$ alkyl (e.g., methyl, ethyl, propyl, or i-propyl). In other embodiments, $Ra_5$ is methyl.

In certain embodiments, $Ra_9$ is L.

Each of $A_2$, $Ra_4$, $Ra_5$, and $nn1$ may be selected from the moieties described above in Formula TL-I, and each of $Ra_6$, $Ra_7$, $Ra_8$, and $Ra_{10}$ may be selected from the moieties described above in Formula TL-I1a-TL-I1d. Each of the moieties defined for one of $A_2$, $Ra_4$, $Ra_5$, $Ra_6$, $Ra_7$, $Ra_8$, $Ra_9$, $Ra_{10}$, and $nn1$, can be combined with any of the moieties defined for the others of $A_2$, $Ra_4$, $Ra_5$, $Ra_6$, $Ra_7$, $Ra_8$, $Ra_9$, $Ra_{10}$, and $nn1$, as described above and in Formula TL-I and TL-I1a-TL-I1d.

In certain embodiments, a Targeting Ligand is a compound of Formula TL-II:

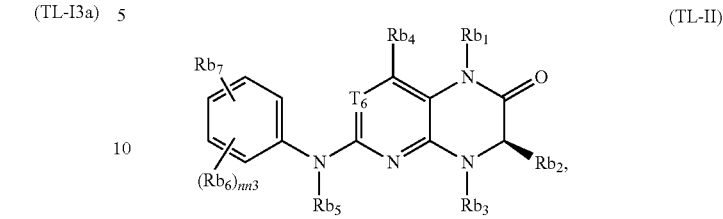

or a pharmaceutically acceptable salt thereof, wherein:
$T_6$ is $CRb_4$ or N;
$Rb_1$, $Rb_2$, and $Rb_5$ are each independently H or $C_1$-$C_3$ alkyl;
$Rb_3$ is $C_3$-$C_6$ cycloalkyl;
each $Rb_4$ is independently H, $C_1$-$C_3$ alkyl, $C_1$-$C_3$ alkoxy, CN, or halogen;
$nn3$ is 0, 1, 2, or 3;
each $Rb_6$ is independently $C_1$-$C_3$ alkyl, $C_1$-$C_3$ alkoxy, CN, or halogen;
$Rb_7$ is $C(O)NRb_8L$, $OL$, $NRb_8L$, or $L$;
$Rb_8$ is H or $C_1$-$C_3$ alkyl; and
$L$ is a Linker.

In certain embodiments, $T_6$ is $CRb_4$.
In certain embodiments, $T_6$ is N.
In certain embodiments, $Rb_1$ is H. In certain embodiments, $Rb_1$ is $C_1$-$C_3$ alkyl (e.g., methyl, ethyl, propyl, or i-propyl). In further embodiments, $Rb_1$ is methyl.

In certain embodiments, $Rb_2$ is H. In certain embodiments, $Rb_2$ is $C_1$-$C_3$ alkyl (e.g., methyl, ethyl, propyl, or i-propyl). In further embodiments, $Rb_2$ is methyl or ethyl.

In certain embodiments, $Rb_5$ is H. In certain embodiments, $Rb_5$ is $C_1$-$C_3$ alkyl (e.g., methyl, ethyl, propyl, or i-propyl).

In certain embodiments, $Rb_3$ is cyclopropyl, cyclobutyl, cyclopentyl, or cyclohexyl. In further embodiments, $Rb_3$ is cyclopentyl.

In certain embodiments, $Rb_4$ is H.
In certain embodiments, $Rb_4$ is $C_1$-$C_3$ alkyl (e.g., methyl, ethyl, propyl, or i-propyl).
In certain embodiments, $Rb_4$ is $C_1$-$C_3$ alkoxy (e.g., methoxy, ethoxy, or propoxy).
In certain embodiments, $Rb_4$ is CN.
In certain embodiments, $Rb_4$ is halogen (e.g., F, Cl, or Br).
In certain embodiments, $nn3$ is 0.
In certain embodiments, $nn3$ is 1.
In certain embodiments, $nn3$ is 2.
In certain embodiments, $nn3$ is 3.
In certain embodiments, at least one $Rb_6$ is $C_1$-$C_3$ alkyl (e.g., methyl, ethyl, propyl, or i-propyl). In further embodiments, at least one $Rb_6$ is methyl.
In certain embodiments, at least one $Rb_6$ is $C_1$-$C_3$ alkoxy (e.g., methoxy, ethoxy, or propoxy). In further embodiments, at least one $Rb_6$ is methoxy.
In certain embodiments, at least one $Rb_6$ is CN.
In certain embodiments, at least one $Rb_6$ is halogen (e.g., F, Cl, or Br).
In certain embodiments, $Rb_7$ is $C(O)NRb_8L$. In further embodiments, $Rb_8$ is H. In other embodiments, $Rb_8$ is $C_1$-$C_3$ alkyl (e.g., methyl, ethyl, propyl, or i-propyl).
In certain embodiments, $Rb_7$ is OL.

In certain embodiments, $Rb_7$ is $NRb_8L$. In further embodiments, $Rb_8$ is H. In other embodiments, $Rb_8$ is $C_1$-$C_3$ alkyl (e.g., methyl, ethyl, propyl, or i-propyl). In other embodiments, $Rb_8$ is methyl.

In certain embodiments, $Rb_7$ is L.

Each of the moieties defined for one of $T_6$, $Rb_1$, $Rb_2$, $Rb_3$, $Rb_4$, $Rb_5$, $Rb_6$, $Rb_7$, $Rb_8$, and nn3, can be combined with any of the moieties defined for the others of $T_6$, $Rb_1$, $Rb_2$, $Rb_3$, $Rb_4$, $Rb_5$, $Rb_6$, $Rb_7$, $Rb_8$, and nn3.

In certain embodiments, $Rb_3$ is cyclopentyl, and $Rb_7$ is $C(O)NRb_8L$.

In certain embodiments, a Targeting Ligand is a compound of Formula TL-III1:

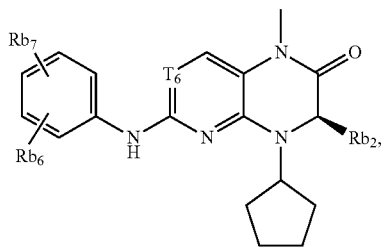

(TL-III1)

or a pharmaceutically acceptable salt thereof, wherein $T_6$, $Rb_2$, $Rb_4$, $Rb_6$, $Rb_7$, and $Rb_8$ are each as defined above in Formula TL-II.

Each of $T_6$, $Rb_2$, $Rb_4$, $Rb_6$, $Rb_7$, and $Rb_8$ may be selected from the moieties described above in Formula TL-II. Each of the moieties defined for one of $T_6$, $Rb_2$, $Rb_4$, $Rb_6$, $Rb_7$, and $Rb_8$, can be combined with any of the moieties defined for the others of $T_6$, $Rb_2$, $Rb_4$, $Rb_6$, $Rb_7$, and $Rb_8$, as described above in Formula TL-II.

In certain embodiments, a Targeting Ligand is a compound of Formula TL-III1a:

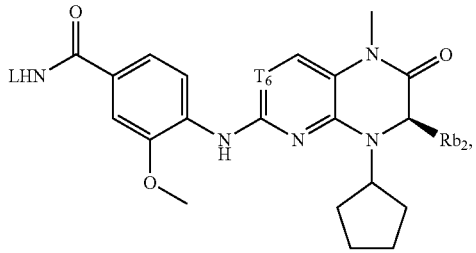

(TL-III1a)

or a pharmaceutically acceptable salt thereof, wherein $T_6$, $Rb_2$, and $Rb_4$ are each as defined above in Formula TL-II.

Each of $T_6$, $Rb_2$, and $Rb_4$ may be selected from the moieties described above in Formula TL-II. Each of the moieties defined for one of $T_6$, $Rb_2$, and $Rb_4$, can be combined with any of the moieties defined for the others of $T_6$, $Rb_2$, and $Rb_4$, as described above in Formula TL-II.

In certain embodiments, a Targeting Ligand is a compound of Formula TL-III:

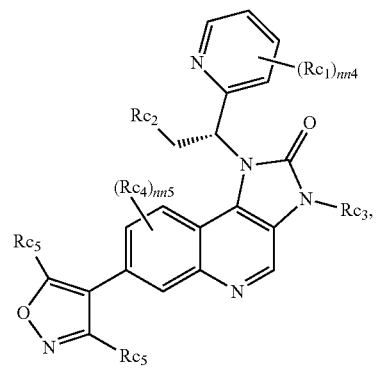

(TL-III)

or a pharmaceutically acceptable salt thereof, wherein:
nn4 is 0 or 1;
$Rc_1$ is $C(O)NRc_6L$, OL, $NRc_6L$, or L;
$Rc_2$ is H, $C_1$-$C_3$ alkyl, $C(O)NRc_6L$, OL, $NRc_6L$, or L;
$Rc_3$ is H, $C_1$-$C_3$ alkyl, $C(O)L$, or L;
nn5 is 0, 1, or 2;
each $Rc_4$ is independently $C_1$-$C_3$ alkyl or $C_1$-$C_3$ alkoxy;
each $Rc_5$ is independently H or $C_1$-$C_3$ alkyl;
$Rc_6$ is independently H or $C_1$-$C_3$ alkyl; and
L is a Linker,
provided that the compound of Formula TL-III is substituted with only one L.

In certain embodiments, nn4 is 0.
In certain embodiments, nn4 is 1.
In certain embodiments, $Rc_1$ is $C(O)NRc_6L$. In further embodiments, $Rc_6$ is H. In other embodiments, $Rc_6$ is $C_1$-$C_3$ alkyl (e.g., methyl, ethyl, propyl, or i-propyl).
In certain embodiments, $Rc_1$ is OL.
In certain embodiments, $Rc_1$ is $NRc_6L$. In further embodiments, $Rc_6$ is H. In other embodiments, $Rc_6$ is $C_1$-$C_3$ alkyl (e.g., methyl, ethyl, propyl, or i-propyl). In other embodiments, $Rc_6$ is methyl.
In certain embodiments, $Rc_1$ is L.
In certain embodiments, $Rc_2$ is H.
In certain embodiments, $Rc_2$ is $C_1$-$C_3$ alkyl (e.g., methyl, ethyl, propyl, or i-propyl). In further embodiments, $Rc_2$ is methyl.
In certain embodiments, $Rc_2$ is $C(O)NRc_6L$. In further embodiments, $Rc_6$ is H. In other embodiments, $Rc_6$ is $C_1$-$C_3$ alkyl (e.g., methyl, ethyl, propyl, or i-propyl).
In certain embodiments, $Rc_2$ is OL.
In certain embodiments, $Rc_2$ is $NRc_6L$. In further embodiments, $Rc_6$ is H. In other embodiments, $Rc_6$ is $C_1$-$C_3$ alkyl (e.g., methyl, ethyl, propyl, or i-propyl). In other embodiments, $Rc_6$ is methyl.
In certain embodiments, $Rc_2$ is L.
In certain embodiments, $Rc_3$ is H.
In certain embodiments, $Rc_3$ is $C_1$-$C_3$ alkyl (e.g., methyl, ethyl, propyl, or i-propyl).
In certain embodiments, $Rc_3$ is $C(O)L$.
In certain embodiments, $Rc_3$ is L.
In certain embodiments, nn5 is 0.
In certain embodiments, nn5 is 1.
In certain embodiments, nn5 is 2.
In certain embodiments, at least one $Rc_4$ is $C_1$-$C_3$ alkyl (e.g., methyl, ethyl, propyl, or i-propyl). In further embodiments, at least one $Rc_4$ is methyl.
In certain embodiments, at least one $Rc_4$ is $C_1$-$C_3$ alkoxy (e.g., methoxy, ethoxy, or propoxy). In further embodiments, at least one $Rc_4$ is methoxy.

In certain embodiments, at least one $Rc_5$ is H.

In certain embodiments, at least one $Rc_5$ is $C_1$-$C_3$ alkyl (e.g., methyl, ethyl, propyl, or i-propyl). In further embodiments, at least one $Rc_5$ is methyl. In further embodiments, two $Rc_5$ are methyl.

Each of the moieties defined for one of $Rc_1$, $Rc_2$, $Rc_3$, $Rc_4$, $Rc_5$, $Rc_6$, nn4, and nn5, can be combined with any of the moieties defined for the others of $Rc_1$, $Rc_2$, $Rc_3$, $Rc_4$, $Rc_5$, $Rc_6$, nn4, and nn5.

In certain embodiments, a Targeting Ligand is a compound of Formula TL-III1-TL-III3:

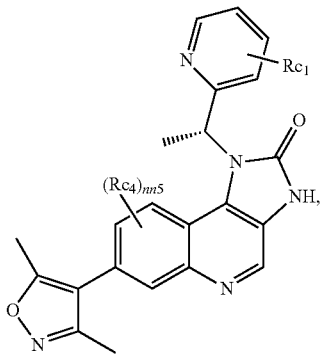
(TL-III1)

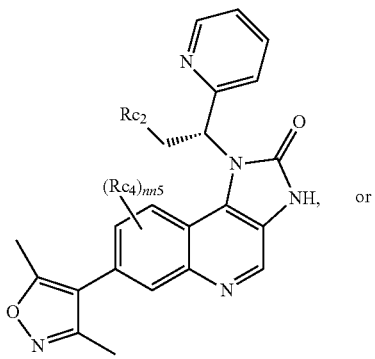
(TL-III2) or

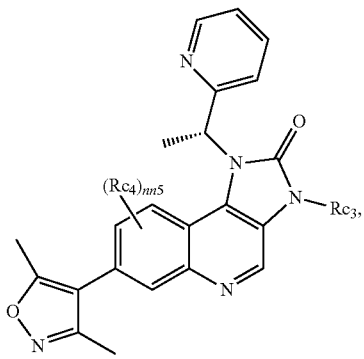
(TL-III3)

or a pharmaceutically acceptable salt thereof, wherein $Rc_1$, $Rc_2$, $Rc_3$, $Rc_4$, and nn5 are each as defined above in Formula TL-III.

Each of $Rc_1$, $Rc_2$, $Rc_3$, $Rc_4$, and nn5 may be selected from the moieties described above in Formula TL-III. Each of the moieties defined for one of $Rc_1$, $Rc_2$, $Rc_3$, $Rc_4$, and nn5, can be combined with any of the moieties defined for the others of $Rc_1$, $Rc_2$, $Rc_3$, $Rc_4$, and nn5, as described above in Formula TL-III.

In certain embodiments, a Targeting Ligand is a compound of Formula TL-IV:

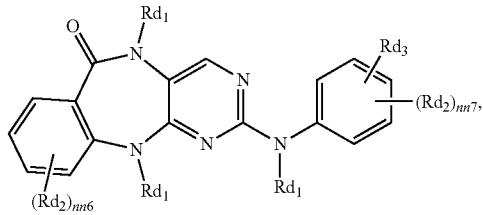
(TL-IV)

or a pharmaceutically acceptable salt thereof, wherein:
each $Rd_1$ is independently H or $C_1$-$C_3$ alkyl;
nn6 is 0, 1, 2, or 3;
nn7 is 0, 1, 2, or 3;
each $Rd_2$ is independently $C_1$-$C_3$ alkyl, $C_1$-$C_3$ alkoxy, CN, or halogen;
$Rd_3$ is $C(O)NRd_4L$, OL, $NRd_4L$, or L;
$Rd_4$ is H or $C_1$-$C_3$ alkyl; and
L is a Linker.

In certain embodiments, $Rd_1$ is H.
In certain embodiments, $Rd_1$ is $C_1$-$C_3$ alkyl (e.g., methyl, ethyl, propyl, or i-propyl). In further embodiments, $Rd_1$ is methyl.

In certain embodiments, nn6 is 0.
In certain embodiments, nn6 is 1.
In certain embodiments, nn6 is 2.
In certain embodiments, nn6 is 3.
In certain embodiments, nn7 is 0.
In certain embodiments, nn7 is 1.
In certain embodiments, nn7 is 2.
In certain embodiments, nn7 is 3.

In certain embodiments, at least one $Rd_2$ is $C_1$-$C_3$ alkyl (e.g., methyl, ethyl, propyl, or i-propyl). In further embodiments, at least one $Rd_2$ is methyl.

In certain embodiments, at least one $Rd_2$ is $C_1$-$C_3$ alkoxy (e.g., methoxy, ethoxy, or propoxy). In further embodiments, at least one $Rd_2$ is methoxy.

In certain embodiments, at least one $Rd_2$ is CN.
In certain embodiments, at least one $Rd_2$ is halogen (e.g., F, Cl, or Br).

In certain embodiments, $Rd_3$ is $C(O)NRd_4L$. In further embodiments, $Rd_4$ is H. In other embodiments, $Rd_4$ is $C_1$-$C_3$ alkyl (e.g., methyl, ethyl, propyl, or i-propyl).

In certain embodiments, $Rd_3$ is OL.

In certain embodiments, $Rd_3$ is $NRd_4L$. In further embodiments, $Rd_4$ is H. In other embodiments, $Rd_4$ is $C_1$-$C_3$ alkyl (e.g., methyl, ethyl, propyl, or i-propyl). In other embodiments, $Rd_4$ is methyl.

In certain embodiments, $Rd_3$ is L.

Each of the moieties defined for one of $Rd_1$, $Rd_2$, $Rd_3$, $Rd_4$, nn6, and nn7, can be combined with any of the moieties defined for the others of $Rd_1$, $Rd_2$, $Rd_3$, $Rd_4$, nn6, and nn7.

In certain embodiments, a Targeting Ligand is a compound of Formula TL-IV 1:

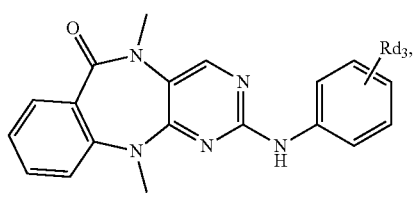
(TL-IV1)

or a pharmaceutically acceptable salt thereof, wherein $Rd_3$ is as defined above in Formula TL-IV. $Rd_3$ may be selected from the moieties described above in Formula TL-IV.

In certain embodiments, a Targeting Ligand is a compound of Formula TL-V:

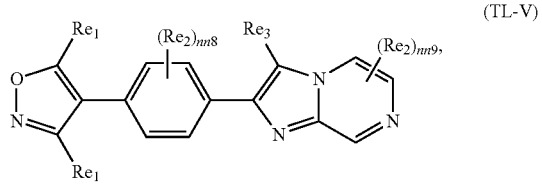
(TL-V)

or a pharmaceutically acceptable salt thereof, wherein:
each $Re_1$ is independently H or $C_1$-$C_3$ alkyl;
nn8 is 0, 1, 2, or 3;
nn9 is 0, 1, 2, or 3;
each $Re_2$ is independently $C_1$-$C_3$ alkyl, $C_1$-$C_3$ alkoxy, CN, or halogen;
$Re_3$ is NH—$(CH_2)_{1-3}$—C(O)NRe$_4$L, C(O)NRe$_4$L, OL, NRe$_4$L, or L;
$Re_4$ is H or $C_1$-$C_3$ alkyl; and
L is a Linker.

In certain embodiments, $Re_1$ is H.
In certain embodiments, $Re_1$ is $C_1$-$C_3$ alkyl (e.g., methyl, ethyl, propyl, or i-propyl). In further embodiments, $Re_1$ is methyl.

In certain embodiments, nn8 is 0.
In certain embodiments, nn8 is 1.
In certain embodiments, nn8 is 2.
In certain embodiments, nn8 is 3.
In certain embodiments, nn9 is 0.
In certain embodiments, nn9 is 1.
In certain embodiments, nn9 is 2.
In certain embodiments, nn9 is 3.
In certain embodiments, at least one $Re_2$ is $C_1$-$C_3$ alkyl (e.g., methyl, ethyl, propyl, or i-propyl). In further embodiments, at least one $Re_2$ is methyl.

In certain embodiments, at least one $Re_2$ is $C_1$-$C_3$ alkoxy (e.g., methoxy, ethoxy, or propoxy). In further embodiments, at least one $Re_2$ is methoxy.

In certain embodiments, at least one $Re_2$ is CN.
In certain embodiments, at least one $Re_2$ is halogen (e.g., F, Cl, or Br).

In certain embodiments, $Re_3$ is NH—$CH_2$—C(O)NRe$_4$L, NH—$(CH_2)_2$—C(O)NRe$_4$L, or NH—$(CH_2)_3$—C(O)NRe$_4$L. In further embodiments, $Re_3$ is NH—$CH_2$—C(O)NRe$_4$L. In further embodiments, $Re_4$ is H. In other embodiments, $Re_4$ is $C_1$-$C_3$ alkyl (e.g., methyl, ethyl, propyl, or i-propyl).

In certain embodiments, $Re_3$ is C(O)NRe$_4$L. In further embodiments, $Re_4$ is H. In other embodiments, $Re_4$ is $C_1$-$C_3$ alkyl (e.g., methyl, ethyl, propyl, or i-propyl).

In certain embodiments, $Re_3$ is OL.
In certain embodiments, $Re_3$ is NRe$_4$L. In further embodiments, $Re_4$ is H. In other embodiments, $Re_4$ is $C_1$-$C_3$ alkyl (e.g., methyl, ethyl, propyl, or i-propyl). In other embodiments, $Re_4$ is methyl.

In certain embodiments, $Re_3$ is L.
Each of the moieties defined for one of $Re_1$, $Re_2$, $Re_3$, $Re_4$, nn8, and nn9, can be combined with any of the moieties defined for the others of $Re_1$, $Re_2$, $Re_3$, $Re_4$, nn8, and nn9.

In certain embodiments, a Targeting Ligand is a compound of Formula TL-V1:

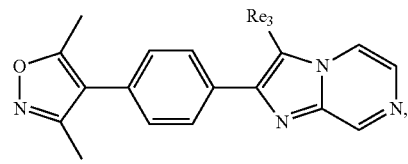
(TL-VI)

or a pharmaceutically acceptable salt thereof, wherein $Re_3$ is as defined above in Formula TL-V. $Re_3$ may be selected from the moieties described above in Formula TL-V.

In certain embodiments, a Targeting Ligand is a compound of Formula TL-VI:

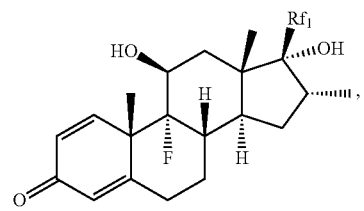
(TL-VI)

or a pharmaceutically acceptable salt thereof, wherein:
$Rf_1$ is C(O)NRf$_2$L, OL, NRf$_2$L, or L;
$Rf_2$ is independently H or $C_1$-$C_3$ alkyl; and
L is a Linker.

In certain embodiments, $Rf_1$ is C(O)NRf$_2$L. In further embodiments, $Rf_2$ is H. In other embodiments, $Rf_2$ is $C_1$-$C_3$ alkyl (e.g., methyl, ethyl, propyl, or i-propyl).

In certain embodiments, $Rf_1$ is OL.
In certain embodiments, $Rf_1$ is NRe$_4$L. In further embodiments, $Rf_2$ is H. In other embodiments, $Rf_2$ is $C_1$-$C_3$ alkyl (e.g., methyl, ethyl, propyl, or i-propyl). In other embodiments, $Rf_2$ is methyl.

In certain embodiments, $Rf_1$ is L.
In certain embodiments, a Targeting Ligand is a compound of Formula TL-VII:

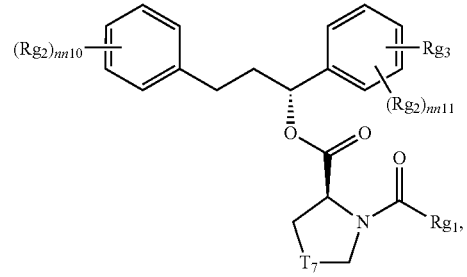
(TL-VII)

or a pharmaceutically acceptable salt thereof, wherein:
$T_7$ is $CH_2$ or $CH_2CH_2$;
$Rg_1$ is C(O)Rg$_5$ or $(CH_2)_{1-3}$Rg$_6$;
nn10 is 0, 1, 2, or 3;
nn11 is 0, 1, 2, or 3;
each $Rg_2$ is independently $C_1$-$C_3$ alkyl, $C_1$-$C_3$ alkoxy, CN, or halogen;
$Rg_3$ is C(O)NRg$_4$L, OL, NRg$_4$L, L, O—$(CH_2)_{1-3}$—C(O)NRg$_4$L, or NHC(O)—$(CH_2)_{1-3}$—C(O)NRg$_4$L;
$Rg_4$ is H or $C_1$-$C_3$ alkyl;

Rg$_5$ is C$_1$-C$_6$ alkyl;

Rg$_6$ is phenyl optionally substituted with C$_1$-C$_3$ alkyl, C$_1$-C$_3$ alkoxy, CN, or halogen; and L is a Linker.

In certain embodiments, T$_7$ is CH$_2$.

In certain embodiments, T$_7$ is CH$_2$CH$_2$.

In certain embodiments, Rg$_1$ is C(O)Rg$_5$.

In certain embodiments, Rg$_1$ is (CH$_2$)—Rg$_6$, (CH$_2$)$_2$—Rg$_6$, or (CH$_2$)$_3$—Rg$_6$.

In certain embodiments, Rg$_5$ is straight-chain C$_1$-C$_6$ or branched C$_3$-C$_6$ alkyl (e.g., methyl, ethyl, propyl, i-propyl, butyl, i-butyl, t-butyl, pentyl, or hexyl).

In certain embodiments, Rg$_6$ is unsubstituted phenyl.

In certain embodiments, Rg$_6$ is phenyl substituted with one, two, three, or more substituents independently selected from C$_1$-C$_3$ alkyl (e.g., methyl, ethyl, propyl, or i-propyl), C$_1$-C$_3$ alkoxy (e.g., methoxy, ethoxy, or propoxy), CN, and halogen (e.g., F, Cl, or Br).

In certain embodiments, nn10 is 0.

In certain embodiments, nn10 is 1.

In certain embodiments, nn10 is 2.

In certain embodiments, nn10 is 3.

In certain embodiments, nn11 is 0.

In certain embodiments, nn11 is 1.

In certain embodiments, nn11 is 2.

In certain embodiments, nn11 is 3.

In certain embodiments, at least one Rg$_2$ is C$_1$-C$_3$ alkyl (e.g., methyl, ethyl, propyl, or i-propyl). In further embodiments, at least one Rg$_2$ is methyl.

In certain embodiments, at least one Rg$_2$ is C$_1$-C$_3$ alkoxy (e.g., methoxy, ethoxy, or propoxy). In further embodiments, at least one Rg$_2$ is methoxy.

In certain embodiments, at least one Rg$_2$ is CN.

In certain embodiments, at least one Rg$_2$ is halogen (e.g., F, Cl, or Br).

In certain embodiments, Rg$_3$ is C(O)NRg$_4$L. In further embodiments, Rg$_4$ is H. In other embodiments, Rg$_4$ is C$_1$-C$_3$ alkyl (e.g., methyl, ethyl, propyl, or i-propyl).

In certain embodiments, Rg$_3$ is OL.

In certain embodiments, Rg$_3$ is NRg$_4$L. In further embodiments, Rg$_4$ is H. In other embodiments, Rg$_4$ is C$_1$-C$_3$ alkyl (e.g., methyl, ethyl, propyl, or i-propyl). In other embodiments, Rg$_4$ is methyl.

In certain embodiments, Rg$_3$ is L.

In certain embodiments, Rg$_3$ is O—(CH$_2$)—C(O)NRg$_4$L, O—(CH$_2$)$_2$—C(O)NRg$_4$L, or O—(CH$_2$)$_3$—C(O)NRg$_4$L. In further embodiments, Rg$_3$ is O—(CH$_2$)—C(O)NRg$_4$L. In further embodiments, Rg$_4$ is H. In other embodiments, Rg$_4$ is C$_1$-C$_3$ alkyl (e.g., methyl, ethyl, propyl, or i-propyl).

In certain embodiments, Rg$_3$ is NHC(O)—(CH$_2$)—C(O)NRg$_4$L, NHC(O)—(CH$_2$)$_2$—C(O)NRg$_4$L, or NHC(O)—(CH$_2$)$_3$—C(O)NRg$_4$L. In further embodiments, Rg$_3$ is NHC(O)—(CH$_2$)—C(O)NRg$_4$L, NHC(O)—(CH$_2$)$_2$—C(O)NRg$_4$L. In further embodiments, Rg$_3$ is NHC(O)—(CH$_2$)$_2$—C(O)NRg$_4$L. In further embodiments, Rg$_4$ is H. In other embodiments, Rg$_4$ is C$_1$-C$_3$ alkyl (e.g., methyl, ethyl, propyl, or i-propyl).

In certain embodiments, the Targeting Ligand is selected from the following, wherein R is a Linker:

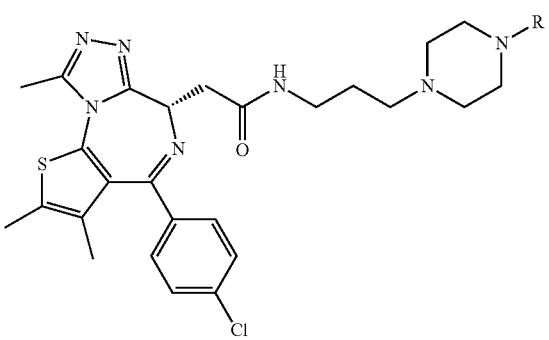

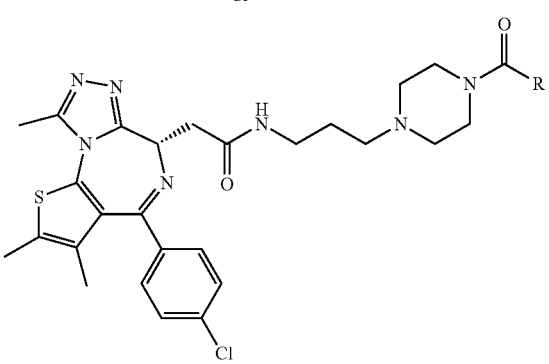

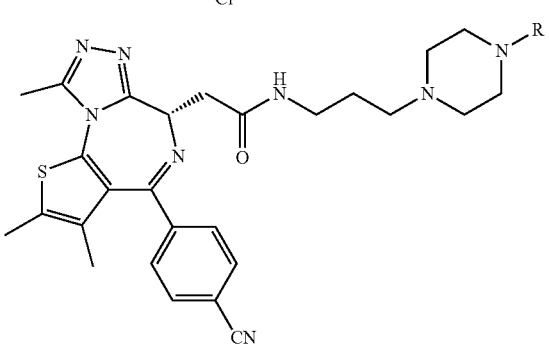

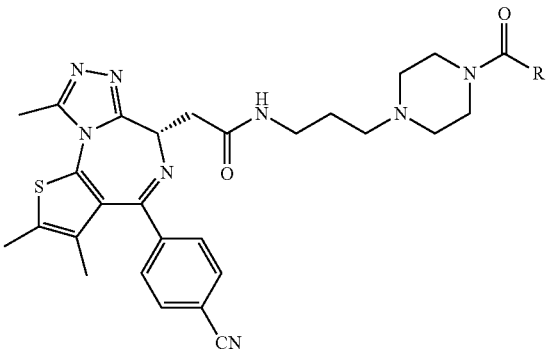

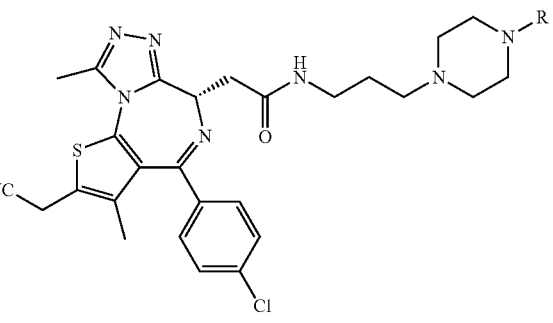

85
-continued
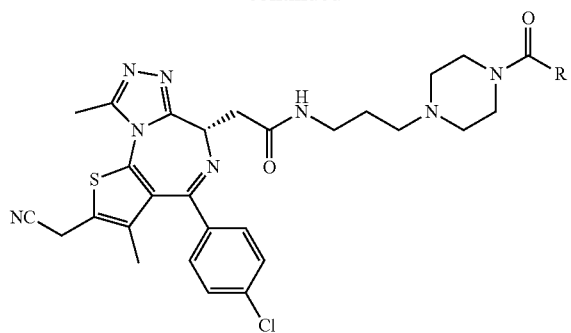
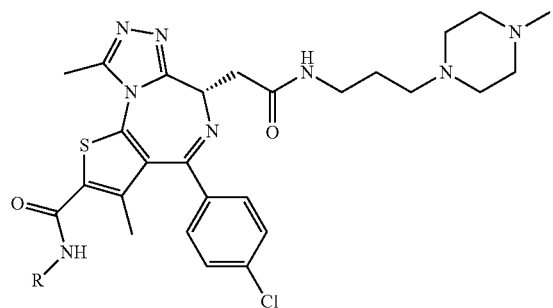
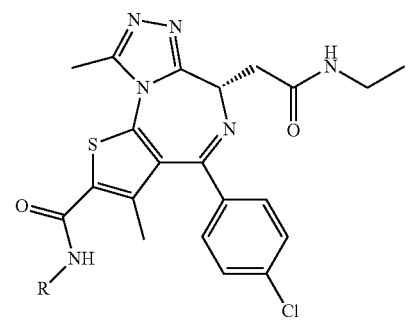
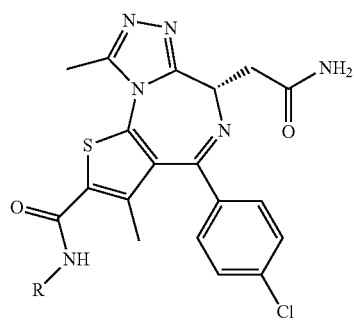
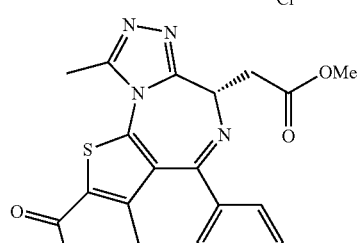
86
-continued
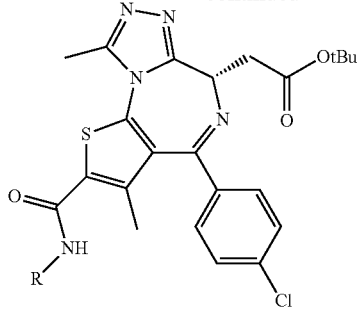
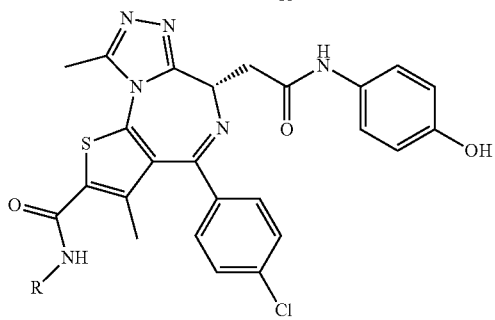
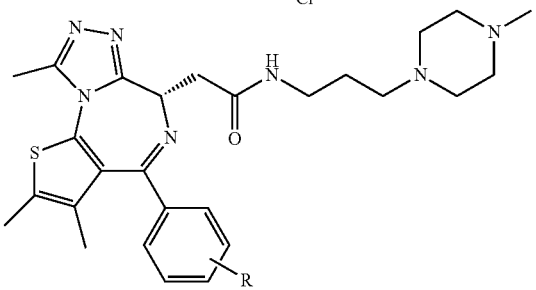
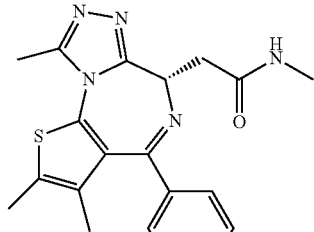
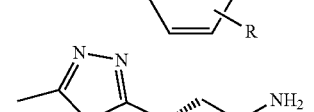
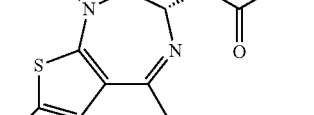
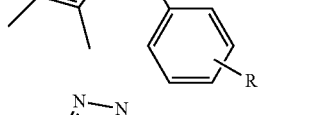
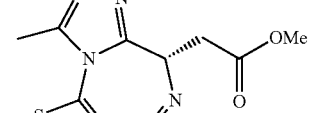
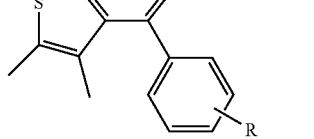

87
-continued
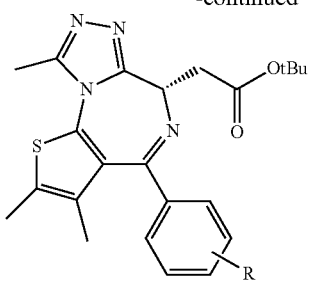
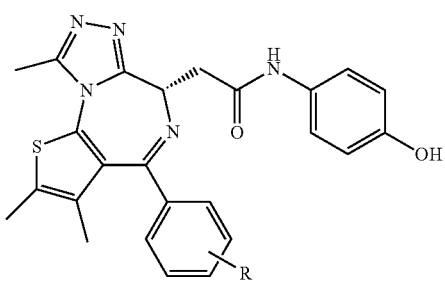
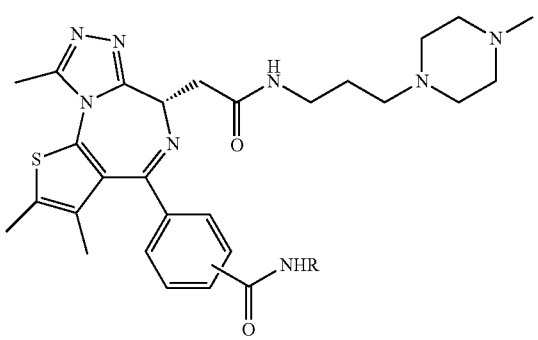
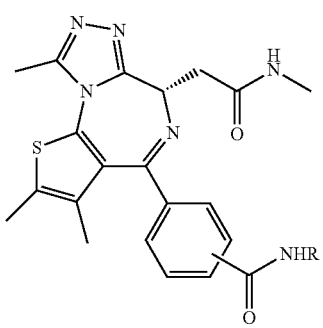
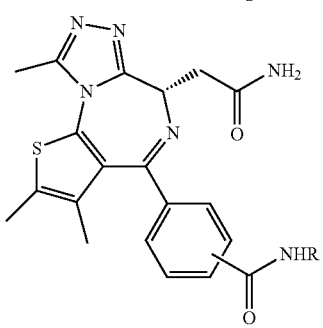
88
-continued
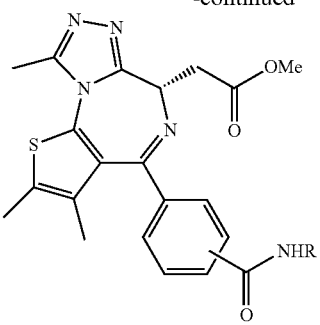
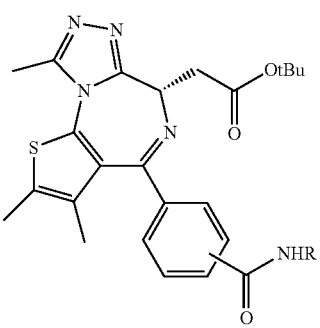
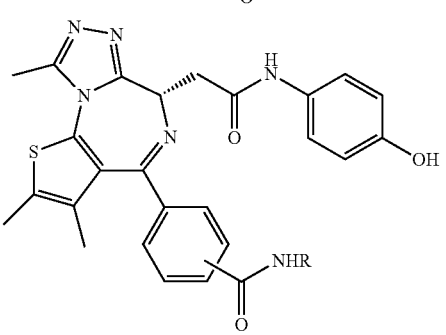
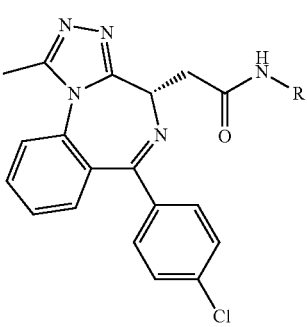
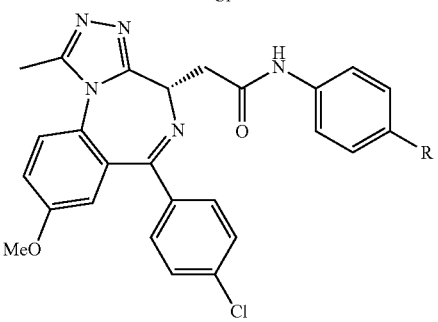

89
-continued
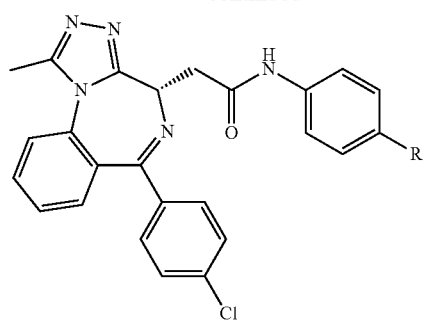
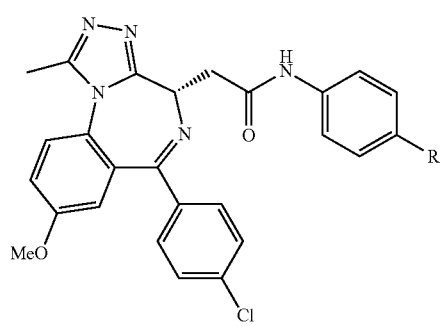
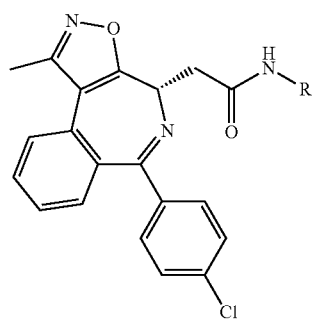
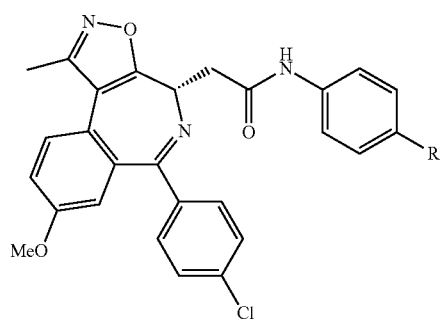
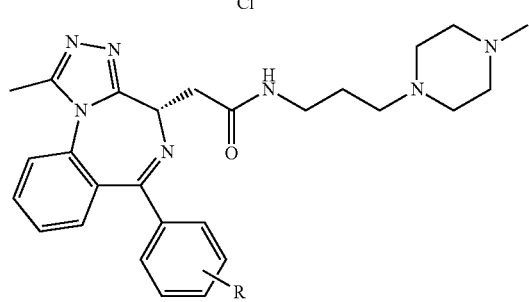
90
-continued
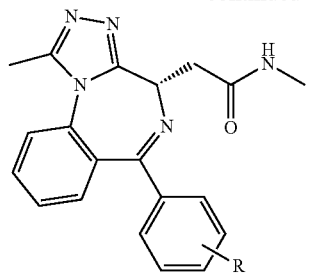
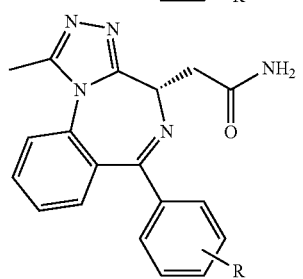
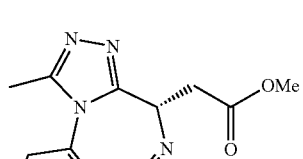
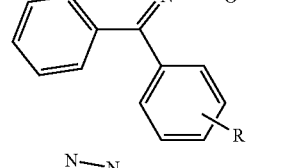
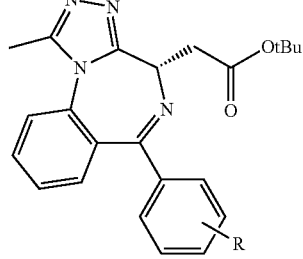
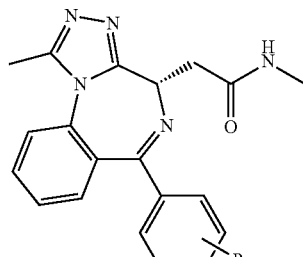
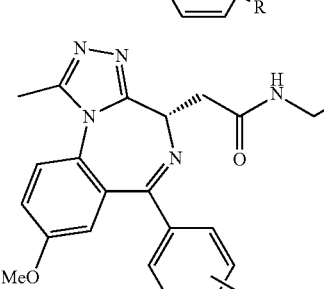

91
-continued
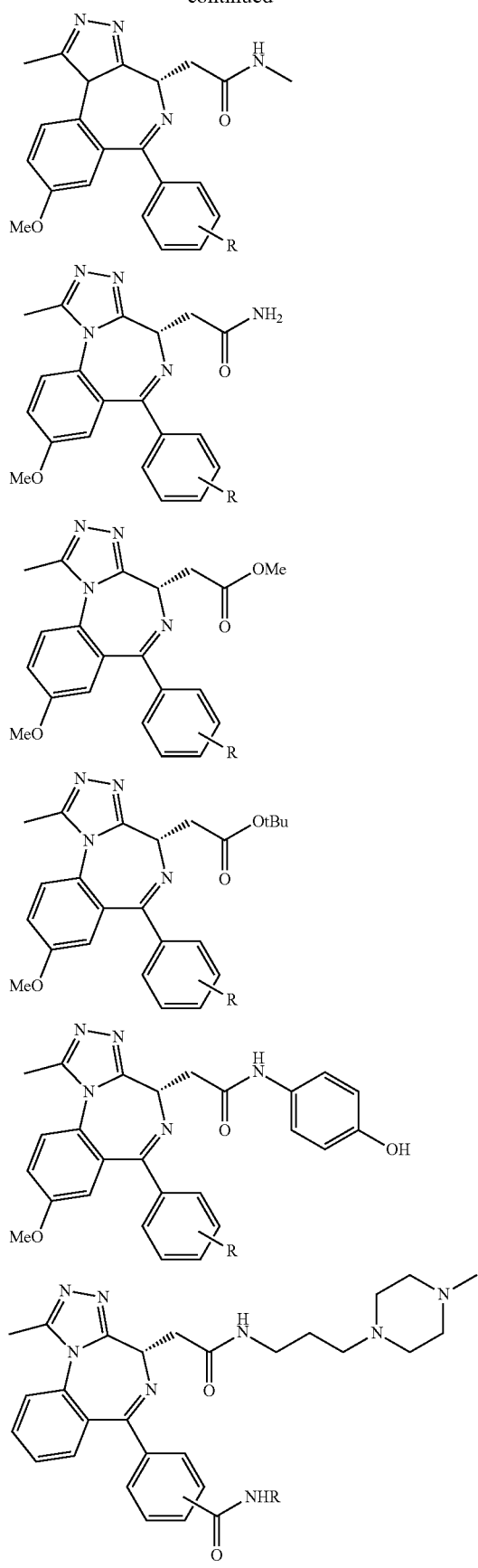
92
-continued
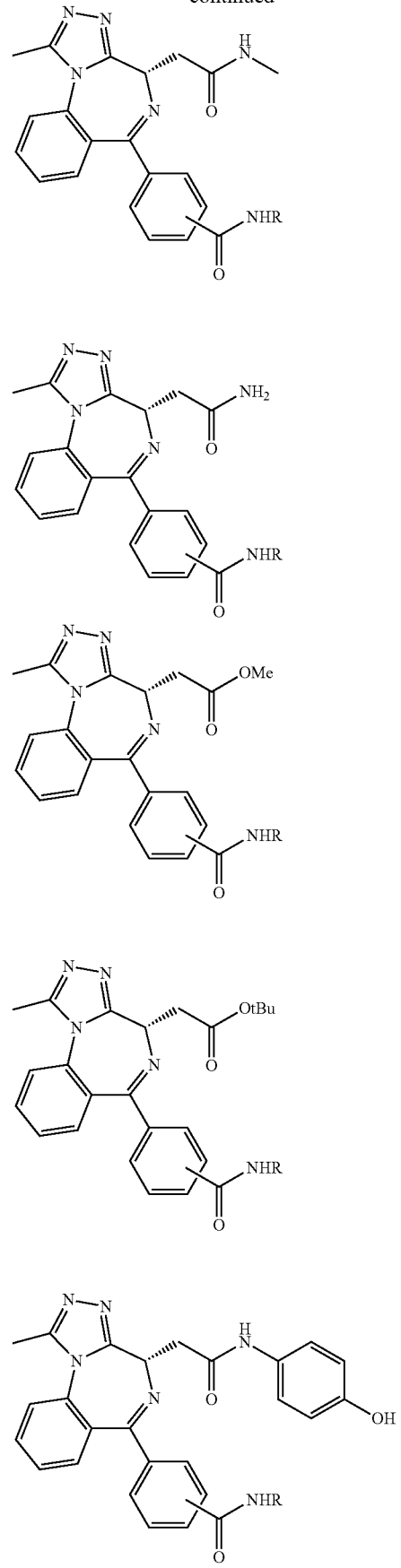

93
-continued
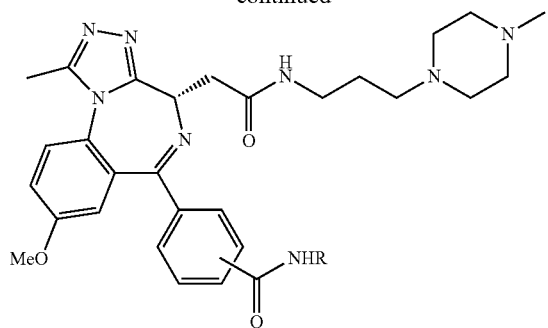
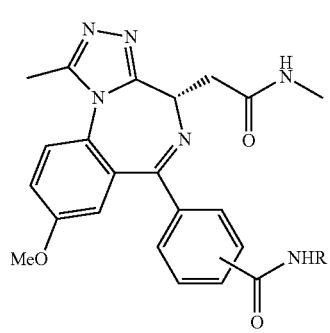
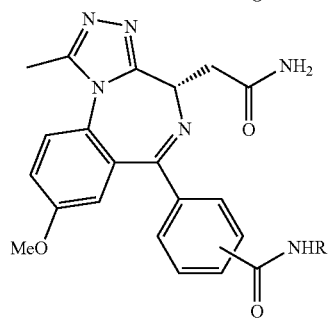
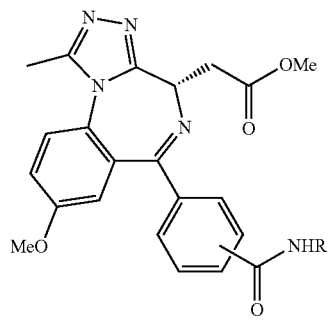
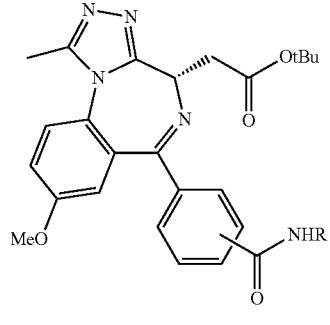
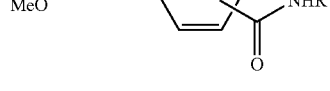
94
-continued
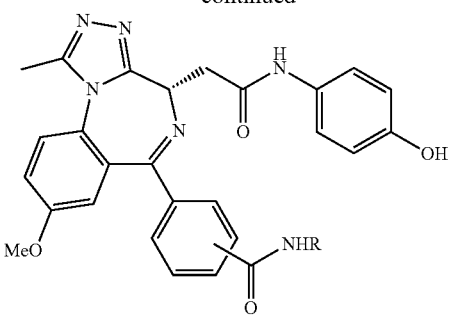
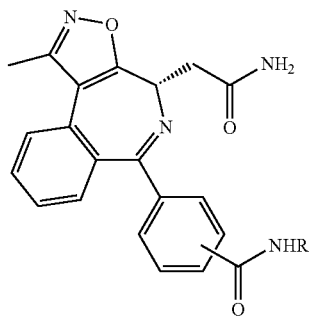
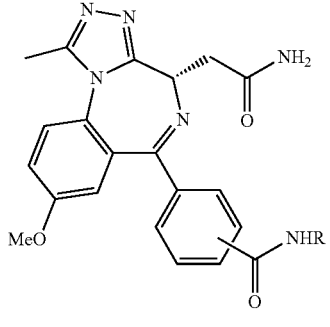
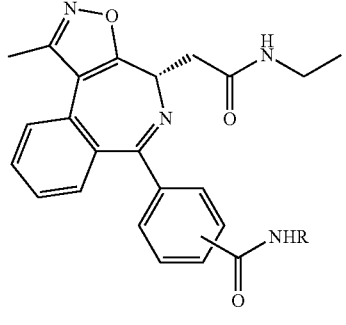
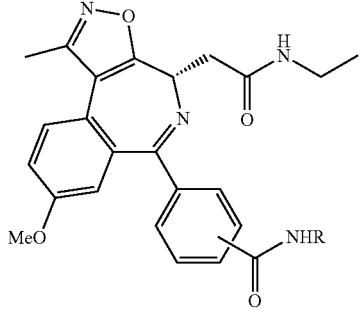
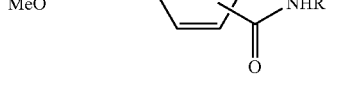

95
-continued
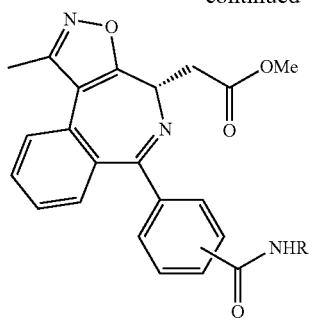
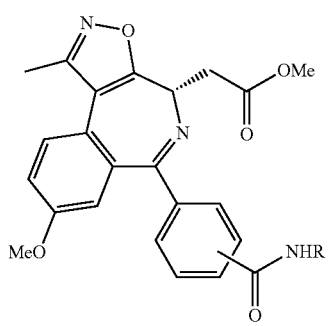
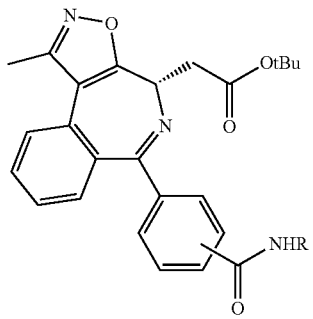
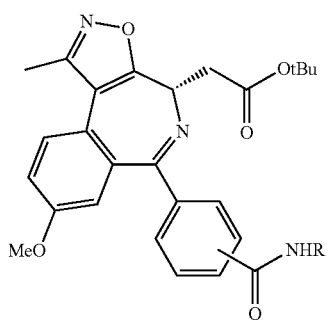
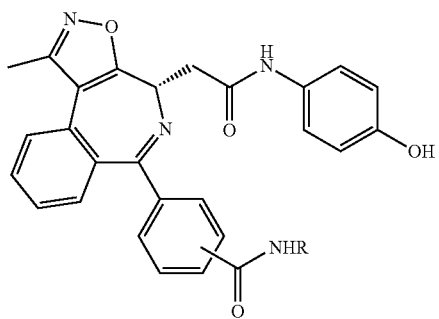
96
-continued
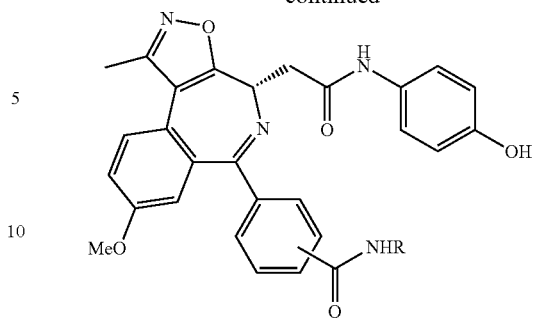
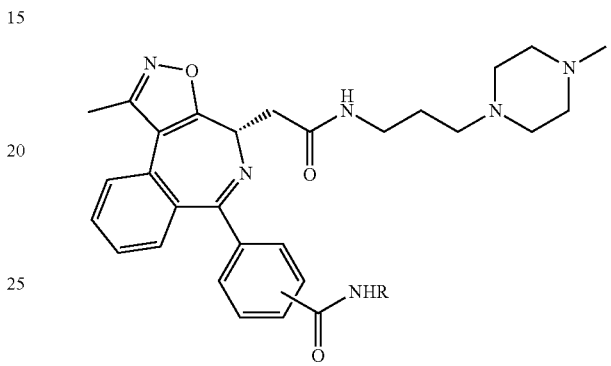
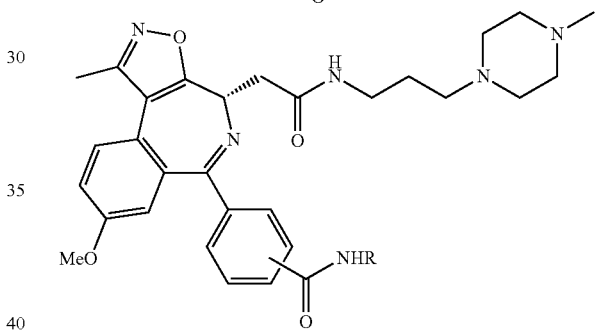
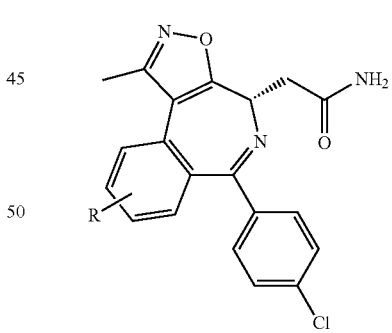
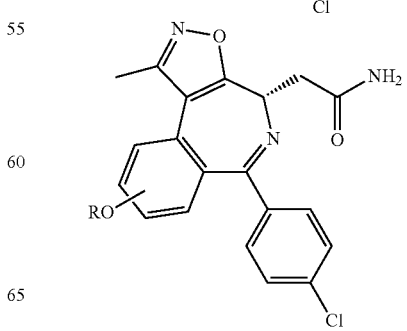

97
-continued
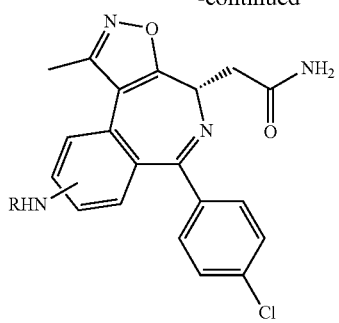
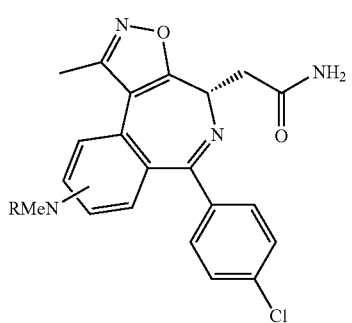
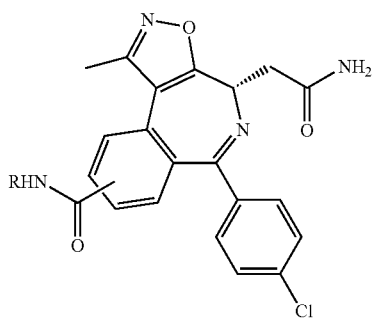
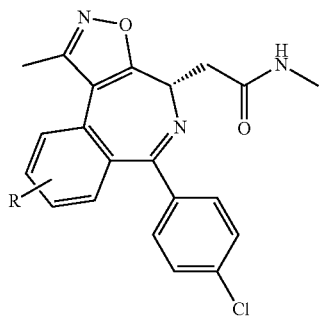
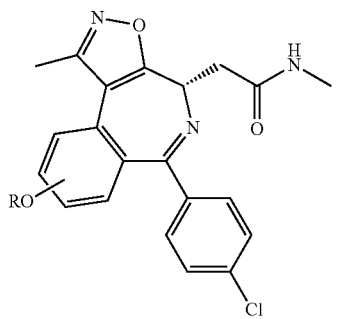
98
-continued
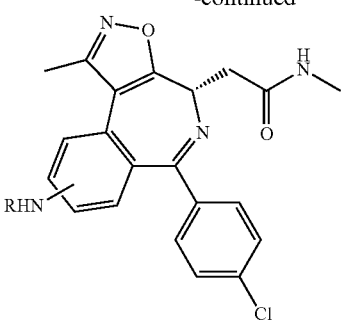
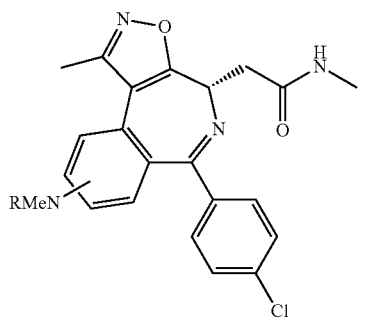
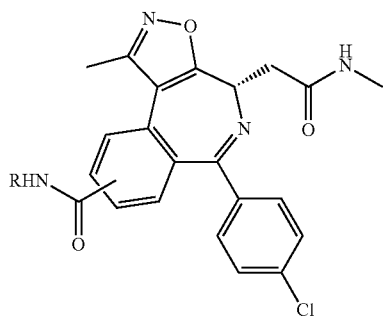
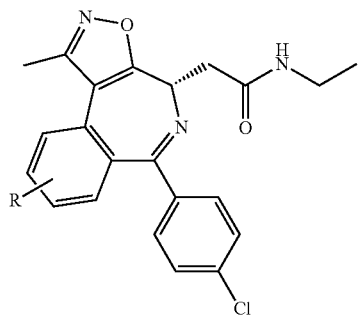
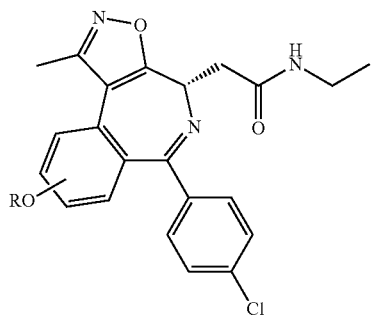

| 99 | 100 |
|---|---|
| -continued | -continued |
| 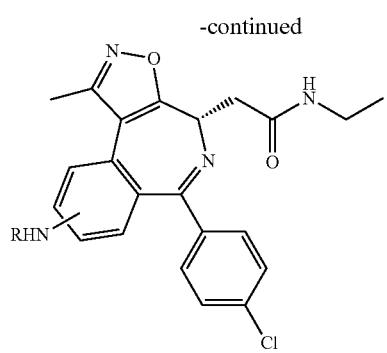 | 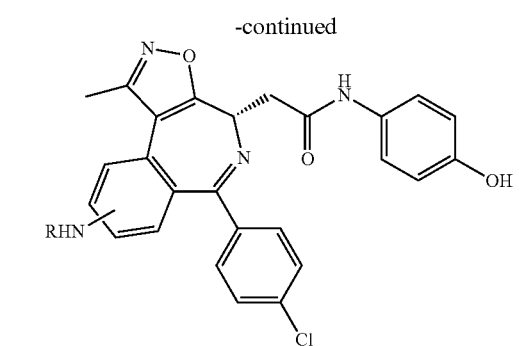 |
| 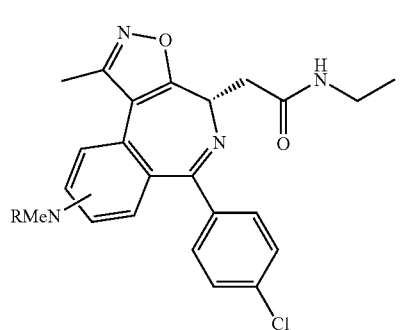 | 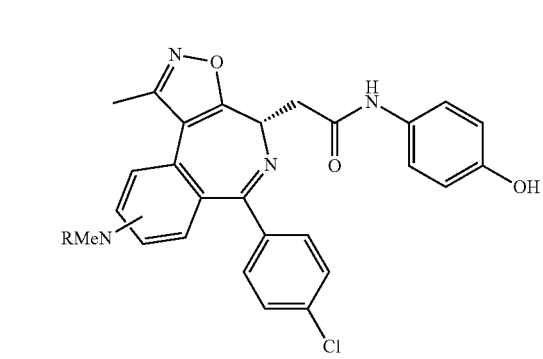 |
| 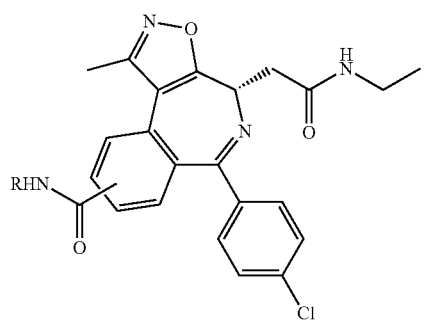 | 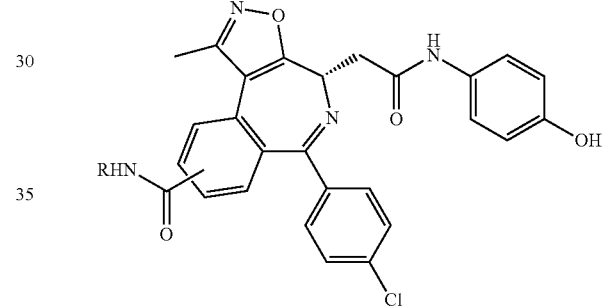 |
| 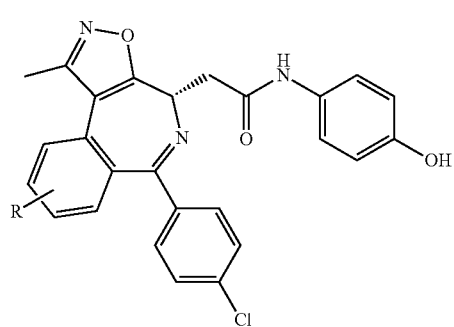 | 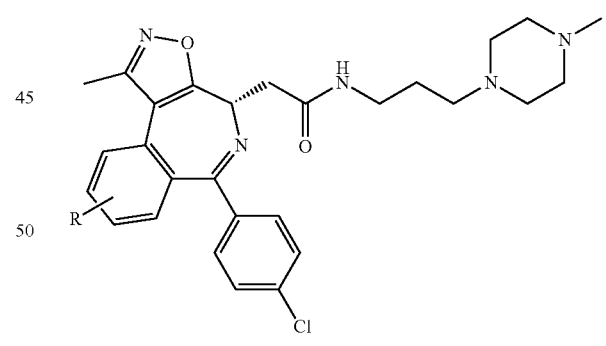 |
| 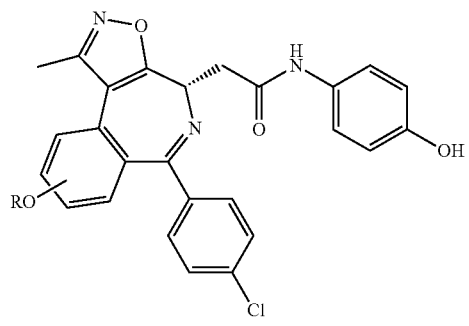 | 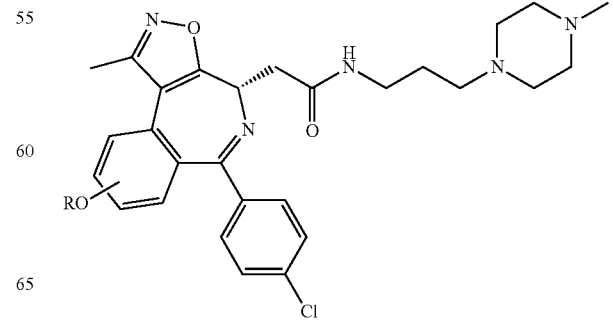 |

101
-continued
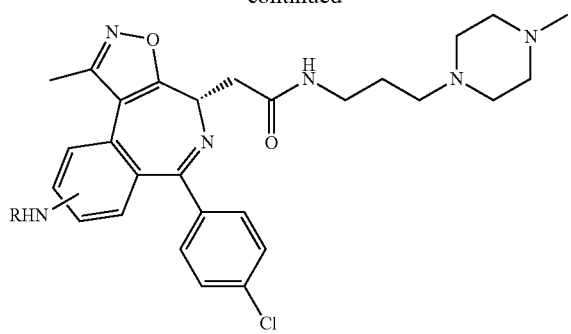
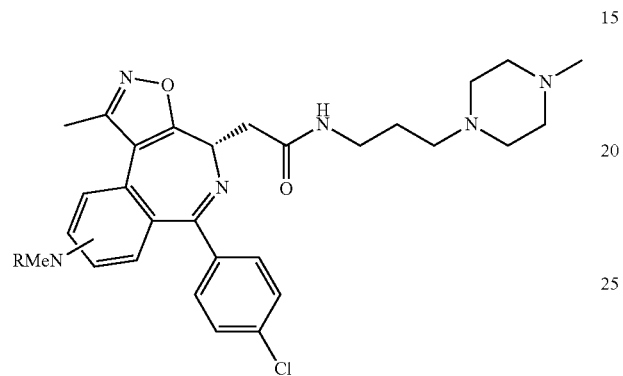
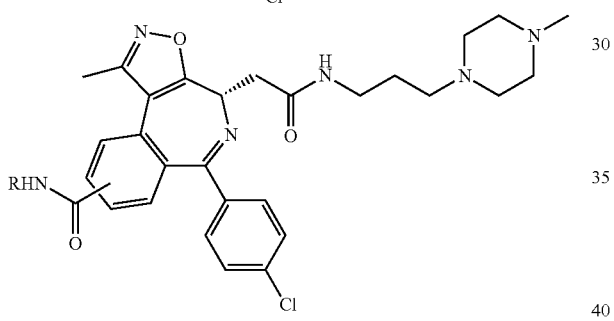
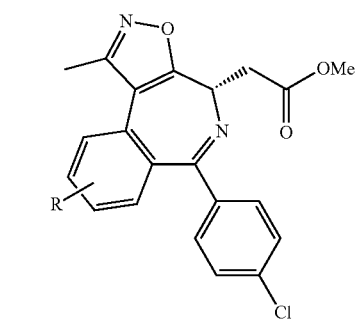
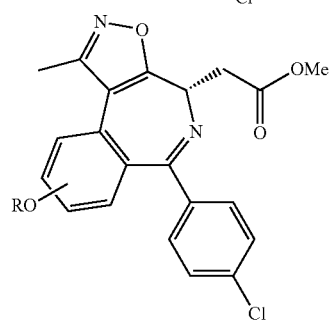
102
-continued
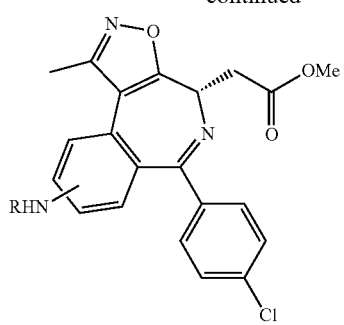
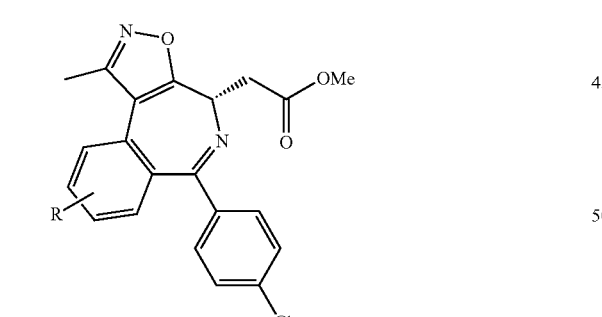
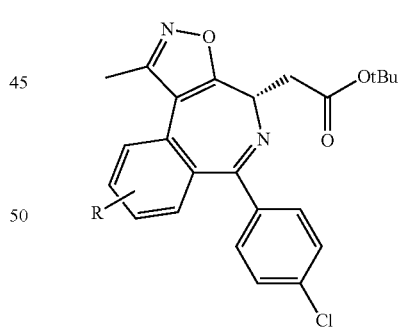
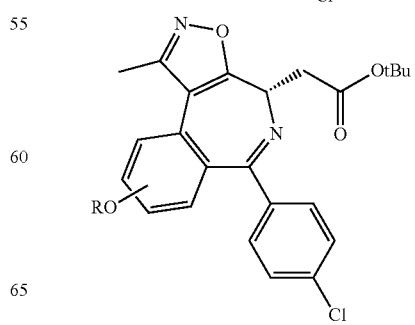

103
-continued
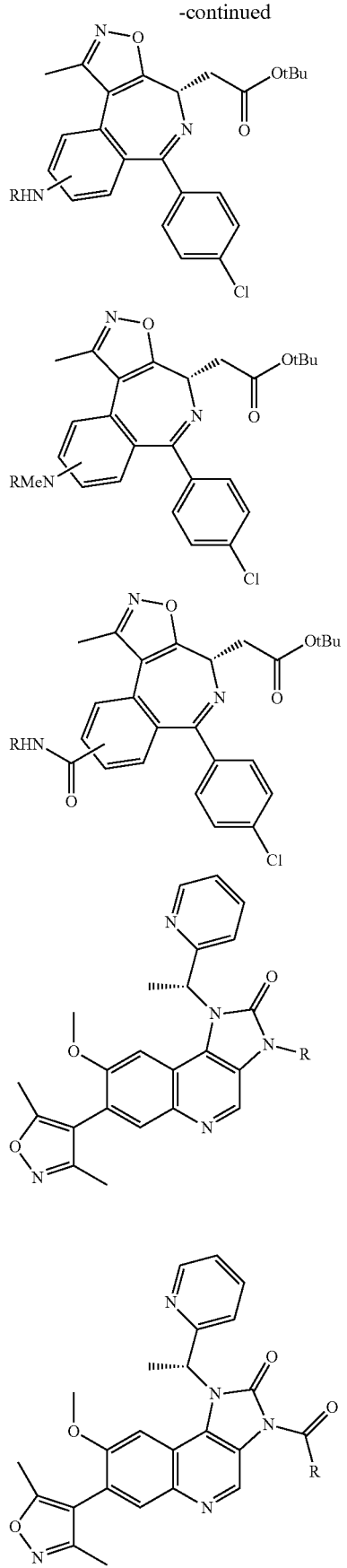
104
-continued
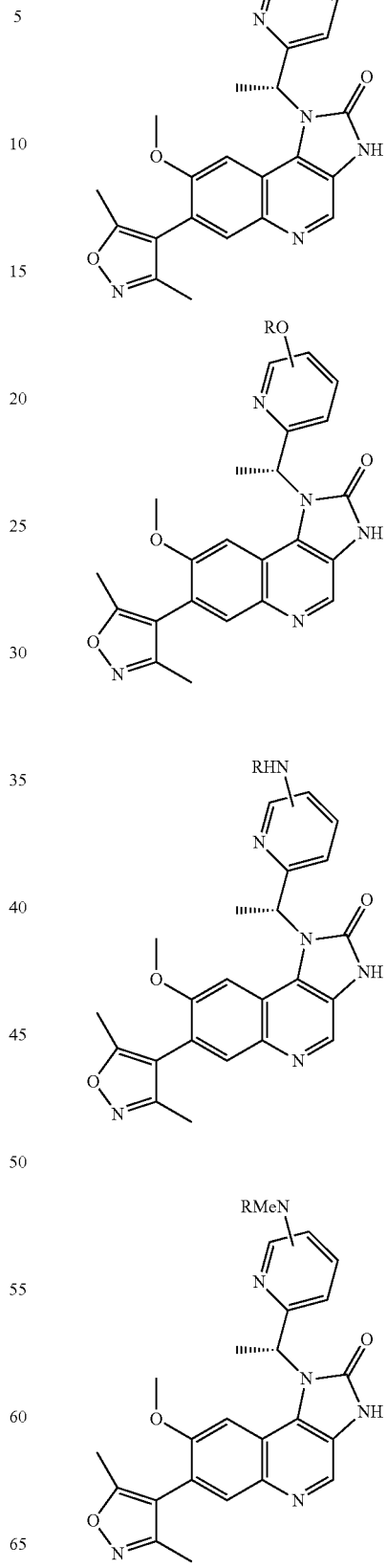

-continued

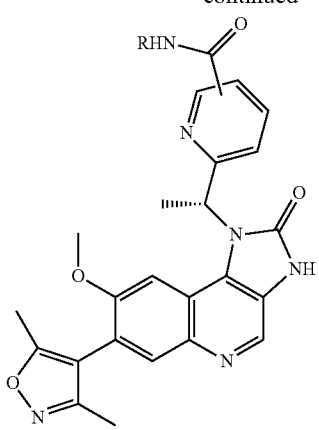

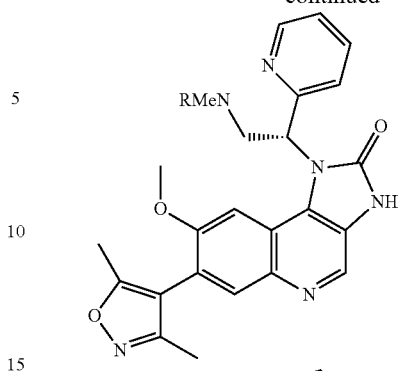

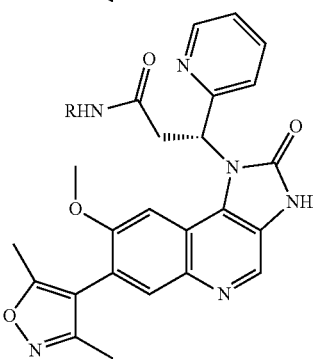

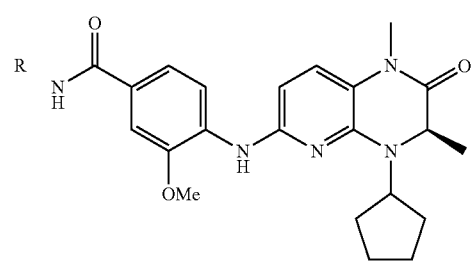

In certain embodiments, the TLs or targets are chosen based on existence (known target protein binding moieties) and ability to develop potent and selective ligands with functional positions that can accommodate a Linker. Some embodiments relate to targets with less selectivity, which may benefit from degradation coupled with proteomics as a measure of compound selectivity or target ID. Such cases include, but are not limited to a) targets that have multiple functionalities that are unable to be targeted by inhibition; b) targets that are resistant to inhibitors without altering their binding; c) targets that have ligands that do not alter the function of the target; and d) targets that would benefit from irreversible inhibition but lack reactive residues that can be targeted with covalent ligands.

In certain embodiments, the present application relates to small molecule inducers of protein degradation, which have numerous advantages over inhibitors of protein function and can a) overcome resistance in certain cases; b) prolong the kinetics of drug effect by destroying the protein requiring resynthesis even after the small molecule has been metabolized; c) target all functions of a protein at once rather than a specific catalytic activity or binding event; d) expand the number of drug targets by including all proteins that a ligand can be developed for, rather than proteins whose activity can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Certain embodiments relate to the loss of 50-100% of the target protein. Other embodiments relate to the loss of 75-95% of the targeted protein.

Some embodiments of present application relate to the bifunctional compounds having the following structures, their synthesis and methods of use:

dBET1

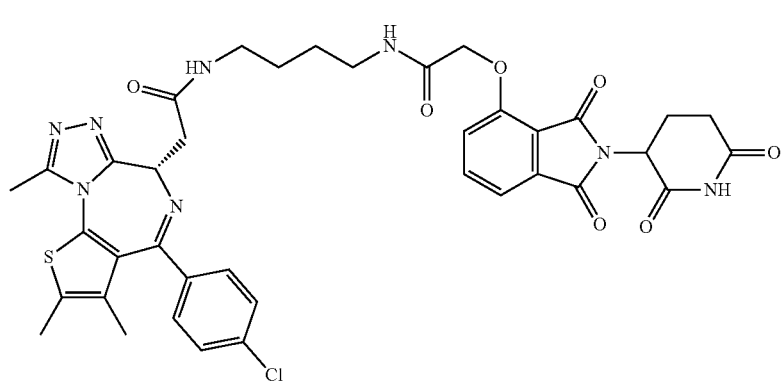

dBET4

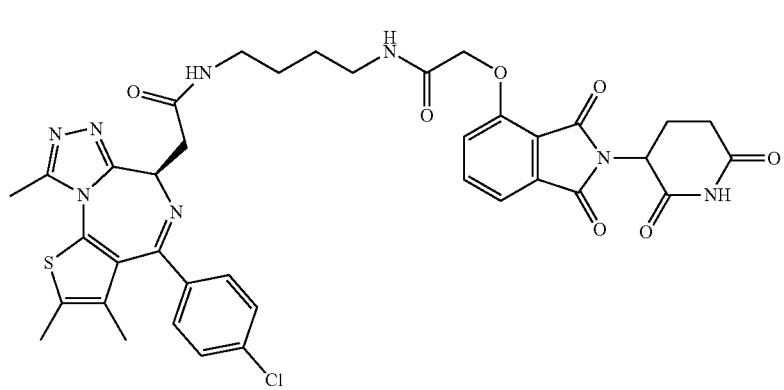

dBET3

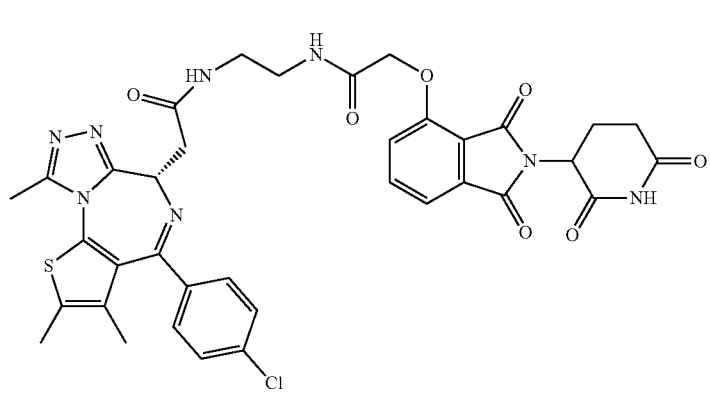

dBET5

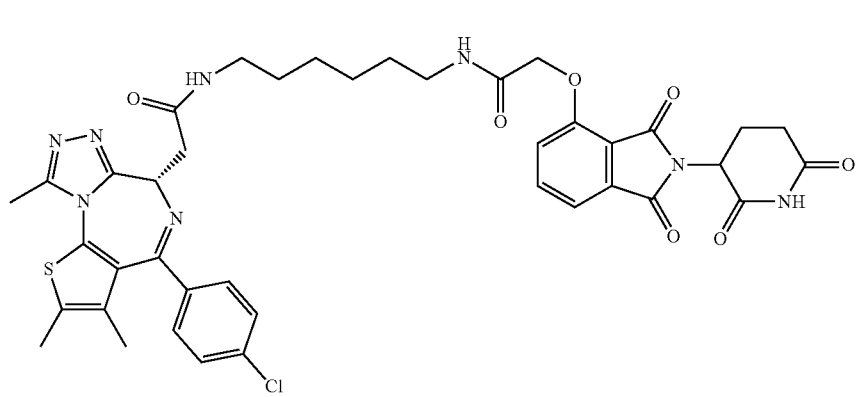

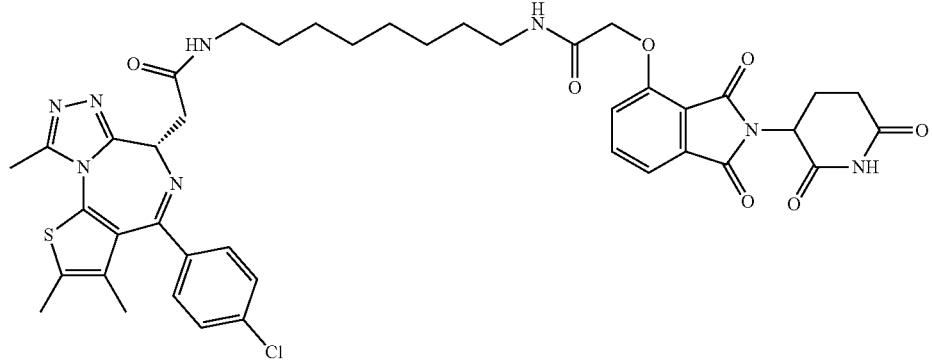
dBET6
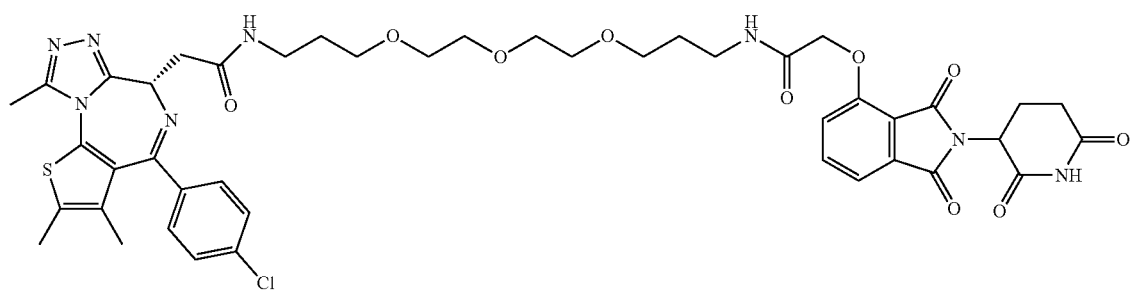
dBET9
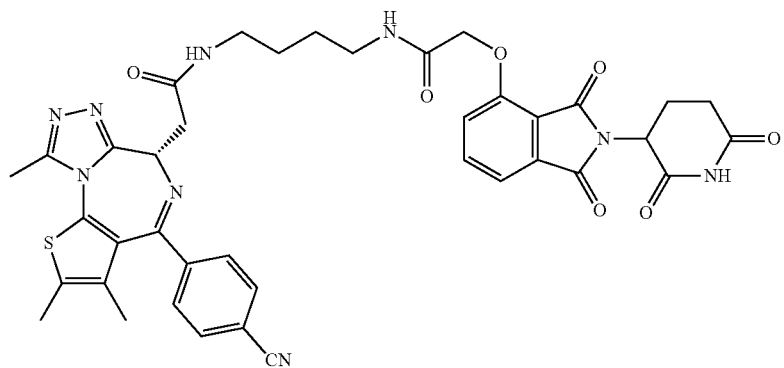
dBET17
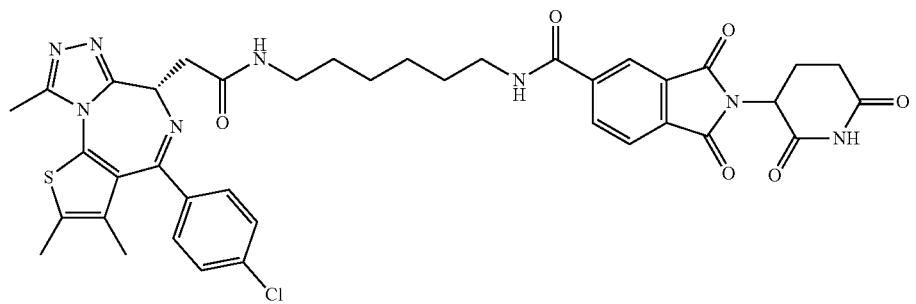
dBET15

111 112
-continued
dBET2
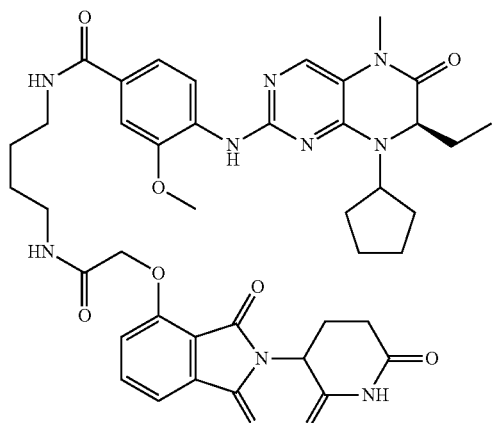
dBET7
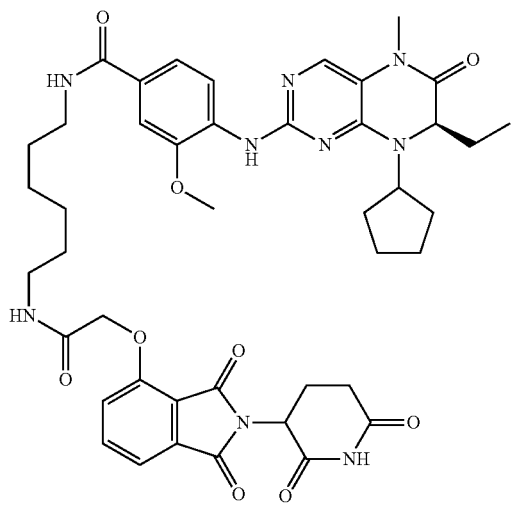
dBET8
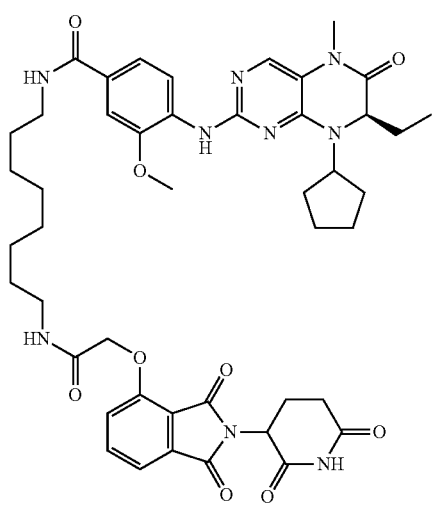
dBET10
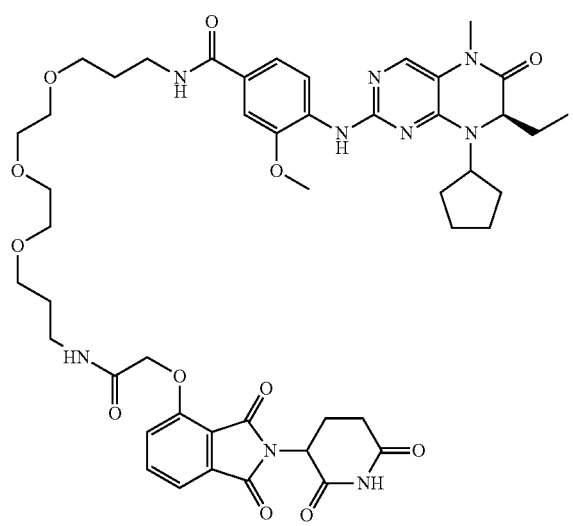
dBET16
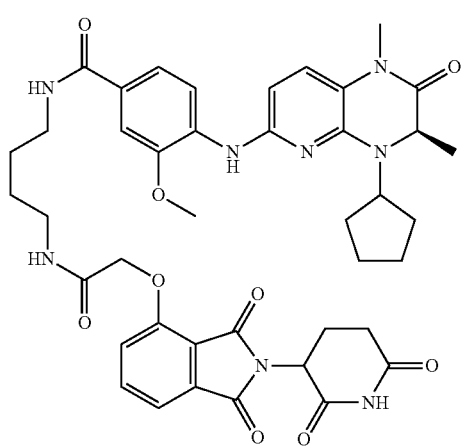

-continued
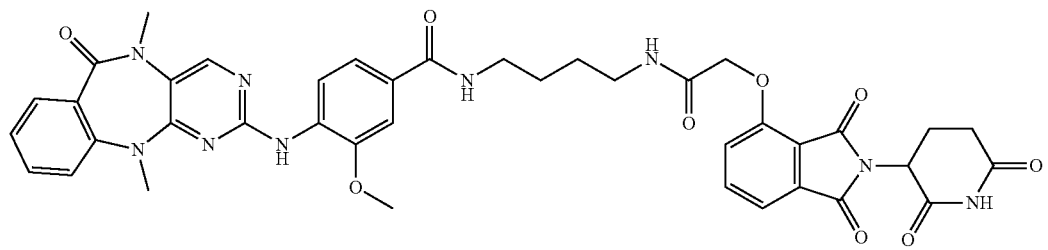
dBET11
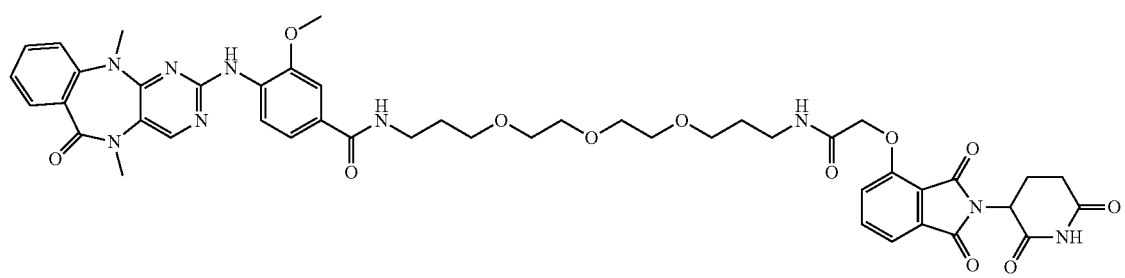
dBET12
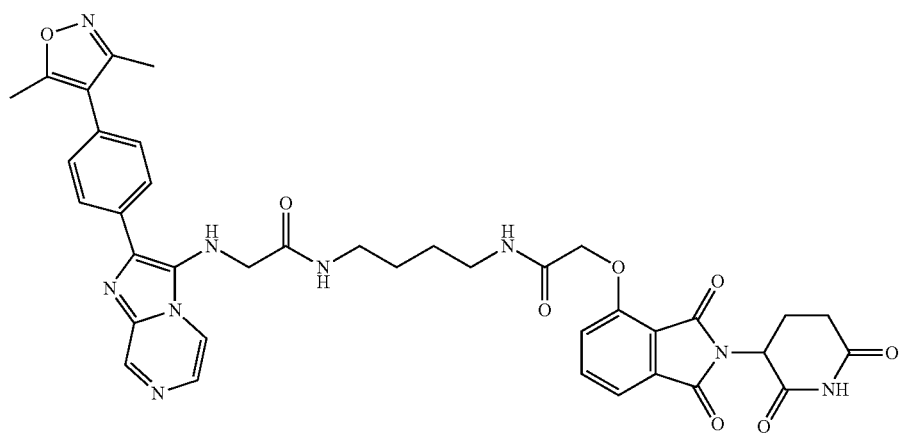
dBET13
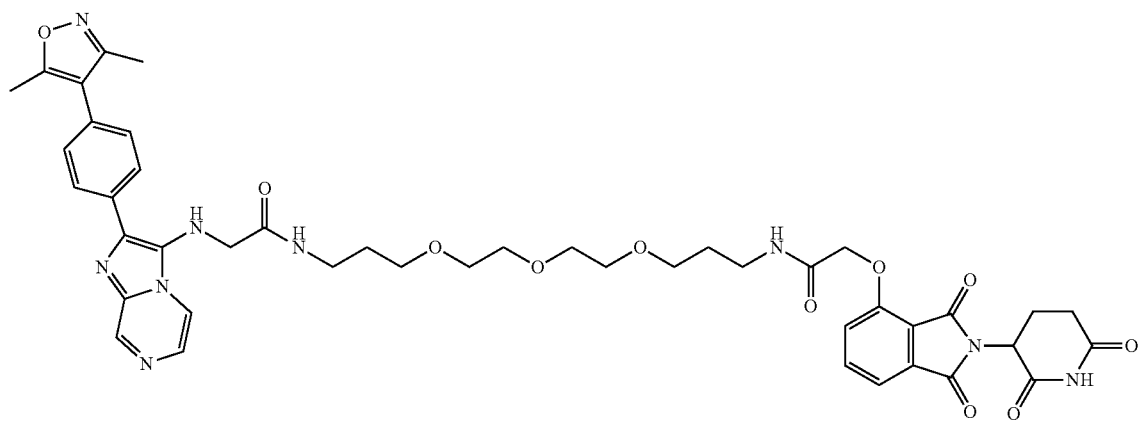
dBET14

-continued
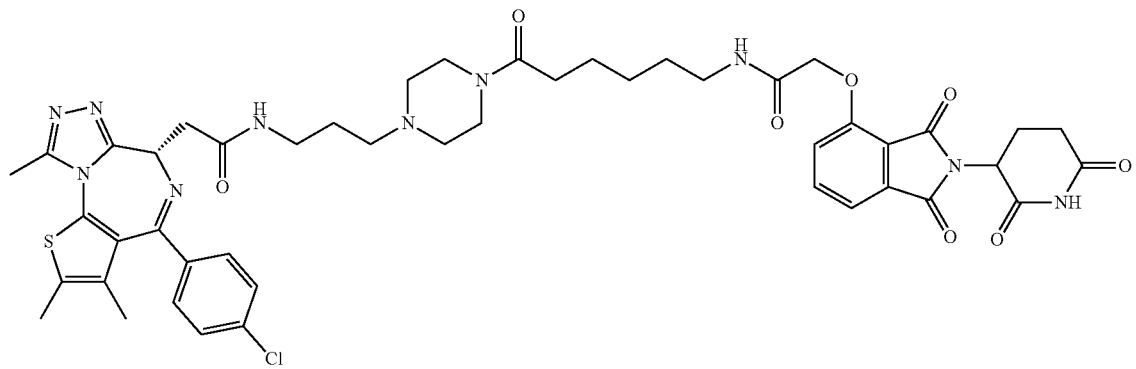
dBET18
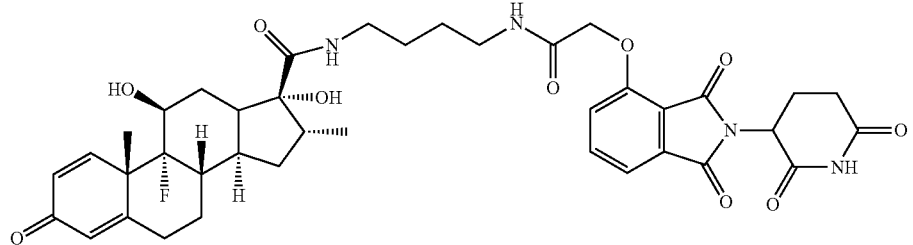
dGR1
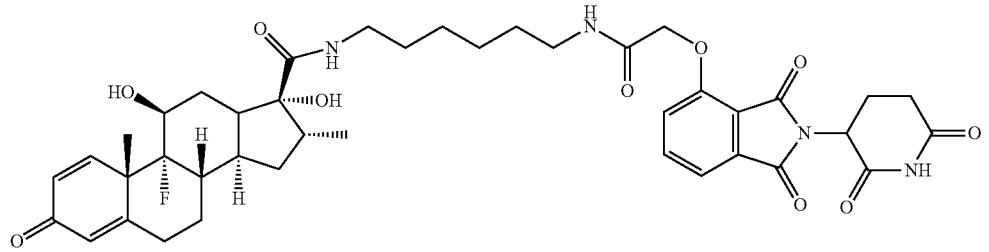
dGR2
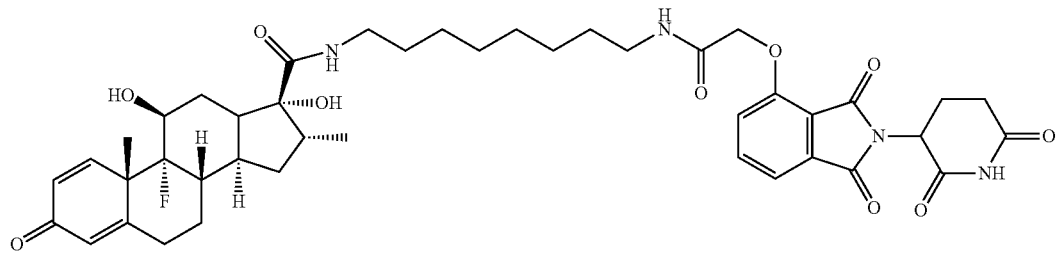
dGR3
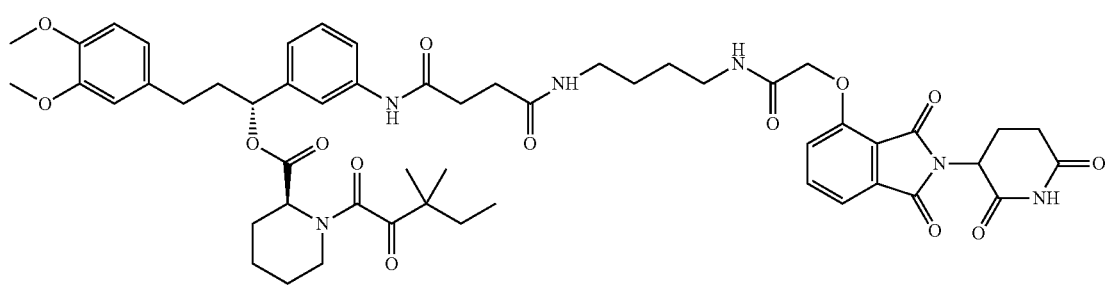
dFKBP-1 dFKBP-2
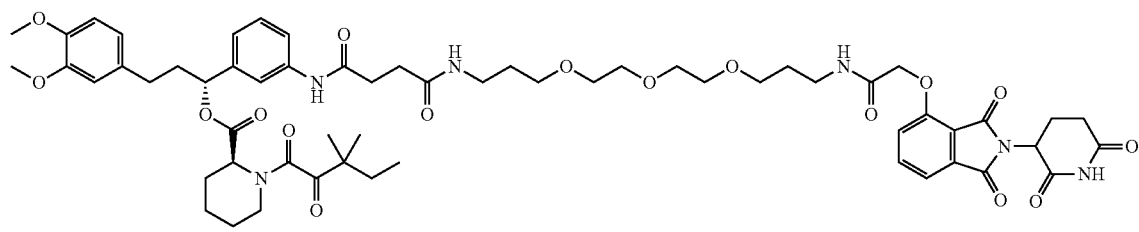
dFKBP-3
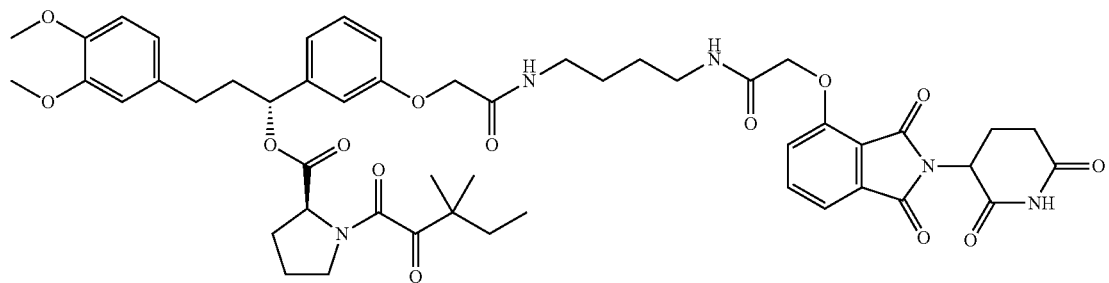
dFKBP-4
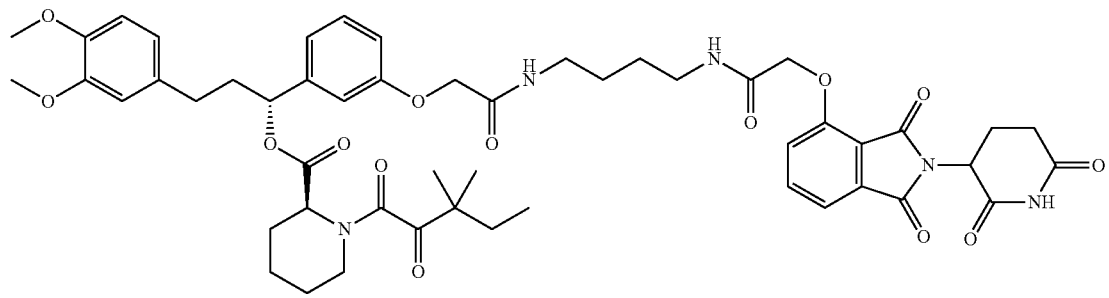
dFKBP-5
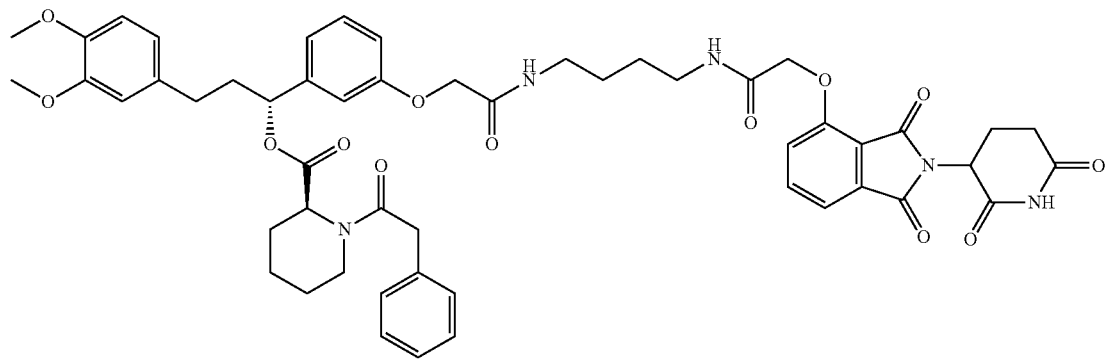

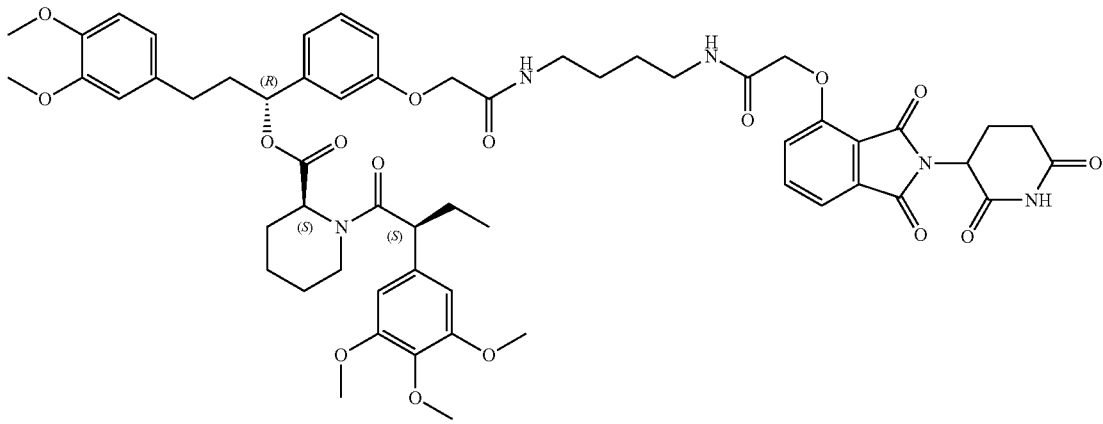

dFKBP-6

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the application are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The application additionally encompasses the compounds as individual isomers substantially free of other isomers and alternatively, as mixtures of various isomers, e.g., racemic mixtures of stereoisomers. In addition to the above-mentioned compounds per se, this application also encompasses pharmaceutically acceptable derivatives of these compounds and compositions comprising one or more compounds of the application and one or more pharmaceutically acceptable excipients or additives.

Compounds of the application may be prepared by crystallization of the compound under different conditions and may exist as one or a combination of polymorphs of the compound forming part of this application. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present application encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

In certain embodiments, the compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, T-cell lymphoma.

Synthesis of the Compounds of the Application

Exemplary synthetic schemes for preparing the bifunctional compounds of the present application are shown in below.

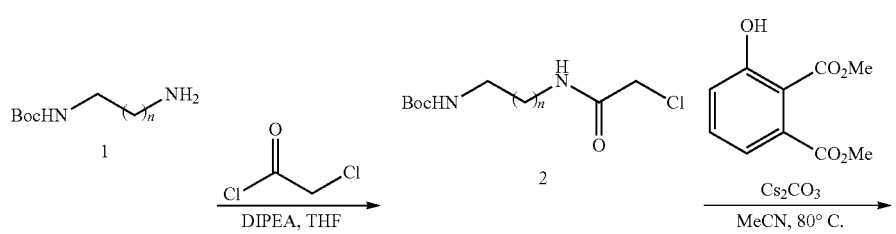

-continued

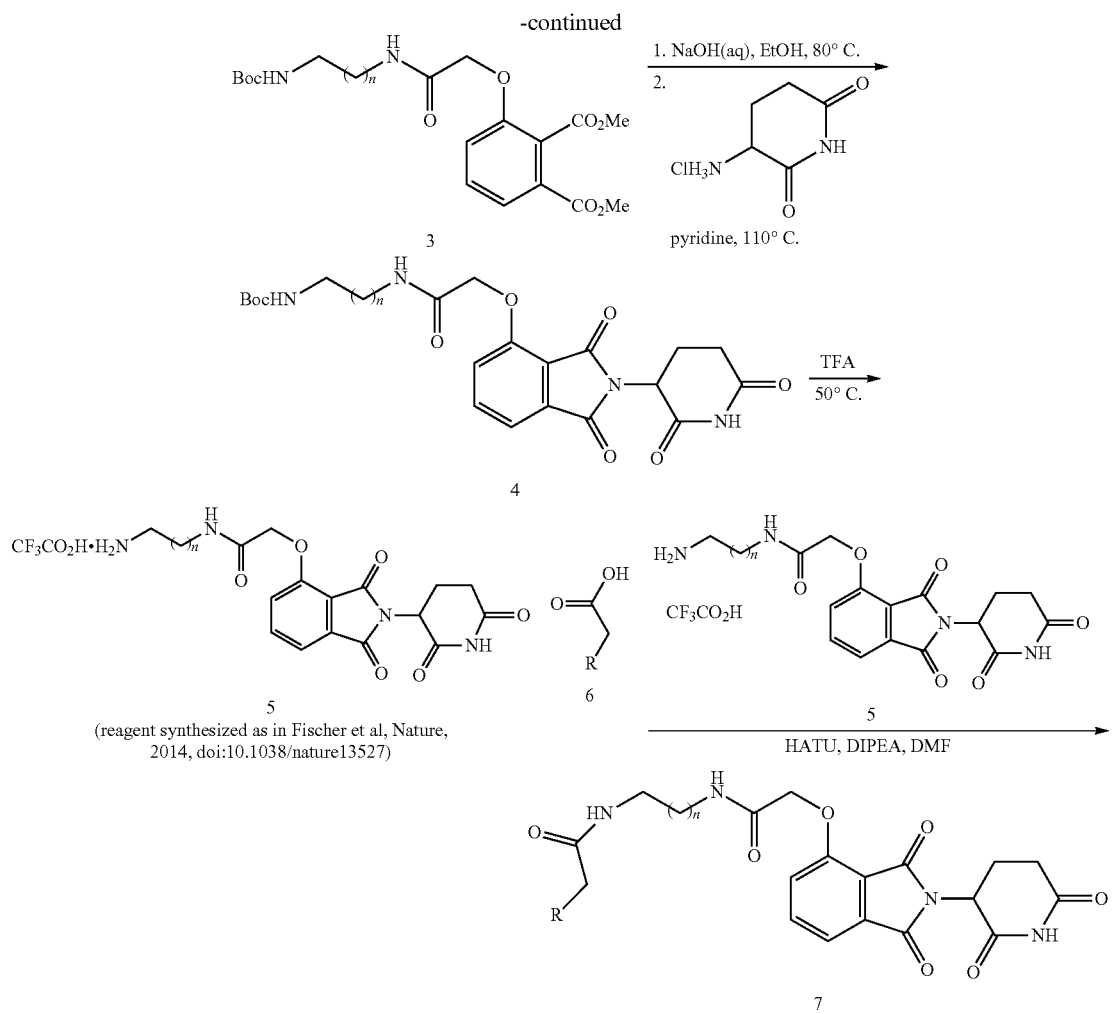

In one aspect of the application, a method for the synthesis of the core structure of Degron-Linker moiety of certain compounds is provided, the method comprising steps of:

a) reacting tert-Butyl (2-aminoethyl)carbamate or its analog (e.g., n=1-20) (1) or its analog (e.g., n=1-20) with chloroacetyl chloride under suitable conditions to generate tert-butyl (2-(2-chloroacetamido)ethyl)carbamate or its analog (e.g., n=1-20) (2);

b) reacting tert-butyl (2-(2-chloroacetamido)ethyl)carbamate or its analog (2) with dimethyl 3-hydroxyphthalate under suitable conditions to provide dimethyl 3-(2-((2-(((tert-butoxycarbonyl)amino)ethyl)amino)-2-oxoethoxy)phthalate or its analog (3);

c) reacting dimethyl 3-(2-((2-(((tert-butoxycarbonyl)amino)ethyl)amino)-2-oxoethoxy)phthalate or its analog (3) with strong base, followed by 3-aminopiperidine-2,6-dione hydrochloride to generate tert-butyl (2-(2-((2-(2,6-dioxopiperidin-3-yl)-1,3-dioxoisoindolin-4-yl)oxy)acetamido)ethyl)carbamate or its analog (4);

d) deprotecting compound (4) to provide diaminoethyl-acetyl-O-thalidomide trifluoroacetate or its analog (5).

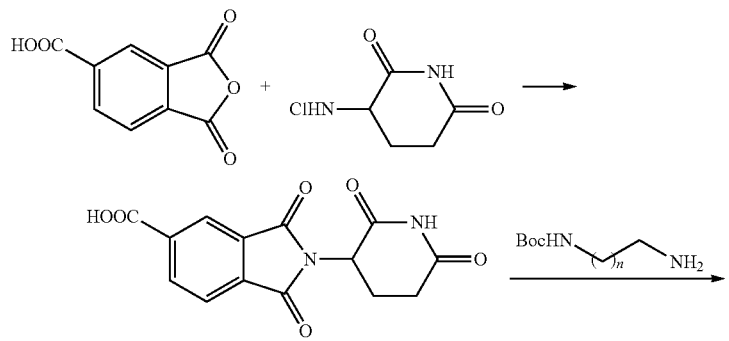

-continued

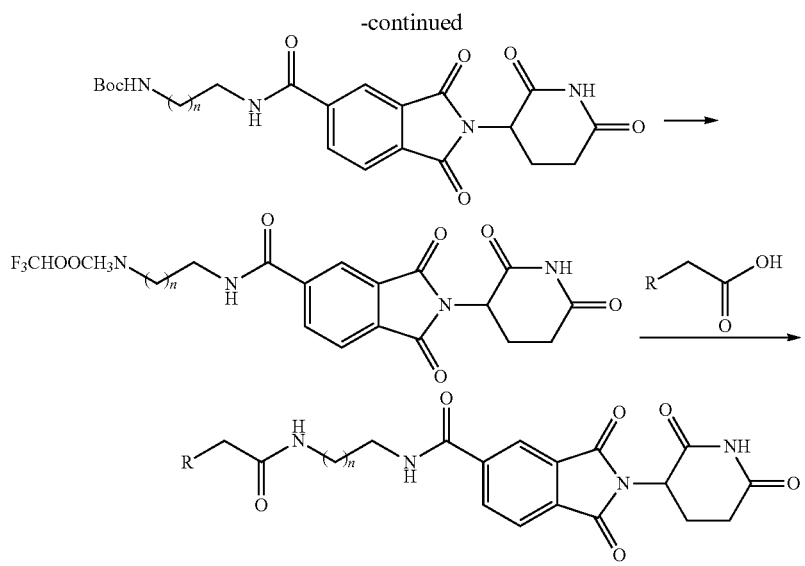

Diaminobutyl-acetyl-O-thalidomide trifluoroacetate can be prepared according to the procedure in Fischer et al. Nature, 2014, 512, 49-53.

In another aspect of the application, a method for the synthesis of the exemplary bifunctional compound is provided, the method comprising reacting a Degron-Linker moiety, for example, compound (5) with an acid derivative of a Target Ligand R—compound (6) under suitable conditions to yield a bifunctional compound (7).

Those of skill in the art will realize that based on this teaching and those known in the art, one could prepare any of the compounds of the present application.

In yet another aspect of the application, methods for producing intermediates useful for the preparation of certain compounds of the application are provided.

In some aspects of the application, the Degron-Linker intermediates can be prepared according to the following steps:

DL5:

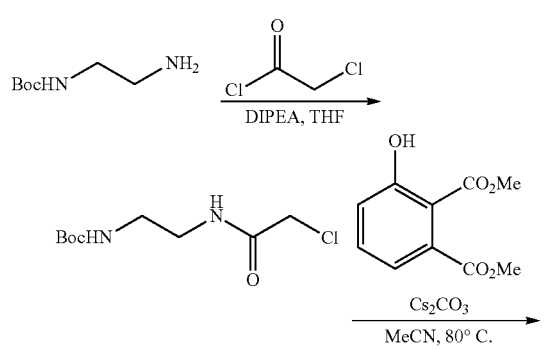

-continued

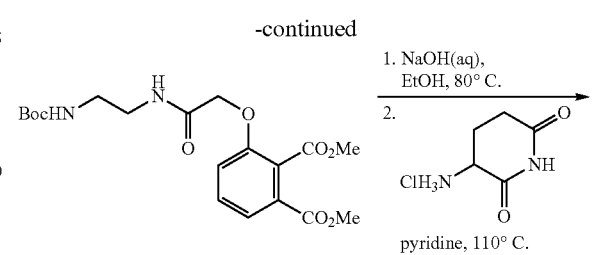

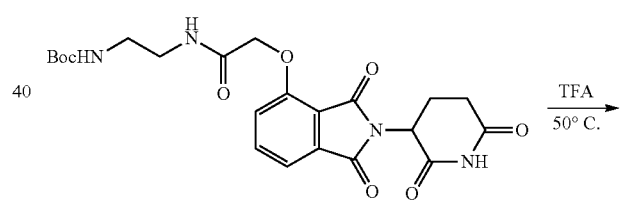

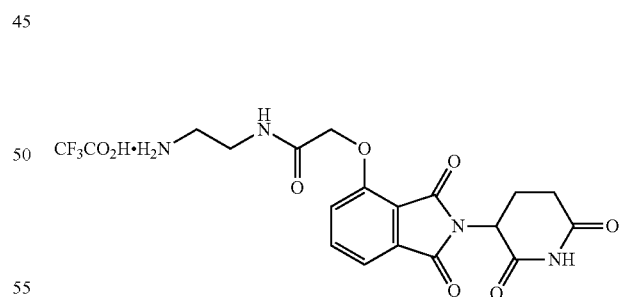

DL6:

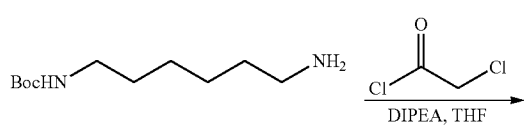

-continued
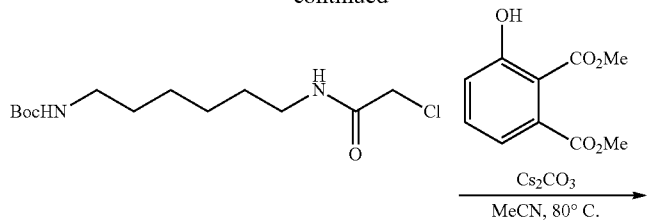
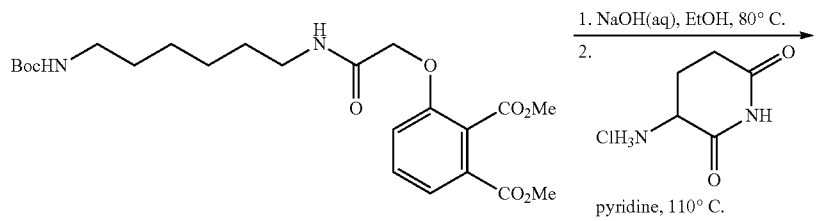
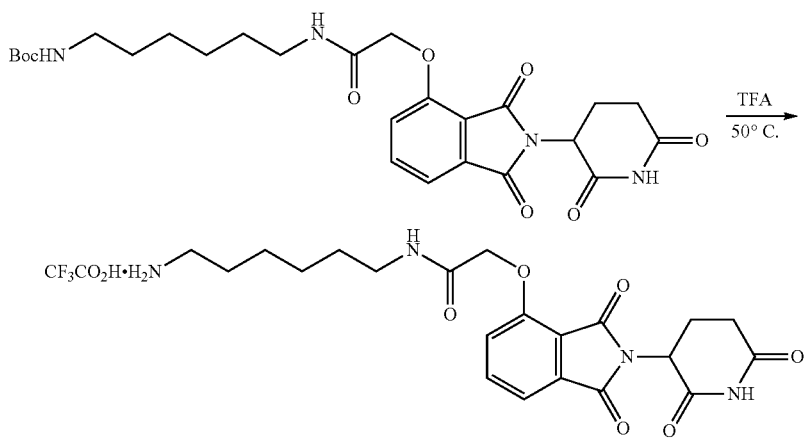
DL7:
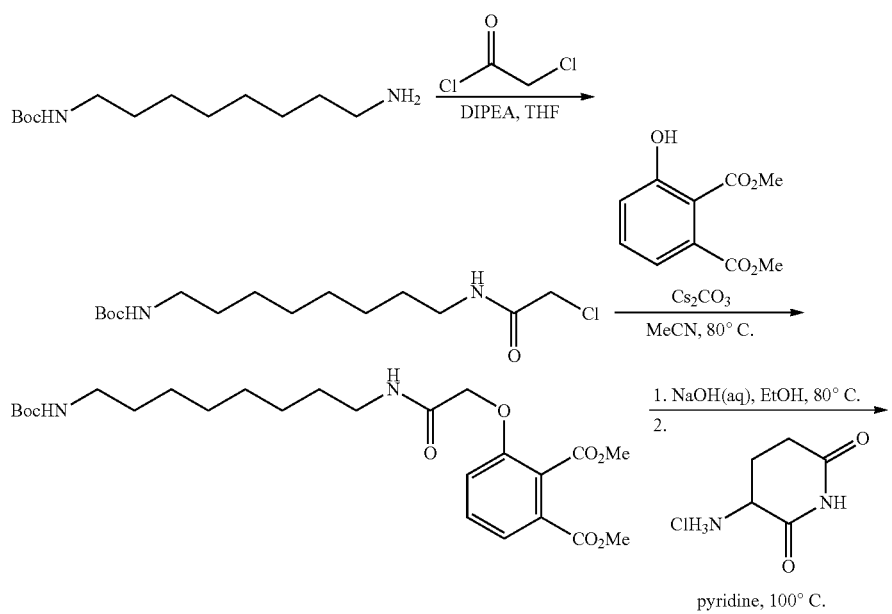

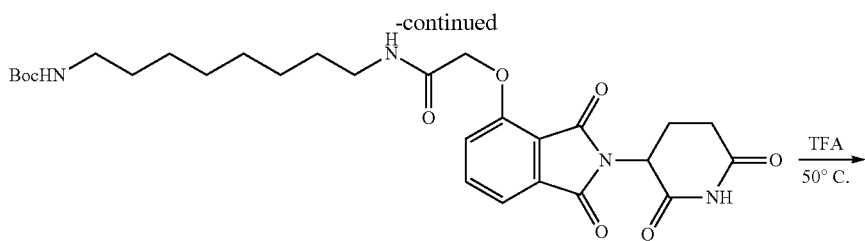
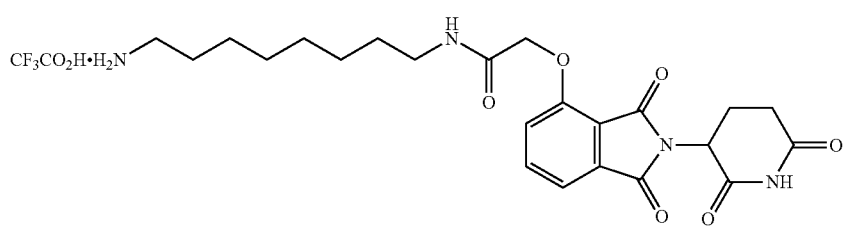
In other aspects of the application, the bifunctional compounds dBET1-dBET6 can be prepared according to the following schemes using a moiety targeting bromodomain:
dBET1:
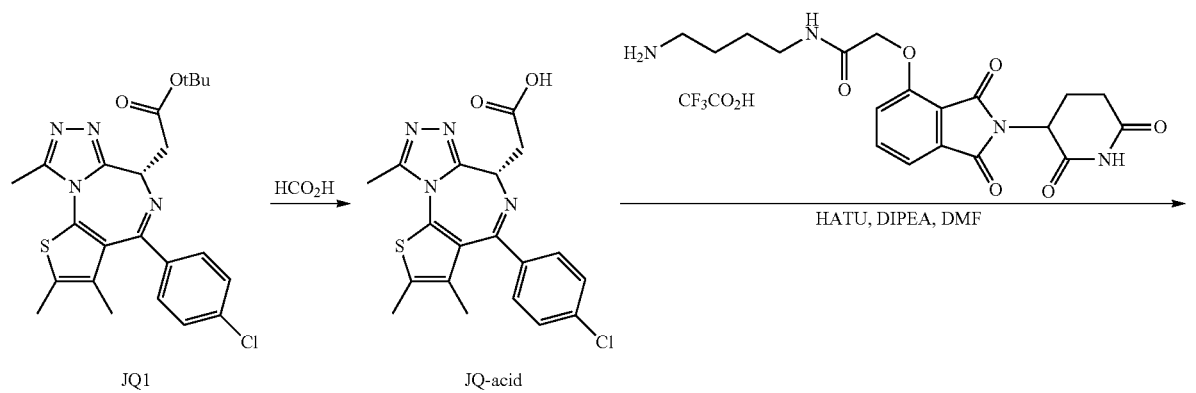
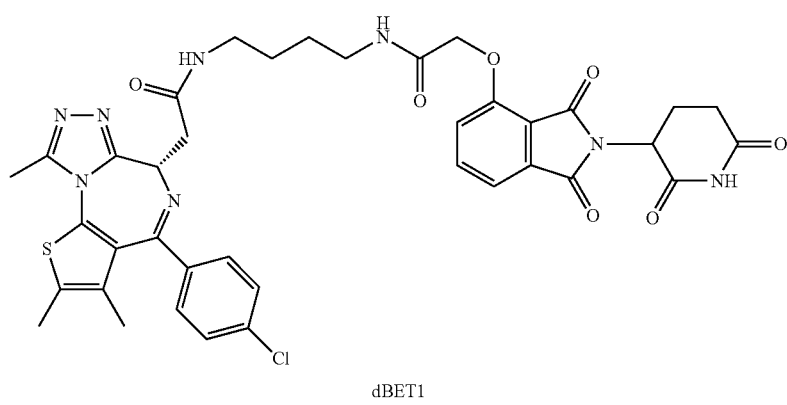

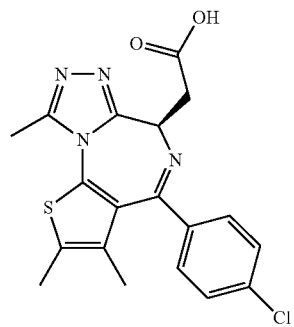
(R)-JQ-acid
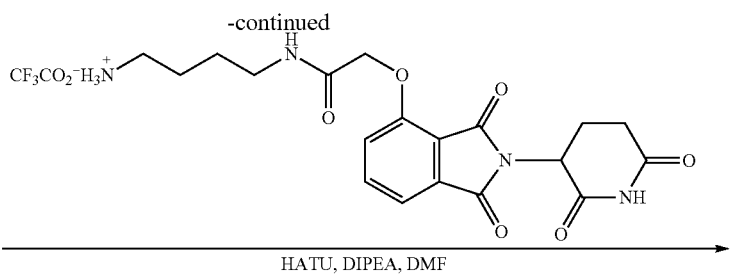
HATU, DIPEA, DMF
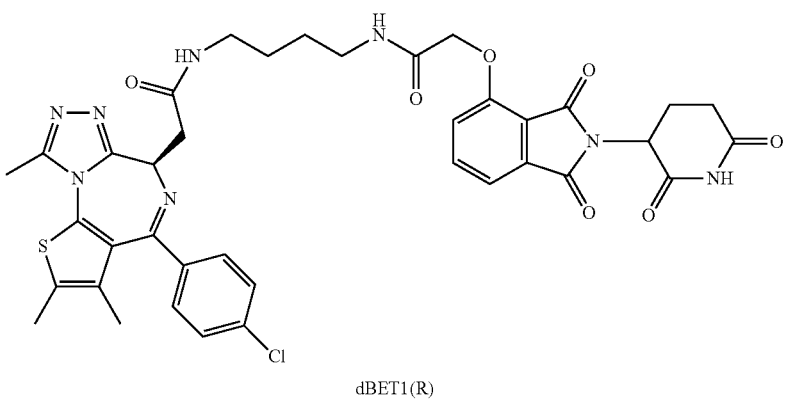
dBET1(R)
dBET2:
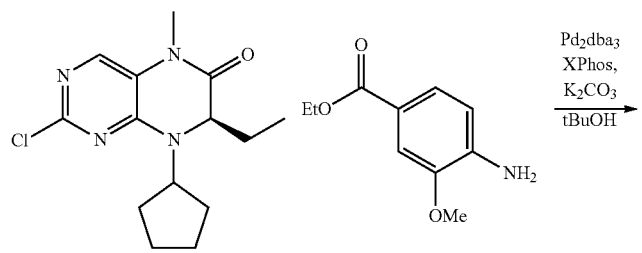
ref: ACIEE, 2011, 50, 9378
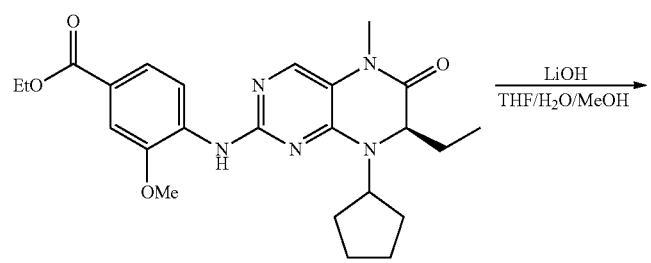
LiOH
THF/H$_2$O/MeOH

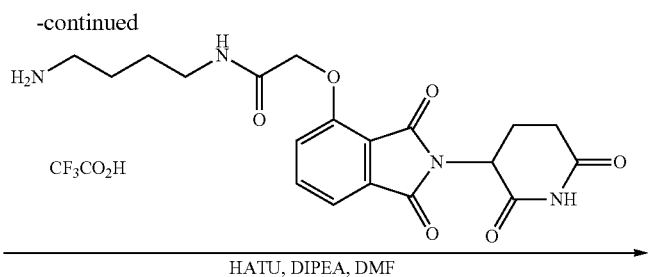
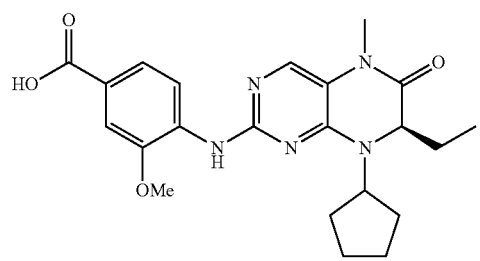 [SMILES: CC[C@@H]1C(=O)N(C)c2cnc(Nc3ccc(C(=O)O)cc3OC)nc2N1C1CCCC1]
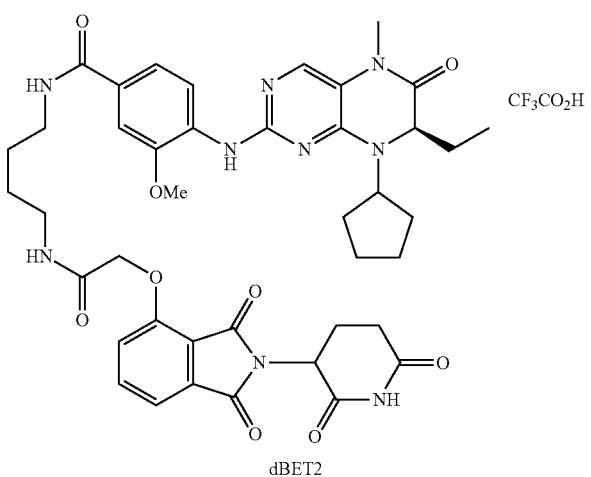
dBET2
dBET3:
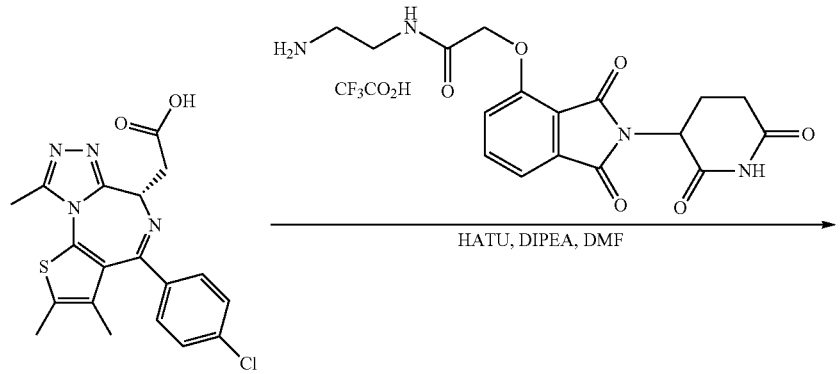
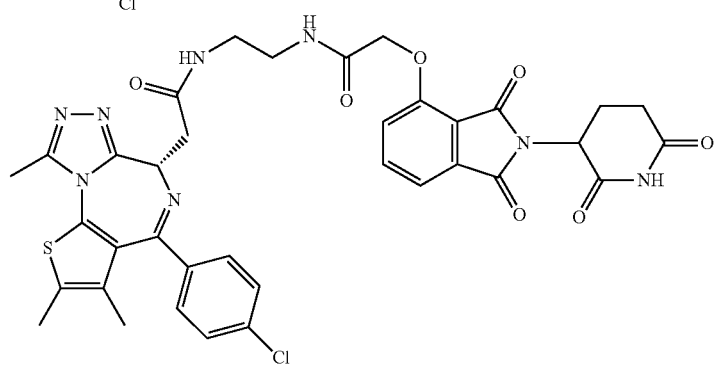
dBET3 dBET4:
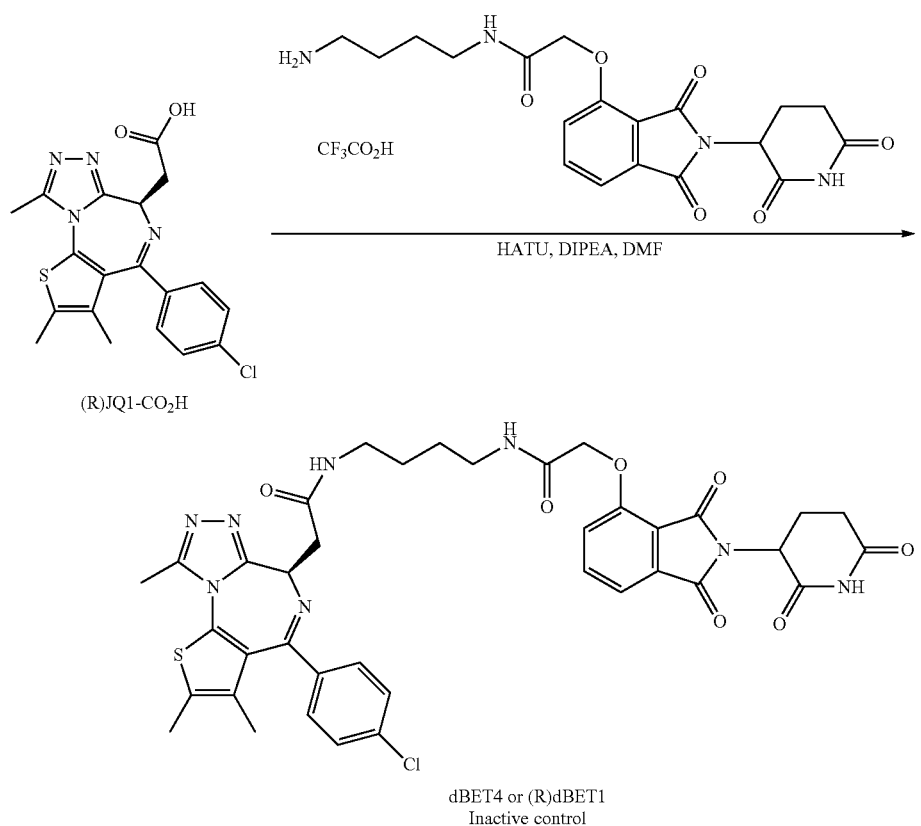
dBET5:
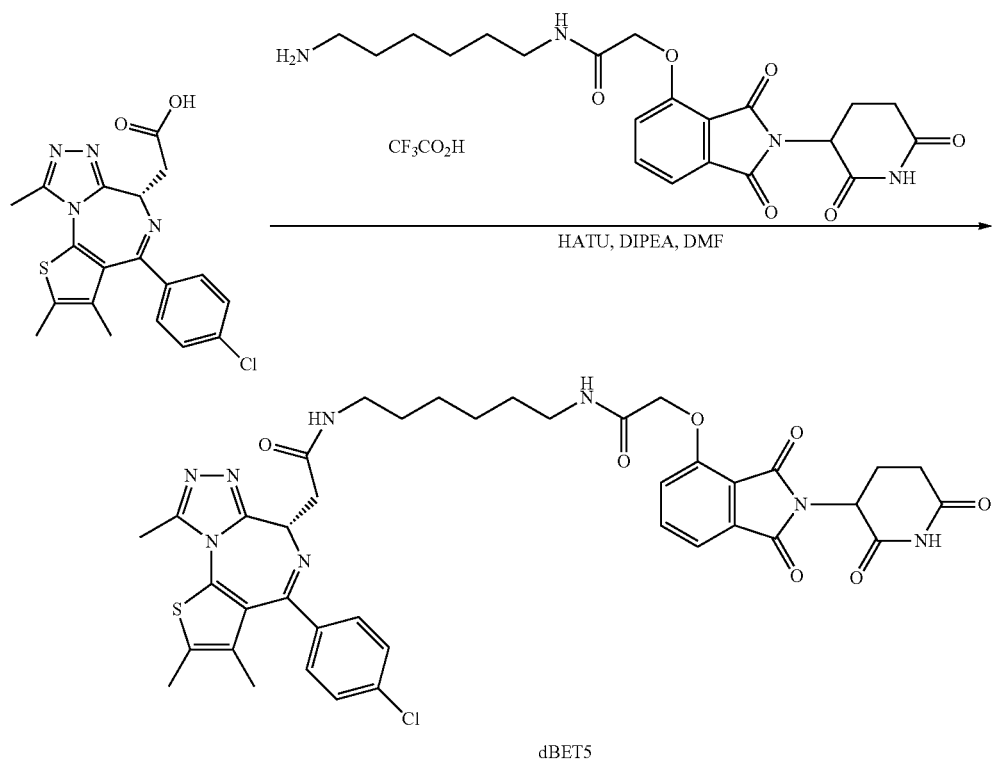

dBET6:
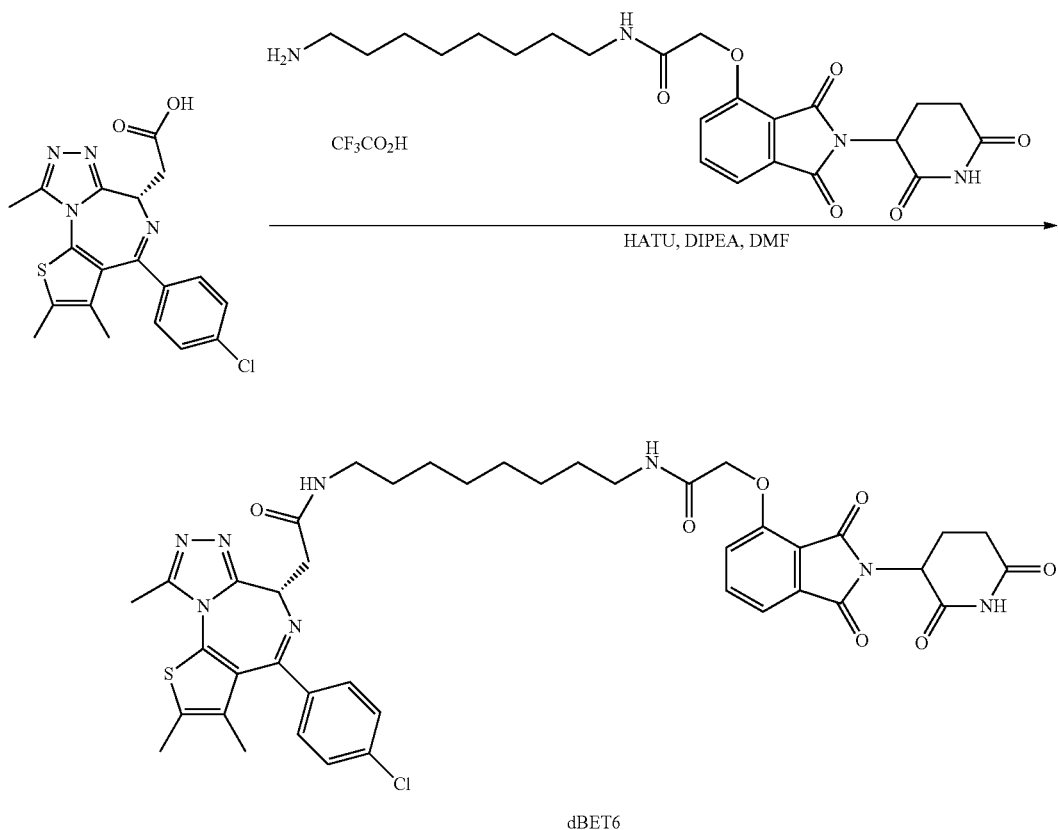
dBET6
In other aspects of the application, the bifunctional compounds dGR1 and dGR2 can be prepared according to the following schemes using TL4 target moiety (dexamethasone):
dGR1:
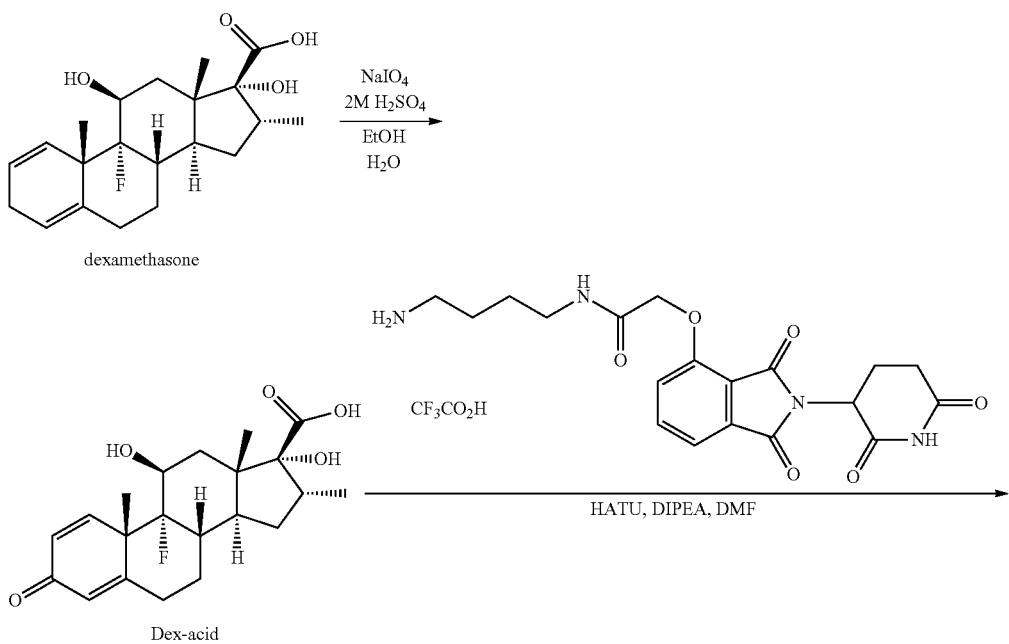

-continued
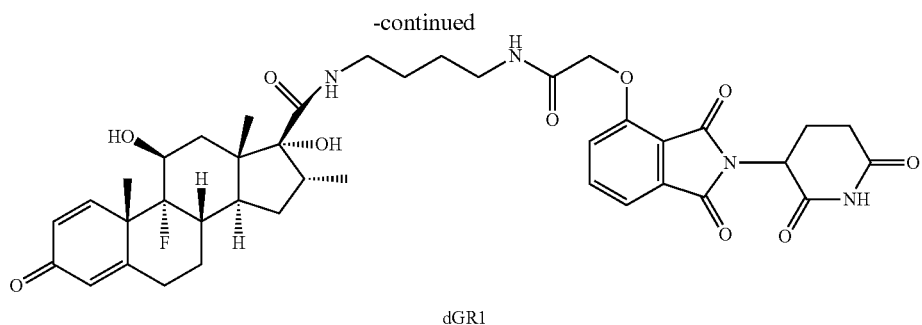
dGR1
dGR2:
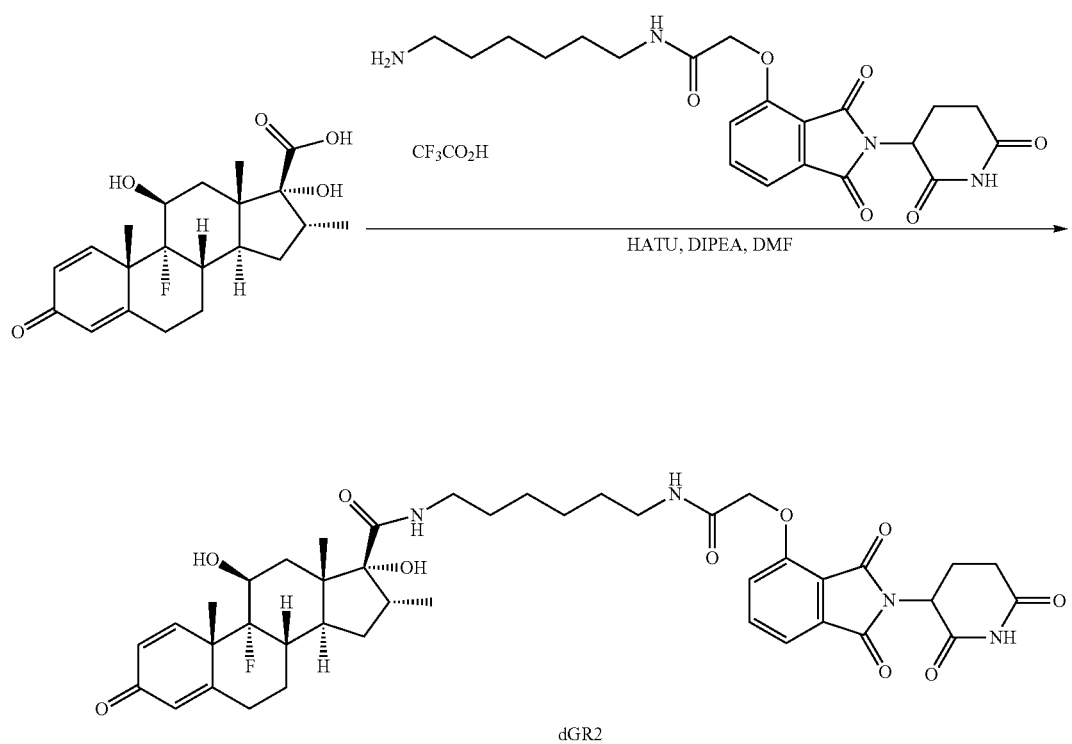
dGR2
In other embodiments of the disclosure, the bifunctional compounds dFKBP-1 and dFKBP-2 can be prepared using TL5 target moiety (AP1479) according to the general methods illustrated above, as shown in the following schemes:
dFKBP-1:
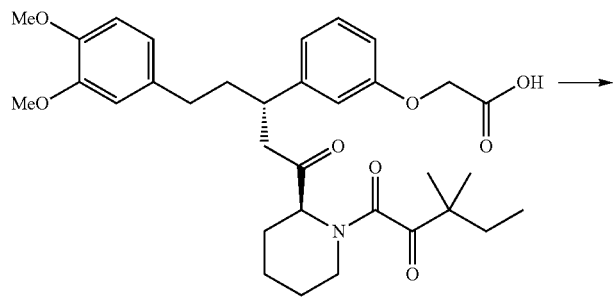

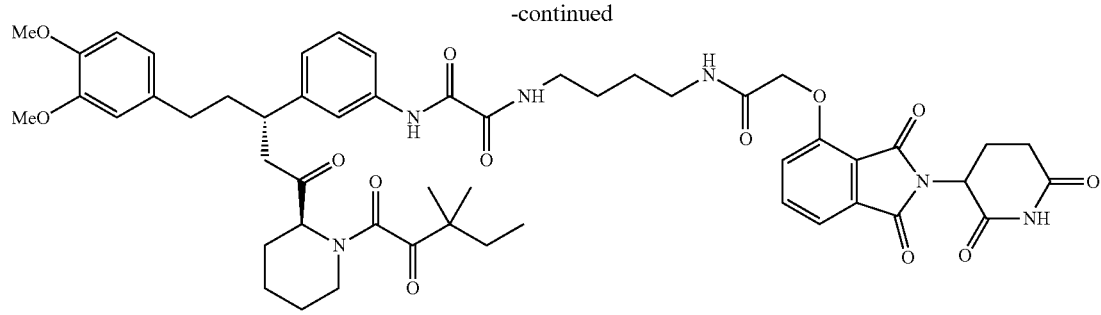
dFKBP-2:
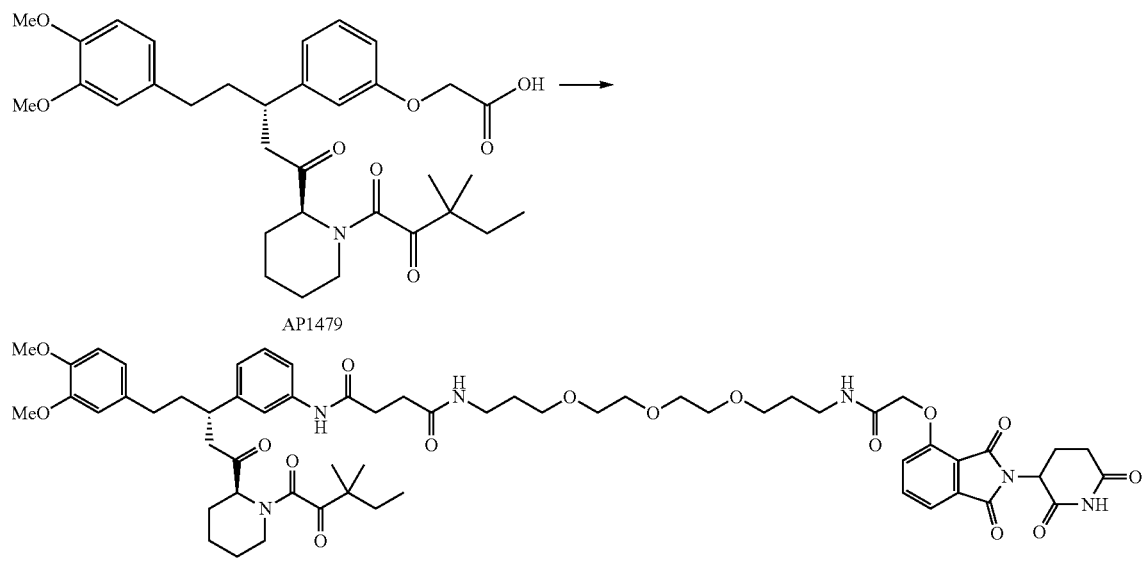
Scheme for Synthesis of Amino Acid-Thalidomide Linker (1)
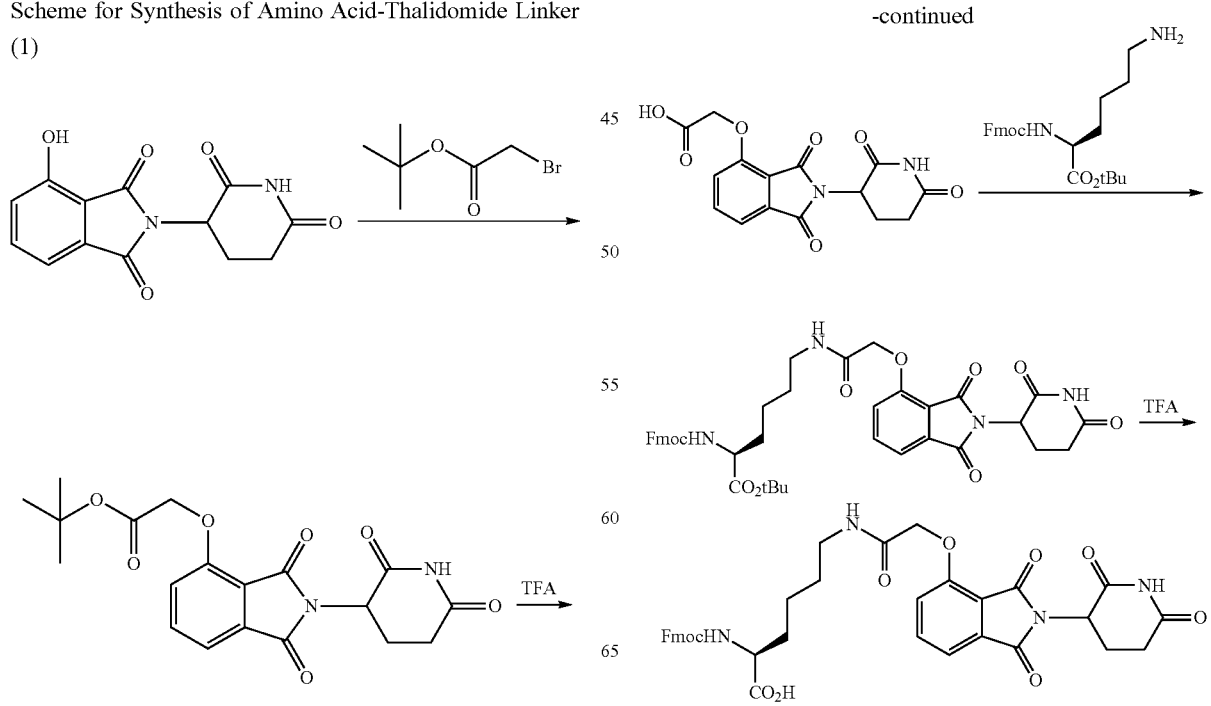

(2)
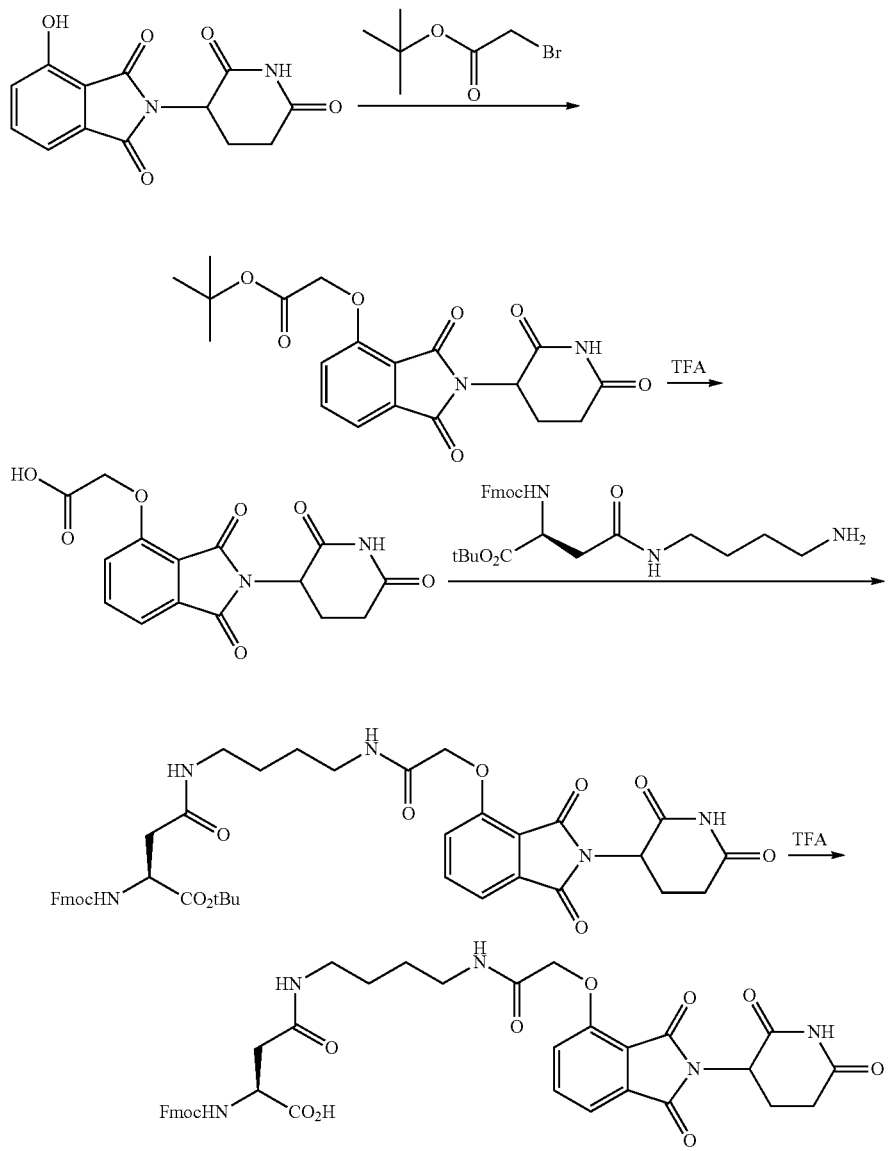
(3)
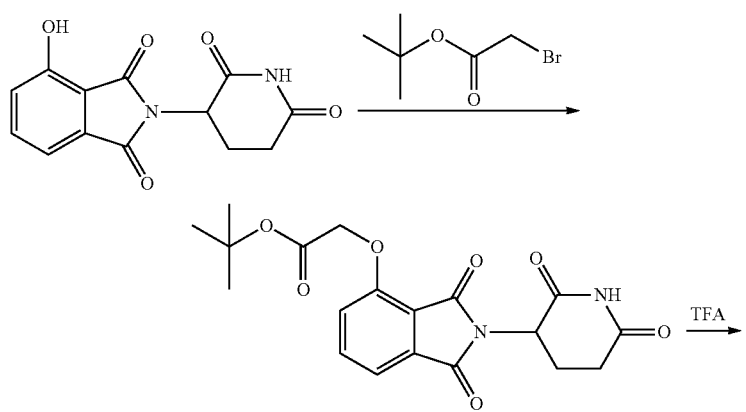

143 144
-continued
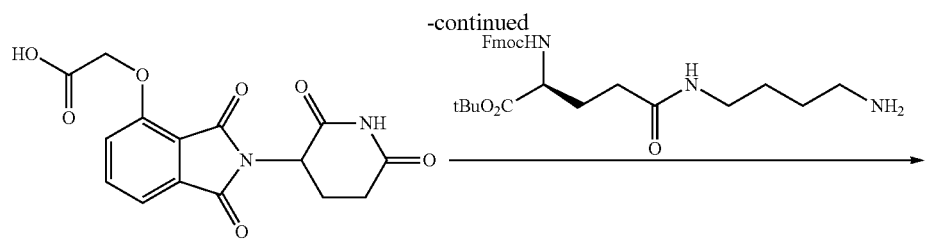
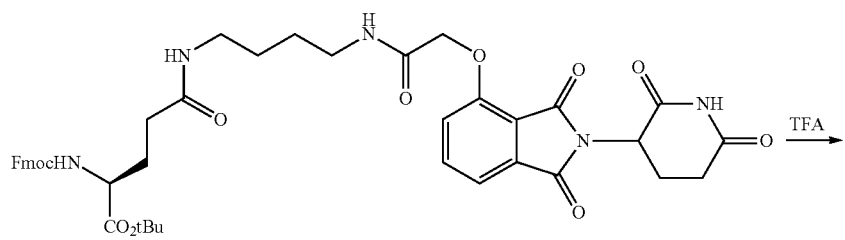
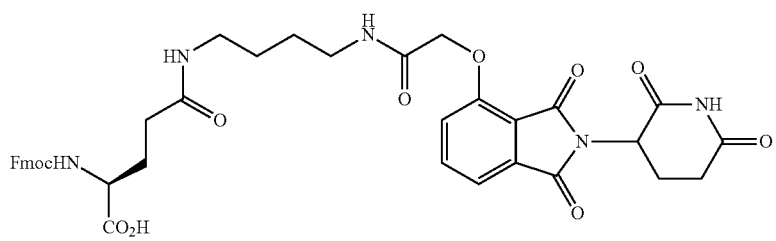
(4)
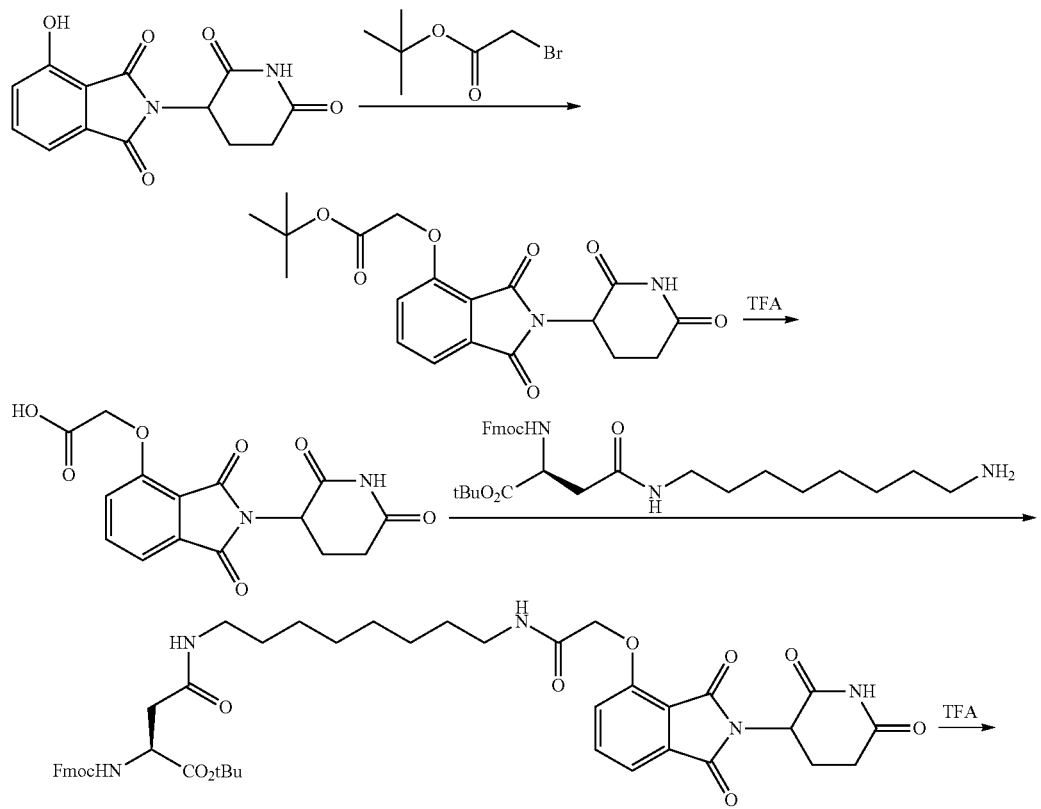

145
146
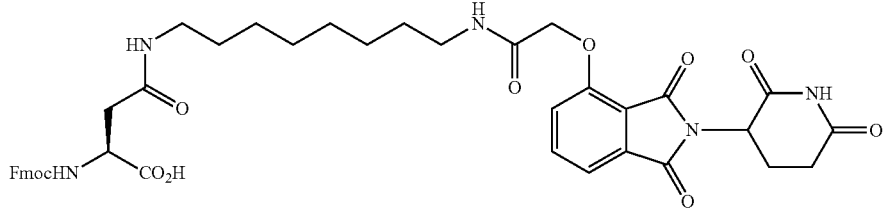
(5)
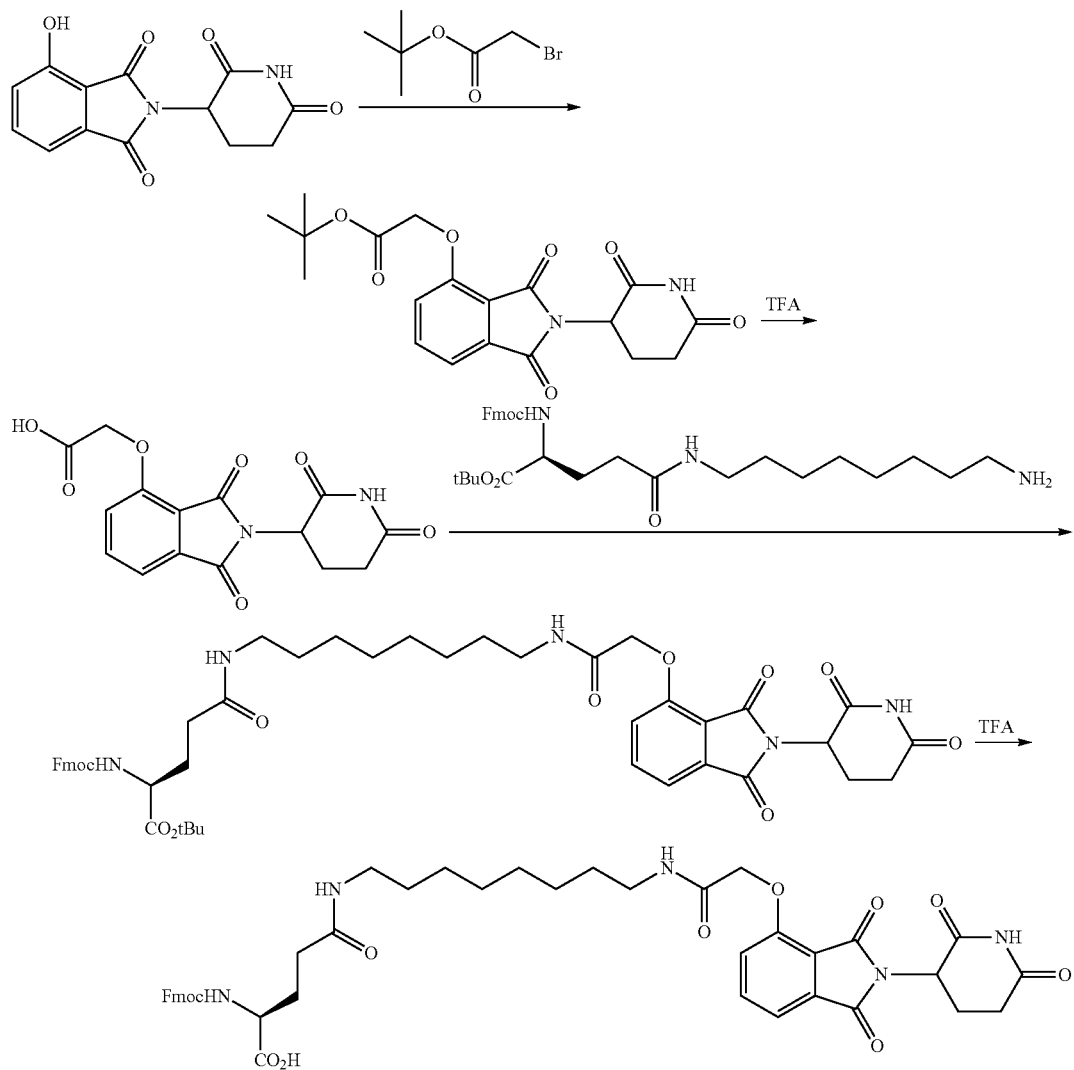
(6)
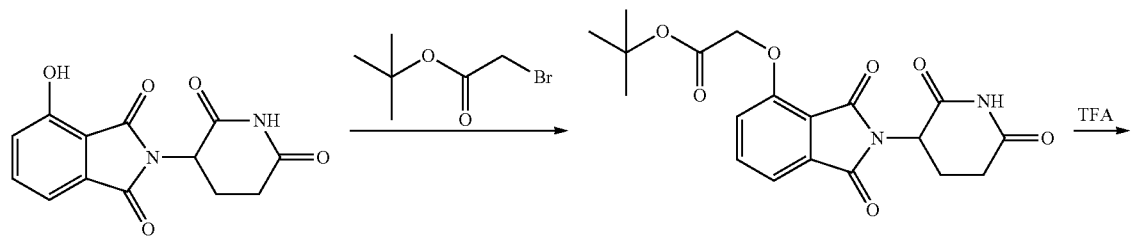

147
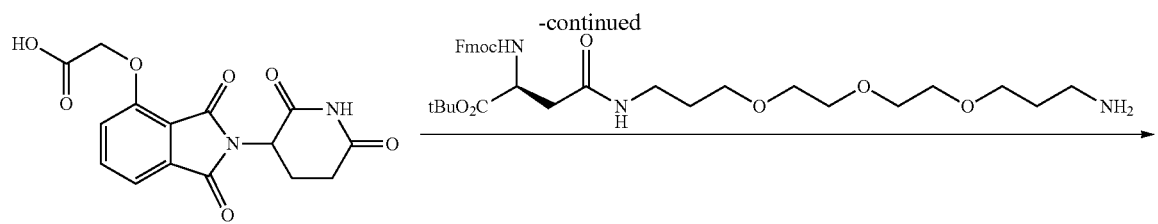
148
-continued
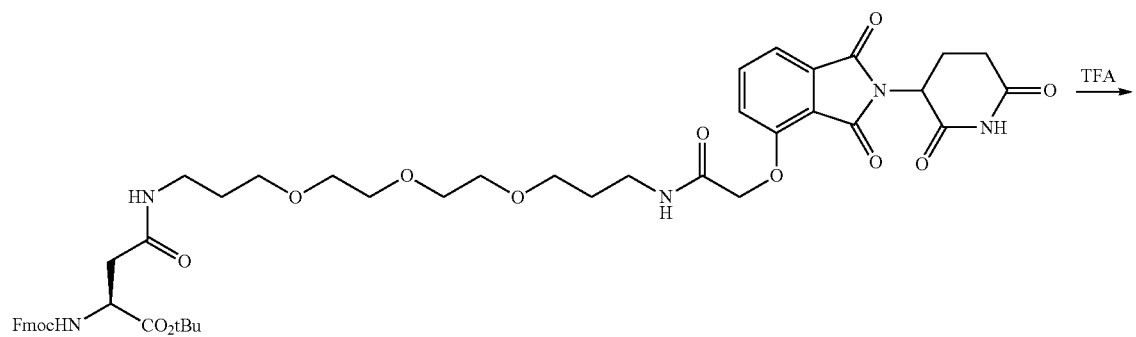
TFA
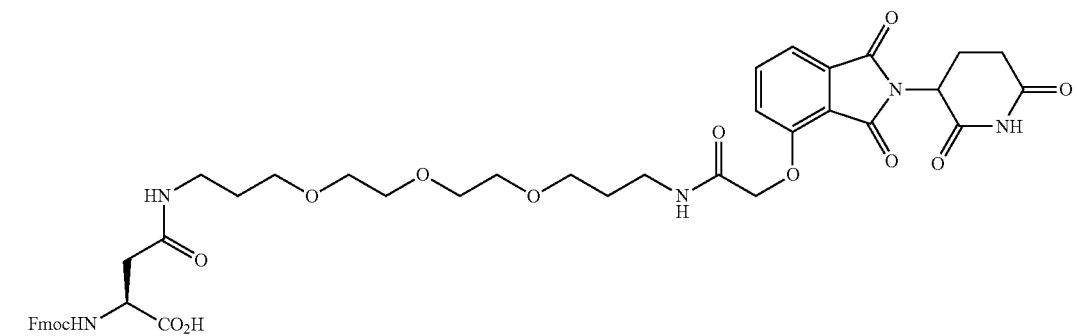
(7)
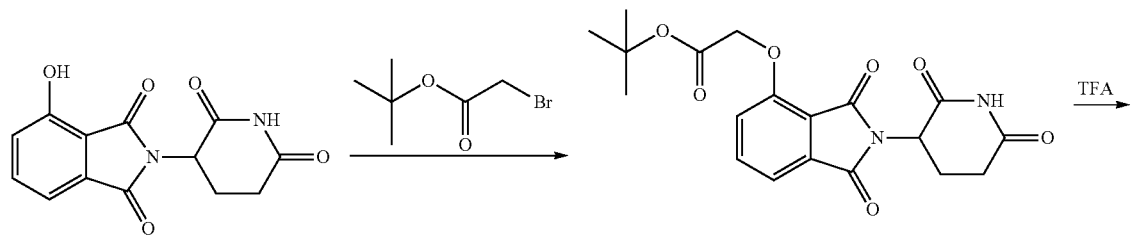
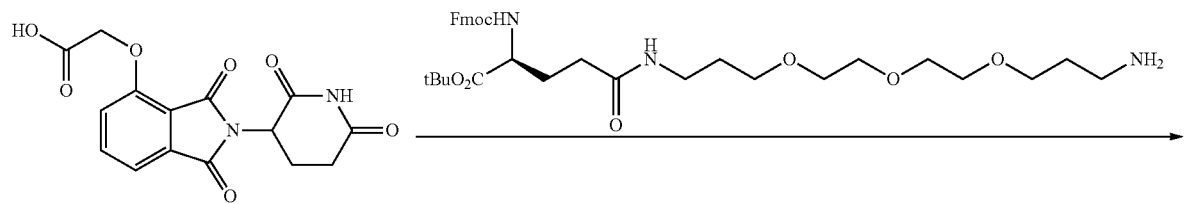

-continued

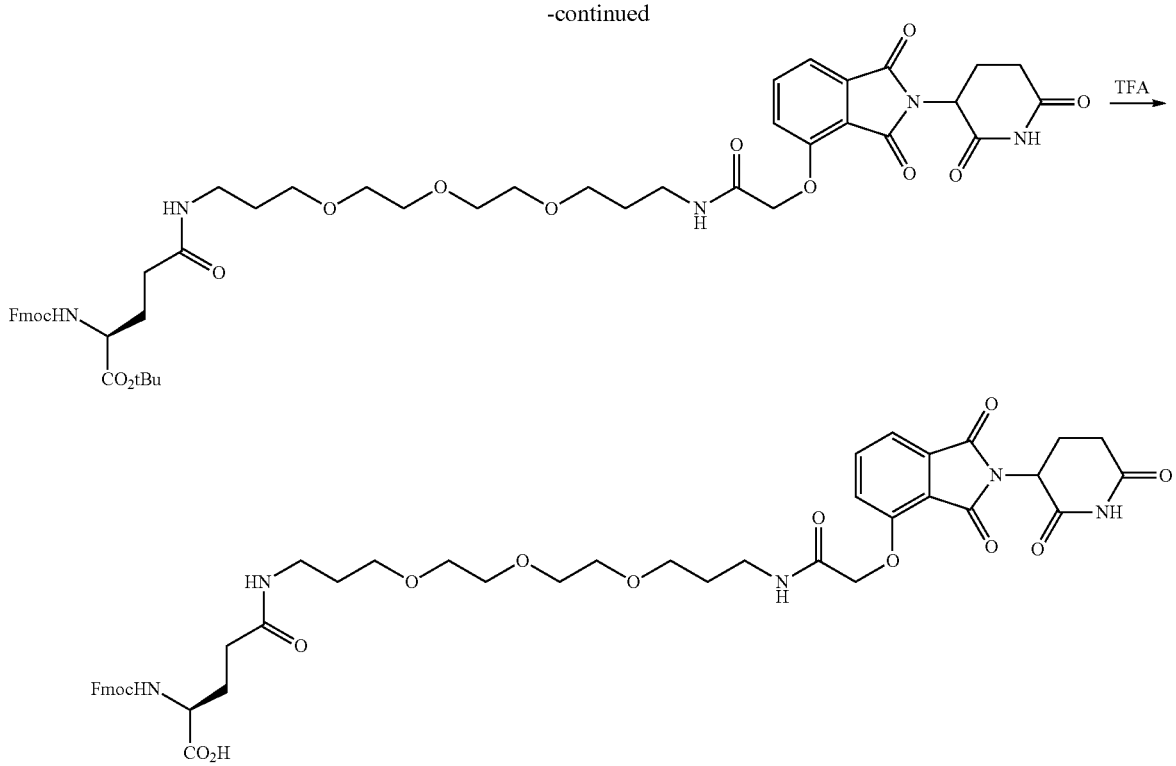

Pharmaceutical Compositions

Accordingly, in another aspect of the present application, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this application may be administered to a patient in need thereof in combination with the administration of one or more other therapeutic agents. For example, additional therapeutic agents for conjoint administration or inclusion in a pharmaceutical composition with a compound of this application may be, for example, an approved chemotherapeutic agent, or it may be any one of a number of agents undergoing approval in the Food and Drug Administration that ultimately obtain approval for the treatment of any disorder associated with cellular hyperproliferation. In certain other embodiments, the additional therapeutic agent is an anticancer agent, as discussed in more detail herein.

It will also be appreciated that certain of the compounds of present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a pro-drug or other adduct or derivative of a compound of this application which upon administration to a patient in need is capable of providing, directly or indirectly, a compound as otherwise described herein, or a metabolite or residue thereof.

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences, 66:1-19 (1977), incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present application additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the application, such as by producing any undesirable biological effect or otherwise interacting in a deleterious manner with any other component(s) of the pharmaceutical composition, its use is contemplated to be within the scope of this application. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present application encompasses pharmaceutically acceptable topical formulations of inventive compounds. The term "pharmaceutically acceptable topical formulation", as used herein, means any formulation which is pharmaceutically acceptable for intradermal administration of a compound of the application by application of the formulation to the epidermis. In certain embodiments of the application, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the application may comprise excipients. Any pharmaceutically acceptable excipient known in the art may be used to prepare the inventive pharmaceutically acceptable topical formulations. Examples of excipients that can be included in the topical formulations of the application include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the application include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the application include, but are not limited to, vitamin E oil, allatoin, dimethicone, glycerin, petrolatum, and zinc oxide.

In certain embodiments, the pharmaceutically acceptable topical formulations of the application comprise at least a compound of the application and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the application include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the application are creams, which may further contain saturated or unsaturated fatty acids such as stearic acid, palmitic acid, oleic acid, palmito-oleic acid, cetyl or oleyl alcohols, and stearic acid being particularly preferred. Creams of the application may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this application. Additionally, the present application contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present application can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent or anticancer agent, or they may achieve different effects (e.g., control of any adverse effects).

For example, other therapies or anticancer agents that may be used in combination with the compounds of the present application include surgery, radiotherapy, endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe).

In certain embodiments, the pharmaceutical compositions of the present application further comprise one or more additional therapeutically active ingredients (e.g., chemotherapeutic and/or palliative). For purposes of the application, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present application provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a prodrug or other adduct or derivative of a compound of this application which upon administration to a patient in need is capable of providing, directly or indirectly, a compound as otherwise described herein, or a metabolite or residue thereof.

Methods of Treatment

In general, methods of using the compounds of the present application comprise administering to a subject in need thereof a therapeutically effective amount of a compound of the present application. The compounds of the application are generally inducers of target protein degradation.

In certain embodiments, compounds of the application are useful in the treatment of proliferative diseases (e.g., cancer, benign neoplasms, inflammatory disease, and autoimmune diseases). In certain embodiments, according to the methods of treatment of the present application, levels of cell proteins of interest, e.g., pathogenic and oncogenic proteins are modulated, or their growth is inhibited by contacting said cells with an inventive compound or composition, as described herein. In other embodiments, the compounds are useful in treating cancer.

Thus, in another aspect of the application, methods for the treatment of cancer are provided comprising administering a therapeutically effective amount of an inventive compound, as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. Preferably, the compounds of present application are administered orally or intravenously. In certain embodiments of the present application a "therapeutically effective amount" of the inventive compound or pharmaceutical composition is that amount effective for killing or inhibiting the growth of tumor cells. The compounds and compositions, according to the method of the present application, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. In certain embodiments of the present application a "therapeutically effective amount" of the inventive compound or pharmaceutical composition is that amount effective for reducing the levels of target proteins. In certain embodiments of the present application a "therapeutically effective amount" of the compound or pharmaceutical composition is that amount effective to kill or inhibit the growth of skin cells.

In certain embodiments, the method involves the administration of a therapeutically effective amount of the compound or a pharmaceutically acceptable derivative thereof to a subject (including, but not limited to a human or animal) in need of it. In certain embodiments, the bifunctional compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer.

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer. In certain embodiments, the inventive anticancer agents are active against solid tumors.

In certain embodiments, the inventive compounds also find use in the prevention of restenosis of blood vessels subject to traumas such as angioplasty and stenting. For example, it is contemplated that the compounds of the application will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing retenosis (See, for example, Presbitero P. et al., "Drug eluting stents do they make the difference?", Minerva Cardioangiol, 2002, 50(5):431-442; Ruygrok P. N. et al., "Rapamycin in cardiovascular medicine", Intern. Med. J., 2003, 33(3):103-109; and Marx S. O. et al., "Bench to bedside: the development of rapamycin and its application to stent restenosis", Circulation, 2001, 104(8):852-855, each of these references is incorporated herein by reference in its entirety). Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248, 127; 6,231,600; 6,203,551; 6,153,252; 6,071,305; 5,891, 507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this application or pharmaceutically acceptable compositions thereof may also be incorporated into compositions for coating implantable medical devices, such as prostheses, artificial valves, vascular grafts, stents and catheters. Accordingly, the present application, in another aspect, includes a composition for coating an implantable device comprising a compound of the present application as described generally above, and in classes and subclasses herein, and a carrier suitable for coating said implantable device. In still another aspect, the present application includes an implantable device coated with a composition comprising a compound of the present application as described generally above, and in classes and subclasses herein, and a carrier suitable for coating said implantable device.

Additionally, the present application provides pharmaceutically acceptable derivatives of the inventive compounds, and methods of treating a subject using these compounds, pharmaceutical compositions thereof, or either of these in combination with one or more additional therapeutic agents.

Another aspect of the application relates to a method of treating or lessening the severity of a disease or condition associated with a proliferation disorder in a patient, said method comprising a step of administering to said patient, a compound of Formula I or a composition comprising said compound.

It will be appreciated that the compounds and compositions, according to the method of the present application, may be administered using any amount and any route of administration effective for the treatment of cancer and/or disorders associated with cell hyperproliferation. For example, when using the inventive compounds for the treatment of cancer, the expression "effective amount" as used herein, refers to a sufficient amount of agent to inhibit cell proliferation, or refers to a sufficient amount to reduce the effects of cancer. The exact amount required will vary from subject to subject, depending on the species, age, and general condition of the subject, the severity of the diseases, the particular anticancer agent, its mode of administration, and the like.

The compounds of the application are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present application will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable carrier in a desired dosage, the pharmaceutical compositions of this application can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the application may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

The present application provides methods for the treatment of a cell proliferative disorder in a subject in need thereof by administering to a subject in need of such treatment, a therapeutically effective amount of a compound of the present application, or a pharmaceutically acceptable salt, prodrug, metabolite, polymorph or solvate thereof. The cell proliferative disorder can be cancer or a precancerous condition. The present application further provides the use of a compound of the present application, or a pharmaceutically acceptable salt, prodrug, metabolite, polymorph or solvate thereof, for the preparation of a medicament useful for the treatment of a cell proliferative disorder.

The present application also provides methods of protecting against a cell proliferative disorder in a subject in need thereof by administering a therapeutically effective amount of compound of the present application, or a pharmaceutically acceptable salt, prodrug, metabolite, polymorph or solvate thereof, to a subject in need of such treatment. The cell proliferative disorder can be cancer or a precancerous condition. The present application also provides the use of compound of the present application, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present application may be used to treat a cancer selected from the group consisting of a hematologic cancer of the present application or a hematologic cell proliferative disorder of the present application. A hematologic cancer of the present application can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present application may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present application may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "treating" or "treat" describes the management and care of a patient for the purpose of combating a disease, condition, or disorder and includes the administration of a compound of the present application, or a pharmaceutically acceptable salt, prodrug, metabolite, polymorph or solvate thereof, to alleviate the symptoms or complications of a disease, condition or disorder, or to eliminate the disease, condition or disorder.

A compound of the present application, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

The compounds described herein (e.g., the bifunctional compounds), once produced, can be characterized using a variety of assays known to those skilled in the art to determine whether the compounds have the desired biological activity. For example, the molecules can be characterized by conventional assays, including but not limited to those assays described below (e.g., treating cells of interest, such as MV4-11 cells, human cell line MM1S, or a human cell line MM1S that is deficient in cereblon, with a test compound and then performing immunoblotting against the indicated proteins such as BRD2, BRD3, and BRD4, or treating certain cells of interest with a test compound and then measuring BRD4 transcript levels via qRT-PCR), to determine whether they have a predicted activity, binding activity and/or binding specificity.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the application

DEFINITIONS

Certain compounds of the present application, and definitions of specific functional groups are also described in more detail below.

It will be appreciated that the compounds, as described herein, may be substituted with any number of substituents or functional moieties. In general, the term "substituted" whether preceded by the term "optionally" or not, and substituents contained in formulas of this application, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this application, heteroatoms such as nitrogen may have hydrogen substituents and/or any permissible substituents of organic compounds described herein which satisfy the valencies of the heteroatoms.

The term "Linker", "linker", "Linker group" or "linker group" as used herein, refers to a chemical moiety utilized to attach one part of a compound of interest to another compound of interest. These binding moieties of the present application are linked to the ubiquitin ligase binding moiety preferably through a Linker in order to present a target protein (to which the protein target moiety is bound) in proximity to the ubiquitin ligase for ubiquitination and degradation. Exemplary Linkers are described herein.

The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present application. In certain other preferred embodiments, synthetic small molecules are utilized.

The term "independently" is used herein to indicate that the variable, such as atom or functional group, which is independently applied, varies independently from application to application. For example, where more than one substituent or atom (carbon or heteroatom, such as oxygen (O), sulfur (S), or nitrogen (N)) occurs, each substituent or atom is independent of another substituent or atom and such substituents or atom can also alternate.

In chemistry, a "derivative" is a compound that is derived from a similar compound by some chemical or physical process. It is also used to mean that a compound can arise from another compound, if one atom is replaced with another atom or group of atoms. A term "structural analogue" can be also used for this meaning.

The term "structural analogue" or term "analogue" has always been used to describe structural and functional similarity. Extended to drugs, this definition implies that the analogue of an existing drug molecule shares structural and pharmacological similarities with the original compound. Formally, this definition allows the establishment of three categories of drug analogues: analogues possessing chemical and pharmacological similarities (direct analogues); analogues possessing structural similarities only (structural analogues); and chemically different compounds displaying similar pharmacological properties (functional analogues). For example, lenalidomide and pomalidomide are among thalidomide analogs, and are believed to act in a similar fashion.

The term "E3 Ubiquitin Ligase" or "Ubiquitin Ligase" (UL) is used herein to describe a target enzyme(s) binding site of ubiquitin ligase moieties in the bifunctional compounds according to the present application. E3 UL is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to monoubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "protein target moiety" or "target protein ligand" is used herein to describe a small molecule, which is capable of binding to or binds to a target protein or other protein or polypeptide of interest and places/presents that protein or polypeptide in proximity to an ubiquitin ligase such that degradation of the protein or polypeptide by ubiquitin ligase may occur. Any protein, which can bind to a protein target moiety and acted on or degraded by an ubiquitin ligase is a target protein according to the present application. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these small molecule target protein.

As used herein, the term "BRD4" or "Brd4" relates to Bromodomain-containing protein 4 is a protein that in humans is encoded by the BRD4 gene. BDR4 is a member of the BET (bromodomain and extra terminal domain) family, along with BRD2, BRD3, and BRDT. BRD4, similar to its BET family members, contains two bromodomains that recognize acetylated lysine residues. An increase in Brd4 expression led to increased P-TEFb-dependent phosphorylation of RNA polymerase II (RNAPII) CTD and stimulation of transcription from promoters in vivo. Conversely, a reduction in Brd4 expression by siRNA reduced CTD phosphorylation and transcription, revealing that Brd4 is a positive regulatory component of P-TEFb. In chromatin immunoprecipitation (ChIP) assays, the recruitment of P-TEFb to a promoter was dependent on Brd4 and was enhanced by an increase in chromatin acetylation. Together, P-TEFb alternately interacts with Brd4 and the inhibitory subunit to maintain functional equilibrium in the cell.

BRD4 is an exemplary, non-enzymatic protein target. BRD4 is a transcriptional co-activator involved in dynamic transcriptional activation and elongation. BRD4 binds to enhancer and promoter regions adjacent to target genes, via recognition of side-chain acetylated lysine on histone proteins and transcription factors (TFs) by twin acetyl-lysine binding modules or bromodomains. Recently, a first direct-acting inhibitor of BET bromodomains (JQ1) was developed (P. Filippakopoulos et al., Nature 468, 1067-1073 (2010)), that displaces BRD4 from chromatin leading to impaired signal transduction from master regulatory TFs to RNA Polymerase II (B. Chapuy et al., Cancer Cell 24, 777-790 (2013); J. E. Delmore et al., Cell 146, 904-917 (2011); J. Lovén et al., Cell 153, 320-334 (2013).). Molecular recognition of the BRD4 bromodomains by JQ1 is stereo-specific, and only the (+)-JQ1 enantiomer (JQ1S; from here forward JQ1) is active; the (−)-JQ1 enantiomer (JQ1R) is inactive. Silencing of BRD4 expression by RNA interference in murine and human models of MM and acute myeloid leukemia (AML) elicited rapid transcriptional downregulation of the MYC oncogene and a potent anti-proliferative response (J. E. Delmore et al., Cell 146, 904-917 (2011); J. Zuber et al., Nature 478, 524-528 (2011)). These and other studies in cancer, inflammation (E. Nicodeme et al., Nature 468, 1119-1123 (2010)) and heart disease (P. Anand et al., Cell 154, 569-582 (2013); J. D. Brown et al., Mol. Cell 56, 219-231 (2014)), establish a desirable mechanistic and translational purpose to target BRD4 for selective degradation.

As used herein, the term "FKBP" relates to a family of proteins that have prolyl isomerase activity and are related to the cyclophilins in function, though not in amino acid sequence (Siekierka et al. Nature 341 (6244): 755-7 (1989)). FKBPs have been identified in many eukaryotes from yeast to humans and function as protein folding chaperones for proteins containing proline residues. Along with cyclophilin, FKBPs belong to the immunophilin family (Balbach et al. Mechanisms of protein folding (2nd ed.). Oxford: Oxford University Press. pp. 212-237 (2000)). Cytosolic signaling protein FKBP12 is notable in humans for binding the immunosuppressant molecule tacrolimus (originally designated FK506), which is used in treating patients after organ transplant and patients suffering from autoimmune disorders (Wang et al. Science 265 (5172): 674-6 (1994)). Tacrolimus has been found to reduce episodes of organ rejection over a related treatment, the drug ciclosporin, which binds cyclophilin (Mayer et al. Transplantation 64 (3): 436-43 (1997)). Both the FKBP-tacrolimus complex and the ciclosporin-cyclophilin complex inhibit a phosphatase called calcineurin, thus blocking signal transduction in the T-lymphocytetransduction pathway (Liu et al. Cell 66 (4): 807-15 (1991)). This therapeutic role is not related to prolyl isomerase activity. AP1497 (Table 1, TL5) is a synthetic pipecolyl α-ketoamide designed to be recognized by FKBP12 (Holt et al., J. Am. Chem. Soc. 115, 9925 (1993))

As used herein the term "CREBBP" relates to CREB binding protein. This gene is ubiquitously expressed and is involved in the transcriptional coactivation of many different transcription factors. First isolated as a nuclear protein that binds to cAMP-response element binding protein (CREB), this gene is now known to play critical roles in embryonic development, growth control, and homeostasis by coupling chromatin remodeling to transcription factor recognition. Chromosomal translocations involving this gene have been associated with acute myeloid leukemia.

As used herein the term "SMARCA4" relates to transcription activator BRG1 also known as ATP-dependent helicase SMARCA4 is a protein that in humans is encoded by the SMARCA4 gene. Mutations in this gene were first recognized in human lung cancer cell lines. It has been demonstrated that BRG1 plays a role in the control of retinoic acid and glucocorticoid-induced cell differentiation in lung cancer and in other tumor types.

As used herein the term "nuclear receptor" relates to a class of proteins found within cells that are responsible for sensing steroid and thyroid hormones and certain other molecules. In response, these receptors work with other proteins to regulate the expression of specific genes, thereby controlling the development, homeostasis, and metabolism of the organism. Since the expression of a large number of genes is regulated by nuclear receptors, ligands that activate these receptors can have profound effects on the organism.

The representative examples which follow are intended to help illustrate the application, and are not intended to, nor should they be construed to, limit the scope of the application. Indeed, various modifications of the application and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this application in its various embodiments and the equivalents thereof.

These and other aspects of the present application will be further appreciated upon consideration of the following Examples, which are intended to illustrate certain particular embodiments of the application but are not intended to limit its scope, as defined by the claims.

EXAMPLES

General Description of Synthetic Methods

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

According to the present application, any available techniques can be used to make or prepare the inventive compounds or compositions including them. For example, a variety of a variety combinatorial techniques, parallel synthesis and/or solid phase synthetic methods such as those discussed in detail below may be used. Alternatively or additionally, the inventive compounds may be prepared using any of a variety of solution phase synthetic methods known in the art.

The starting materials, intermediates, and compounds of this application may be isolated and purified using conventional techniques, including filtration, distillation, crystallization, chromatography, and the like. They may be characterized using conventional methods, including physical constants and spectral data.

Synthesis of Exemplary Compounds

Unless otherwise indicated, starting materials are either commercially available or readily accessible through laboratory synthesis by anyone reasonably familiar with the art. Described generally below, are procedures and general guidance for the synthesis of compounds as described generally and in subclasses and species herein.

Example 1

Synthesis of dBET1

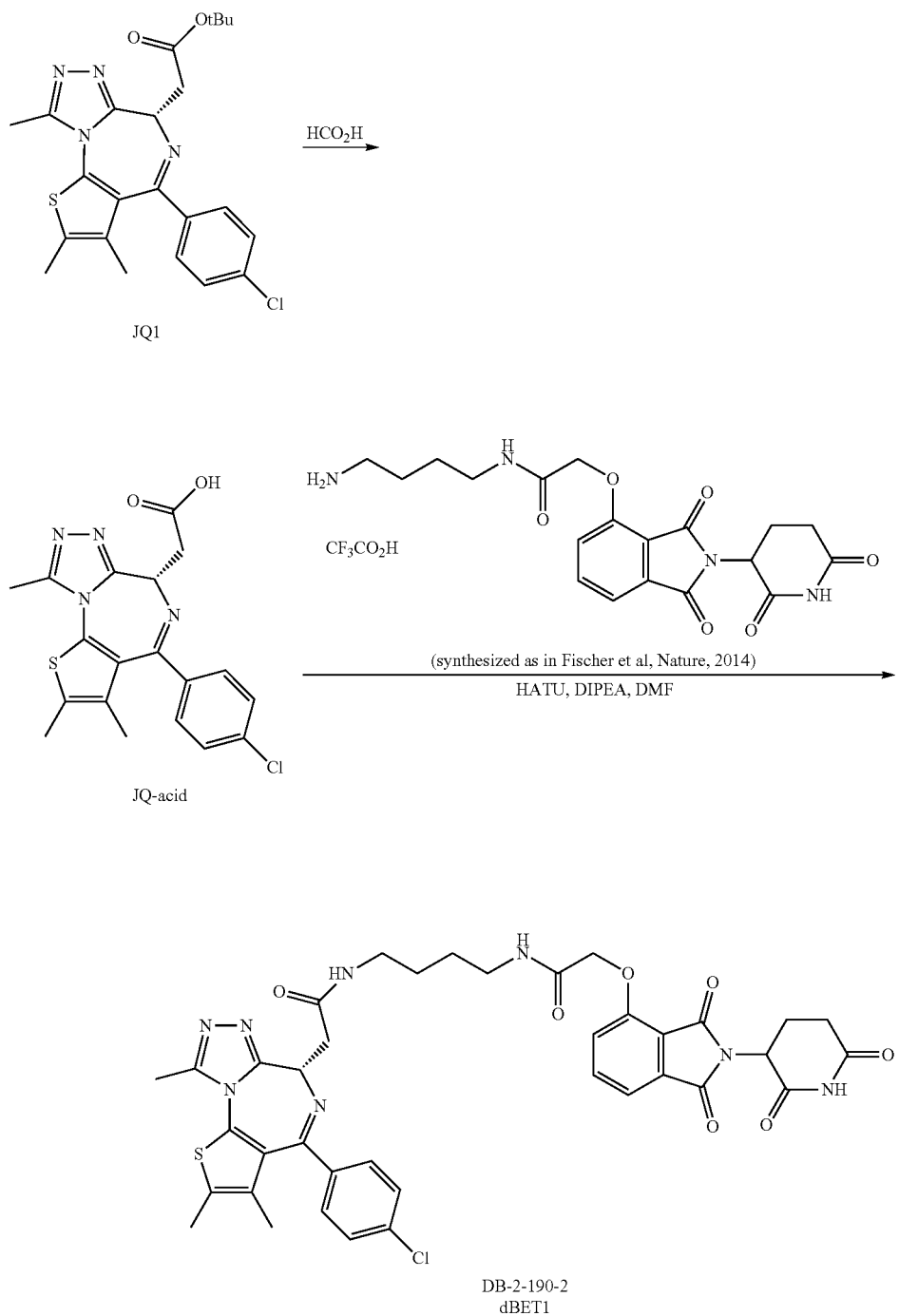

DB-2-190-2
dBET1

(1) Synthesis of JQ-Acid

JQ1 (1.0 g, 2.19 mmol, 1 eq) was dissolved in formic acid (11 mL, 0.2 M) at room temperature and stirred for 75 hours. The mixture was concentrated under reduced pressure to give a yellow solid (0.99 g, quant yield) that was used without purification. $^1$H NMR (400 MHz, Methanol-$d_4$) δ 7.50-7.36 (m, 4H), 4.59 (t, J=7.1 Hz, 1H), 3.51 (d, J=7.1 Hz, 2H), 2.70 (s, 3H), 2.45 (s, 3H), 1.71 (s, 3H). LCMS 401.33 (M+H).

167.76, 166.73, 166.70, 156.26, 138.40, 138.23, 137.44, 134.83, 133.92, 133.40, 132.30, 132.28, 131.97, 131.50, 129.87, 121.85, 119.31, 118.00, 69.53, 54.90, 50.54, 40.09, 39.83, 38.40, 32.12, 27.74, 27.65, 23.61, 14.42, 12.97, 11.57. LCMS 785.44 (M+H).

Example 2

Synthesis of dBET4

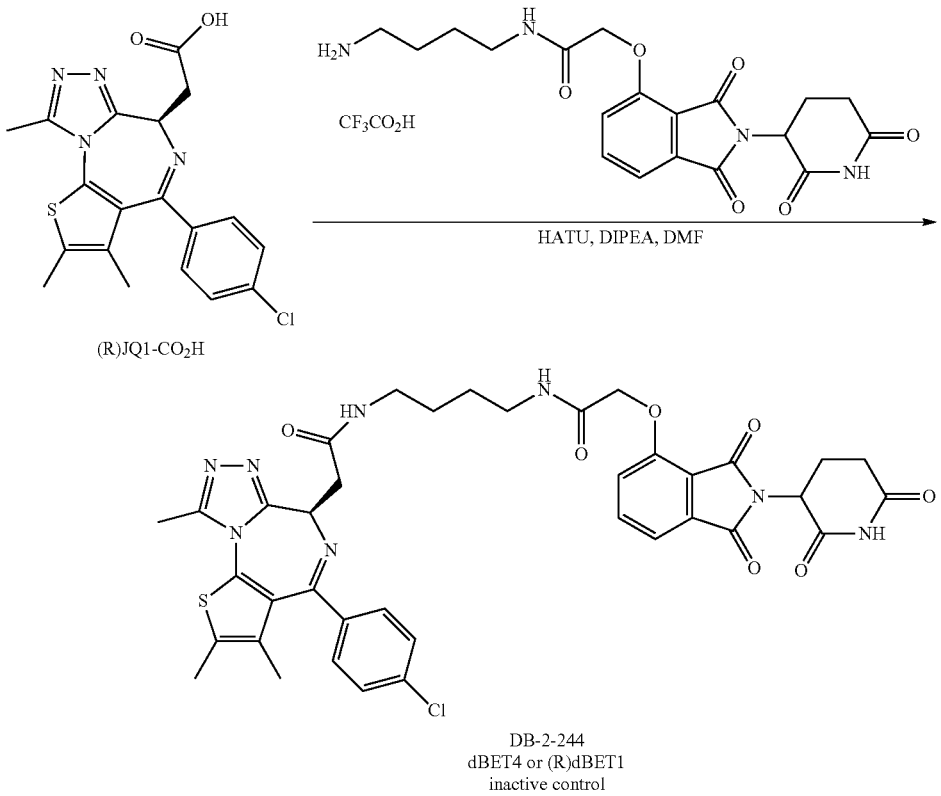

DB-2-244
dBET4 or (R)dBET1
inactive control

N-(4-aminobutyl)-2-((2-(2,6-dioxopiperidin-3-yl)-1,3-dioxoisoindolin-4-yl)oxy)acetamidetrifluoroacetate was synthesized according to the previously published procedure (Fischer et al. Nature 2014, 512, 49).

(2) Synthesis of dBET1

JQ-acid (11.3 mg, 0.0281 mmol, 1 eq) and N-(4-aminobutyl)-2-((2-(2,6-dioxopiperidin-3-yl)-1,3-dioxoisoindolin-4-yl)oxy)acetamide trifluoroacetate (14.5 mg, 0.0281 mmol, 1 eq) were dissolved in DMF (0.28 mL, 0.1 M) at room temperature. DIPEA (14.7 microliters, 0.0843 mmol, 3 eq) and HATU (10.7 mg, 0.0281 mmol, 1 eq) were then added and the mixture was stirred for 19 hours. The mixture was then purified by preparative HPLC to give dBET1 as a yellow solid (15.90 mg, 0.0202 mmol, 72%). $^1$H NMR (400 MHz, Methanol-$d_4$) δ 7.77 (dd, J=8.3, 7.5 Hz, 1H), 7.49 (d, J=7.3 Hz, 1H), 7.47-7.37 (m, 5H), 5.07 (dd, J=12.5, 5.4 Hz, 1H), 4.74 (s, 2H), 4.69 (dd, J=8.7, 5.5 Hz, 1H), 3.43-3.32 (m, 3H), 3.29-3.25 (m, 2H), 2.87-2.62 (m, 7H), 2.43 (s, 3H), 2.13-2.04 (m, 1H), 1.72-1.58 (m, 7H). $^{13}$C NMR (100 MHz, cd$_3$od) δ 174.41, 172.33, 171.27, 171.25, 169.87, 168.22, A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.438 mL, 0.0438 mmol 1.2 eq) was added to (R)-JQ-acid (prepared from (R)-JQ1 in an analogous method to JQ-acid) (14.63 mg, 0.0365 mmol, 1 eq) at room temperature. DIPEA (19.1 microliters, 0.1095 mmol, 3 eq) and HATU (15.3 mg, 0.0402 mmol, 1.1 eq) were added and the mixture was stirred for 24 hours, then diluted with MeOH and concentrated under reduced pressure. The crude material was purified by preparative HPLC to give a yellow solid (20.64 mg, 0.0263 mmol, 72%). $^1$H NMR (400 MHz, Methanol-$d_4$) δ 7.79 (dd, J=8.4, 7.4 Hz, 1H), 7.51 (d, J=7.3 Hz, 1H), 7.47-7.39 (m, 5H), 5.11-5.06 (m, 1H), 4.75 (s, 2H), 4.68 (dd, J=8.8, 5.5 Hz, 1H), 3.47-3.31 (m, 5H), 2.83-2.65 (m, 7H), 2.44 (s, 3H), 2.13-2.06 (m, 1H), 1.68 (s, 3H), 1.67-1.60 (m, 4H). $^{13}$C NMR (100 MHz, cd$_3$od) δ 174.43, 172.40, 171.29, 169.92, 168.24, 167.82, 166.71, 156.31, 153.14, 138.38, 138.24, 137.54, 134.88, 133.86, 133.44, 132.29, 132.00, 131.49, 129.88, 122.46, 121.90, 119.38, 118.02, 69.59, 54.96, 50.55, 40.09, 39.84, 38.45, 32.14, 27.75, 27.65, 23.62, 14.41, 12.96, 11.56. MS 785.48 (M+H).

Example 3

Synthesis of dBET3

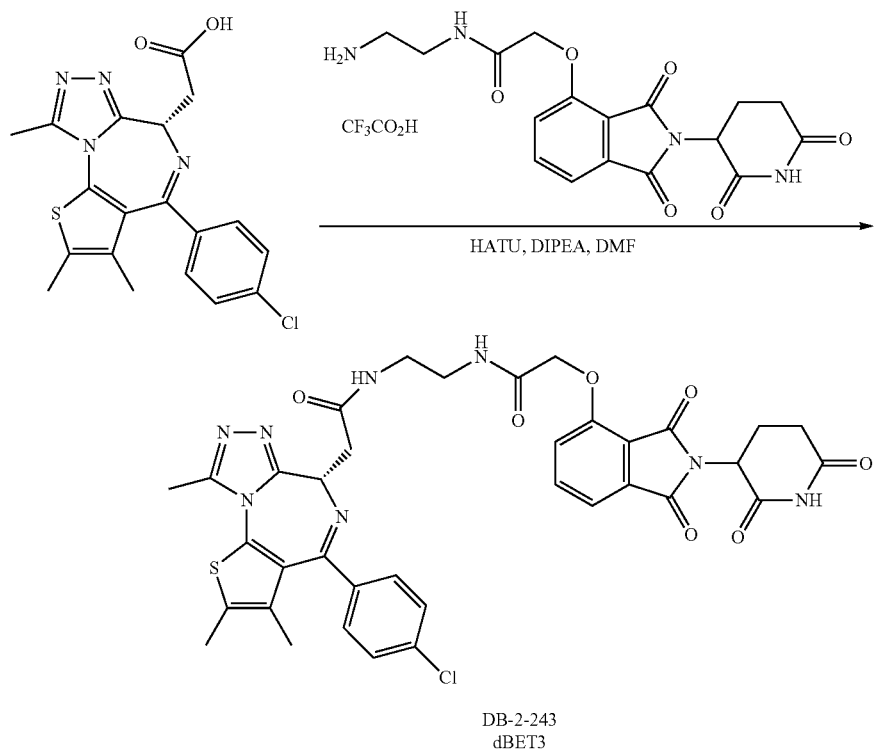

DB-2-243
dBET3

A 0.1 M solution of N-(2-aminoethyl)-2-((2-(2,6-dioxopiperidin-3-yl)-1,3-dioxoisoindolin-4-yl)oxy)acetamide trifluoroacetate in DMF (0.475 mL, 0.0475 mmol, 1.2 eq) was added to JQ-acid (15.86 mg, 0.0396 mmol, 1 eq) at room temperature. DIPEA (20.7 microliters, 0.1188 mmol, 3 eq) and HATU (16.5 mg, 0.0435 mmol, 1.1 eq) were then added and the mixture was stirred for 24 hours, then purified by preparative HPLC to give a yellow solid (22.14 mg, 0.0292 mmol, 74%). $^1$H NMR (400 MHz, Methanol-$d_4$) δ 7.82-7.75 (m, 1H), 7.52-7.32 (m, 6H), 5.04 (dd, J=11.6, 5.5 Hz, 1H), 4.76 (d, J=3.2 Hz, 2H), 4.66 (d, J=6.6 Hz, 1H), 3.58-3.35 (m, 6H), 2.78-2.58 (m, 6H), 2.48-2.41 (m, 3H), 2.11-2.02 (m, 1H), 1.70 (d, J=11.8 Hz, 3H). $^{13}$C NMR (100 MHz, cd$_3$od) δ 174.38, 171.26, 171.19, 170.26, 168.86, 168.21, 167.76, 166.72, 156.27, 153.14, 138.44, 138.36, 138.19, 134.87, 133.71, 132.31, 131.57, 131.51, 129.90, 129.86, 121.81, 119.36, 117.95, 69.48, 54.83, 50.52, 40.09, 39.76, 38.30, 32.09, 23.63, 14.40, 11.61. LCMS 757.41 (M+H).

Example 4

Synthesis of dBET5

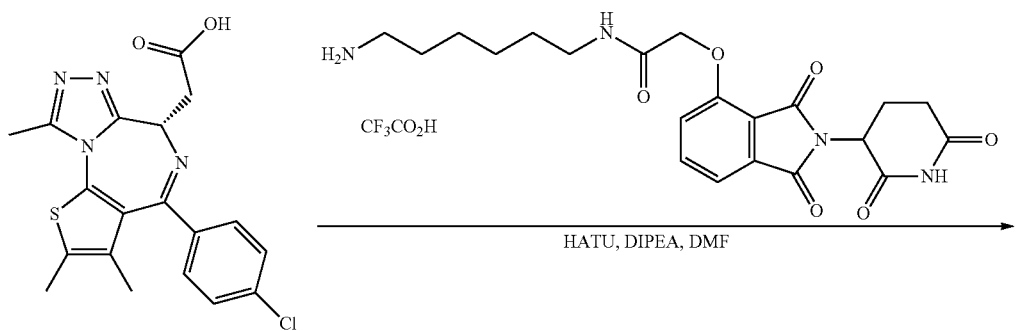

-continued

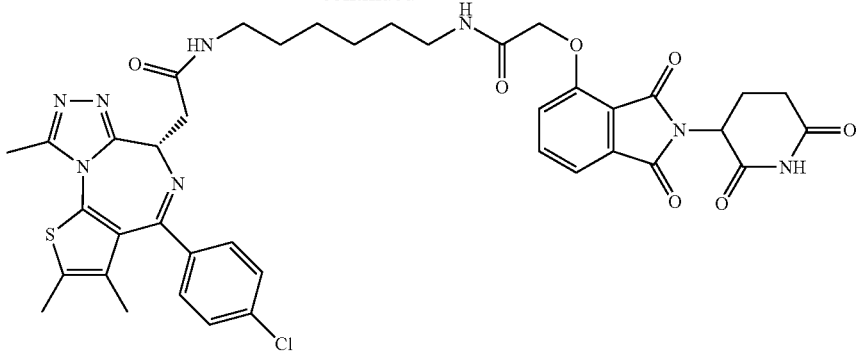

DB-2-264
dBET5

A 0.1 M solution of N-(6-aminohexyl)-2-((2-(2,6-dioxopiperidin-3-yl)-1,3-dioxoisoindolin-4-yl)oxy)acetamide trifluoroacetate in DMF (0.247 mL, 0.0247 mmol, 1 eq) was added to JQ-acid (9.9 mg, 0.0247 mmol, 1 eq) at room temperature. DIPEA (12.9 microliters, 0.0741 mmol, 3 eq) and HATU (9.4 mg, 0.0247 mmol, 1 eq) were then added. The mixture was stirred for 21 hours, then diluted with MeOH and concentrated under reduced pressure. The crude material was purified by preparative HPLC to give a yellow solid (13.56 mg, 0.0167 mmol, 67%). $^1$H NMR (400 MHz, Methanol-$d_4$) δ 7.82-7.78 (m, 1H), 7.53 (dd, J=7.3, 2.0 Hz, 1H), 7.49-7.37 (m, 5H), 5.10 (dt, J=12.4, 5.3 Hz, 1H), 4.76 (s, 2H), 4.70 (dd, J=8.7, 5.5 Hz, 1H), 3.42-3.33 (m, 2H), 3.25 (dt, J=12.3, 6.0 Hz, 3H), 2.87-2.67 (m, 7H), 2.48-2.42 (m, 3H), 2.14-2.09 (m, 1H), 1.69 (d, J=4.8 Hz, 3H), 1.58 (s, 4H), 1.42 (d, J=5.2 Hz, 4H). $^{13}$C NMR (100 MHz, cd$_3$od) δ 174.51, 171.31, 171.26, 169.82, 168.27, 168.26, 167.75, 156.26, 150.46, 138.20, 134.92, 133.92, 133.47, 132.34, 132.01, 131.52, 129.88, 121.69, 119.34, 117.95, 111.42, 69.39, 54.97, 50.56, 40.39, 40.00, 38.40, 32.15, 30.46, 30.16, 27.58, 27.48, 23.64, 14.41, 12.96, 11.55. LCMS 813.38.

Example 5

Synthesis of dBET6

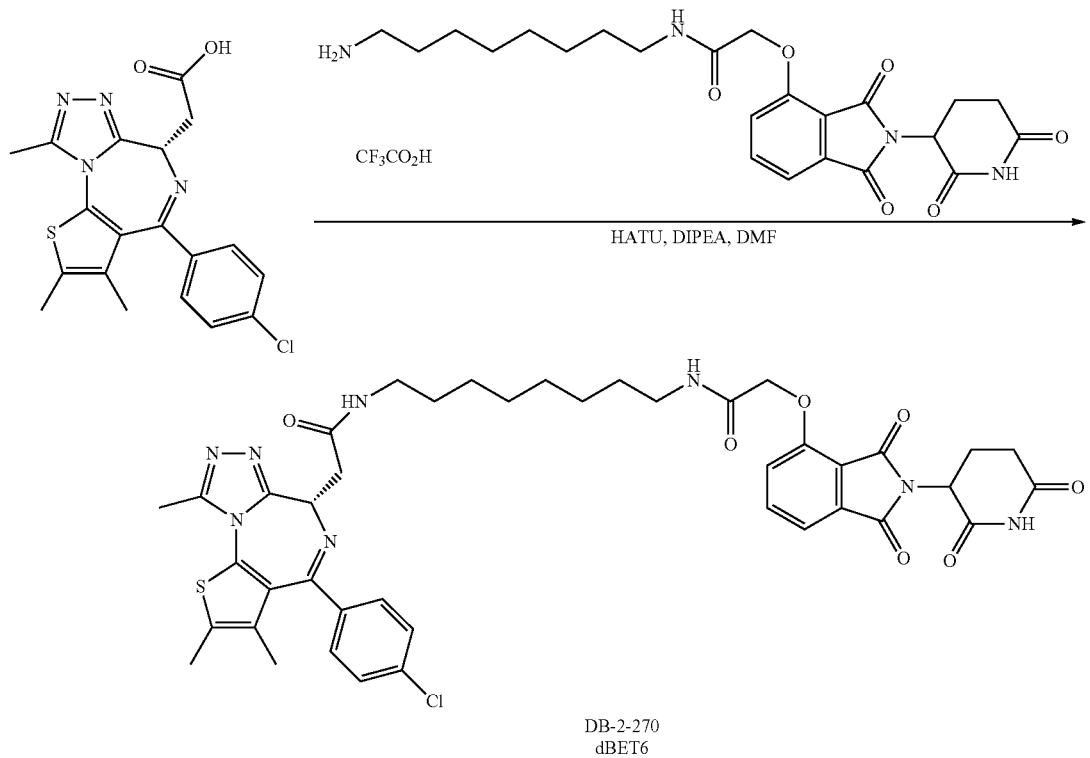

DB-2-270
dBET6

A 0.1 M solution of N-(8-aminooctyl)-2-((2-(2,6-dioxopiperidin-3-yl)-1,3-dioxoisoindolin-4-yl)oxy)acetamide trifluoroacetate in DMF (0.191 mL, 0.0191 mmol, 1 eq) was added to JQ-acid (7.66 mg, 0.0191 mmol, 1 eq) at room temperature. DIPEA (10 microliters, 0.0574 mmol, 3 eq) and HATU (7.3 mg, 0.0191 mmol, 1 eq) were added and the mixture was stirred for 22 hours, diluted with MeOH, and concentrated under reduced pressure. The crude material was purified by preparative HPLC to give a cream colored solid. (8.53 mg, 0.0101 mmol, 53%). $^1$H NMR (400 MHz, Methanol-$d_4$) δ 7.80 (dd, J=8.4, 7.4 Hz, 1H), 7.53 (d, J=7.4 Hz, 1H), 7.49-7.36 (m, 5H), 5.10 (dt, J=12.3, 5.3 Hz, 1H), 4.75 (s, 2H), 4.69 (dd, J=8.8, 5.3 Hz, 1H), 3.42 (dd, J=15.0, 8.9 Hz, 1H), 3.30-3.18 (m, 4H), 2.90-2.64 (m, 7H), 2.45 (s, 3H), 2.13 (dtt, J=10.8, 5.2, 2.6 Hz, 1H), 1.71 (d, J=4.4 Hz, 3H), 1.56 (d, J=6.2 Hz, 4H), 1.33 (d, J=17.1 Hz, 8H). $^{13}$C NMR (100 MHz, cd$_3$od) δ 174.50, 172.38, 171.30, 169.81, 168.28, 167.74, 166.64, 156.25, 138.38, 138.20, 137.55, 134.92, 133.88, 133.42, 132.27, 132.02, 131.50, 129.85, 121.66, 119.30, 117.95, 69.37, 55.01, 50.58, 40.51, 40.12, 38.44, 32.18, 30.46, 30.33, 30.27, 30.21, 27.91, 27.81, 23.63, 14.42, 12.96, 11.55. LCMS 841.64 (M+H).

Example 6

Synthesis of dBET9

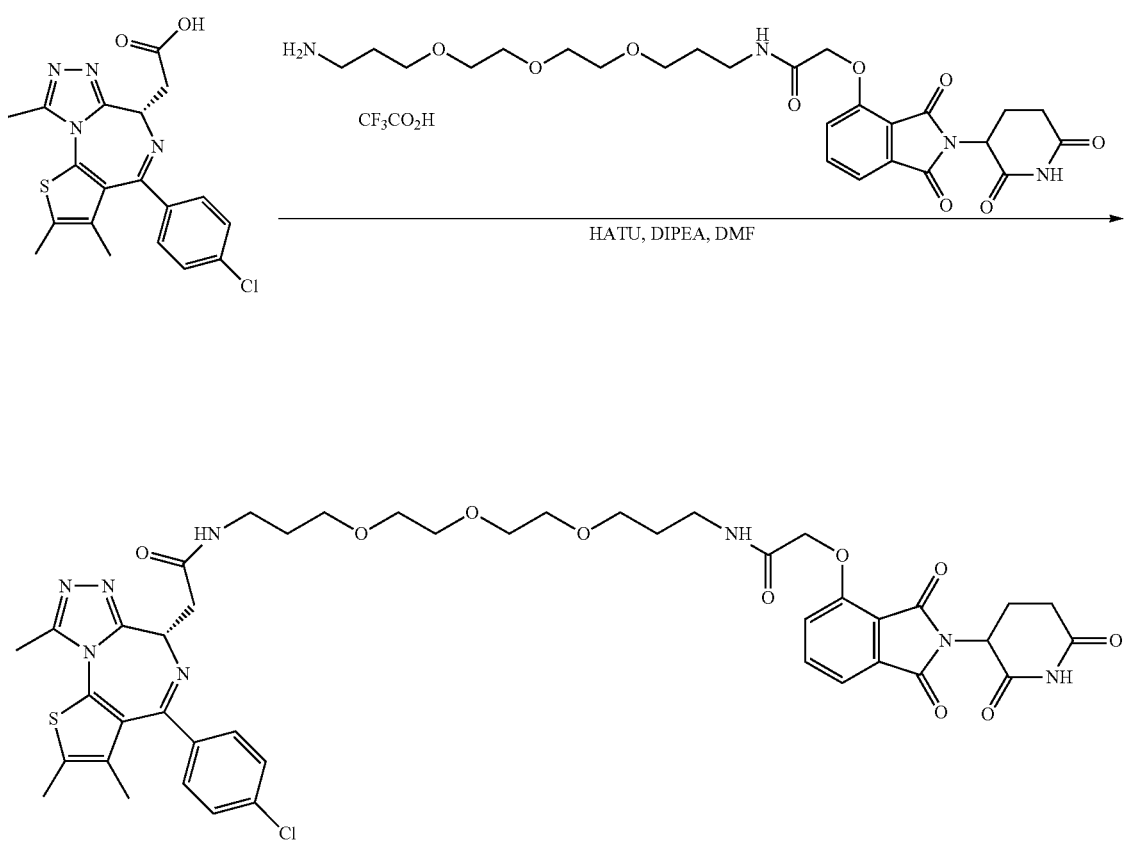

dBET9

A 0.1M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.321 mL, 0.0321 mmol, 1 eq) was added to JQ-acid (12.87 mg, 0.0321 mmol, 1 eq) at room temperature. DIPEA (16.8 microliters, 0.0963 mmol, 3 eq) and HATU (12.2 mg, 0.0321 mmol, 1 eq) were added and the mixture was stirred for 24 hours, diluted with MeOH, and concentrated under reduced pressure. The crude material was purified by preparative HPLC to give a yellow oil. (16.11 mg, 0.0176 mmol, 55%).
$^1$H NMR (400 MHz, Methanol-$d_4$) δ 7.79 (dd, J=8.4, 7.4 Hz, 1H), 7.52 (d, J=7.2 Hz, 1H), 7.49-7.36 (m, 5H), 5.10 (dd, J=12.5, 5.5 Hz, 1H), 4.78-4.67 (m, 3H), 3.64-3.52 (m, 11H), 3.48-3.32 (m, 6H), 2.94-2.64 (m, 7H), 2.52-2.43 (m, 3H), 2.18-2.08 (m, 1H), 1.81 (p, J=6.3 Hz, 4H), 1.73-1.67 (m, 3H). LCMS 918.45 (M+H).

Example 7

Synthesis of dBET17

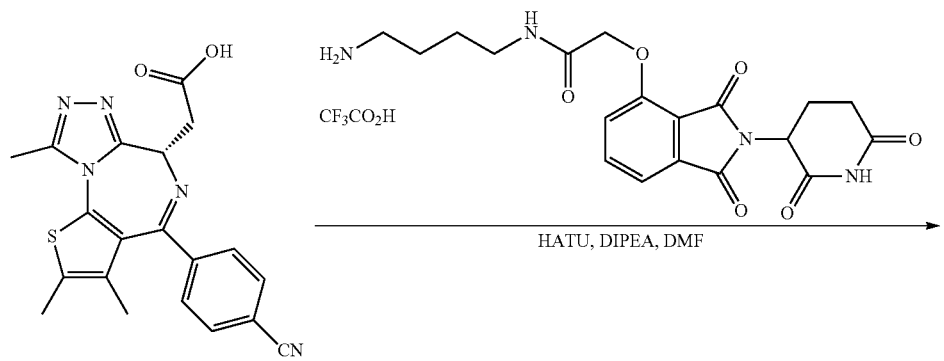

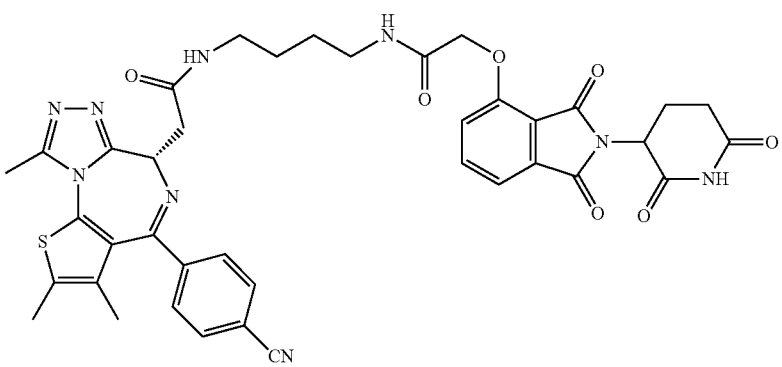

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.281 mL, 0.0281 mmol 1 eq) was added to (S)-2-(4-(4-cyanophenyl)-2,3,9-trimethyl-6H-thieno[3,2-f][1,2,4]triazolo[4,3-a][1,4]diazepin-6-yl)acetic acid (11 mg, 0.0281 mmol, 1 eq) at room temperature. DIPEA (14.7 microliters, 0.0843 mmol, 3 eq) and HATU (10.7 mg, 0.0281 mmol, 1 eq) were added and the mixture was stirred for 24 hours, diluted with EtOAc and washed with saturated sodium bicarbonate, water and brine. The organic layer was dried over sodium sulfate, filtered and condensed. Purification by column chromatography (ISCO, 4 g silica column 0-10% MeOH/DCM) gave a white solid (14.12 mg, 0.0182 mmol, 65%).

$^1$H NMR (400 MHz, Methanol-$d_4$) δ 7.82-7.72 (m, 3H), 7.61 (dd, J=8.5, 2.0 Hz, 2H), 7.51 (d, J=7.9 Hz, 1H), 7.44-7.40 (m, 1H), 5.11-5.05 (m, 1H), 4.76 (s, 2H), 4.66 (dd, J=9.0, 5.1 Hz, 1H), 3.48-3.32 (m, 4H), 3.30-3.23 (m, 1H), 2.87-2.61 (m, 7H), 2.43 (s, 3H), 2.10 (dt, J=10.7, 5.2 Hz, 1H), 1.70-1.59 (m, 7H). $^{13}$C NMR (100 MHz, cd$_3$od) δ 174.42, 172.65, 171.27, 169.92, 168.25, 167.80, 165.88, 156.31, 143.55, 138.24, 134.88, 133.92, 133.50, 133.39, 131.72, 131.46, 130.55, 121.93, 119.39, 119.21, 118.02, 115.17, 69.59, 55.50, 50.55, 40.10, 39.83, 38.86, 32.11, 27.78, 27.67, 23.62, 14.41, 12.91, 11.64. LCMS 776.39 (M+H).

Example 8

Synthesis of dBET15

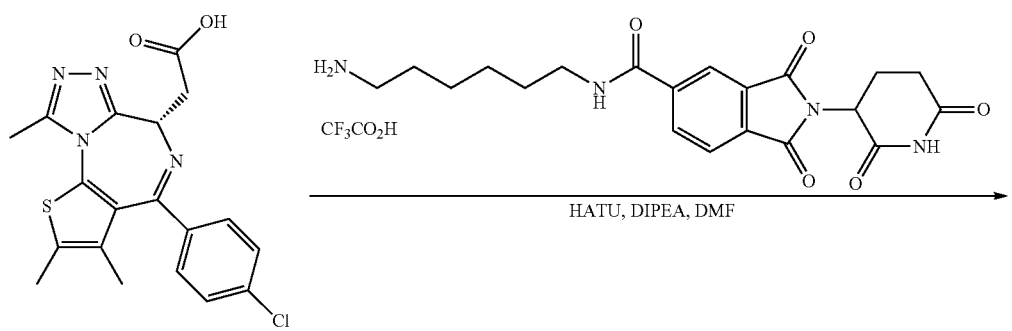

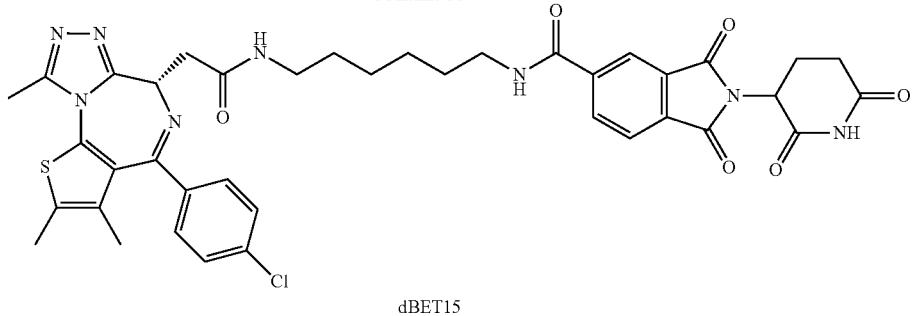

dBET15

N-(6-aminohexyl)-2-(2,6-dioxopiperidin-3-yl)-1,3-dioxoisoindoline-5-carboxamide trifluoroacetate (13.29 mg, 0.258 mmol, 1 eq) and JQ-acid (10.3 mg, 0.0258 mmol, 1 eq) were dissolved in DMF (0.26 mL). DIPEA (13.5 microliters, 0.0775 mmol, 3 eq) was added, followed by HATU (9.8 mg, 0.0258 mmol, 1 eq) and the mixture was stirred at room temperature. After 24 hours, the material was diluted with DCM and purified by column chromatography (ISCO, 0-15% MeOH/DCM) followed by preparative HPLC to give a pale yellow solid (11.44 mg, 0.0146 mmol 57%).

$^1$H NMR (400 MHz, Methanol-$d_4$) δ 8.29-8.23 (m, 2H), 7.93 (dd, J=8.1, 4.2 Hz, 1H), 7.50-7.34 (m, 4H), 5.17-5.11 (m, 1H), 4.75-4.69 (m, 1H), 3.53-3.32 (m, 6H), 3.25 (dd, J=13.8, 6.7 Hz, 1H), 2.90-2.67 (m, 6H), 2.49-2.38 (m, 3H), 2.18-2.10 (m, 1H), 1.64 (d, J=22.4 Hz, 6H), 1.47 (s, 4H). $^{13}$C NMR (100 MHz, cd$_3$od) δ 174.48, 171.17, 168.05, 168.03, 167.99, 167.70, 166.63, 141.81, 138.40, 137.47, 135.09, 134.77, 134.74, 133.96, 133.94, 133.38, 132.24, 132.05, 131.44, 129.85, 124.57, 123.12, 123.09, 54.98, 50.78, 40.88, 40.08, 38.37, 32.13, 30.40, 30.23, 27.34, 27.26, 23.58, 14.40, 12.96, 11.54. LCMS 783.43 (M+H).

Example 9

Synthesis of dBET2

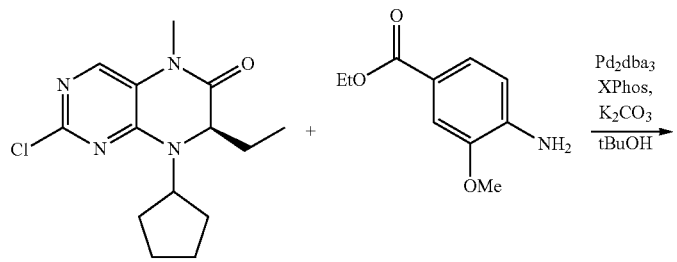

ref: ACIEE, 2011, 50, 9378

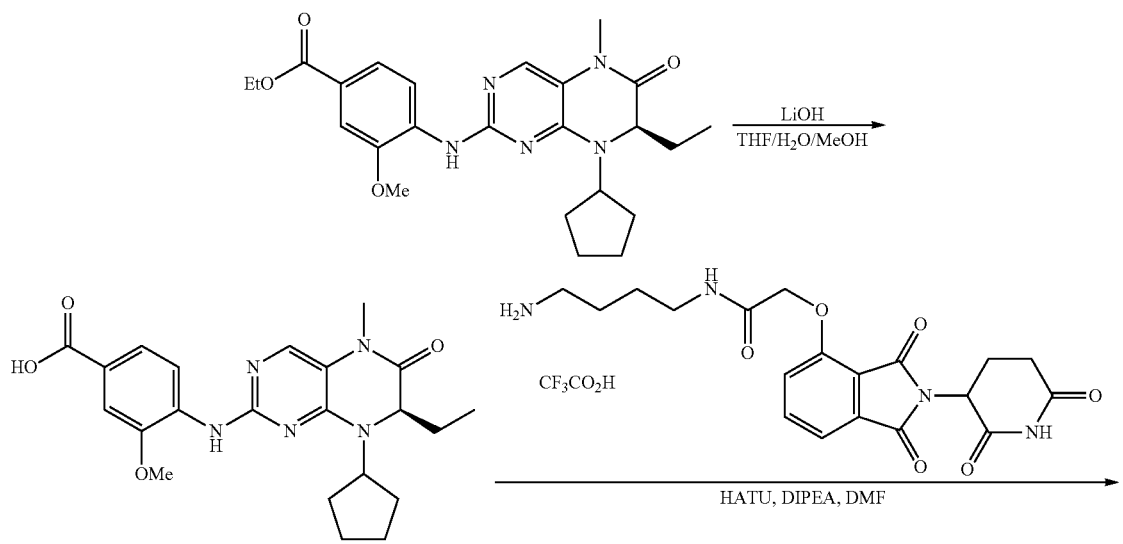

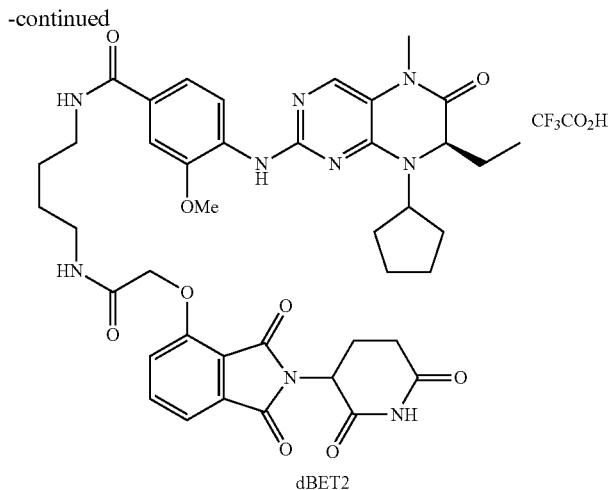

dBET2

(1) Synthesis of (R)-ethyl 4-((8-cyclopentyl-7-ethyl-5-methyl-6-oxo-5,6,7,8-tetrahydropteridin-2-yl)amino)-3-methoxybenzoate

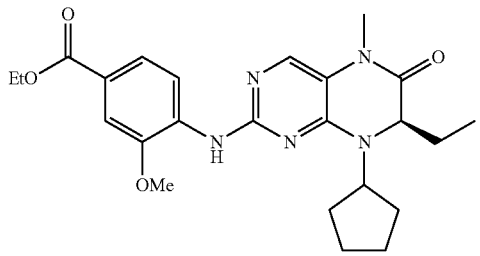

(R)-2-chloro-8-cyclopentyl-7-ethyl-5-methyl-7,8-dihydropteridin-6(5H)-one (44.2 mg, 0.15 mmol, 1 eq), ethyl 4-amino-3-methoxybenzoate (35.1 mg, 0.18 mmol, 1.2 eq), $Pd_2dba_3$ (6.9 mg, 0.0075 mmol, 5 mol %), XPhos (10.7 mg, 0.0225 mmol, 15 mol %) and potassium carbonate (82.9 mg, 0.60 mmol, 4 eq) were dissolved in tBuOH (1.5 mL, 0.1 M) and heated to 100° C. After 21 hours, the mixture was cooled to room temperature, filtered through celite, washed with DCM and concentrated under reduced pressure. Purification by column chromatography (ISCO, 4 g silica column, 0-100% EtOAc/hexanes over an 18 minute gradient) gave a yellow oil (52.3 mg, 0.115 mmol, 77%). $^1$H NMR (400 MHz, Chloroform-d) δ 8.57 (d, J=8.5 Hz, 1H), 7.69 (td, J=6.2, 2.9 Hz, 2H), 7.54 (d, J=1.8 Hz, 1H), 4.52 (t, J=7.9 Hz, 1H), 4.37 (q, J=7.1 Hz, 2H), 4.23 (dd, J=7.9, 3.7 Hz, 1H), 3.97 (s, 3H), 3.33 (s, 3H), 2.20-2.12 (m, 1H), 2.03-1.97 (m, 1H), 1.86 (ddd, J=13.9, 7.6, 3.6 Hz, 4H), 1.78-1.65 (m, 4H), 1.40 (t, J=7.1 Hz, 3H), 0.88 (t, J=7.5 Hz, 3H). LCMS 454.32 (M+H).

(2) Synthesis of (R)-4-((8-cyclopentyl-7-ethyl-5-methyl-6-oxo-5,6,7,8-tetrahydropteridin-2-yl)amino)-3-methoxybenzoic acid

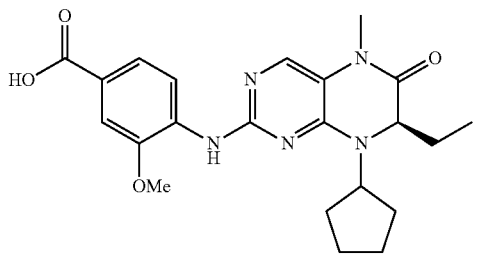

(R)-ethyl 4-((8-cyclopentyl-7-ethyl-5-methyl-6-oxo-5,6,7,8-tetrahydropteridin-2-yl)amino)-3-methoxybenzoate (73.8 mg, 0.163 mmol, 1 eq) and LiOH (11.7 mg, 0.489 mmol, 3 eq) were dissolved in MeOH (0.82 mL) THF (1.63 mL) and water (0.82 mL). After 20 hours, an additional 0.82 mL of water was added and the mixture was stirred for an additional 24 hours before being purified by preparative HPLC to give a cream colored solid (53 mg, 0.125 mmol, 76%). $^1$H NMR (400 MHz, Methanol-$d_4$) δ 7.97 (d, J=8.4 Hz, 1H), 7.67 (dd, J=8.3, 1.6 Hz, 1H), 7.64-7.59 (m, 2H), 4.38 (dd, J=7.0, 3.2 Hz, 1H), 4.36-4.29 (m, 1H), 3.94 (s, 3H), 3.30 (s, 3H), 2.13-1.98 (m, 2H), 1.95-1.87 (m, 2H), 1.87-1.76 (m, 2H), 1.73-1.57 (m, 4H), 0.86 (t, J=7.5 Hz, 3H). $^{13}$C NMR (100 MHz, $cd_3od$) δ 168.67, 163.72, 153.59, 150.74, 150.60, 130.95, 127.88, 125.97, 123.14, 121.68, 116.75, 112.35, 61.76, 61.66, 56.31, 29.40, 29.00, 28.68, 28.21, 23.57, 23.41, 8.69. LCMS 426.45 (M+H).

(3) Synthesis of dBET2

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.183 mL, 0.0183 mmol 1.2 eq) was added to (R)-4-((8-cyclopentyl-7-ethyl-5-methyl-6-oxo-5,6,7,8-tetrahydropteridin-2-yl)amino)-3-methoxybenzoic acid (6.48 mg, 0.0152 mmol, 1 eq) at room temperature. DIPEA (7.9 microliters, 0.0456 mmol, 3 eq) and HATU (6.4 mg, 0.0168 mmol, 1.1 eq) were added and the mixture was stirred for 23 hours, before being purified by preparative HPLC to give a yellow solid (9.44 mg, 0.0102 mmol, 67%). $^1$H NMR (400 MHz, Methanol-$d_4$) δ 7.84-7.77 (m, 2H), 7.58 (d, J=1.8 Hz, 2H), 7.53-7.46 (m, 2H), 7.42 (d, J=8.4 Hz, 1H), 5.11-5.05 (m, 1H), 4.76 (s, 2H), 4.48 (dd, J=6.5, 3.1 Hz, 1H), 4.33-4.24 (m, 1H), 3.95 (s, 3H), 3.49-3.35 (m, 4H), 2.97 (d, J=10.5 Hz, 3H), 2.89-2.65 (m, 5H), 2.17-1.99 (m, 4H), 1.89 (dd, J=14.5, 7.3 Hz, 2H), 1.69-1.54 (m, 6H), 1.36 (dt, J=7.6, 3.9 Hz, 1H), 0.85 (t, J=7.5 Hz, 3H). $^{13}$C NMR (100 MHz, $cd_3od$) δ 176.52, 174.48, 173.05, 171.34, 169.99, 168.91, 168.25, 167.80, 164.58, 156.34, 154.48, 153.10, 150.63, 138.22, 134.89, 133.96, 129.53, 123.93, 121.87, 120.78, 119.36, 117.99, 111.54, 69.55, 63.29, 63.10, 56.68, 50.55, 40.71, 39.86, 32.15, 29.43, 29.26, 28.73, 28.63, 27.81, 27.77, 24.25, 23.63, 8.47. LCMS 810.58 (M+H).

Example 10

Synthesis of dBET7

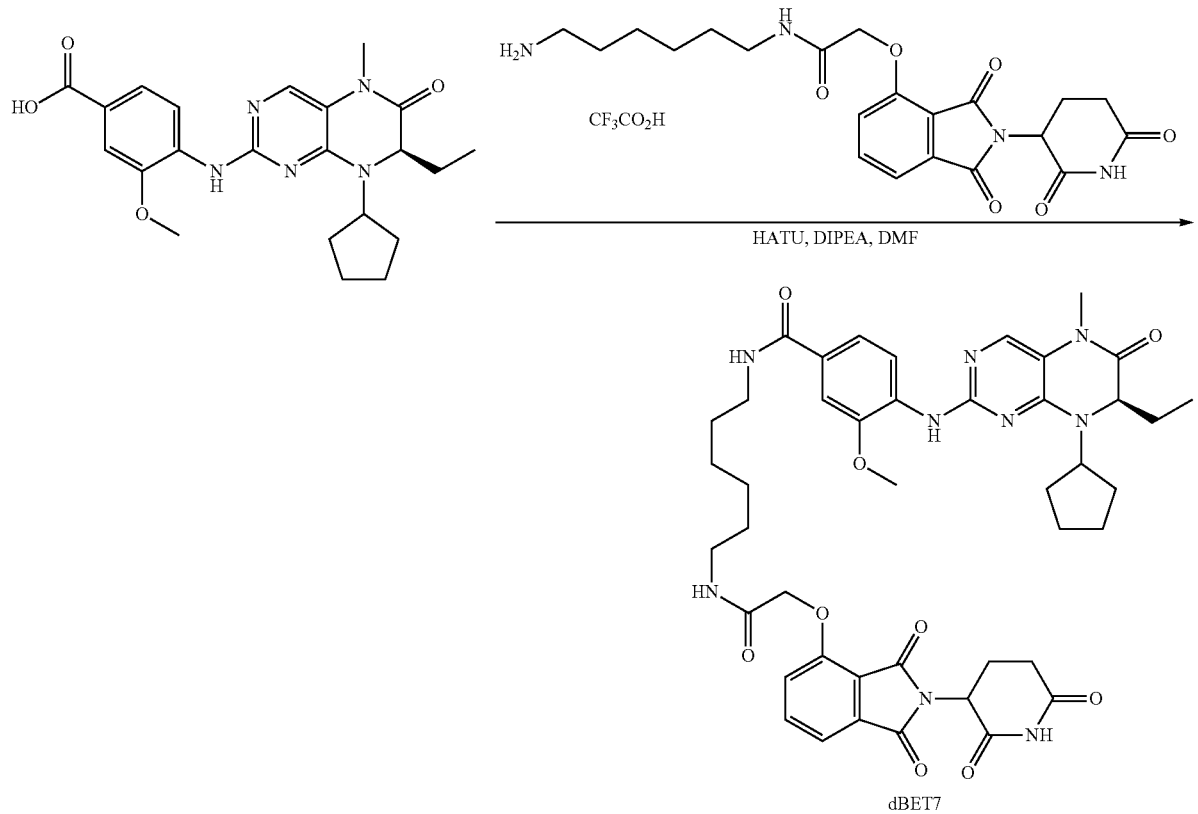

A 0.1 M solution N-(6-aminohexyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 19 hours, before being purified by preparative HPLC to give the desired trifluoracetate salt as a yellow solid (13.62 mg, 0.0143 mmol, 77%).

$^1$H NMR (400 MHz, Methanol-d$_4$) δ 7.80 (t, J=8.3 Hz, 2H), 7.61-7.57 (m, 2H), 7.55-7.49 (m, 2H), 7.42 (d, J=8.4 Hz, 1H), 5.13 (dd, J=12.6, 5.5 Hz, 1H), 4.75 (s, 2H), 4.48 (dd, J=6.5, 3.2 Hz, 1H), 4.33-4.24 (m, 1H), 3.97 (s, 3H), 3.40 (t, J=7.1 Hz, 2H), 3.34 (d, J=6.7 Hz, 2H), 3.30 (s, 3H), 2.98 (d, J=8.5 Hz, 1H), 2.89-2.82 (m, 1H), 2.79-2.63 (m, 3H), 2.17-2.00 (m, 4H), 1.91 (dt, J=14.4, 7.1 Hz, 3H), 1.61 (dt, J=13.4, 6.6 Hz, 7H), 1.47-1.41 (m, 3H), 0.86 (t, J=7.5 Hz, 3H). $^{13}$C NMR (100 MHz, cd$_3$od) δ 174.54, 171.37, 169.84, 168.84, 168.27, 167.74, 164.59, 156.26, 154.47, 153.18, 150.69, 138.19, 134.91, 134.05, 129.47, 124.78, 124.01, 121.65, 120.77, 119.29, 117.92, 117.86, 111.55, 69.34, 63.31, 63.13, 56.67, 50.53, 40.97, 39.96, 32.16, 30.42, 30.19, 29.42, 29.26, 28.72, 28.62, 27.65, 27.46, 24.26, 23.65, 8.47. LCMS 838.60 (M+H).

Example 11

Synthesis of dBET8

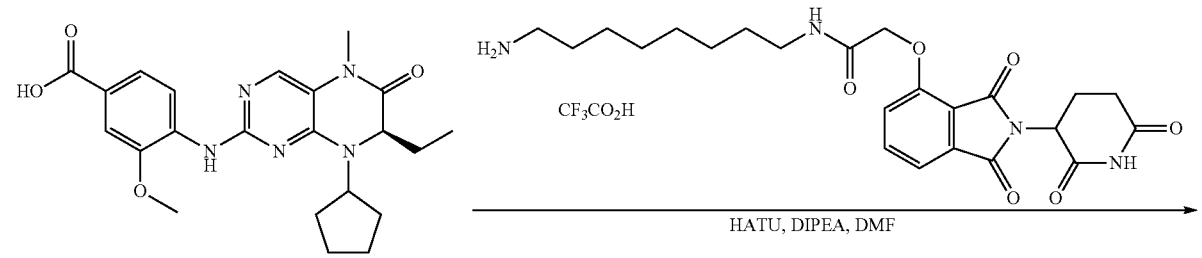

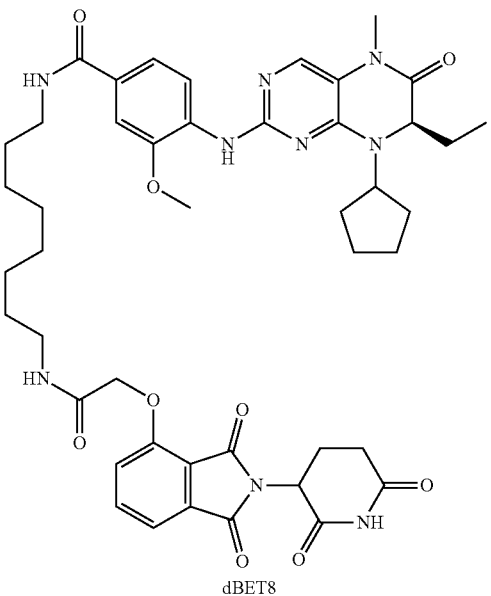

dBET8

A 0.1 M solution N-(8-aminooctyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 16 hours, before being purified by preparative HPLC to give the desired trifluoracetate salt as an off-white solid (7.15 mg, 0.007296 mmol, 39%).

$^1$H NMR (400 MHz, Methanol-d$_4$) δ 7.83-7.77 (m, 2H), 7.61-7.56 (m, 2H), 7.55-7.50 (m, 2H), 7.42 (d, J=8.5 Hz, 1H), 5.13 (dd, J=12.6, 5.5 Hz, 1H), 4.75 (s, 2H), 4.49 (dd, J=6.6, 3.3 Hz, 1H), 4.33-4.24 (m, 1H), 3.97 (s, 3H), 3.39 (t, J=7.1 Hz, 2H), 3.34-3.32 (m, 2H), 3.30 (s, 3H), 3.01-2.83 (m, 2H), 2.82-2.65 (m, 3H), 2.17-2.01 (m, 4H), 1.91 (dt, J=14.2, 7.4 Hz, 1H), 1.68-1.54 (m, 7H), 1.37 (s, 7H), 0.86 (t, J=7.5 Hz, 3H). $^{13}$C NMR (100 MHz, cd$_3$od) δ 174.52, 171.35, 169.81, 168.85, 168.28, 167.74, 164.58, 156.27, 154.47, 153.89, 150.64, 138.19, 134.93, 134.18, 129.52, 129.41, 124.91, 123.83, 121.67, 120.76, 119.31, 117.95, 117.89, 111.57, 69.37, 63.37, 63.17, 56.67, 50.58, 41.12, 40.12, 32.19, 30.43, 30.28, 30.22, 30.19, 29.40, 29.25, 28.71, 28.62, 27.94, 27.75, 24.29, 23.65, 8.46. LCMS 866.56 (M+H).

Example 12

Synthesis of dBET10

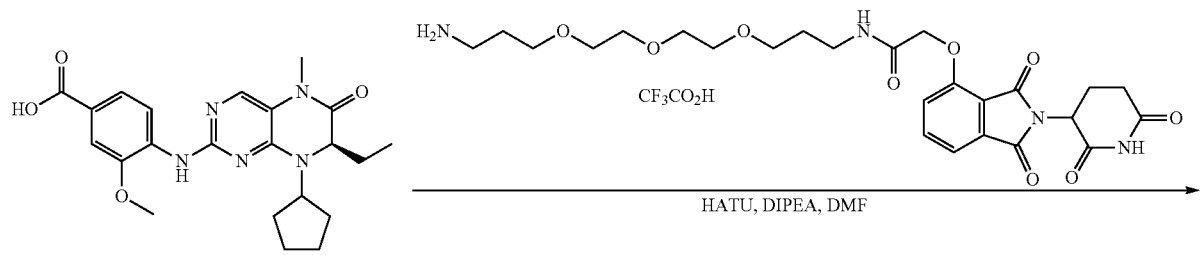

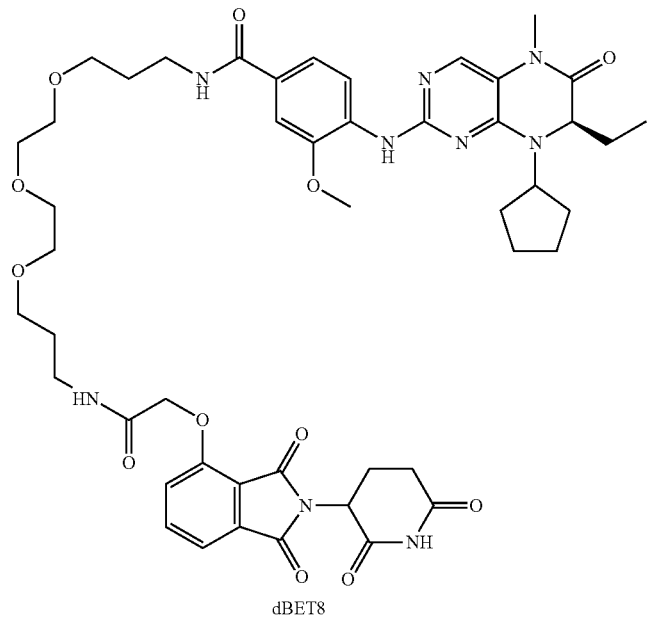

dBET8

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.172 mL, 0.0172 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.3 mg, 0.0172 mmol, 1 eq) at room temperature. DIPEA (9.0 microliters, 0.0515 mmol, 3 eq) and HATU (6.5 mg, 0.0172 mmol, 1 eq) were added and the mixture was stirred for 23 hours, before being purified by preparative HPLC to give the desired trifluoroacetate salt as an off-white oil (10.7 mg, 0.0101 mmol, 59%).

$^1$H NMR (400 MHz, Methanol-$d_4$) δ 7.78 (d, J=8.3 Hz, 1H), 7.75 (dd, J=8.4, 7.4 Hz, 1H), 7.56-7.51 (m, 2H), 7.49-7.44 (m, 2H), 7.36 (d, J=8.4 Hz, 1H), 5.08 (dd, J=12.4, 5.4 Hz, 1H), 4.69 (s, 2H), 4.44 (dd, J=6.7, 3.2 Hz, 1H), 4.30-4.21 (m, 1H), 3.92 (s, 3H), 3.59-3.42 (m, 12H), 3.35 (t, J=6.7 Hz, 2H), 3.25 (s, 3H), 2.95-2.64 (m, 5H), 2.13-1.95 (m, 4H), 1.91-1.71 (m, 7H), 1.65-1.48 (m, 4H), 0.81 (t, J=7.5 Hz, 3H). $^{13}$C NMR (100 MHz, cd$_3$od) δ 174.50, 171.35, 169.83, 168.77, 168.25, 167.68, 164.57, 156.26, 154.47, 153.05, 150.59, 138.19, 134.92, 133.89, 129.53, 124.57, 123.98, 121.72, 120.75, 119.26, 117.95, 117.86, 111.54, 71.51, 71.46, 71.28, 71.20, 70.18, 69.65, 69.41, 63.27, 63.07, 56.71, 50.57, 38.84, 37.59, 32.17, 30.41, 30.32, 29.46, 29.26, 28.73, 28.64, 24.27, 23.65, 8.49. LCMS 942.62 (M+H).

Example 13

Synthesis of dBET16

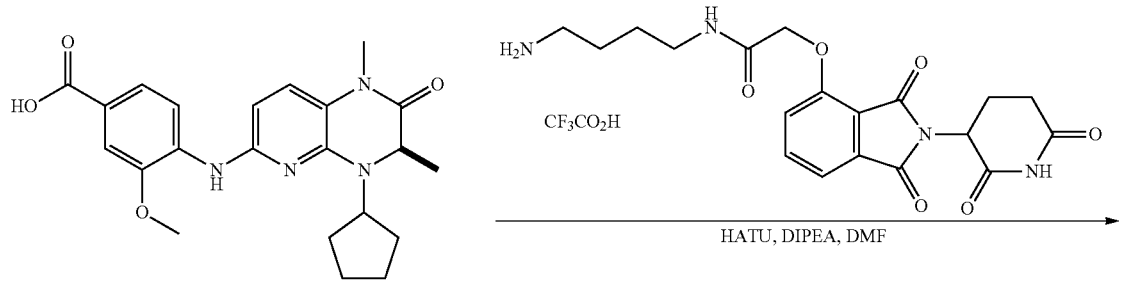

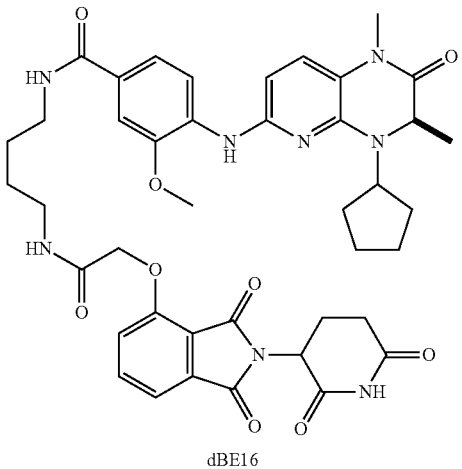

dBE16

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.402 mL, 0.0402 mmol 1 eq) was added (R)-4-((4-cyclopentyl-1,3-dimethyl-2-oxo-1,2,3,4-tetrahydropyrido[2,3-b]pyrazin-6-yl)amino)-3-methoxybenzoic acid (16.55 mg, 0.0402 mmol, 1 eq) at room temperature. DIPEA (21 microliters, 0.1206 mmol, 3 eq) and HATU (15.3 mg, 0.0402 mmol, 1 eq) were added and the mixture was stirred for 21 hours, before being purified by preparative HPLC, followed by column chromatography (ISCO, 12 g NH2-silica column, 0-15% MeOH/DCM, 20 min gradient) to give HPLC to give a brown solid (10.63 mg, 0.0134 mmol, 33%).

$^1$H NMR (400 MHz, Methanol-$d_4$) δ 8.22 (d, J=8.4 Hz, 1H), 7.78 (dd, J=8.4, 7.4 Hz, 1H), 7.73-7.68 (m, 1H), 7.49 (d, J=7.4 Hz, 2H), 7.46-7.39 (m, 2H), 6.98 (d, J=8.8 Hz, 1H), 5.97-5.87 (m, 1H), 5.06 (dd, J=12.6, 5.4 Hz, 1H), 4.76 (s, 2H), 3.98 (s, 3H), 3.61 (s, 2H), 3.44-3.36 (m, 4H), 2.92 (s, 1H), 2.78 (dd, J=14.3, 5.2 Hz, 1H), 2.68 (ddd, J=17.7, 8.2, 4.5 Hz, 2H), 2.36-2.26 (m, 2H), 2.10-1.90 (m, 5H), 1.76-1.62 (m, 6H), 1.31 (d, J=16.0 Hz, 4H). LCMS 795.38 (M+H).

Example 14

Synthesis of dBET11

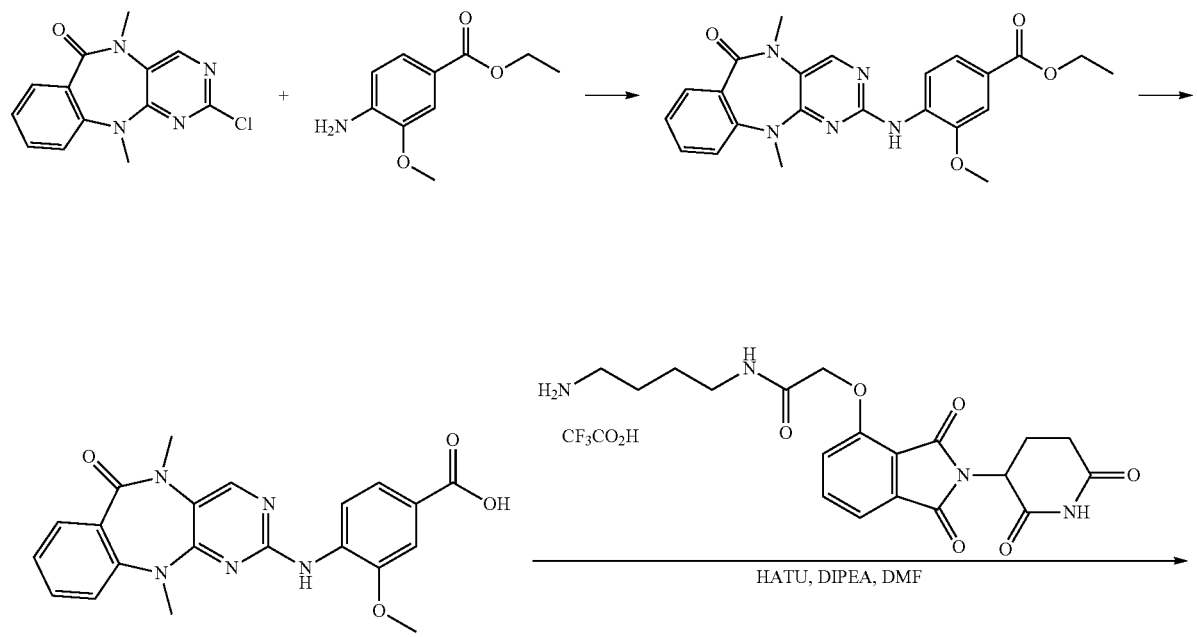

-continued

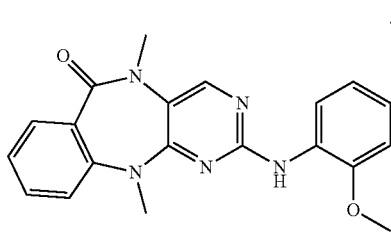 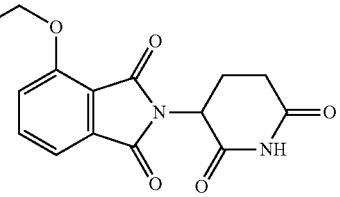

dBET11

(1) Synthesis of ethyl 4-((5,11-dimethyl-6-oxo-6,11-dihydro-5H-benzo[e]pyrimido[5,4-b][1,4]diazepin-2-yl)amino)-3-methoxybenzoate 2-chloro-5,11-dimethyl-5H-benzo[e]pyrimido[5,4-b][1,4]diazepin-6(11H)-one (82.4 mg, 0.30 mmol, 1 eq), ethyl 4-amino-3-methoxybenzoate (70.3 mg, 0.36 mmol, 1.2 eq) $Pd_2dba_3$ (13.7 mg, 0.015 mmol, 5 mol %), XPhos (21.5 mg, 0.045 mmol, 15 mol %) and potassium carbonate (166 mg, 1.2 mmol, 4 eq) were dissolved in tBuOH (3.0 mL) and heated to 100° C. After 17 hours, the mixture was cooled room temperature and filtered through celite. The mixture was purified by column chromatography (ISCO, 12 g silica column, 0-100% EtOAc/hexanes, 19 min gradient) to give an off white solid (64.3 mg, 0.148 mmol, 49%).

$^1$H NMR (400 MHz, 50% $cd_3od/cdcl_3$) δ 8.51 (d, J=8.5 Hz, 1H), 8.17 (s, 1H), 7.73 (ddd, J=18.7, 8.1, 1.7 Hz, 2H), 7.52 (d, J=1.8 Hz, 1H), 7.46-7.41 (m, 1H), 7.15-7.10 (m, 2H), 4.34 (q, J=7.1 Hz, 4H), 3.95 (s, 3H), 3.47 (s, 3H), 3.43 (s, 3H), 1.38 (t, J=7.1 Hz, 3H). $^{13}$C NMR (100 MHz, 50% $cd_3od/cdcl_3$) δ 169.28, 167.39, 164.29, 155.64, 151.75, 149.73, 147.45, 146.22, 133.88, 133.18, 132.37, 126.44, 124.29, 123.70, 123.36, 122.26, 120.58, 118.05, 116.83, 110.82, 61.34, 56.20, 38.62, 36.25, 14.51. LCMS 434.33 (M+H).

(2) Synthesis of 4-((5,11-dimethyl-6-oxo-6,11-dihydro-5H-benzo[e]pyrimido[5,4-b][1,4]diazepin-2-yl)amino)-3-methoxybenzoic acid Ethyl 4-((5,11-dimethyl-6-oxo-6,11-dihydro-5H-benzo[e]pyrimido[5,4-b][1,4]diazepin-2-yl)amino)-3-methoxybenzoate (108.9 mg, 0.251 mmol, 1 eq) and LiOH (18 mg) were dissolved in THF (2.5 mL) and water (1.25 mL). After 24 hours, MeOH (0.63 mL) was added to improved solubility) and stirred for an additional 24 hours before being diluted with MeOH and purified by preparative HPLC to give a light yellow solid (41.31 mg).

$^1$H NMR (400 MHz, Methanol-$d_4$) δ 8.51 (d, J=8.5 Hz, 1H), 8.22 (s, 1H), 7.73 (ddd, J=11.8, 8.1, 1.7 Hz, 2H), 7.57 (d, J=1.8 Hz, 1H), 7.49-7.44 (m, 1H), 7.19-7.11 (m, 2H), 3.97 (s, 3H), 3.48 (s, 3H), 3.45 (s, 3H). LCMS 406.32 (M+H).

(3) Synthesis of dBET11

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.190 mL, 0.0190 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid (7.71 mg, 0.0190 mmol, 1 eq) at room temperature. DIPEA (9.9 microliters, 0.0571 mmol, 3 eq) and HATU (7.2 mg, 0.0190 mmol, 1 eq) were added and the mixture was stirred for 22 hours, before being purified by preparative HPLC to give HPLC to give the desired trifluoracetate salt as a cream colored solid (6.72 mg, 0.00744 mmol, 39%).

$^1$H NMR (400 MHz, Methanol-$d_4$) δ 8.46 (d, J=8.3 Hz, 1H), 8.21 (s, 1H), 7.79-7.73 (m, 2H), 7.52 (d, J=7.1 Hz, 1H), 7.50-7.43 (m, 3H), 7.33 (d, J=8.2 Hz, 1H), 7.15 (dd, J=7.7, 5.9 Hz, 2H), 4.98 (dd, J=12.0, 5.5 Hz, 1H), 4.69 (s, 2H), 3.97 (s, 3H), 3.49 (s, 3H), 3.46-3.34 (m, 7H), 2.81-2.67 (m, 3H), 2.13-2.08 (m, 1H), 1.69 (dt, J=6.6, 3.5 Hz, 4H). $^{13}$C NMR (100 MHz, $cd_3od$) δ 173.40, 170.10, 169.68, 169.00, 168.85, 167.60, 167.15, 164.77, 156.01, 155.42, 151.83, 150.03, 148.21, 137.82, 134.12, 133.48, 132.58, 132.52, 128.11, 126.72, 124.54, 122.33, 121.06, 120.63, 118.77, 118.38, 117.94, 117.62, 109.67, 68.90, 56.33, 49.96, 40.16, 39.48, 38.72, 36.34, 31.82, 27.24, 23.16. LCMS 790.48 (M+H).

Example 15

Synthesis of dBET12

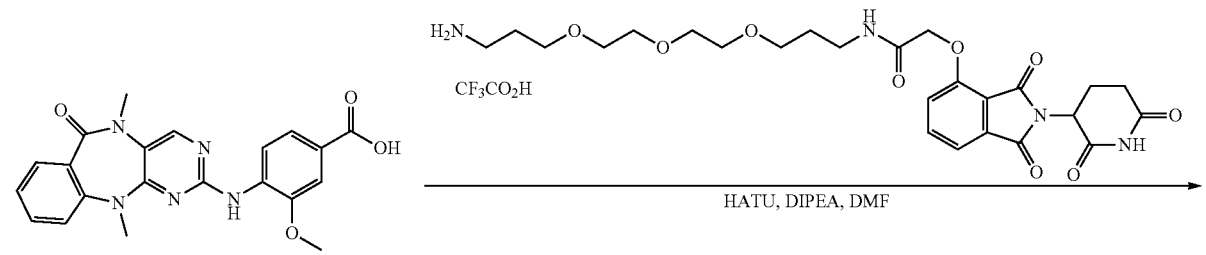

-continued

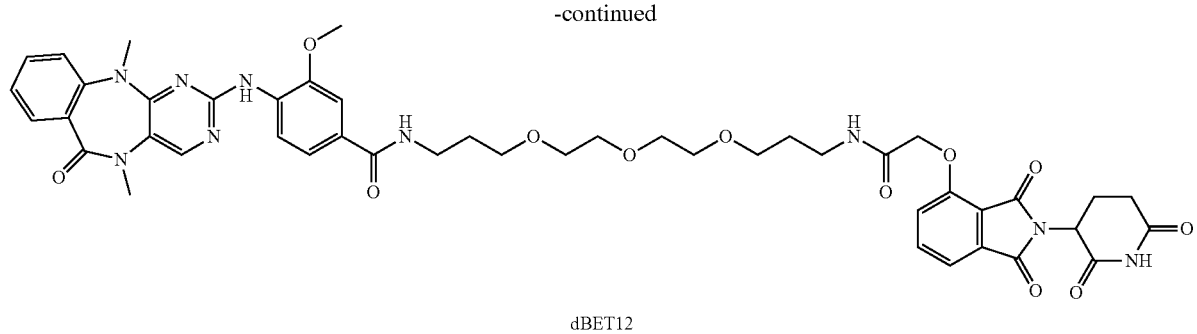

dBET12

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid (7.53 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 22 hours, before being purified by preparative HPLC to give HPLC to give the desired trifluoracetate salt as a cream colored solid (7.50 mg, 0.00724 mmol, 39%).

$^1$H NMR (400 MHz, Methanol-$d_4$) δ 8.46 (d, J=8.9 Hz, 1H), 8.21 (s, 1H), 7.73 (dd, J=15.2, 7.8 Hz, 2H), 7.50-7.42 (m, 3H), 7.28 (d, J=8.5 Hz, 1H), 7.15 (t, J=7.7 Hz, 2H), 5.01 (dd, J=11.8, 5.8 Hz, 1H), 4.68 (s, 2H), 3.97 (s, 3H), 3.67-3.58 (m, 7H), 3.58-3.43 (m, 10H), 3.39 (t, J=6.8 Hz, 2H), 3.35 (s, 2H), 2.97 (s, 1H), 2.84-2.70 (m, 3H), 2.16-2.07 (m, 1H), 1.93-1.76 (m, 4H). LCMS 922.57 (M+H).

Example 16

Synthesis of dBET13

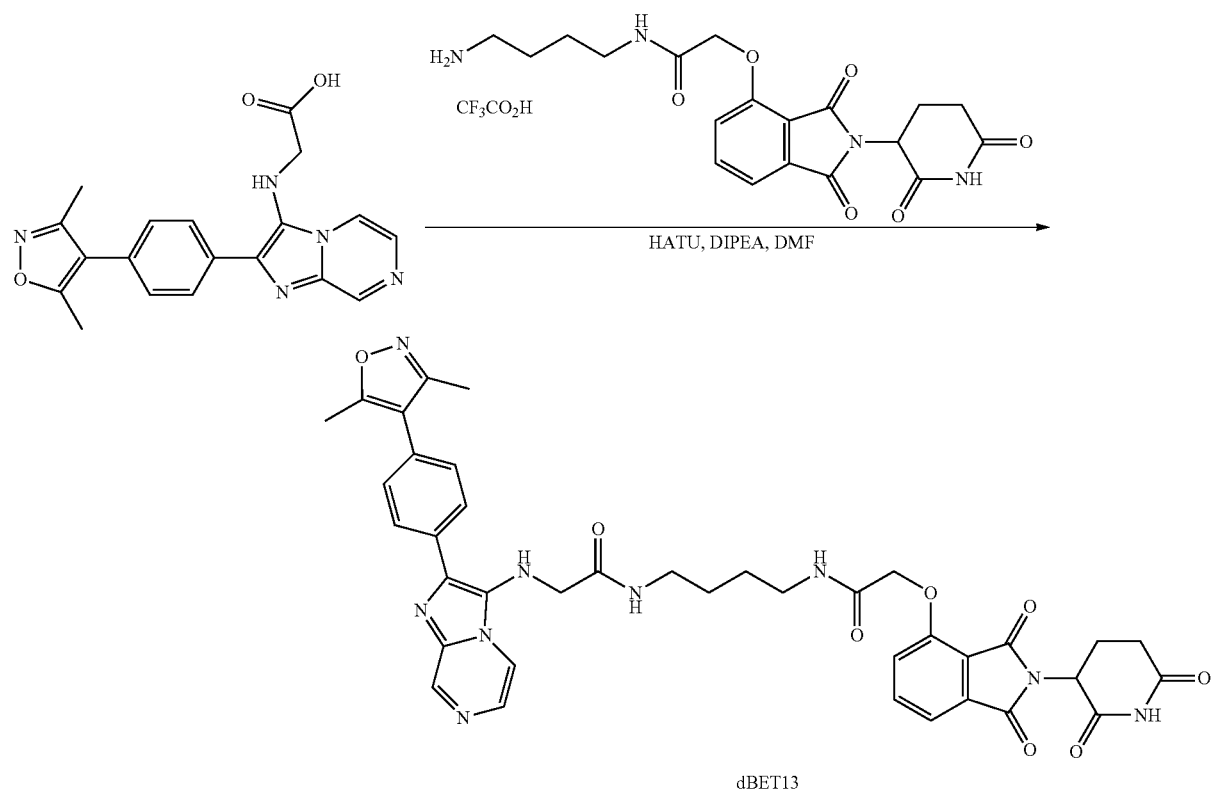

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.501 mL, 0.0501 mmol 1 eq) was added to 2-((2-(4-(3,5-dimethylisoxazol-4-yl)phenyl)imidazo[1,2-a]pyrazin-3-yl)amino)acetic acid (synthesized as in McKeown et al, J. Med. Chem, 2014, 57, 9019) (18.22 mg, 0.0501 mmol, 1 eq) at room temperature. DIPEA (26.3 microliters, 0.150 mmol, 3 eq) and HATU (19.0 mg, 0.0501 mmol, 1 eq) were added and the mixture was stirred for 21 hours, before being purified by preparative HPLC to give HPLC to give the desired trifluoracetate salt as a dark yellow oil (29.66 mg, 0.0344 mmol, 69%). $^1$H NMR (400 MHz, Methanol-d$_4$) δ 9.09 (s, 1H), 8.65 (d, J=5.2 Hz, 1H), 8.14-8.06 (m, 2H), 7.94-7.88 (m, 1H), 7.80-7.74 (m, 1H), 7.59-7.47 (m, 3H), 7.40 (dd, J=8.4, 4.7 Hz, 1H), 5.11-5.06 (m, 1H), 4.72 (d, J=9.8 Hz, 2H), 3.90 (s, 2H), 3.25-3.22 (m, 1H), 3.12 (t, J=6.4 Hz, 1H), 2.96 (s, 2H), 2.89-2.79 (m, 1H), 2.76-2.62 (m, 2H), 2.48-2.42 (m, 3H), 2.29 (s, 3H), 2.10 (ddq, J=10.2, 5.3, 2.7 Hz, 1H), 1.49-1.45 (m, 2H), 1.37 (dd, J=6.7, 3.6 Hz, 2H). $^{13}$C NMR (100 MHz, cd$_3$od) δ 174.45, 171.98, 171.35, 169.88, 168.17, 167.85, 167.40, 159.88, 156.28, 141.82, 138.26, 135.85, 134.82, 133.09, 132.06, 130.75, 129.67, 122.07, 121.94, 119.30, 118.98, 118.06, 117.24, 69.56, 50.56, 40.05, 39.73, 32.13, 27.53, 23.62, 18.71, 17.28, 11.64, 10.85. LCMS 748.49 (M+H).

Example 17

Synthesis of dBET14 dimethylisoxazol-4-yl)phenyl)imidazo[1,2-a]pyrazin-3-yl) amino)acetic acid (synthesized as in McKeown et al, J. Med. Chem, 2014, 57, 9019) (18.52 mg, 0.0510 mmol, 1 eq) at room temperature. DIPEA (26.6 microliters, 0.153 mmol, 3 eq) and HATU (19.4 mg, 0.0510 mmol, 1 eq) were added and the mixture was stirred for 22 hours, before being purified by preparative HPLC to give HPLC to give the desired trifluoracetate salt as a dark yellow oil (32.63 mg, 0.0328 mmol, 64%).

$^1$H NMR (400 MHz, Methanol-d$_4$) δ 9.09 (s, 1H), 8.66 (d, J=5.4 Hz, 1H), 8.17-8.08 (m, 2H), 7.92 (d, J=5.6 Hz, 1H), 7.77 (dd, J=8.4, 7.4 Hz, 1H), 7.60-7.47 (m, 3H), 7.39 (d, J=8.4 Hz, 1H), 5.09 (dd, J=12.4, 5.5 Hz, 1H), 4.71 (s, 2H), 3.91 (s, 2H), 3.62-3.46 (m, 10H), 3.38 (dt, J=16.0, 6.4 Hz, 3H), 3.18 (t, J=6.8 Hz, 2H), 2.97 (s, 1H), 2.89-2.81 (m, 1H), 2.78-2.66 (m, 2H), 2.47 (s, 3H), 2.31 (s, 3H), 2.16-2.08 (m, 1H), 1.79 (dt, J=12.8, 6.5 Hz, 2H), 1.64 (t, J=6.3 Hz, 2H). $^{13}$C NMR (100 MHz, cd$_3$od) δ 174.48, 171.88, 171.34, 169.80, 168.22, 167.69, 167.42, 159.87, 156.24, 141.87,

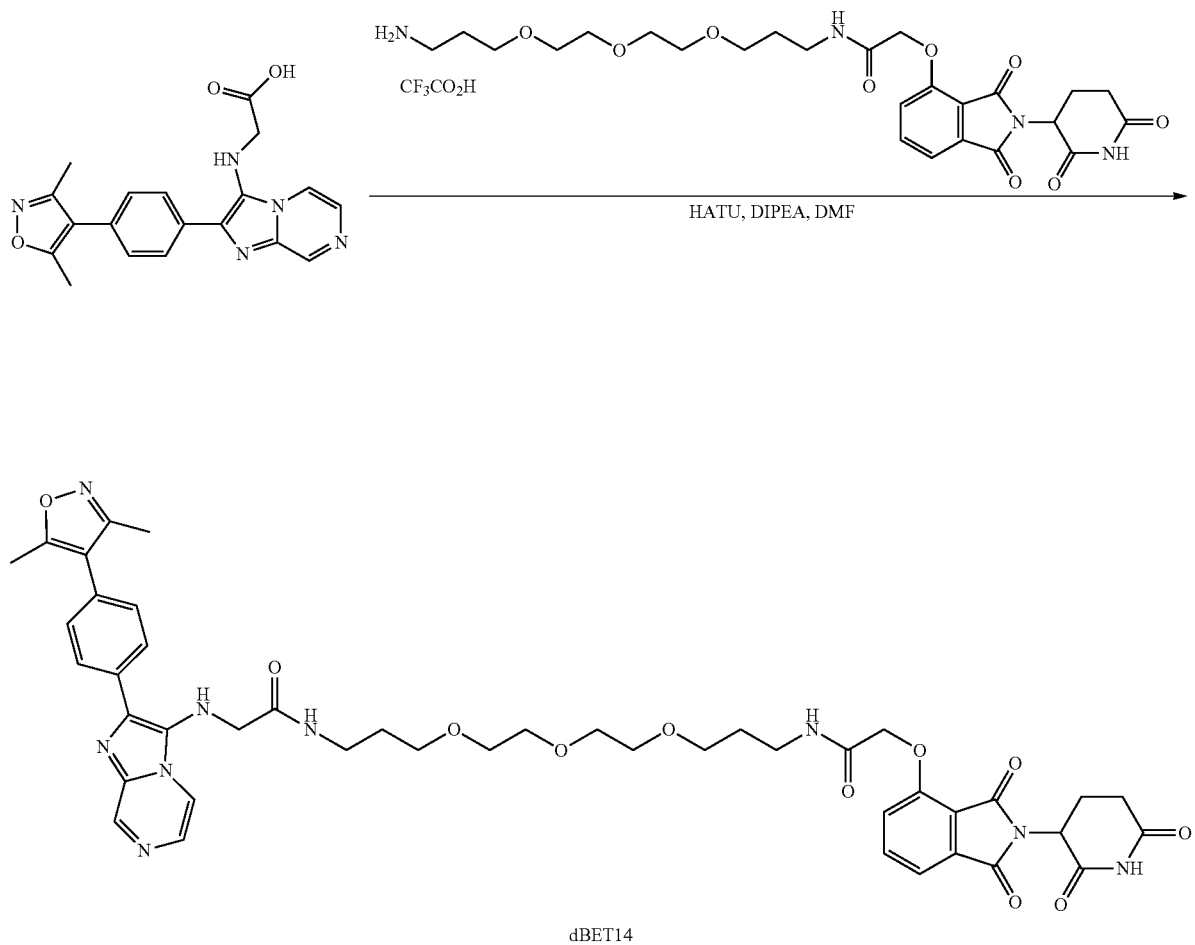

A 0.1 M solution N-(3-(2-(2-(3-aminopropoxy)ethoxy) ethoxy)propyl)-2-((2-(2,6-dioxopiperidin-3-yl)-1,3-dioxoisoindolin-4-yl)oxy)acetamide trifluoroacetate in DMF (0.510 mL, 0.0510 mmol 1 eq) was added to 2-((2-(4-(3,5-

138.21, 135.89, 134.88, 133.13, 132.04, 130.76, 129.67, 122.08, 121.69, 119.20, 117.94, 117.23, 71.44, 71.22, 71.10, 69.92, 69.62, 69.38, 50.57, 49.64, 38.11, 37.55, 32.16, 30.30, 30.20, 23.63, 11.67, 10.88. LCMS 880.46 (M+H).

201 202
Example 18
Synthesis of dBET18
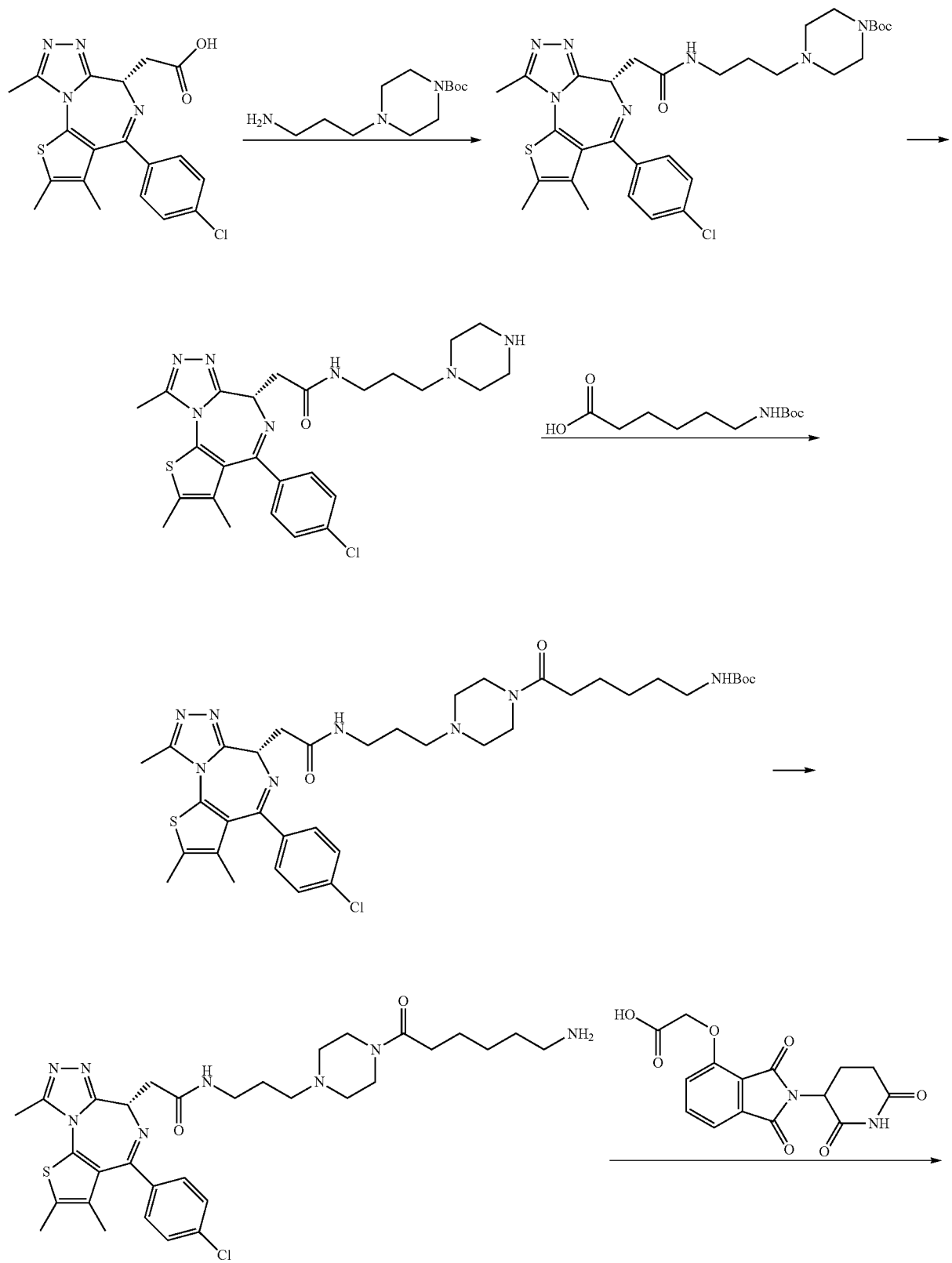

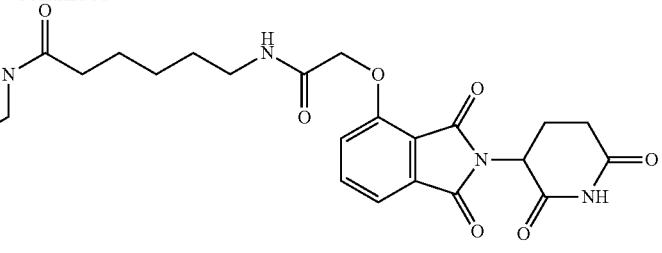
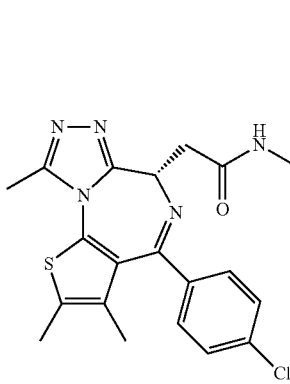

dBET18

(1) Synthesis of (S)-tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate JQ-acid (176.6 mg, 0.441 mmol, 1 eq) was dissolved in DMF (4.4 mL) at room temperature. HATU (176 mg, 0.463 mmol, 1.05 eq) was added, followed by DIPEA (0.23 mL), 1.32 mmol, 3 eq). After 10 minutes, tert-butyl 4-(3-aminopropyl)piperazine-1-carboxylate (118 mg, 0.485 mmol, 1.1 eq) was added as a solution in DMF (0.44 mL). After 24 hours, the mixture was diluted with half saturated sodium bicarbonate and extracted twice with DCM and once with EtOAc. The combined organic layer was dried over sodium sulfate, filtered and condensed. Purification by column chromatography (ISCO, 24 g silica column, 0-15% MeOH/DCM, 23 minute gradient) gave a yellow oil (325.5 mg, quant yield)

$^1$H NMR (400 MHz, Chloroform-d) δ 7.67 (t, J=5.3 Hz, 1H), 7.41-7.28 (m, 4H), 4.58 (dd, J=7.5, 5.9 Hz, 1H), 3.52-3.23 (m, 8H), 2.63 (s, 9H), 2.37 (s, 3H), 1.80-1.69 (m, 2H), 1.64 (s, 3H), 1.42 (s, 9H). $^{13}$C NMR (100 MHz, cdcl$_3$) δ 171.41, 164.35, 155.62, 154.45, 150.20, 136.92, 136.64, 132.19, 131.14, 130.98, 130.42, 129.98, 128.80, 80.24, 56.11, 54.32, 52.70, 38.96, 37.85, 28.42, 25.17, 14.43, 13.16, 11.82. LCMS 626.36 (M+H).

(2) Synthesis of (S)-2-(4-(4-chlorophenyl)-2,3,9-trimethyl-6H-thieno[3,2-f][1,2,4]triazolo[4,3-a][1,4]diazepin-6-yl)-N-(3-(piperazin-1-yl)propyl)acetamide (S)-tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate (325.5 mg) was dissolved in DCM (5 mL) and MeOH (0.5 mL). A solution of 4M HCl in dioxane (1 mL) was added and the mixture was stirred for 16 hours, then concentrated under a stream of nitrogen to give a yellow solid (231.8 mg) which was used without further purification.

$^1$H NMR (400 MHz, Methanol-d$_4$) δ 7.64-7.53 (m, 4H), 5.05 (t, J=7.1 Hz, 1H), 3.81-3.66 (m, 6H), 3.62-3.33 (m, 9H), 3.30 (p, J=1.6 Hz, 1H), 2.94 (s, 3H), 2.51 (s, 3H), 2.09 (dq, J=11.8, 6.1 Hz, 2H), 1.72 (s, 3H). $^{13}$C NMR (100 MHz, cd$_3$od) δ 171.78, 169.38, 155.83, 154.03, 152.14, 140.55, 136.33, 134.58, 134.53, 133.33, 132.73, 130.89, 130.38, 56.07, 53.54, 41.96, 37.22, 36.23, 25.11, 14.48, 13.14, 11.68. LCMS 526.29 (M+H).

(3) Synthesis of (S)-tert-butyl (6-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)-6-oxohexyl)carbamate (S)-2-(4-(4-chlorophenyl)-2,3,9-trimethyl-6H-thieno[3,2-f][1,2,4]triazolo[4,3-a][1,4]diazepin-6-yl)-N-(3-(piperazin-1-yl)propyl)acetamide (62.1 mg) and 6-((tert-butoxycarbonyl)amino)hexanoic acid (24.0 mg, 0.1037 mmol, 1 eq) were dissolved in DMF (1 mL). DIPEA (72.2 microliters, 0.4147 mmol, 4 eq) was added, followed by HATU (39.4 mg, 0.1037 mmol, 1 eq) and the mixture was stirred for 25 hours. The mixture was diluted with half saturated sodium bicarbonate and extracted three times with DCM. The combined organic layer was dried over sodium sulfate, filtered and condensed. Purification by column chromatography (ISCO, 4 g silica column, 0-15% MeOH/DCM, 15 minute gradient) gave a yellow oil (71.75 mg, 0.0970 mmol, 94%).

$^1$H NMR (400 MHz, Chloroform-d) δ 7.61 (s, 1H), 7.43-7.28 (m, 4H), 4.63 (s, 1H), 4.61-4.56 (m, 1H), 3.82-3.21 (m, 10H), 3.11-3.01 (m, 2H), 2.61 (d, J=24.3 Hz, 9H), 2.38 (s, 3H), 2.28 (t, J=7.4 Hz, 2H), 1.73 (dq, J=13.8, 7.4 Hz, 2H), 1.63-1.55 (m, 2H), 1.53-1.24 (m, 14H). $^{13}$C NMR (100 MHz, cdcl$_3$) δ 171.63, 171.11, 164.34, 156.17, 155.66, 150.21, 136.96, 136.72, 132.25, 131.14, 131.01, 130.47, 130.00, 128.85, 79.11, 56.42, 54.46, 53.06, 52.82, 45.04, 41.02, 40.47, 39.29, 38.33, 33.00, 29.90, 28.54, 26.60, 25.29, 24.86, 14.47, 13.20, 11.86. LCMS 739.37 (M+H).

(4) Synthesis of (S)-N-(3-(4-(6-aminohexanoyl)piperazin-1-yl)propyl)-2-(4-(4-chlorophenyl)-2,3,9-trimethyl-6H-thieno[3,2-f][1,2,4]triazolo[4,3-a][1,4]diazepin-6-yl)acetamide (S)-tert-butyl (6-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)-6-oxohexyl)carbamate (71.75 mg, 0.0970 mmol, 1 eq) was dissolved in DCM (2 mL) and MeOH (0.2 mL). A solution of 4M HCl in dioxane (0.49 mL) was added and the mixture was stirred for 2 hours, then concentrated under a stream of nitrogen, followed by vacuum to give a yellow foam (59.8 mg, 0.0840 mmol, 87%).

$^1$H NMR (400 MHz, Methanol-d$_4$) δ 7.68-7.53 (m, 4H), 5.04 (d, J=6.6 Hz, 1H), 4.66 (d, J=13.6 Hz, 1H), 4.23 (d, J=13.6 Hz, 1H), 3.63-3.34 (m, 7H), 3.29-3.00 (m, 5H), 2.95 (d, J=6.0 Hz, 5H), 2.51 (d, J=9.2 Hz, 5H), 2.08 (s, 2H), 1.77-1.62 (m, 7H), 1.45 (dt, J=15.3, 8.6 Hz, 2H). $^{13}$C NMR (100 MHz, cd$_3$od) δ 173.77, 171.84, 169.35, 155.85, 153.99, 140.56, 136.40, 134.58, 133.35, 132.70, 130.39, 55.83, 53.57, 52.92, 52.70, 43.57, 40.55, 39.67, 37.33, 36.25, 33.17, 28.26, 26.94, 25.33, 25.26, 14.49, 13.15, 11.65. LCMS 639.35 (M+H).

(5) Synthesis of dBET18

(S)-N-(3-(4-(6-aminohexanoyl)piperazin-1-yl)propyl)-2-(4-(4-chlorophenyl)-2,3,9-trimethyl-6H-thieno[3,2-f][1,2,4]triazolo[4,3-a][1,4]diazepin-6-yl)acetamide dihydrochloride (20.0 mg, 0.0281 mmol, 1 eq) and 2-((2-(2,6-dioxopiperidin-3-yl)-1,3-dioxoisoindolin-4-yl)oxy)acetic acid (9.32 mg, 0.0281 mmol, 1 eq) were dissolved in DMF (0.281 mL). DIPEA (19.6 microliters, 0.1124 mmol, 4 eq) was added, followed by HATU (10.7 mg, 0.0281 mmol, 1 eq). After 24 hours, the mixture was diluted with MeOH and purified by preparative HPLC to give the desired trifluoracetate salt.

$^1$H NMR (400 MHz, Methanol-$d_4$) δ 7.83-7.79 (m, 1H), 7.54 (d, J=7.1 Hz, 1H), 7.45 (q, J=8.8 Hz, 5H), 5.12 (dd, J=12.5, 5.4 Hz, 1H), 4.76 (s, 2H), 4.68 (t, J=7.3 Hz, 1H), 3.59-3.32 (m, 8H), 3.28-3.18 (m, 4H), 2.87 (ddd, J=19.0, 14.7, 5.3 Hz, 2H), 2.80-2.65 (m, 6H), 2.44 (d, J=6.8 Hz, 5H), 2.33-2.25 (m, 1H), 2.14 (dd, J=9.8, 4.9 Hz, 1H), 2.06-1.89 (m, 3H), 1.70 (s, 3H), 1.61 (dq, J=14.4, 7.3, 6.9 Hz, 4H), 1.45-1.37 (m, 2H). $^{13}$C NMR (100 MHz, cd$_3$od) δ 174.52, 173.97, 173.69, 171.44, 169.88, 168.26, 167.83, 166.72, 156.36, 138.28, 137.84, 134.89, 133.52, 132.12, 131.83, 131.38, 129.89, 121.87, 119.32, 118.01, 69.52, 55.64, 55.03, 52.79, 50.58, 43.69, 39.77, 38.57, 36.89, 33.47, 32.16, 29.93, 27.34, 25.76, 25.45, 23.63, 14.39, 12.94, 11.66. LCMS 953.43 (M+H).

Example 19

Synthesis of dGR1

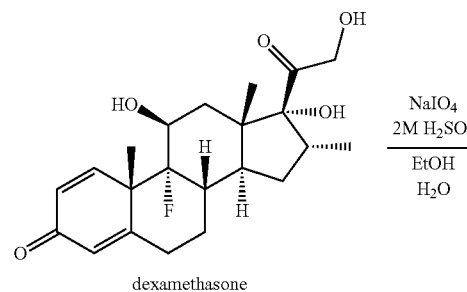

dexamethasone

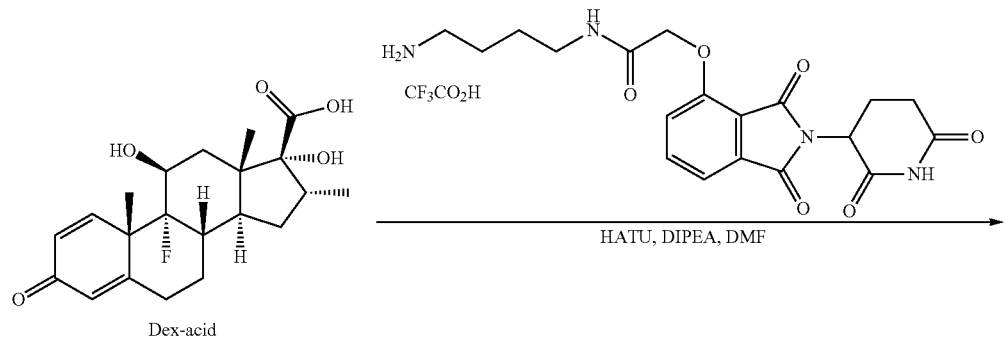

Dex-acid

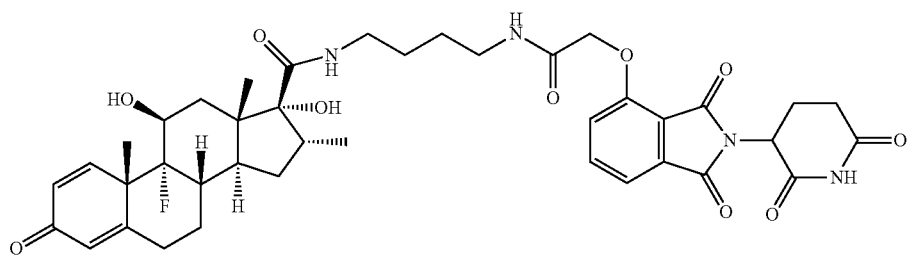

DB-2-247
dGR1

Example 20
Synthesis of dGR2
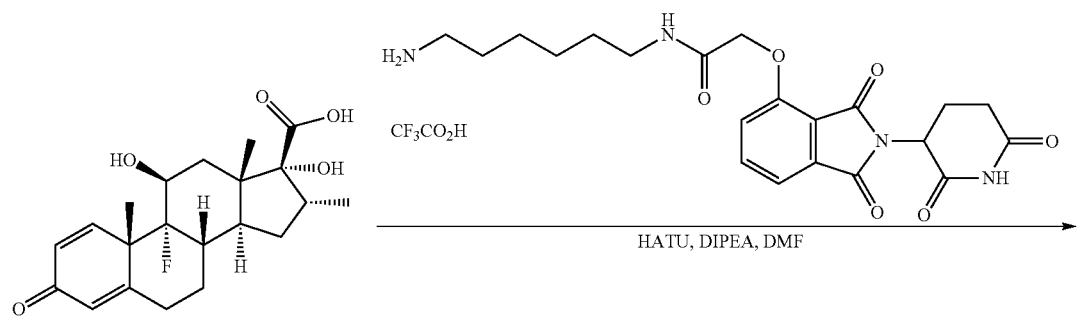
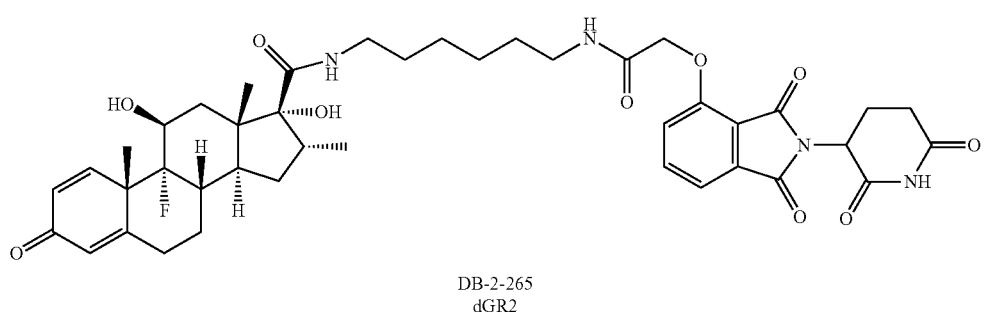
DB-2-265
dGR2
Example 21
Synthesis of dGR3
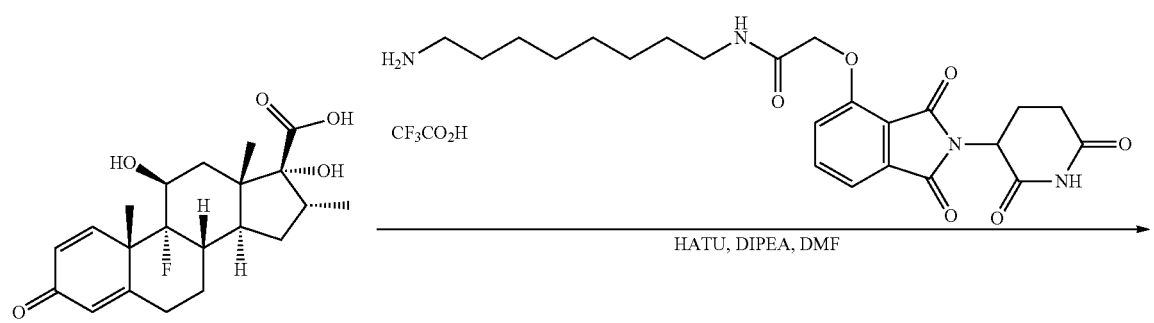
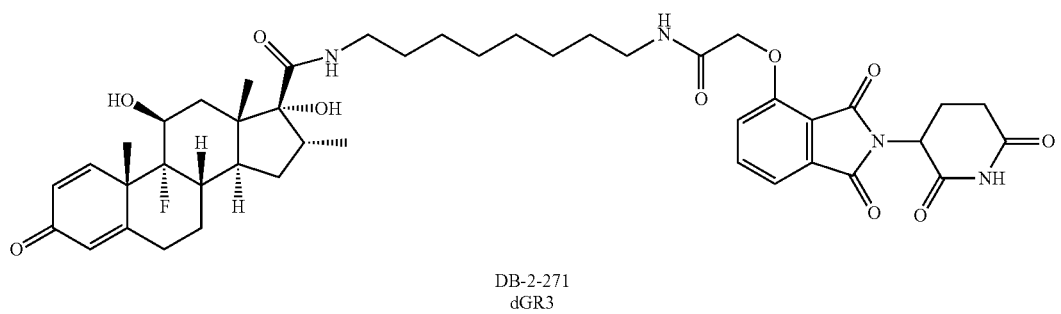
DB-2-271
dGR3

Example 22

Synthesis of dFKBP-1

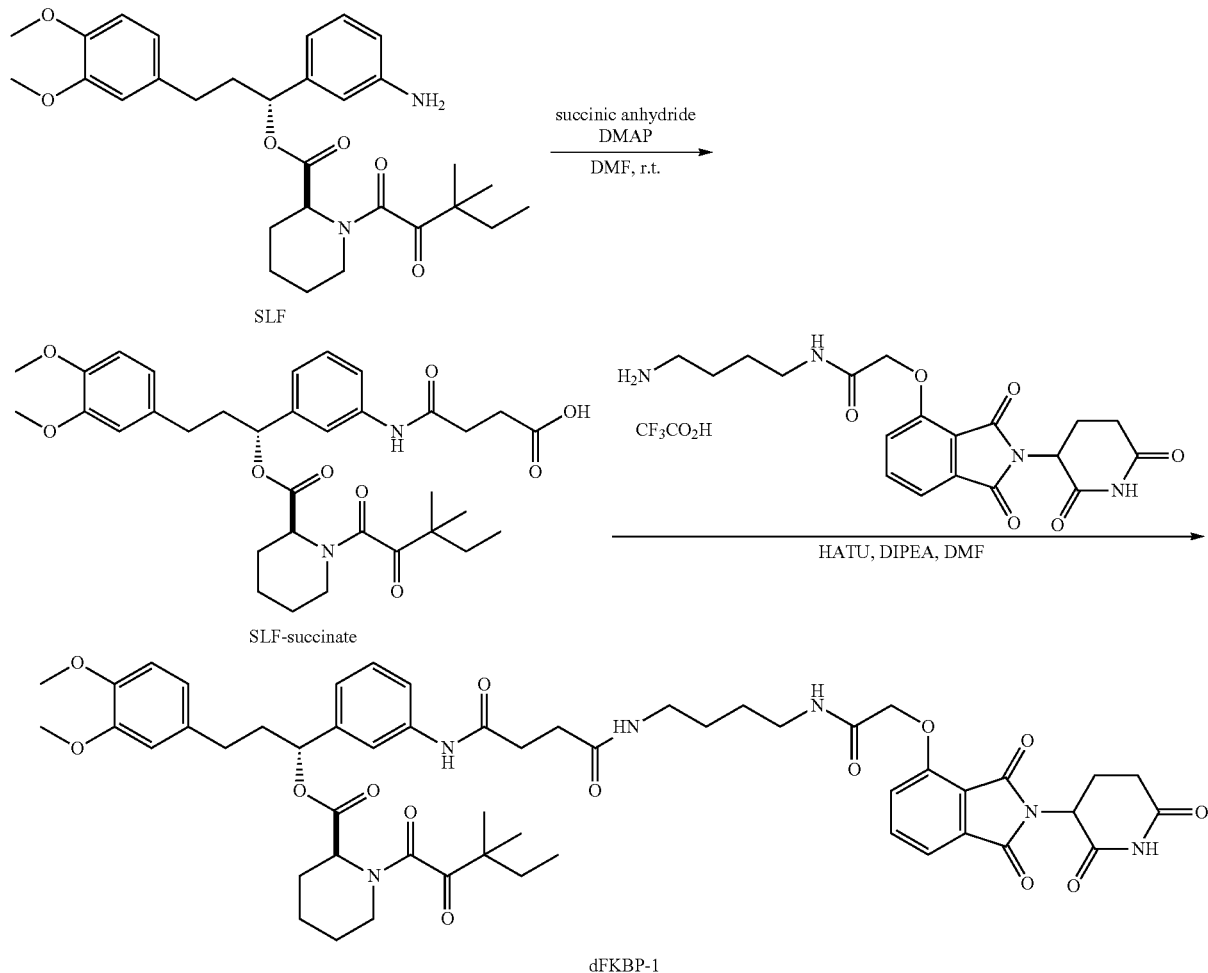

(1) Synthesis of SLF-Succinate

SLF (25 mg, 2.5 mL of a 10 mg/mL solution in MeOAc, 0.0477 mmol, 1 eq) was combined with DMF (0.48 mL, 0.1 M) and succinic anhydride (7.2 mg, 0.0715 mmol, 1.5 eq) and stirred at room temperature for 24 hours. Low conversion was observed and the mixture was placed under a stream of $N_2$ to remove the MeOAc. An additional 0.48 mL of DMF was added, along with an additional 7.2 mg succinic anhydride and DMAP (5.8 mg, 0.0477 mmol, 1 eq). The mixture was then stirred for an additional 24 hours before being purified by preparative HPLC to give SLF-succinate as a yellow oil (24.06 mg, 0.0385 mmol, 81%).

$^1$H NMR (400 MHz, Methanol-d4) δ 7.62 (d, J=10.7 Hz, 1H), 7.44 (d, J=8.0 Hz, 1H), 7.26 (td, J=7.9, 2.7 Hz, 1H), 7.07-6.97 (m, 1H), 6.80 (dd, J=8.1, 2.1 Hz, 1H), 6.74-6.66 (m, 2H), 5.73 (dd, J=8.1, 5.5 Hz, 1H), 5.23 (d, J=4.8 Hz, 1H), 3.83 (s, 3H), 3.81 (s, 3H), 3.39-3.29 (m, 4H), 3.21 (td, J=13.2, 3.0 Hz, 1H), 2.68-2.50 (m, 5H), 2.37-2.19 (m, 2H), 2.12-2.02 (m, 1H), 1.79-1.61 (m, 4H), 1.49-1.30 (m, 2H), 1.27-1.05 (m, 6H), 0.82 (dt, J=41.2, 7.5 Hz, 3H). LCMS 624.72 (M+H).

(2) Synthesis of dFKBP-1

N-(4-aminobutyl)-2-((2-(2,6-dioxopiperidin-3-yl)-1,3-dioxoisoindolin-4-yl)oxy)acetamide trifluoroacetate (9.9 mg, 0.0192 mmol, 1 eq) was added to SLF succinate (11.98 mg, 0.0192 mmol, 1 eq) as a solution in 0.192 mL DMF (0.1 M). DIPEA (10.0 microliters, 0.0575 mmol, 3 eq) was added, followed by HATU (7.3 mg, 0.0192 mmol, 1 eq). The mixture was stirred for 17 hours, then diluted with MeOH and purified by preparative HPLC to give dFKBP-1 (7.7 mg, 0.00763 mmol, 40%) as a yellow solid.

$^1$H NMR (400 MHz, Methanol-d4) δ 7.81 (s, 1H), 7.77-7.70 (m, 1H), 7.55-7.49 (m, 2H), 7.26 (dd, J=8.0, 5.3 Hz, 2H), 7.05-6.99 (m, 1H), 6.77 (d, J=8.8 Hz, 1H), 6.66 (d, J=6.8 Hz, 2H), 5.77-5.72 (m, 1H), 5.24 (d, J=4.8 Hz, 1H), 4.99 (dd, J=12.3, 5.7 Hz, 1H), 4.68-4.59 (m, 2H), 3.82 (s, 3H), 3.81 (s, 3H), 3.32 (dt, J=3.3, 1.6 Hz, 4H), 3.26-3.14 (m, 3H), 2.79 (dd, J=18.9, 10.2 Hz, 3H), 2.64-2.48 (m, 5H), 2.34 (d, J=14.4 Hz, 1H), 2.22 (d, J=9.2 Hz, 1H), 2.14-2.02 (m, 2H), 1.78-1.49 (m, 9H), 1.43-1.30 (m, 2H), 1.20-1.04 (m, 6H), 0.90-0.76 (m, 3H). 13C NMR (100 MHz, cd3od) δ 208.51, 173.27, 172.64, 171.63, 169.93, 169.51, 168.04, 167.69, 167.09, 166.71, 154.92, 149.05, 147.48, 140.76, 138.89, 137.48, 133.91, 133.67, 129.36, 122.19, 120.61, 120.54, 119.82, 118.41, 118.12, 117.79, 112.12, 111.76, 68.54, 56.10, 55.98, 51.67, 46.94, 44.57, 39.32, 39.01, 38.23, 32.64, 31.55, 31.43, 26.68, 26.64, 25.08, 23.52, 23.21, 22.85, 21.27, 8.76. LCMS 1009.66 (M+H).

Example 23

Synthesis of dFKBP-2

(1) Synthesis of tert-butyl (1-chloro-2-oxo-7,10,13-trioxa-3-azahexadecan-16-yl)carbamate tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24 hours, the mixture was diluted with EtOAc and washed with saturated sodium bicarbonate, water then brine. The organic layer was dried over sodium sulfate, filtered and condensed to give a yellow oil (1.416 g) that was carried forward without further purification.

$^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl3) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of dimethyl 3-((2,2-dimethyl-4,20-dioxo-3,9,12,15-tetraoxa-5,19-diazahenicosan-21-yl)oxy)phthalate tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography

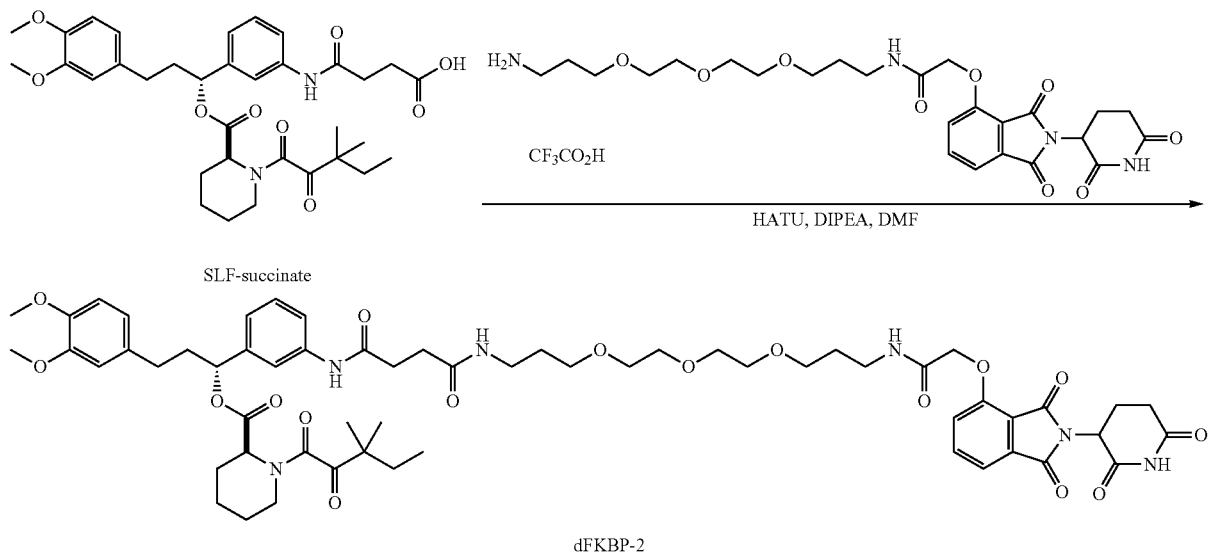

SLF-succinate dFKBP-2

(ISCO, 24 g silica column, 0-15% MeOH/DCM 22 minute gradient) to give a yellow oil (1.5892 g, 2.78 mmol, 89% over two steps).

$^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl3) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate Dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil.

$^1$H NMR (400 MHz, Methanol-d4) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd3od) δ 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

(4) Synthesis of dFKBP-2

N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (12.5 mg, 0.0193 mmol, 1 eq) was added to SLF-succinate (12.08 mg, 0.0193 mmol, 1 eq) as a solution in 0.193 mL in DMF (0.1 M). DIPEA (10.1 microliters, 0.0580 mmol, 3 eq) and HATU (7.3 mg, 0.0193 mmol, 1 eq) were added and the mixture was stirred for 19 hours. The mixture was then diluted with MeOH and purified by preparative HPLC to give dFKBP-2 (9.34 mg, 0.00818 mmol, 42%) as a yellow oil.

$^1$H NMR (400 MHz, 50% MeOD/Chloroform-d) δ 7.76-7.70 (m, 1H), 7.58-7.45 (m, 3H), 7.26 (t, J=8.2 Hz, 2H), 7.05-6.98 (m, 1H), 6.77 (d, J=7.9 Hz, 1H), 6.71-6.63 (m, 2H), 5.73 (dd, J=8.1, 5.6 Hz, 1H), 5.23 (d, J=5.4 Hz, 1H), 5.03-4.95 (m, 1H), 4.64 (s, 2H), 3.82 (s, 3H), 3.80 (s, 3H), 3.62-3.52 (m, 8H), 3.47 (t, J=6.1 Hz, 2H), 3.44-3.33 (m, 3H), 3.27-3.14 (m, 3H), 2.84-2.70 (m, 3H), 2.64-2.47 (m, 6H), 2.34 (d, J=14.1 Hz, 1H), 2.24 (dd, J=14.3, 9.3 Hz, 2H), 2.13-2.00 (m, 2H), 1.83 (p, J=6.3 Hz, 2H), 1.67 (dtd, J=38.4, 16.8, 14.8, 7.0 Hz, 7H), 1.51-1.26 (m, 3H), 1.22-1.05 (m, 6H), 0.80 (dt, J=39.8, 7.5 Hz, 3H). $^{13}$C NMR (100 MHz, cdcl3) δ 208.64, 173.39, 173.01, 171.76, 170.11, 169.62, 168.24, 167.92, 167.36, 166.69, 155.02, 149.23, 147.66, 140.94, 139.18, 137.57, 134.09, 133.91, 129.49, 122.32, 120.75, 120.52, 119.93, 118.42, 117.75, 112.33, 111.98, 70.77, 70.51, 70.40, 69.45, 69.04, 68.48, 56.10, 51.88, 47.09, 44.78, 38.40, 37.48, 36.91, 32.80, 32.71, 31.70, 31.59, 31.55, 29.53, 29.30, 26.77, 25.22, 23.63, 23.33, 22.98, 21.43. LCMS 1141.71 (M+H).

Example 24

Synthesis of dFKBP-3

SLF-succinate was prepared according to step (1) of the synthesis of dFKBP-1.

A 0.1 M solution of N-(4-aminobutyl)-2-((2-(2,6-dioxopiperidin-3-yl)-1,3-dioxoisoindolin-4-yl)oxy)acetamide trifluoroacetate (0.233 mL, 0.0233 mmol, 1 eq) was added to 2-(3-((R)-3-(3,4-dimethoxyphenyl)-1-(((S)-1-(3,3-dimethyl-2-oxopentanoyl)pyrrolidine-2-carbonyl)oxy)propyl)phenoxy)acetic acid (13.3 mg, 0.0233 mmol, 1 eq). DIPEA (12.2 microliters, 0.0700 mmol, 3 eq) was added, followed by HATU (8.9 mg, 0.0233 mmol, 1 eq). The mixture was stirred for 23 hours, then diluted with MeOH and purified by preparative HPLC to give a white solid (10.72 mg mg, 0.0112 mmol, 48%).

$^1$H NMR (400 MHz, Methanol-d$_4$) δ 7.79-7.74 (m, 1H), 7.52 (d, J=7.4 Hz, 1H), 7.33 (d, J=8.4 Hz, 1H), 7.26 (t, J=8.1 Hz, 1H), 6.97-6.90 (m, 2H), 6.89-6.84 (m, 1H), 6.79 (dd, J=8.2, 1.9 Hz, 1H), 6.73-6.64 (m, 2H), 5.73-5.65 (m, 1H), 5.07-4.99 (m, 1H), 4.67 (s, 2H), 4.57-4.51 (m, 1H), 4.48 (dd, J=5.7, 2.5 Hz, 2H), 3.82 (d, J=1.9 Hz, 3H), 3.80 (s, 3H), 3.66-3.39 (m, 3H), 2.88-2.48 (m, 6H), 2.42-1.87 (m, 9H), 1.73-1.51 (m, 6H), 1.19-0.92 (m, 6H), 0.75 (dt, J=56.7, 7.5 Hz, 3H). LCMS 954.52 (M+H).

Example 25

Synthesis of dFKBP-4

SLF-succinate was prepared according to step (1) of the synthesis of dFKBP-1.

A 0.1 M solution of N-(4-aminobutyl)-2-((2-(2,6-dioxopiperidin-3-yl)-1,3-dioxoisoindolin-4-yl)oxy)acetamide trifluoroacetate (0.182 mL, 0.0182 mmol, 1 eq) was added to 2-(3-((R)-3-(3,4-dimethoxyphenyl)-1-(((S)-1-(3,3-dimethyl-2-oxopentanoyl)piperidine-2-carbonyl)oxy)propyl)phenoxy)acetic acid (10.6 mg, 0.0182 mmol, 1 eq). DIPEA (9.5 microliters, 0.0545 mmol, 3 eq) was added, followed by HATU (6.9 mg, 0.0182 mmol, 1 eq). The mixture was stirred for 26 hours, then diluted with MeOH and purified by preparative HPLC to give a white solid (9.74 mg, 0.01006 mmol, 55%).

$^1$H NMR (400 MHz, Methanol-d$_4$) δ 7.75 (dd, J=8.3, 7.4 Hz, 1H), 7.53 (d, J=2.3 Hz, 1H), 7.33-7.25 (m, 2H), 7.00-6.84 (m, 3H), 6.79 (dd, J=8.1, 2.5 Hz, 1H), 6.72-6.65 (m, 2H), 5.75-5.70 (m, 1H), 5.23 (d, J=4.9 Hz, 1H), 5.05-4.96 (m, 1H), 4.66 (s, 2H), 4.46 (s, 2H), 3.82 (s, 3H), 3.81 (s, 3H), 3.39-3.32 (m, 4H), 3.20-3.12 (m, 1H), 2.82-2.69 (m, 3H), 2.62-2.49 (m, 2H), 2.37-2.00 (m, 5H), 1.78-1.30 (m, 11H), 1.24-1.08 (m, 6H), 0.81 (dt, J=32.9, 7.5 Hz, 3H). LCMS 968.55 (M+H).

Example 26

Synthesis of dFKBP-5

SLF-succinate was prepared according to step (1) of the synthesis of dFKBP-1.

A 0.1 M solution of N-(4-aminobutyl)-2-((2-(2,6-dioxopiperidin-3-yl)-1,3-dioxoisoindolin-4-yl)oxy)acetamide trifluoroacetate (0.205 mL, 0.0205 mmol, 1 eq) was added to 2-(3-((R)-3-(3,4-dimethoxyphenyl)-1-(((S)-1-(2-phenylacetyl)piperidine-2-carbonyl)oxy)propyl)phenoxy)acetic acid (11.8 mg, 0.0205 mmol, 1 eq). DIPEA (10.7 microliters, 0.0615 mmol, 3 eq) was added, followed by HATU (7.8 mg, 0.0205 mmol, 1 eq). The mixture was stirred for 29 hours, then diluted with MeOH and purified by preparative HPLC to give a white solid (10.62 mg, 0.01106 mmol, 54%).

$^1$H NMR (400 MHz, Methanol-d$_4$) δ 7.77-7.72 (m, 1H), 7.52 (s, 1H), 7.31-7.11 (m, 7H), 6.92-6.77 (m, 4H), 6.68-6.62 (m, 2H), 5.70-5.64 (m, 1H), 5.38 (d, J=3.8 Hz, 1H), 4.99 (d, J=4.6 Hz, 1H), 4.65 (s, 2H), 4.45-4.39 (m, 2H), 3.80 (dd, J=6.7, 2.4 Hz, 8H), 3.13-3.03 (m, 1H), 2.83-2.68 (m, 3H), 2.63-2.45 (m, 3H), 2.34-1.93 (m, 6H), 1.71-1.52 (m, 7H), 1.34-1.20 (m, 3H). LCMS 960.54 (M+H).

Example 27

Synthesis of diaminoethyl-acetyl-O-thalidomide trifluoroacetate

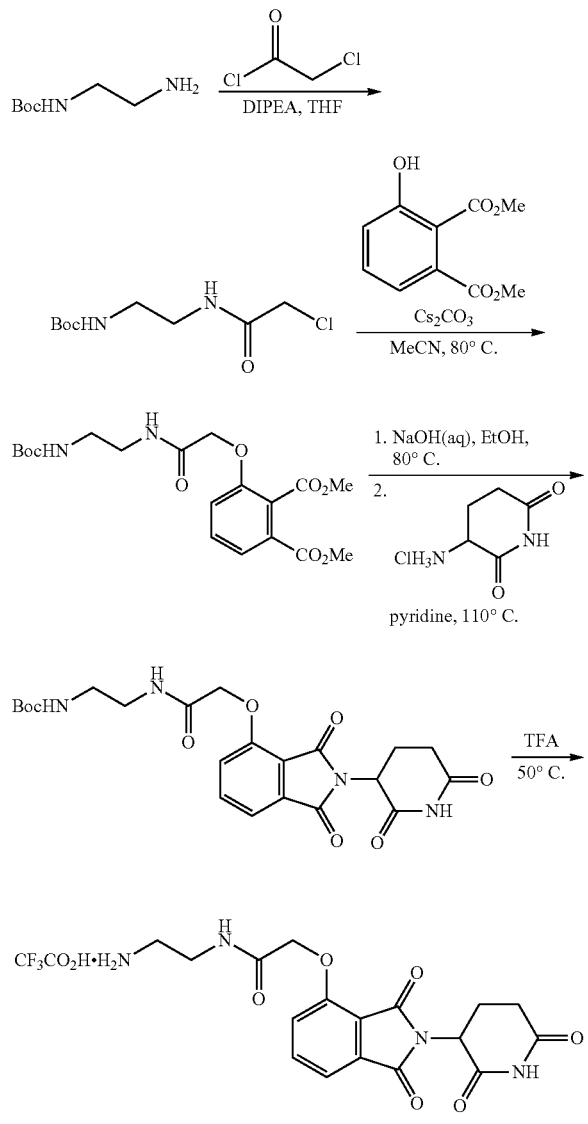

(1) Synthesis of tert-Butyl (2-(2-chloroacetamido)ethyl)carbamate

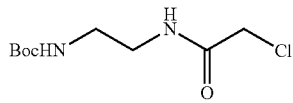 [SMILES: CC(C)(C)OC(=O)NCCNC(=O)CCl]

tert-butyl (2-aminoethyl)carbamate (0.40 mL, 2.5 mmol, 1 eq) was dissolved in THF (25 mL, 0.1 M) and DIPEA (0.44 mL, 2.5 mmol, 1 eq) at 0° C. Chloroacetyl chloride (0.21 mL, 2.75 mmol, 1.1 eq) was added and the mixture was allowed to warm to room temperature. After 22 hours, the mixture was diluted with EtOAc and washed with saturated sodium bicarbonate, water and brine. The organic layer was dried with sodium sulfate, filtered and concentrated under reduced pressure to give a white solid (0.66 g, quantitative yield) that carried forward to the next step without further purification. $^1$H NMR (400 MHz, Chloroform-d) δ 7.16 (s, 1H), 4.83 (s, 1H), 4.04 (s, 2H), 3.42 (q, J=5.4 Hz, 2H), 3.32 (q, J=5.6 Hz, 2H), 1.45 (s, 9H). LCMS 237.30 (M+H).

(2) Synthesis of dimethyl 3-(2-((2-(((tert-butoxycarbonyl)amino)ethyl)amino)-2-oxoethoxy)phthalate

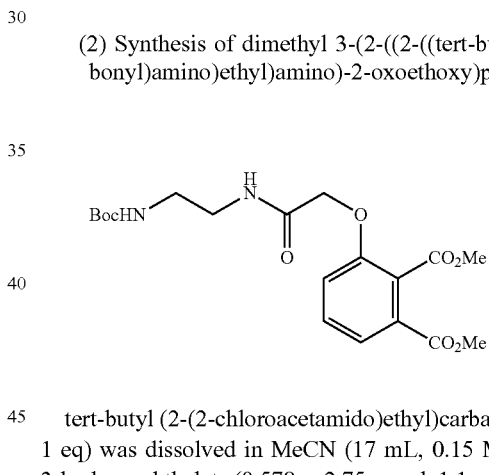

tert-butyl (2-2-chloroacetamido)ethyl)carbamate (0.66 g, 1 eq) was dissolved in MeCN (17 mL, 0.15 M). Dimethyl 3-hydroxyphthalate (0.578 g, 2.75 mmol, 1.1 eq) and cesium carbonate (2.24 g, 6.88 mmol, 2.75 eq) were then added. The flask was fitted with a reflux condenser and heated to 80° C. for 32 hours. The mixture was then cooled to room temperature, diluted with EtOAc and washed three times with water. The organic layer was dried over sodium sulfate, filtered and concentrated under reduced pressure. Purification by column chromatography (ISCO, 4 g silica column, 0-15% MeOH/DCM over a 15 minute gradient) gave a yellow solid (0.394 g, 0.960 mmol, 38% over 2 steps). $^1$H NMR (400 MHz, Chloroform-d) δ 7.65-7.56 (m, 1H), 7.50-7.41 (m, 1H), 7.27 (s, 1H), 7.11 (dd, J=8.4, 4.1 Hz, 2H), 5.17 (s, 1H), 4.57 (d, J=6.3 Hz, 2H), 3.94 (s, 2H), 3.88 (s, 2H), 3.40 (p, J=5.8 Hz, 4H), 3.32-3.19 (m, 4H), 1.39 (d, J=5.7 Hz, 13H). $^{13}$C NMR (100 MHz, cdcl$_3$) δ 168.37, 168.23, 165.73, 156.13, 154.71, 131.24, 130.09, 124.85, 123.49, 117.24, 79.42, 68.48, 53.22, 52.83, 40.43, 39.54, 28.44. LCMS 411.45 (M+H).

(3) Synthesis of diaminoethyl-acetyl-O-thalidomide trifluoroacetate

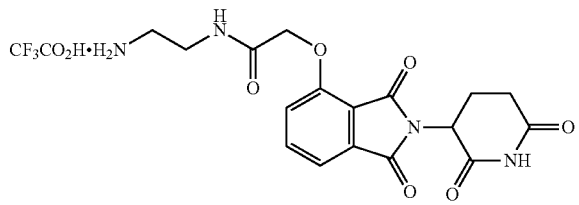

Dimethyl 3-(2-((2-((tert-butoxycarbonyl)amino)ethyl)amino)-2-oxoethoxy)phthalate (0.39 g, 0.970 mmol, 1 eq) was dissolved in EtOH (9.7 mL, 0.1 M). Aqueous 3M NaOH (0.97 mL, 2.91 mmol, 3 eq) was added and the mixture was heated to 80° C. for 3 hours. The mixture was cooled to room temperature, diluted with 50 mL DCM, 5 mL 1 M HCl and 20 mL water. The layers were separated and the organic layer was washed with 20 mL water. The combined aqueous layers were then extracted 3 times with 50 mL chloroform. The combined organic layers were dried over sodium sulfate, filtered and concentrated under reduced pressure to give a yellow solid (0.226 g) that was carried forward without further purification. LCMS 383.36.

The resultant yellow solid (0.226 g) and 3-aminopiperidine-2,6-dione hydrochloride (0.102 g, 0.6197 mmol, 1 eq) were dissolved in pyridine (6.2 mL, 0.1 M) and heated to 110° C. for 16 hours. The mixture was cooled to room temperature and concentrated under reduced pressure to give tert-butyl (2-(2-((2-(2,6-dioxopiperidin-3-yl)-1,3-dioxoisoindolin-4-yl)oxy)acetamido)ethyl)carbamate as a poorly soluble black tar (0.663 g) which was carried forward without purification (due to poor solubility). LCMS 475.42 (M+H).

The crude tert-butyl (2-(2-((2-(2,6-dioxopiperidin-3-yl)-1,3-dioxoisoindolin-4-yl)oxy)acetamido)ethyl)carbamate was dissolved in TFA (10 mL) and heated to 50° C. for 3.5 hours, then concentrated under reduced pressure. Purification by preparative HPLC gave a red oil (176.7 mg, 0.362 mmol, 37% over 3 steps). $^1$H NMR (400 MHz, Methanol-d$_4$) δ 7.85-7.76 (m, 1H), 7.57-7.50 (m, 1H), 7.48-7.41 (m, 1H), 5.13 (dd, J=12.6, 5.5 Hz, 1H), 4.81 (s, 2H), 3.62 (td, J=5.6, 1.8 Hz, 2H), 3.14 (t, J=5.8 Hz, 2H), 2.97 (s, 1H), 2.80-2.66 (m, 2H), 2.15 (dddd, J=10.1, 8.0, 5.8, 2.8 Hz, 1H). $^{13}$C NMR (100 MHz, cd$_3$od) δ 173.09, 170.00, 169.99, 166.78, 166.62, 154.93, 136.88, 133.46, 120.71, 117.93, 116.77, 68.29, 49.17, 39.37, 38.60, 30.73, 22.19. LCMS 375.30 (M+H for free base).

Example 28

Synthesis of diaminobutyl-acetyl-O-thalidomide trifluoroacetate

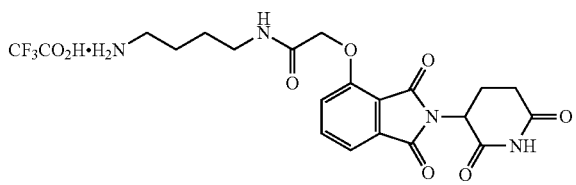

Diaminobutyl-acetyl-O-thalidomide trifluoroacetate was prepared according to the procedure in Fischer et al. *Nature*, 2014, 512, 49-53.

Example 29

Synthesis of diaminohexyl-acetyl-O-thalidomide trifluoroacetate

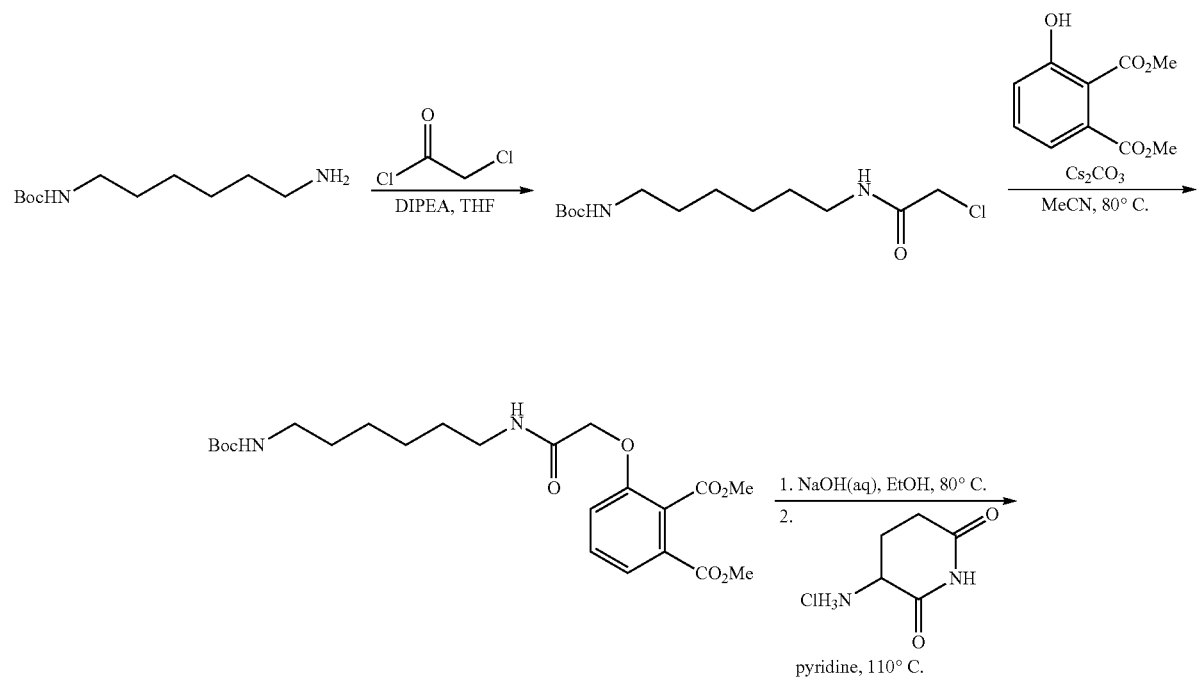

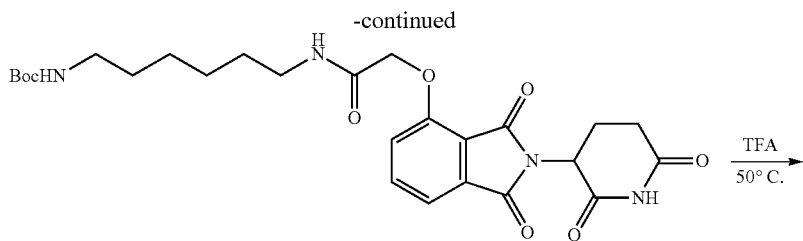

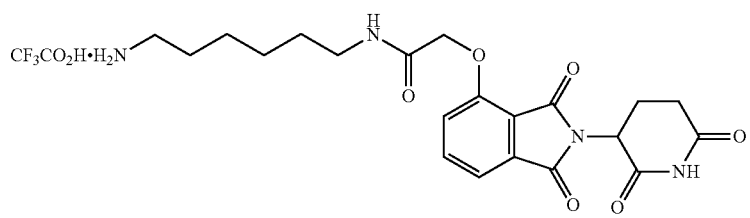

(1) Synthesis of tert-butyl (6-(2-chloroacetamido)hexyl)carbamate

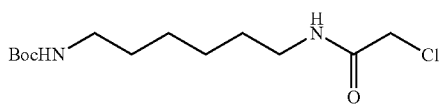 [SMILES: CC(C)(C)OC(=O)NCCCCCCNC(=O)CCl]

tert-butyl (6-aminohexyl)carbamate (0.224 mL, 1.0 mmol, 1 eq) was dissolved in THF (10 mL, 0.1 M). DIPEA (0.17 mL, 1.0 mmol, 1 eq) was added and the mixture was cooled to 0° C. Chloroacetyl chloride (88 microliters, 1.1 mmol, 1.1 eq) was added and the mixture was warmed to room temperature and stirred for 18 hours. The mixture was then diluted with EtOAc and washed with saturated sodium bicarbonate, water and brine. The organic layer was dried over sodium sulfate, filtered and concentrated under reduced pressure to give a white solid (0.2691 g, 0.919 mmol, 92%). $^1$H NMR (400 MHz, Chloroform-d) δ 6.60 (s, 1H), 4.51 (s, 1H), 4.05 (s, 2H), 3.30 (q, J=6.9 Hz, 2H), 3.11 (d, J=6.7 Hz, 2H), 1.57-1.46 (m, 4H), 1.44 (s, 9H), 1.38-1.32 (m, 4H). LCMS 293.39 (M+H).

(2) Synthesis of dimethyl 3-(2-((6-(((tert-butoxycarbonyl)amino)hexyl)amino)-2-oxoethoxy)phthalate

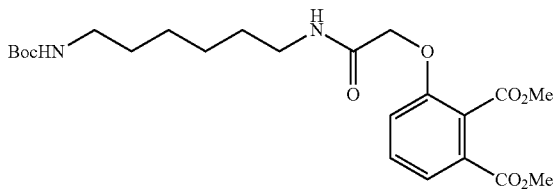 [SMILES: COC(=O)c1cccc(OCC(=O)NCCCCCCNC(=O)OC(C)(C)C)c1C(=O)OC]

tert-butyl (6-(2-chloroacetamido)hexyl)carbamate (0.2691 g, 0.919 mmol, 1 eq) was dissolved in MeCN (9.2 mL, 0.1 M). Dimethyl 3-hydroxyphthalate (0.212 g, 1.01 mmol, 1.1 eq) and cesium carbonate (0.823 g, 2.53 mmol, 2.75 eq) were added. The flask was fitted with a reflux condenser and heated to 80° C. for 14 hours. The mixture was cooled to room temperature and diluted with EtOAc, washed three times with water and back extracted once with EtOAc. The combined organic layers were dried over sodium sulfate, filtered and concentrated under reduced pressure. The crude material was purified by column chromatography (ISCO, 12 g silica column, 0-15% MeOH/DCM 15 minute gradient) to give a yellow oil (0.304 g, 0.651 mmol, 71%). $^1$H NMR (400 MHz, Chloroform-d) δ 7.66-7.58 (m, 1H), 7.44 (td, J=8.2, 1.6 Hz, 1H), 7.15-7.08 (m, 1H), 6.96 (s, 1H), 4.56 (s, 2H), 3.92 (t, J=1.6 Hz, 3H), 3.88 (t, J=1.6 Hz, 3H), 3.27 (q, J=6.9 Hz, 2H), 3.10-3.00 (m, 2H), 1.41 (s, 13H), 1.33-1.22 (m, 4H). $^{13}$C NMR (100 MHz, cdcl$_3$) δ 167.97, 167.37, 165.58, 155.95, 154.37, 130.97, 129.74, 124.94, 123.26, 116.81, 78.96, 68.04, 52.89, 52.87, 52.69, 52.67, 40.41, 38.96, 29.88, 29.13, 28.39, 26.33, 26.30. LCMS 467.49.

(3) Synthesis of diaminohexyl-acetyl-O-thalidomide trifluoroacetate

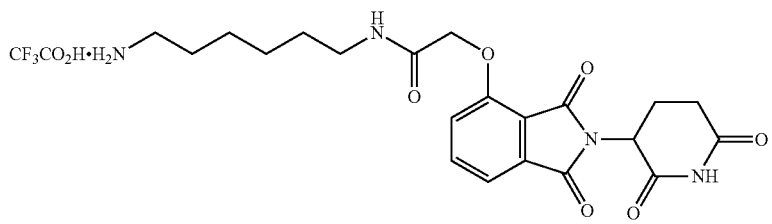

Dimethyl 3-(2-((6-((tert-butoxycarbonyl)amino)hexyl)amino)-2-oxoethoxy)phthalate (0.304 g, 0.651 mmol, 1 eq) was dissolved in EtOH (6.5 mL, 0.1 M). Aqueous 3M NaOH (0.65 mL, 1.953 mmol, 3 eq) was added and the mixture was heated to 80° C. for 18 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow foam (0.290 g) that was carried forward without further purification. LCMS 439.47.

The resultant yellow solid (0.290 g) and 3-aminopiperidine-2,6-dione hydrochloride (0.113 g, 0.69 mmol, 1 eq) were dissolved in pyridine (6.9 mL, 0.1 M) and heated to 110° C. for 17 hours. The mixture was cooled to room temperature and concentrated under reduced pressure to give tert-butyl (6-(2-((2-(2,6-dioxopiperidin-3-yl)-1,3-dioxoisoindolin-4-yl)oxy)acetamido)hexyl)carbamate as a black solid (0.4216 g) which was carried forward without purification (due to poor solubility). LCMS 531.41 (M+H).

The crude tert-butyl (6-(2-((2-(2,6-dioxopiperidin-3-yl)-1,3-dioxoisoindolin-4-yl)oxy)acetamido)hexyl)carbamate (0.4216 g) was dissolved in TFA (10 mL) and heated to 50° C. for 2 hours. The mixture was concentrated under reduced pressure, then concentrated under reduced pressure. Purification by preparative HPLC gave a brown solid (379.2 mg). $^1$H NMR (400 MHz, Methanol-$d_4$) δ 7.79 (dd, J=8.4, 7.4 Hz, 1H), 7.52 (d, J=7.2 Hz, 1H), 7.42 (d, J=8.4 Hz, 1H), 5.13 (dd, J=12.6, 5.5 Hz, 1H), 4.75 (s, 2H), 3.32 (t, J=7.6 Hz, 2H), 2.96-2.89 (m, 2H), 2.89-2.65 (m, 3H), 2.16 (ddt, J=10.4, 5.4, 2.9 Hz, 1H), 1.63 (dp, J=20.6, 7.1 Hz, 4H), 1.51-1.34 (m, 4H). $^{13}$C NMR (100 MHz, cd$_3$od) δ 174.57, 171.42, 169.90, 168.24, 167.79, 156.23, 138.23, 134.87, 121.69, 119.22, 117.98, 69.36, 50.53, 40.64, 39.91, 32.14, 30.01, 28.44, 27.23, 26.96, 23.63. LCMS 431.37 (M+H).

Example 30

Synthesis of diaminooctyl-acetyl-O-thalidomide trifluoroacetate

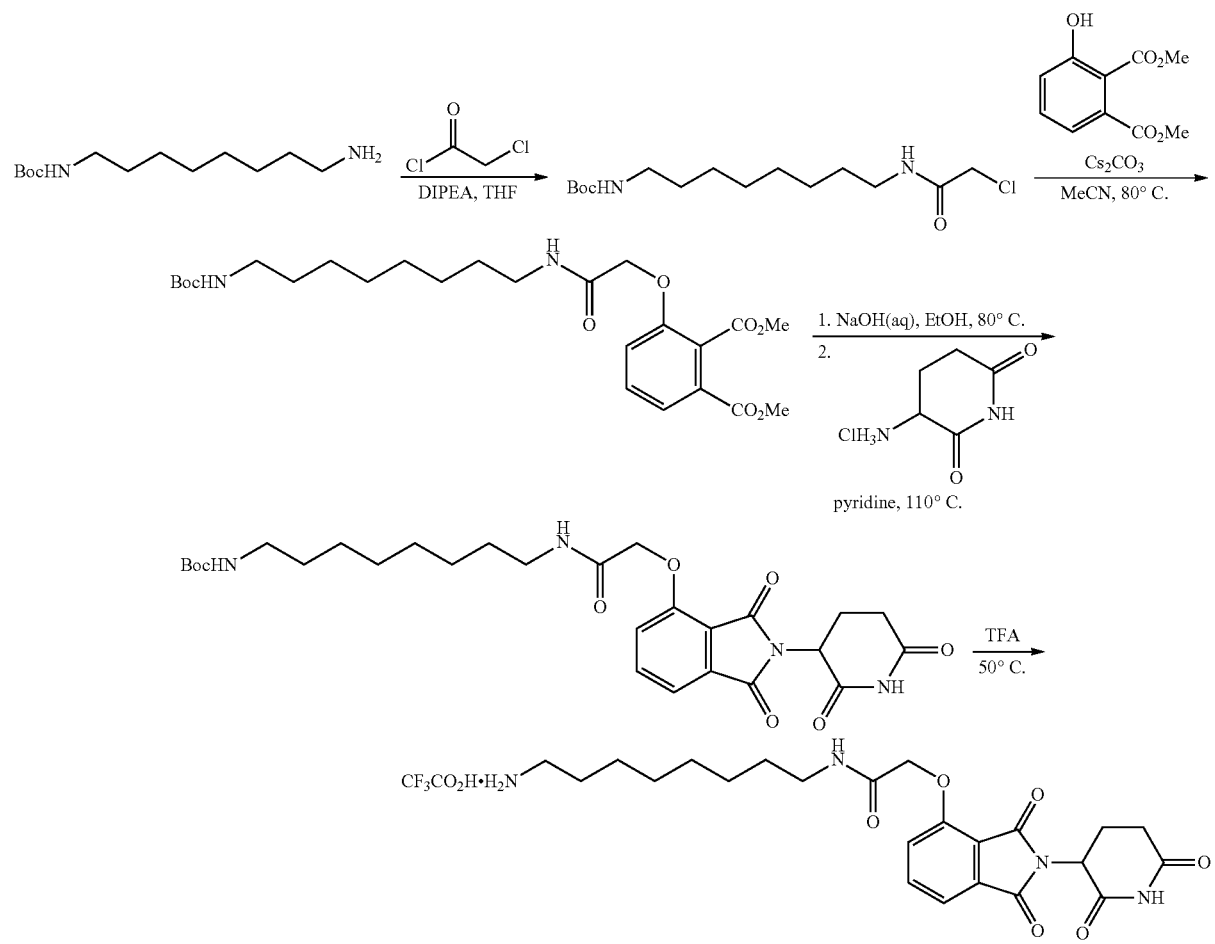

(1) Synthesis of tert-Butyl (8-(2-chloroacetamido)octyl)carbamate

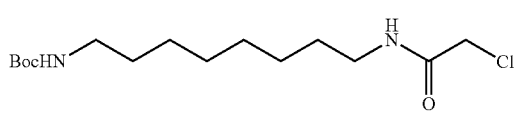 [SMILES: CC(C)(C)OC(=O)NCCCCCCCCNC(=O)CCl]

Octane-1,8-diamine (1.65 g, 11.45 mmol, 5 eq) was dissolved in chloroform (50 mL). A solution of di-tert-butyl dicarbonate (0.54 g, 2.291 mmol, 1 eq) in chloroform (10 mL) was added slowly at room temperature and stirred for 16 hours before being concentrated under reduced pressure. The solid material was resuspended in a mixture of DCM, MeOH, EtOAc and 0.5 N NH$_3$ (MeOH), filtered through celite and concentrated under reduced pressure. Purification by column chromatography (ISCO, 12 g NH2-silica column, 0-15% MeOH/DCM over a 15 minute gradient) gave a mixture (1.75 g) of the desired product and starting material which was carried forward without further purification.

This mixture was dissolved in THF (72 mL) and DIPEA (1.25 mL, 7.16 mmol) and cooled to 0° C. Chloroacetyl chloride (0.63 mL, 7.88 mmol) was added and the mixture was allowed to warm to room temperature. After 16 hours, the mixture was diluted with EtOAc and washed with saturated sodium bicarbonate, water and brine. The resultant mixture was purified by column chromatography (ISCO, dry load onto silica, 24 g column, 0-100% EtOAc/hexanes, over a 21 minute gradient) to give a white solid (0.56 g, 1.745 mmol, 76% over 2 steps). $^1$H NMR (400 MHz, Chloroform-d) δ 6.55 (s, 1H), 4.48 (s, 1H), 4.05 (s, 2H), 3.30 (q, J=6.9 Hz, 2H), 3.10 (d, J=6.2 Hz, 2H), 1.44 (s, 12H), 1.31 (s, 9H). $^{13}$C NMR (100 MHz, cdcl$_3$) δ 165.86, 156.14, 77.36, 42.86, 40.73, 40.00, 30.18, 29.44, 29.26, 28.59, 26.86, 26.82. LCMS 321.34 (M+H).

(2) Synthesis of dimethyl 3-(2-((8-((tert-butoxycarbonyl)amino)octyl)amino)-2-oxoethoxy)phthalate

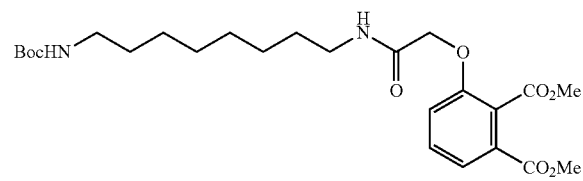 [SMILES: COC(=O)c1cccc(OCC(=O)NCCCCCCCCNC(=O)OC(C)(C)C)c1C(=O)OC]

tert-butyl (8-(2-chloroacetamido)octyl)carbamate (0.468 g, 1.46 mmol, 1 eq) was dissolved in MeCN (15 mL, 0.1 M). Dimethyl 3-hydroxyphthalate (0.337 g, 1.60 mmol, 1.1 eq) and cesium carbonate (1.308 g, 4.02 mmol, 2.75 eq) were added. The flask was fitted with a reflux condenser and heated to 80° C. for 18 hours. The mixture was cooled to room temperature and diluted water and extracted once with chloroform and twice with EtOAc. The combined organic layers were dried over sodium sulfate, filtered and concentrated under reduced pressure.

The crude material was purified by column chromatography (ISCO, 24 g silica column, 0-15% MeOH/DCM 20 minute gradient) to give a yellow oil (0.434 g, 0.878 mmol, 60%). $^1$H NMR (400 MHz, Chloroform-d) δ 7.57 (dd, J=7.9, 0.8 Hz, 1H), 7.40 (t, J=8.1 Hz, 1H), 7.07 (dd, J=8.4, 0.7 Hz, 1H), 6.89 (t, J=5.3 Hz, 1H), 4.63 (s, 1H), 4.52 (s, 2H), 3.88 (s, 3H), 3.83 (s, 3H), 3.22 (q, J=6.9 Hz, 2H), 3.01 (q, J=6.4 Hz, 2H), 1.36 (s, 12H), 1.20 (s, 9H). $^{13}$C NMR (100 MHz, cdcl$_3$) δ 167.89, 167.29, 165.54, 155.97, 154.38, 130.95, 129.69, 124.96, 123.23, 116.86, 78.82, 68.05, 52.83, 52.82, 52.66, 52.64, 40.54, 39.06, 29.97, 29.19, 29.10, 29.06, 28.40, 26.66, 26.61. LCMS 495.42 (M+H).

(3) Synthesis of diaminooctyl-acetyl-O-thalidomide trifluoroacetate

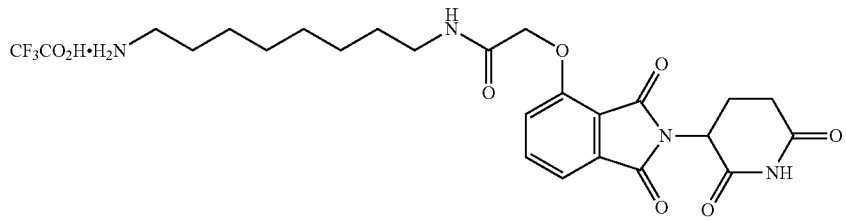

Dimethyl 3-(2-((8-((tert-butoxycarbonyl)amino)octyl)amino)-2-oxoethoxy)phthalate (0.434 g, 0.878 mmol, 1 eq) was dissolved in EtOH (8.8 mL, 0.1 M) Aqueous 3M NaOH (0.88 mL, 2.63 mmol, 3 eq) was added and the mixture was heated to 80° C. for 24 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow solid (0.329 g) that was carried forward without further purification. LCMS 467.41.

The resultant yellow solid (0.329 g) and 3-aminopiperidine-2,6-dione hydrochloride (0.121 g, 0.734 mmol, 1 eq) were dissolved in pyridine (7.3 mL, 0.1 M) and heated to 110° C. for 20 hours. The mixture was cooled to room temperature and concentrated under reduced pressure to give tert-butyl (8-(2-((2-(2,6-dioxopiperidin-3-yl)-1,3-dioxoisoindolin-4-yl)oxy)acetamido) octyl) carbamate as a black tar (0.293 g) which was carried forward without purification (due to poor solubility). LCMS 559.45 (M+H).

The crude tert-butyl (8-(2-((2-(2,6-dioxopiperidin-3-yl)-1,3-dioxoisoindolin-4-yl)oxy)acetamido)octyl)carbamate (0.293 g) was dissolved in TFA (10 mL) and heated to 50° C. for 4 hours. The mixture was concentrated under reduced pressure, then concentrated under reduced pressure. Purification by preparative HPLC gave a brown residue (114.69 mg, 23% over 3 steps). $^1$H NMR (400 MHz, Methanol-d$_4$) δ 7.84-7.78 (m, 1H), 7.54 (d, J=7.3 Hz, 1H), 7.43 (d, J=8.5 Hz, 1H), 5.13 (dd, J=12.5, 5.5 Hz, 1H), 4.76 (s, 2H), 3.32 (d, J=4.1 Hz, 1H), 3.30 (d, J=3.3 Hz, 1H), 2.94-2.84 (m, 3H), 2.80-2.70 (m, 2H), 2.19-2.12 (m, 1H), 1.67-1.55 (m, 4H), 1.40-1.34 (m, 8H). $^{13}$C NMR (100 MHz, cd$_3$od) δ 174.57, 171.37, 169.85, 168.26, 167.78, 156.26, 138.22, 134.91, 121.70, 119.28, 117.97, 69.37, 50.57, 40.76, 40.08, 32.17, 30.19, 30.05, 30.01, 28.52, 27.68, 27.33, 23.63. LCMS 459.41 (M+H).

Example 31

Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24

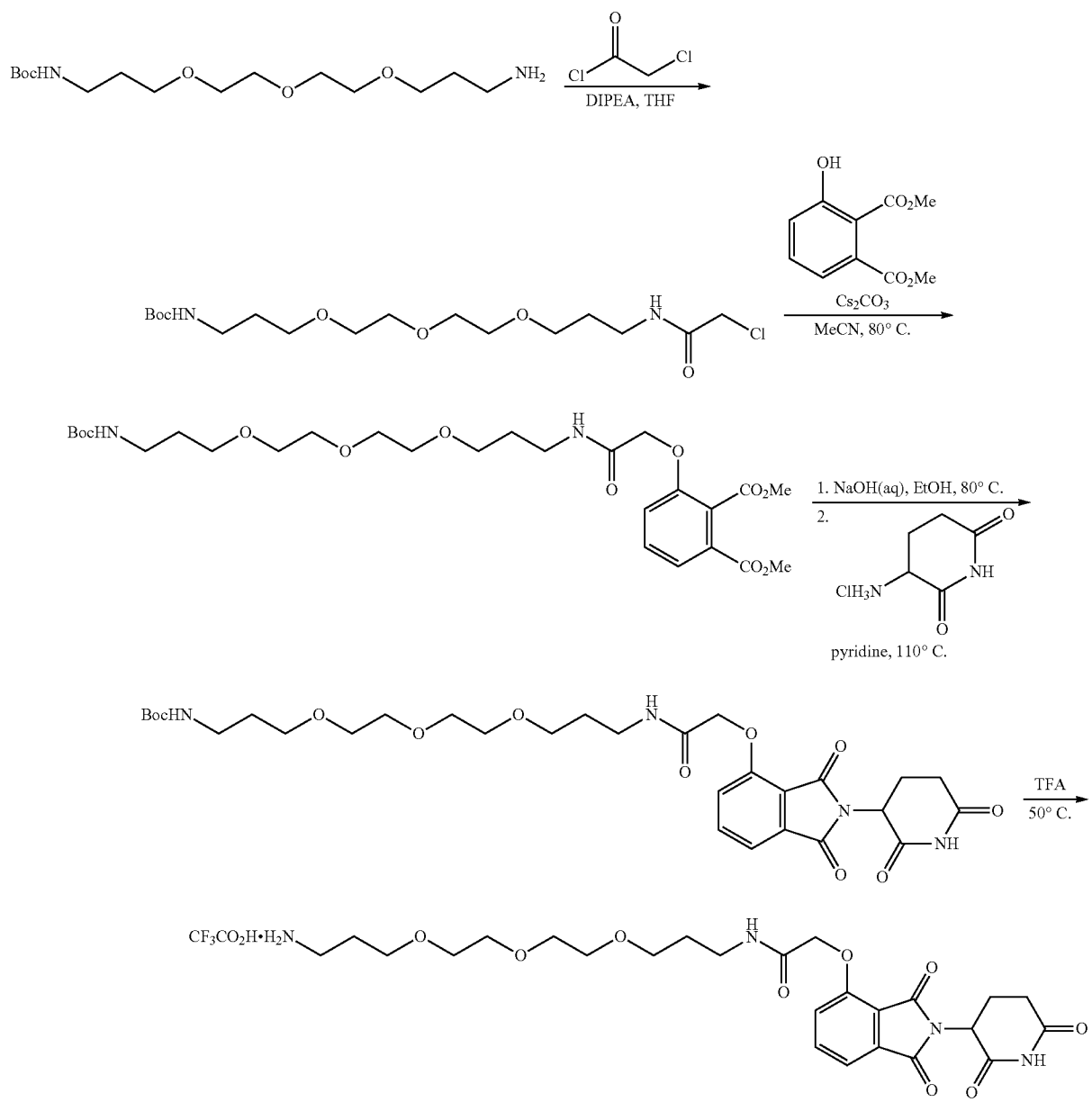

(1) Synthesis of tert-butyl (1-chloro-2-oxo-7,10,13-trioxa-3-azahexadecan-16-yl)carbamate

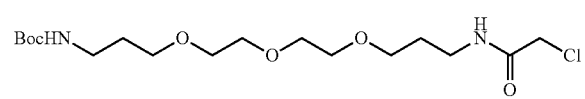 [SMILES: CC(C)(C)OC(=O)NCCCOCCOCCOCCCNC(=O)CCl]

hours, the mixture was diluted with EtOAc and washed with saturated sodium bicarbonate, water then brine. The organic layer was dried over sodium sulfate, filtered and condensed to give a yellow oil (1.416 g) that was carried forward without further purification. $^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl$_3$) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of dimethyl 3-((2,2-dimethyl-4,20-dioxo-3,9,12,15-tetraoxa-5,19-diazahenicosan-21-yl)oxy)phthalate

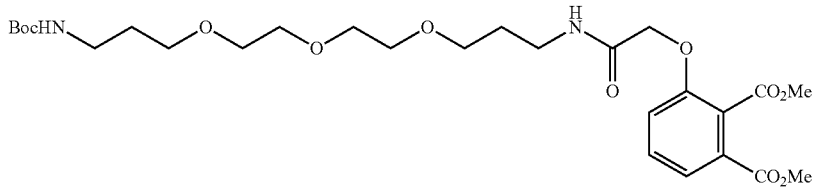 [SMILES: COC(=O)c1cccc(OCC(=O)NCCCOCCOCCOCCCNC(=O)OC(C)(C)C)c1C(=O)OC]

tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography (ISCO, 24 g silica column, 0-15% MeOH/DCM 22 minute gradient) to give a yellow oil (1.5892 g, 2.78 mmol, 89% over two steps). $^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl$_3$) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil. $^1$H NMR (400 MHz, Methanol-d$_4$) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd$_3$od) δ 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

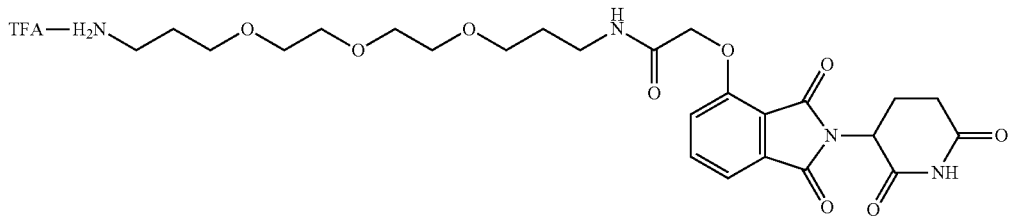

Example 32

Synthesis of N-(6-aminohexyl)-2-(2,6-dioxopiperidin-3-yl)-1,3-dioxoisoindoline-5-carboxamide

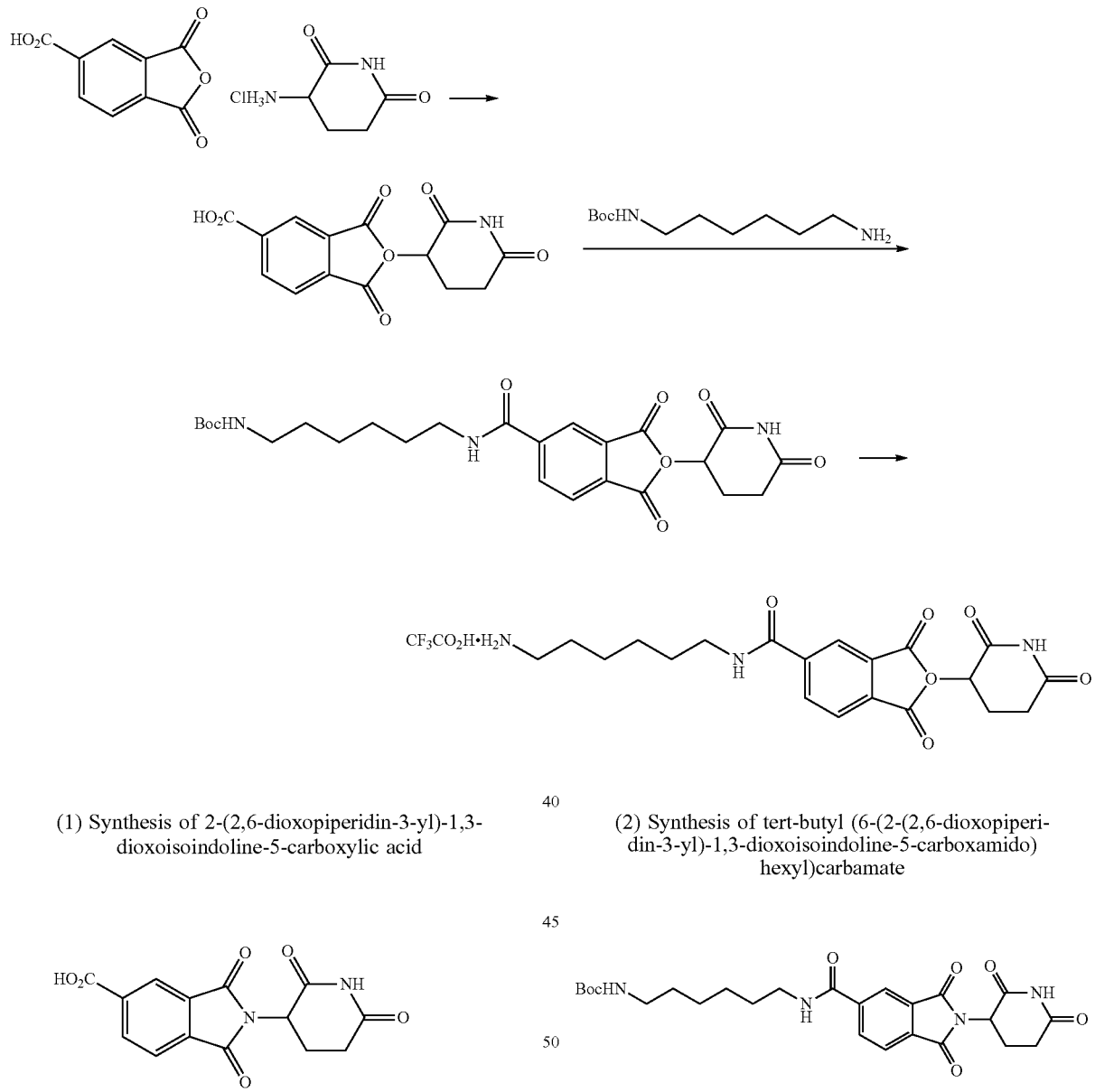

(1) Synthesis of 2-(2,6-dioxopiperidin-3-yl)-1,3-dioxoisoindoline-5-carboxylic acid 1,3-dioxo-1,3-dihydroisobenzofuran-5-carboxylic acid (0.192 g, 1 mmol, 1 eq) and 3-aminopiperidine-2,6-dione hydrochloride (0.165 g, 1 mmol, 1 eq) were dissolved in DMF (2.5 mL) and acetic acid (5 mL) and heated to 80° C. for 24 hours. The mixture was then concentrated under reduced pressure and diluted with EtOH, from which a precipitate slowly formed. The precipitate was washed twice with EtOH to give a white solid (84.8 mg, 0.28 mmol, 28%). $^1$H NMR (400 MHz, DMSO-d$_6$) δ 13.74 (s, 1H), 11.12 (s, 1H), 8.39 (dd, J=7.8, 1.4 Hz, 1H), 8.26 (s, 1H), 8.04 (d, J=7.8 Hz, 1H), 5.18 (dd, J=12.8, 5.4 Hz, 1H), 2.93-2.88 (m, 1H), 2.84 (d, J=4.7 Hz, OH), 2.66-2.50 (m, 2H), 2.12-1.99 (m, 1H). LCMS 303.19 (M+H).

(2) Synthesis of tert-butyl (6-(2-(2,6-dioxopiperidin-3-yl)-1,3-dioxoisoindoline-5-carboxamido)hexyl)carbamate 2-(2,6-dioxopiperidin-3-yl)-1,3-dioxoisoindoline-5-carboxylic acid (22.7 mg, 0.0751 mmol, 1 eq) and HATU (31.4 mg, 0.0826 mmol, 1.1 eq) were dissolved in DMF (0.75 mL). After 5 minutes, DIPA (39.2 microliters, 0.225 mmol, 3 eq) was added. After an additional 5 minutes, tert-butyl (6-aminohexyl)carbamate (19.5 mg, 0.0901 mmol, 1.2 eq) was added as a solution in DMF (0.75 mL). The mixture was stirred for 20 hours, then diluted with EtOAc. The organic layer was washed three times with brine, dried over sodium sulfate and concentrated under reduced pressure. Purification by column chromatography (ISCO, 4 g column, 0-10% MeOH/DCM, 25 minute gradient) to give a yellow oil (17.18 mg, 0.03432 mmol, 46%). $^1$H NMR (400 MHz, Chloroform-d) δ 8.29 (d, J=6.2 Hz, 2H), 8.16 (s, 1H), 7.94 (d, J=8.4 Hz, 1H), 6.91 (s, 1H), 5.00 (dd, J=12.4, 5.3 Hz, 1H), 4.58 (s, 1H), 3.47 (q, J=6.7 Hz, 2H), 3.14 (q, J=8.5, 7.3 Hz, 2H), 2.97-2.69 (m, 3H), 2.17 (ddd, J=10.4, 4.8, 2.6 Hz, 1H), 1.65 (p, J=6.9 Hz, 2H), 1.53-1.32 (m, 15H). $^{13}$C NMR (100 MHz, cdcl$_3$) δ 174.69, 170.77, 167.86, 166.67, 165.27, 156.49, 141.06, 133.95, 133.71, 132.13, 124.21, 122.27, 77.36, 49.71, 39.75, 31.54, 30.27, 29.22, 28.57, 25.70, 25.37, 22.73. LCMS 501.28 (M+H).

(3) Synthesis of N-(6-aminohexyl)-2-(2,6-dioxopiperidin-3-yl)-1,3-dioxoisoindoline-5-carboxamide

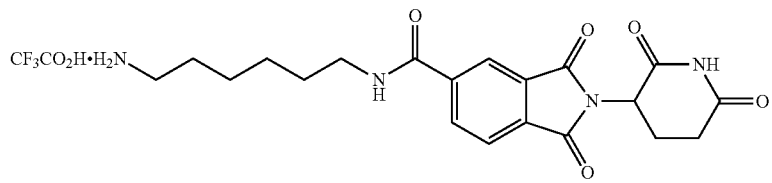

tert-butyl (6-(2-(2,6-dioxopiperidin-3-yl)-1,3-dioxoisoindoline-5-carboxamido)hexyl)carbamate (17.18 mg, 0.343 mmol, 1 eq) was dissolved in TFA (1 mL) and heated to 50° C. for 2 hours. The mixture was concentrated under reduced pressure to give a yellow oil (13.29 mg) which was deemed sufficiently pure without further purification. $^1$H NMR (400 MHz, Methanol-d$_4$) δ 8.27 (dd, J=9.3, 1.3 Hz, 2H), 7.99 (d, J=7.6 Hz, 1H), 5.18 (dd, J=12.5, 5.4 Hz, 1H), 3.48-3.40 (m, 2H), 2.96-2.84 (m, 3H), 2.76 (ddd, J=17.7, 8.1, 3.7 Hz, 2H), 2.20-2.12 (m, 1H), 1.75-1.63 (m, 4H), 1.53-1.43 (m, 4H). LCMS 401.31 (M+H).

Example 33

Synthesis of 2-((2-(2,6-dioxopiperidin-3-yl)-1,3-dioxoisoindolin-4-yl)oxy)acetic acid

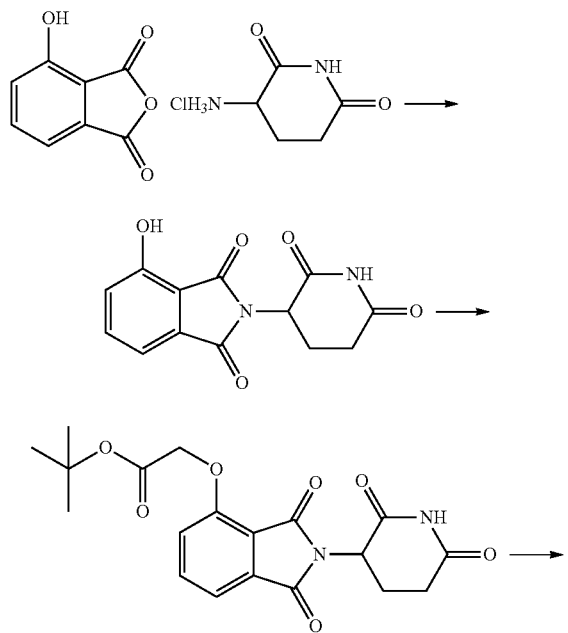

(1) Synthesis of 2-(2,6-dioxopiperidin-3-yl)-4-hydroxyisoindoline-1,3-dione

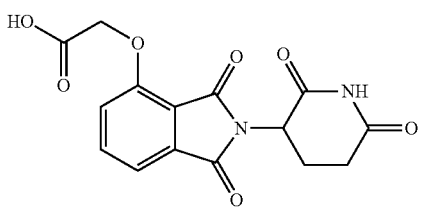

4-hydroxyisobenzofuran-1,3-dione (0.773 g, 4.71 mmol, 1 eq) and 3-aminopiperidine-2,6-dione hydrochloride (0.775 g, 4.71 mmol, 1 eq) were dissolved in pyridine (19 mL) and heated to 110° C. for 16 hours. The mixture was concentrated under reduced pressure and purified by column chromatography (ISCO, 12 g silica column, 0-10% MeOH/DCM, 25 minute gradient) to give an off white solid (1.14 g, 4.16 mmol, 88%). $^1$H NMR (400 MHz, DMSO-d$_6$) δ 11.19 (s, 1H), 11.07 (s, 1H), 7.65 (dd, J=8.3, 7.3 Hz, 1H), 7.31 (d, J=7.2 Hz, 1H), 7.24 (d, J=8.4 Hz, 1H), 5.07 (dd, J=12.8, 5.4 Hz, 1H), 2.88 (ddd, J=17.7, 14.2, 5.4 Hz, 1H), 2.63-2.50 (m, 2H), 2.11-1.95 (m, 1H). LCMS 275.11 (M+H).

(2) Synthesis of tert-butyl 2-((2-(2,6-dioxopiperidin-3-yl)-1,3-dioxoisoindolin-4-yl)oxy)acetate

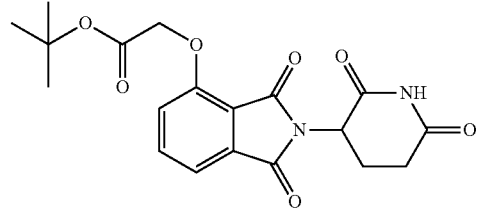 [SMILES: CC(C)(C)OC(=O)COc1cccc2c1C(=O)N(C1CCC(=O)NC1=O)C2=O]

2-(2,6-dioxopiperidin-3-yl)-4-hydroxyisoindoline-1,3-dione (218.8 mg, 0.798 mmol, 1 eq) was dissolved in DMF (8 mL). Potassium carbonate (165.9 mg, 1.20 mmol, 1.5 eq) was added, followed by tert-butyl bromoacetate (118 microliters, 0.798 mmol, 1 eq) and the mixture was stirred at room temperature for 3 hours. The mixture was diluted with EtOAc and washed once with water and twice with brine. Purification by column chromatography (ISCO, 12 g silica column, 0-100% EtOAc/hex, 17 minute gradient) gave a white solid (0.26 g, 0.669 mmol, 84%). $^1$H NMR (400 MHz, Chloroform-d) δ 8.74 (s, 1H), 7.61 (dd, J=8.4, 7.3 Hz, 1H), 7.46-7.41 (m, 1H), 7.06 (d, J=8.3 Hz, 1H), 4.98-4.92 (m, 1H), 4.74 (s, 2H), 2.83-2.69 (m, 3H), 2.12-2.04 (m, 1H), 1.43 (s, 9H). $^{13}$C NMR (100 MHz, cdcl$_3$) δ 171.58, 168.37, 166.96, 166.87, 165.49, 155.45, 136.27, 133.89, 119.78, 117.55, 116.83, 83.05, 66.52, 49.20, 31.37, 28.03, 22.55. LCMS 411.23 (M+Na).

(3) Synthesis of 2-((2-(2,6-dioxopiperidin-3-yl)-1,3-dioxoisoindolin-4-yl)oxy)acetic acid

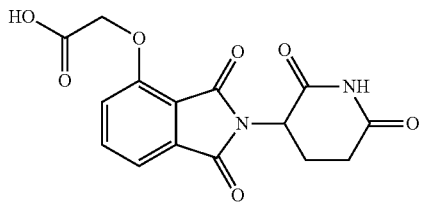 [SMILES: O=C(O)COc1cccc2c1C(=O)N(C1CCC(=O)NC1=O)C2=O]

tert-butyl 2-((2-(2,6-dioxopiperidin-3-yl)-1,3-dioxoisoindolin-4-yl)oxy)acetate (47.5 mg, 0.122 mmol, 1 eq) was dissolved in TFA (1.3 mL) at room temperature. After 3 hours, the mixture was diluted with DCM and concentrated under reduced pressure to yield a white solid (42.27 mg), which was deemed sufficiently pure without further purification. $^1$H NMR (400 MHz, Methanol-d$_4$) δ 7.76 (dd, J=8.5, 7.3 Hz, 1H), 7.50 (d, J=7.3 Hz, 1H), 7.34 (d, J=8.5 Hz, 1H), 5.11 (dd, J=12.5, 5.5 Hz, 1H), 4.96 (s, 2H), 2.87 (ddd, J=17.8, 14.2, 5.0 Hz, 1H), 2.80-2.65 (m, 2H), 2.18-2.09 (m, 1H). LCMS 333.15 (M+H).

Figure 1C:
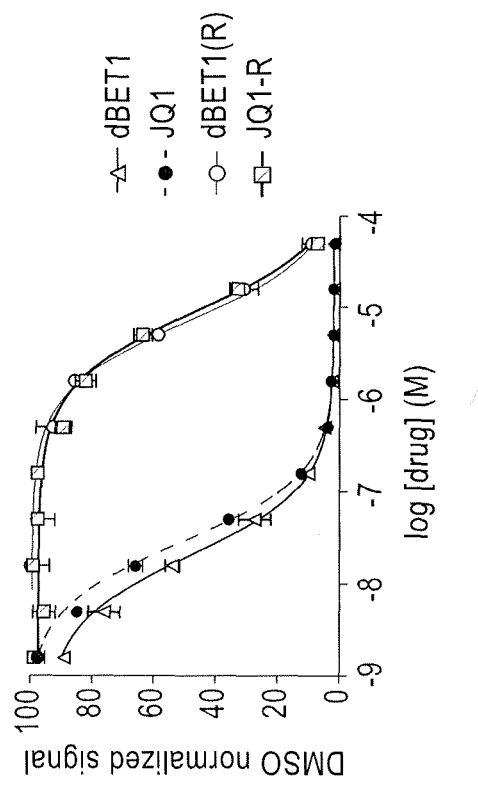
Figure 11A:
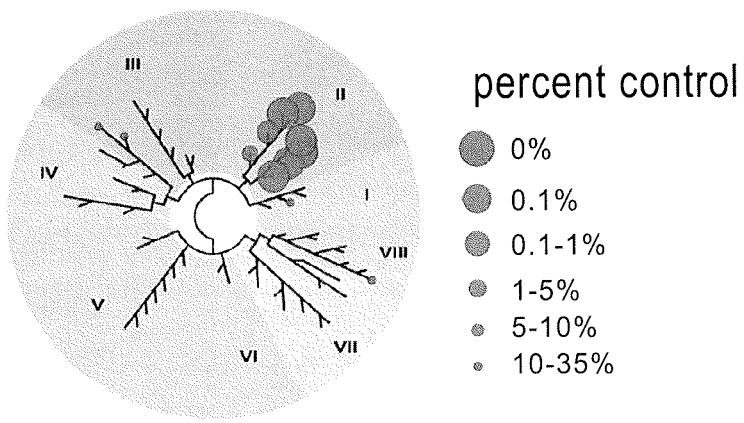
FIGS. 11A-11C (i.e.

Example 34 dBET1 Treatment Downregulates BRD4 Levels dBET1 showed potent binding to the first bromodomain of BRD4 (BRD4(1); IC$_{50}$=20 nM), while the epimeric dBET1(R) was comparatively inactive (IC$_{50}$=6.9 μM) (FIG. 1C). In comparison, the IC$_{50}$ JQ1 and JQ1-R are 20 nM and 8.8 μM, respectively (FIG. 1C). Selectivity profiling confirmed potent and BET-specific target engagement among 32 bromodomains studied by phage display and displacement (FIG. 11A) (Table 2).

TABLE 2

Single Point Screening of dBET1 using BromoScan dBET1, 1 μM

| DiscoveRx Gene Symbol | Percent Control |
|---|---|
| ATAD2A | 44 |
| ATAD2B | 62 |
| BAZ2A | 90 |
| BAZ2B | 59 |
| BRD1 | 50 |
| BRD2(1) | 0 |
| BRD2(2) | 0 |
| BRD3(1) | 0 |
| BRD3(2) | 0 |

TABLE 2-continued

Single Point Screening of dBET1 using BromoScan dBET1, 1 μM

| DiscoveRx Gene Symbol | Percent Control |
|---|---|
| BRD4(1) | 0.25 |
| BRD4(2) | 0 |
| BRD7 | 96 |
| BRD9 | 96 |
| BRDT(1) | 1.6 |
| BRDT(2) | 0 |
| BRPF1 | 44 |
| BRPF3 | 82 |
| CECR2 | 65 |
| CREBBP | 32 |
| EP300 | 30 |
| FALZ | 26 |
| GCN5L2 | 96 |
| PBRM1(2) | 98 |
| PBRM1(5) | 100 |
| PCAF | 61 |
| SMARCA2 | 34 |
| SMARCA4 | 47 |
| TAF1(2) | 56 |
| TAF1L(2) | 92 |
| TRIM24(PHD, Bromo.) | 100 |
| TRIM33(PHD, Bromo.) | 100 |
| WDR9(2) | 36 |

Figure 1H:
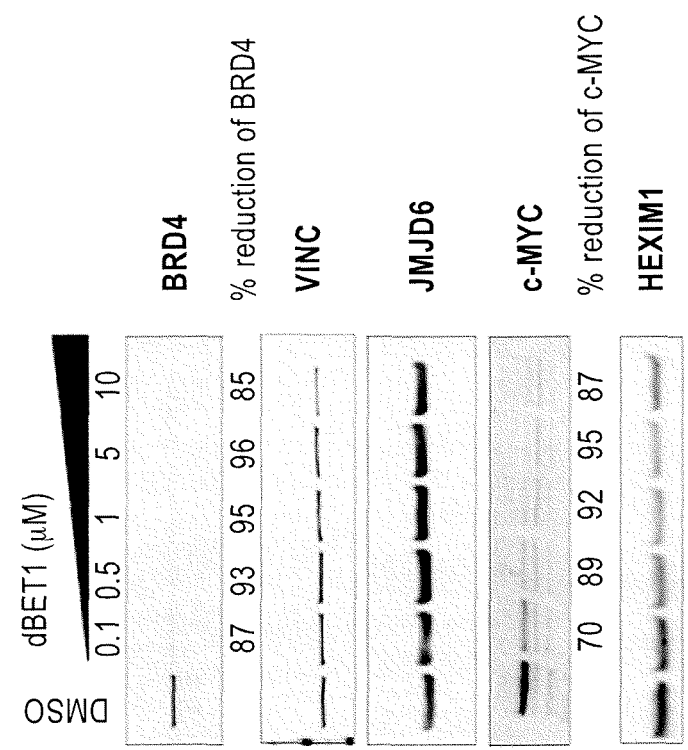
Figure 1G:
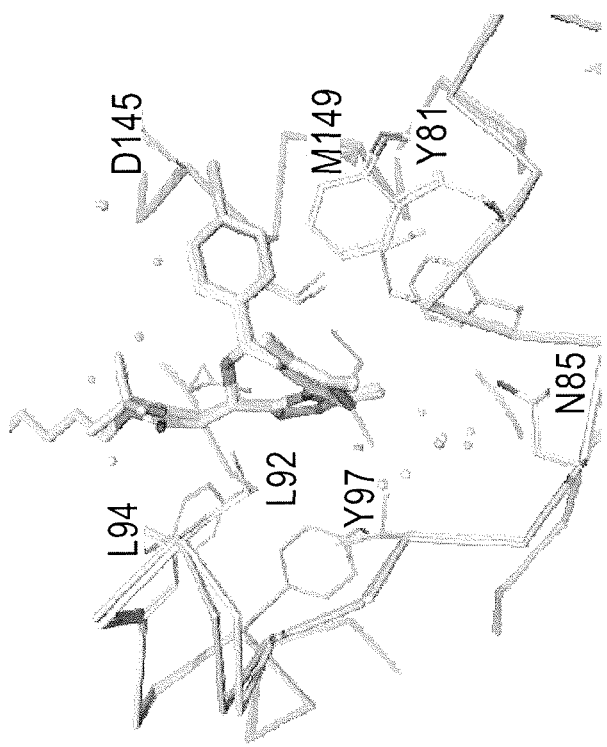

A high-resolution crystal structure (1.0 Å) of dBET1 bound to BRD4(1) confirmed the mode of molecular recognition as comparable to JQ1 (FIGS. 1D and 1G). Ordered density for the dBET1 ligand was found only to the first two carbon atoms of the butane spacer, suggesting conformational flexibility of the conjugated phthalimide. Using the dBET1-BRD4(1) crystal structure and the recently reported structure of CRBN bound to thalidomide (E. S. Fischer et al., Nature 512, 49-53 (2014)), the feasibility of ternary complex formation was modeled in silico. An extended conformation of dBET1 was capable of bridging ordered BRD4(1) and CRBN in numerous sampled conformations without destructive steric interactions (FIG. 1E). The modular nature of CRL complexes suggests that chemical recruitment of BRD4 may lead to CRBN-dependent degradation (E. S. Fischer et al., Cell 147, 1024-1039 (2011); M. D. Petroski, R. J. Deshaies, Nat. Rev. Mol. Cell Biol. 6, 9-2).

Figure 11B:
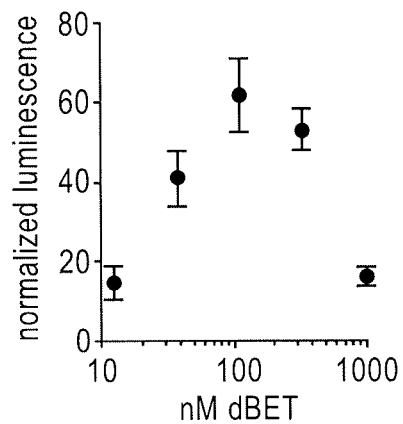
Figure 11C:
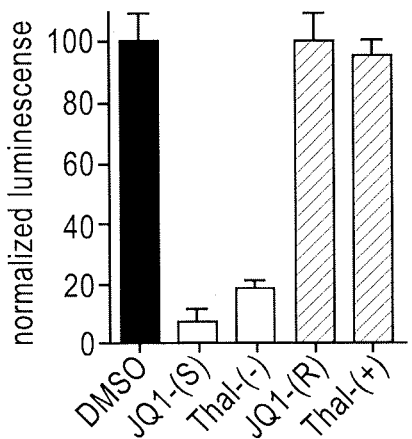

The chemical adaptor function of dBET1 was assessed by a homogeneous proximity assay for recombinant, human CRBN-DDB1 and BRD4 using AlphaScreen technology. As shown in FIG. 11B, luminescence arising from proximity of acceptor (CRBN-bound) and donor (BRD4-bound) beads was increased in the presence of low (10-100 nM) concentrations of dBET1. At higher concentrations of dBET1 (e.g., 1 μM), luminescence diminished, consistent with independent occupancy of CRBN and BRD4 binding sites by excess dBET1 (the hook effect). Inhibition of chemical adaptor function was accomplished with competitive co-incubation with free JQ1 or thalidomide, each in a stereo-specific manner (FIG. 11C).

To functionally assess the effect of dBET1 on BRD4 in cells, a human AML cell line (MV4-11) was treated for 18 hours with increasing concentrations of dBET1 and assayed for endogenous BRD4 levels by immunoblot. Pronounced loss of BRD4 (>85%) was observed with concentrations of dBET1 as low as 100 nM (FIG. 1F). MV4-11 cells were treated with DMSO or increasing concentrations of dBET1 for 24 hours, lysed in RIPA buffer. Immunoblotting was performed against the indicated proteins. In addition, BRD4 and c-MYC levels were quantified relative to vinculin levels in cells treated with increasing concentrations of dBET1

(FIG. 1H). Notably, JMJD6, a protein that physically interacts with BRD4 was not affected (FIG. 1H). Moreover, HEXIM1 levels which usually increase after BRD4 inhibitor treatment via a transcriptional control mechanism were moderately decreased as well (FIG. 1H).

Figure 2A:
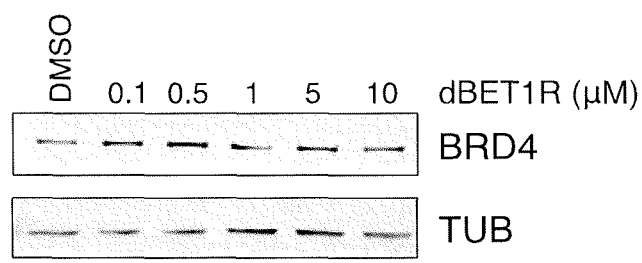
FIGS. 2A-2Q (i.e.

Molecular recognition of the BRD4 bromodomains by JQ1 is stereo-specific, and only the (+)-JQ1 enantiomer is active; the (−)-JQ1 enantiomer (JQ1R) is inactive (FIGS. 1A, 1B, and 1C and FIGS. 5A and B). The epimeric dBET1(R) compound lacks BRD4 binding (>300 fold weaker binding in homogenous assays) and was inactive, demonstrating that BRD4 degradation requires target protein engagement (FIG. 2A).

Example 35

Degradation of BRD2, BRD3, and BRD4 by dBET1

MV4-11 cells were treated with DMSO or 100 nM dBET1 for various timepoints between 1 and 24 hours. Cells were lysed in RIPA buffer. Immunoblotting was performed. While BRD3 and BRD4 showed comparable kinetics, BRD2 levels equilibrated faster at later timepoints. The results are shown in FIG. 2K.

Figure 2B:
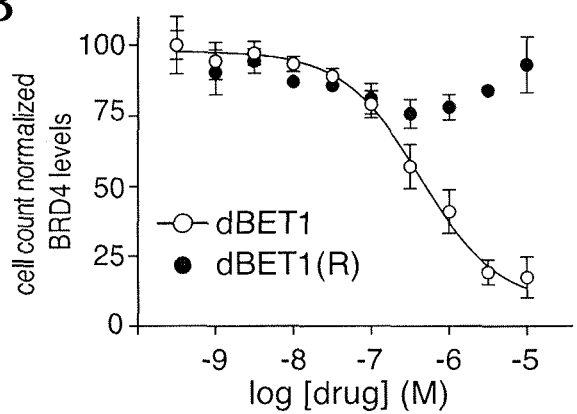
Figure 2C:
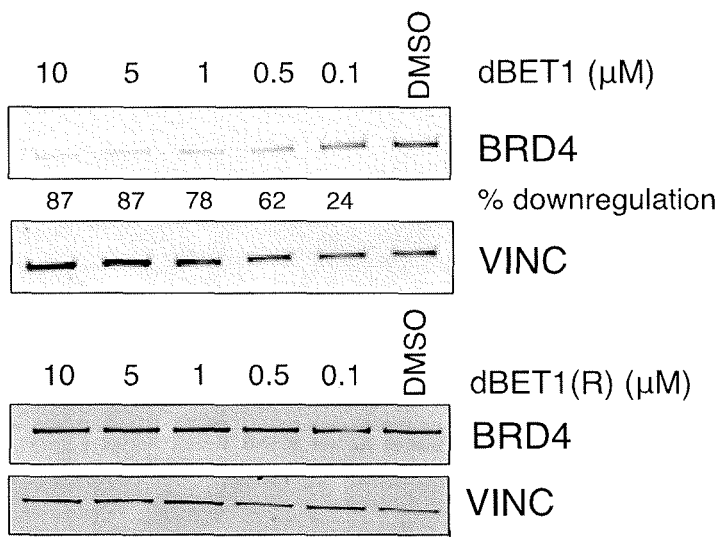
Figure 2D:
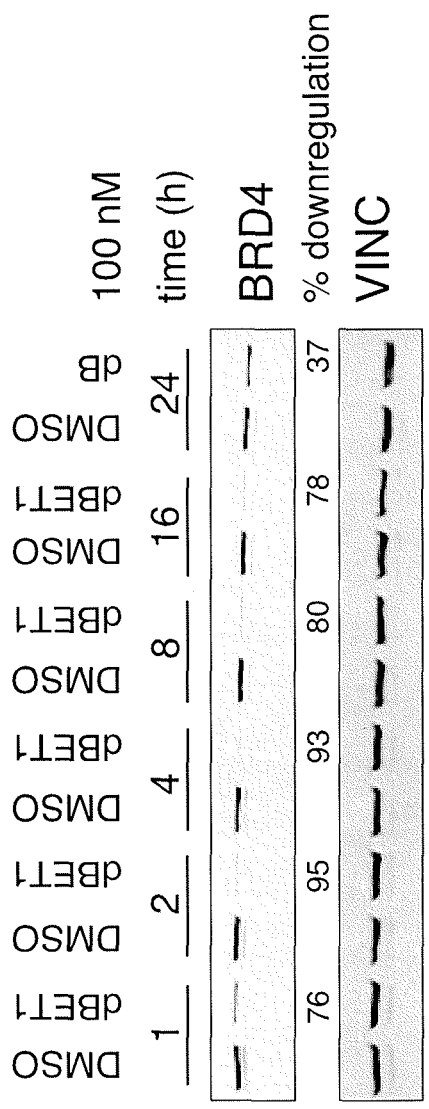
Figure 2F:
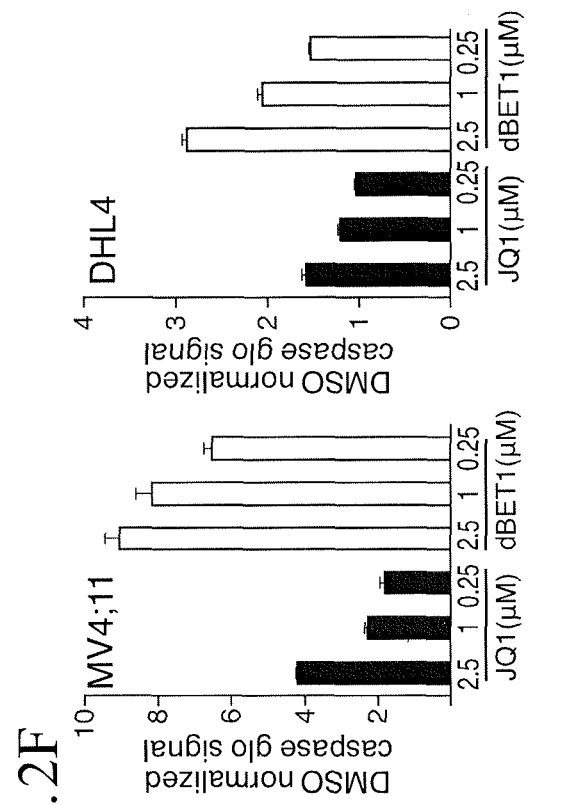
Figure 2E:
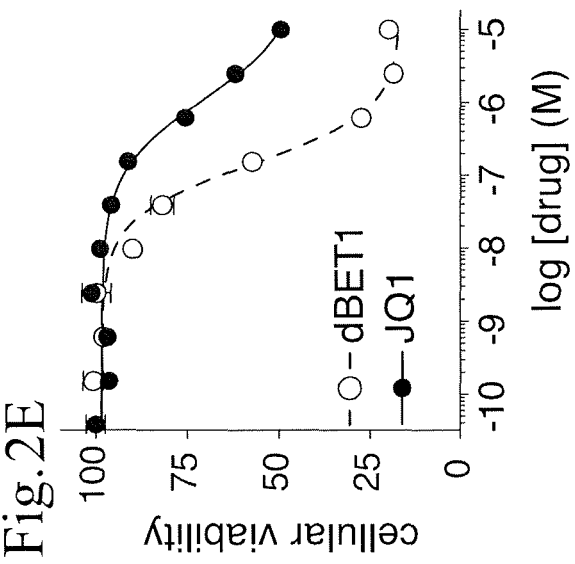
Figure 2H:
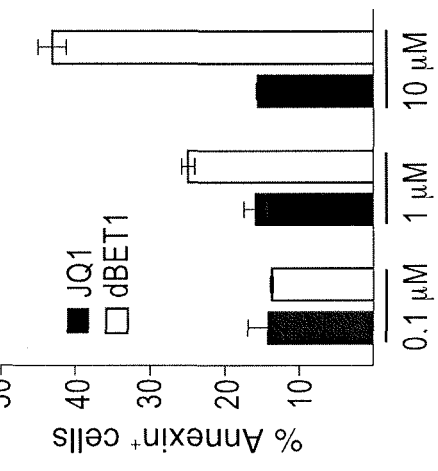
Figure 2G:
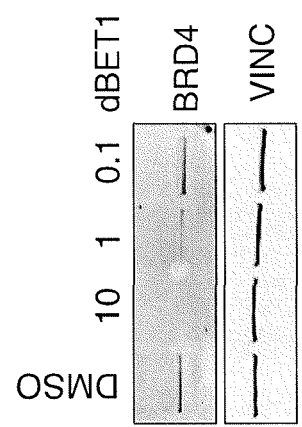
Figure 2J:
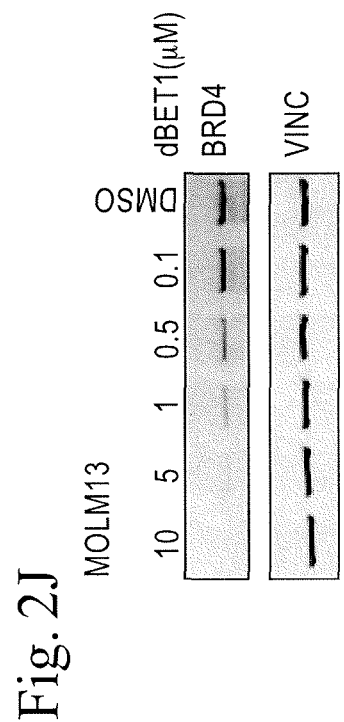
Figure 2I:
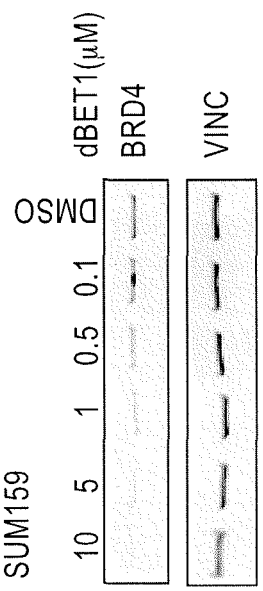
Figure 2K:
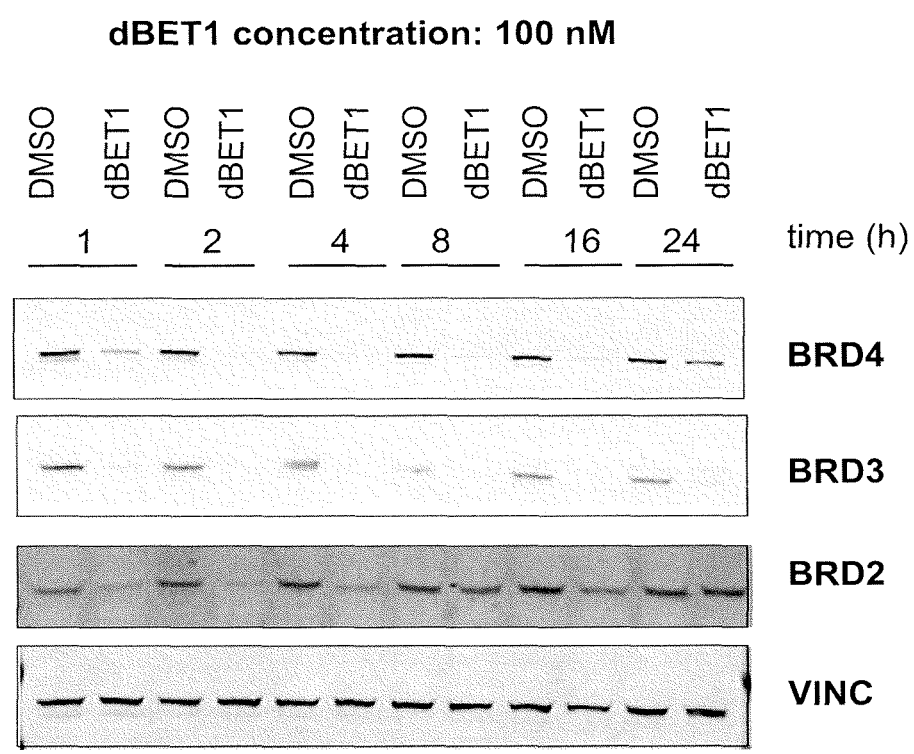

To quantify dose-responsive effects on BRD4 protein stability, a cell-count normalized, immunofluorescence-based high-content assay was developed in an adherent human cancer cell line (SUM149 breast cancer cells (FIG. 2B). Potent downregulation of total BRD4 was observed for dBET1 ($EC_{50}$=430 nM) without apparent activity for dBET1(R). These observations were confirmed by immunoblot in SUM149, which were used for baseline normalization of the assay (FIG. 2C). Additional cultured adherent and non-adherent human cancer cell lines showed comparable response (SUM159, MOLM13) (FIGS. 2I and 2J).

Figure 2L:
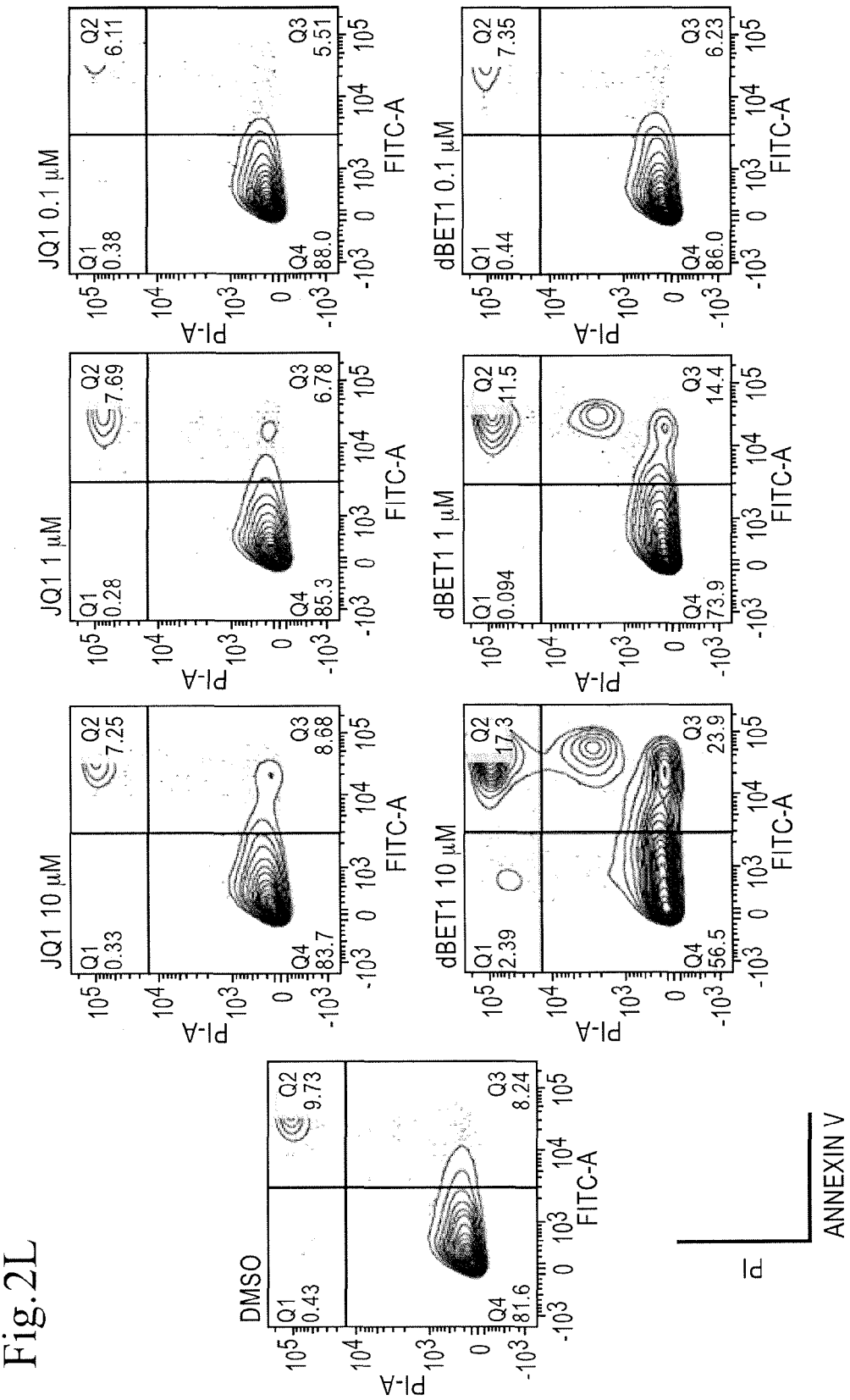
Figure 2M:
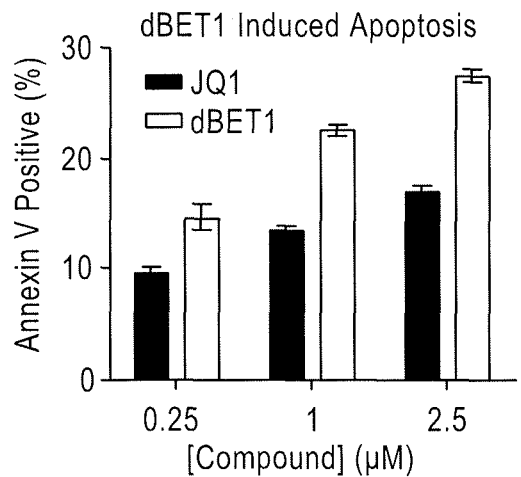
Figure 2N:
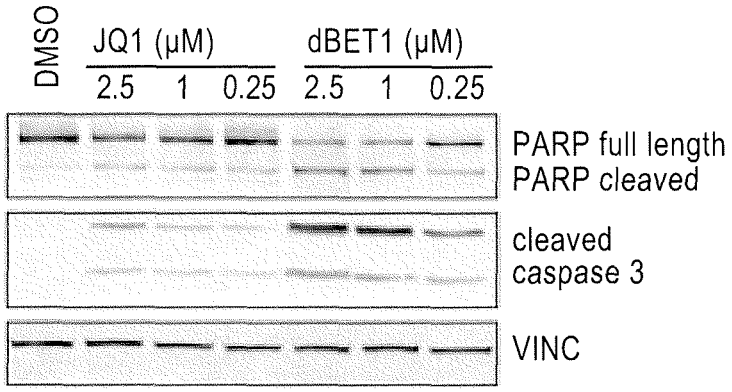
Figure 2O:
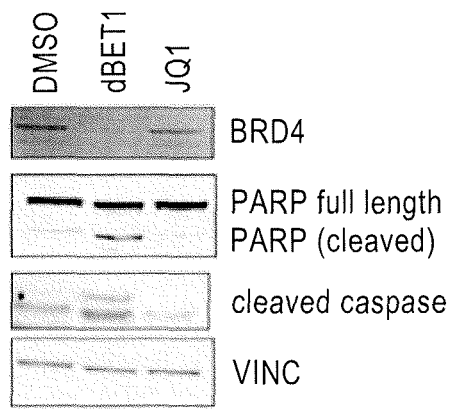
Figure 2P:
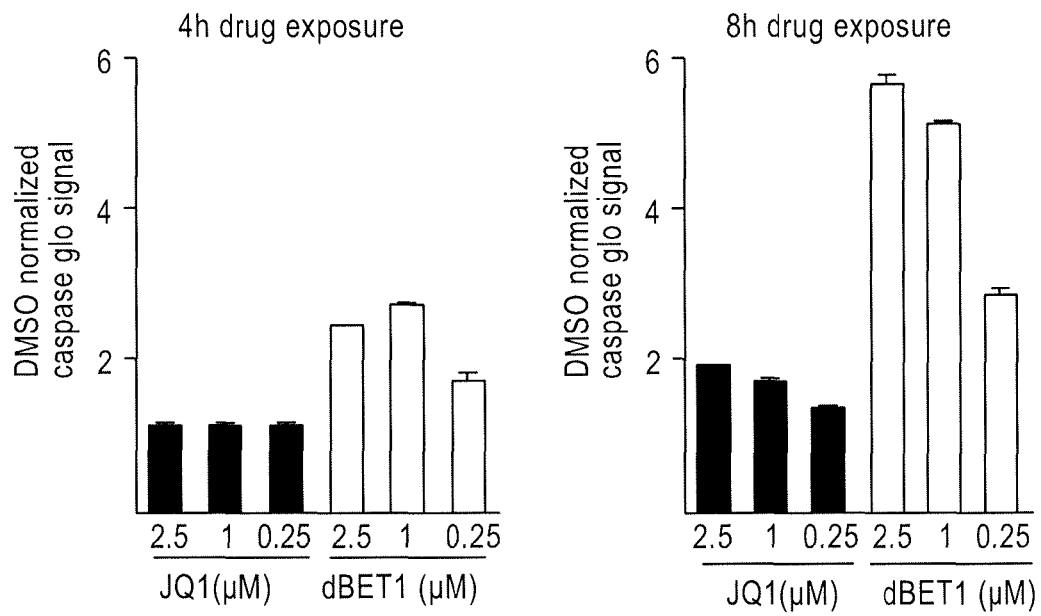
Figure 2Q:
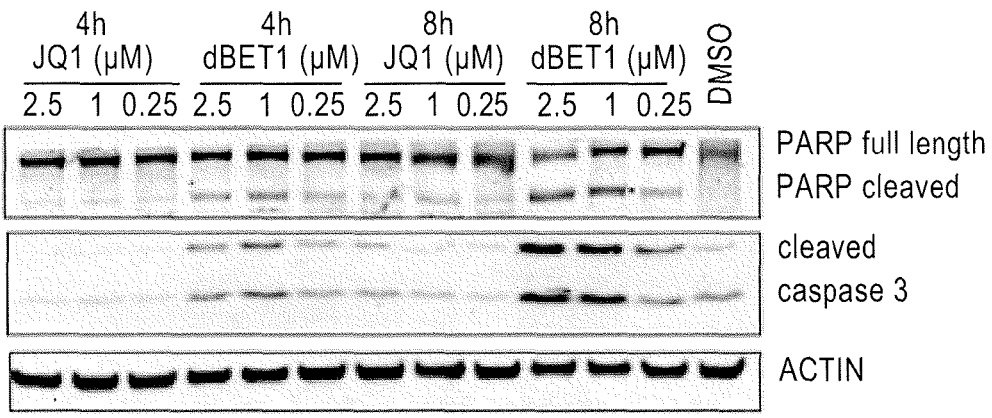

The kinetics of BRD4 degradation were determined in a time course experiment using 100 nM dBET1 in MV4-11 cells. Marked depletion of BRD4 was observed at 1 hour and complete degradation was observed at 2 hours of treatment (FIG. 2D). Degradation of BRD4 by dBET1 was associated with a potent inhibitory effect on MV4-11 cell proliferation at 24 hours (measured by ATP content, $IC_{50}$=0.14 µM, compared to $IC_{50}$=1.1 µM (FIG. 2E), consistent with the reported, pronounced inhibitory effect of RNA silencing of BRD4 in this and other models of MLL-rearranged leukemia (J. Zuber et al., Nature 478, 524-528 (2011)). Moreover, dBET1 induced a potent apoptotic consequence in MV4-11 as measured by activated caspase cleavage (Caspase-GLO) (FIG. 2F), cleavage of poly(ADP-ribose) polymerase (PARP), and cleavage of Caspase-3 (FIG. 2N) and Annexin V staining (FIG. 2M). The apoptotic response to dBET1 was confirmed in additional cultured human cell lines including DHL4 (B-cell lymphoma) (FIG. 2F). Kinetic studies of apoptotic response were then performed in MV4-11 cells cultured for either 4 or 8 hours followed by drug washout. Induction of apoptosis was assessed at 24 hours. While pulsed treatment with JQ1 did not yield a pronounced apoptotic response, significantly increased apoptosis was observed after only 4 h of dBET1 treatment that was enhanced at 8 h (FIGS. 2P and 2Q).

The rapid biochemical activity and robust apoptotic response of cultured cell lines to dBET1 established the feasibility of assessing effects on primary human AML cells, where ex vivo proliferation is negligible in short-term cultures. Exposure of primary leukemic patient blasts to dBET1 elicited dose-proportionate depletion of BRD4 (immunoblot) (FIG. 2G) and induction of apoptosis (Annexin V staining) (FIGS. 2H and 2L). Importantly, the effect of BRD4 degradation by dBET1 elicited a significantly greater apoptotic response in primary AML cells and AML cell lines than displacement of BRD4 by JQ1 (FIG. 2H). Together, these data demonstrated ligand-dependent target protein degradation and supported that target degradation can elicit a more pronounced biological consequence than domain-specific target inhibition.

Figure 12A:
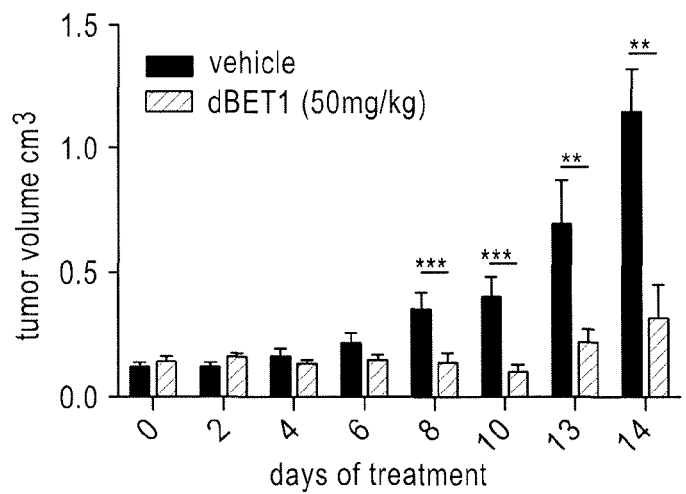
FIGS. 12A-12E (i.e.
Figure 12B:
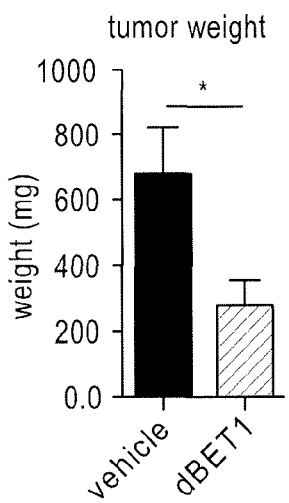
Figure 12C:
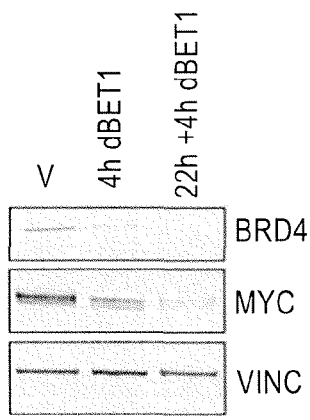
Figure 12E:
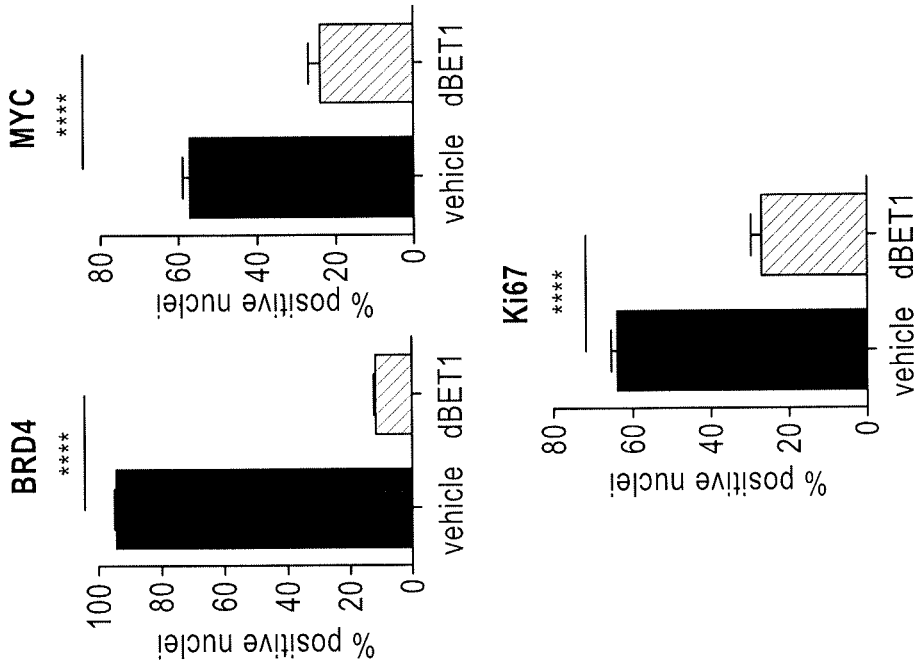
Figure 12D:
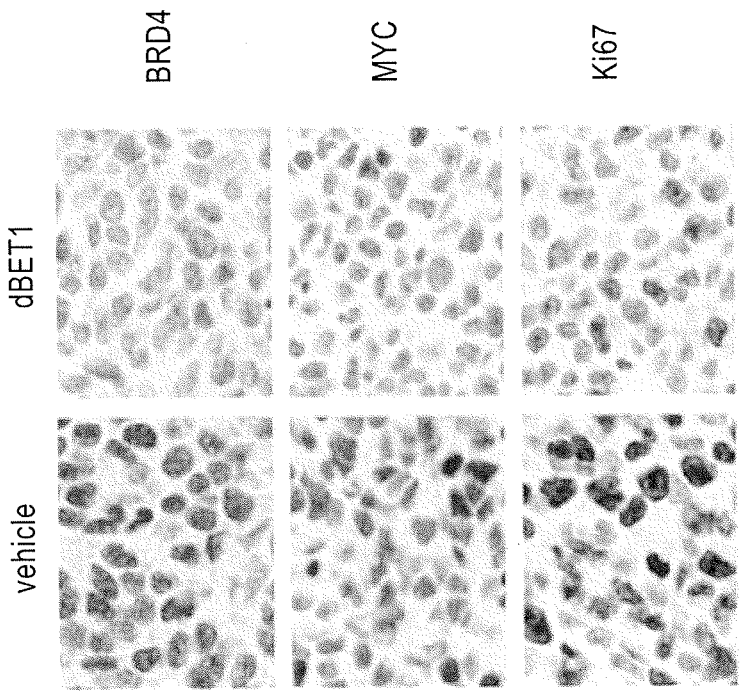
Figures 13A, 13B:
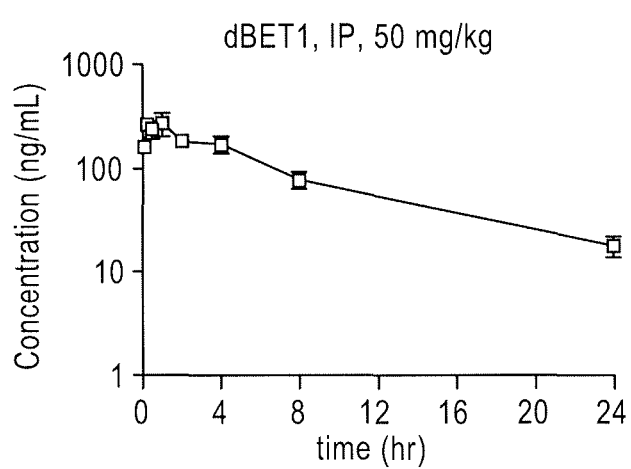
FIGS. 13A-13D (i.e.
Figure 13C:
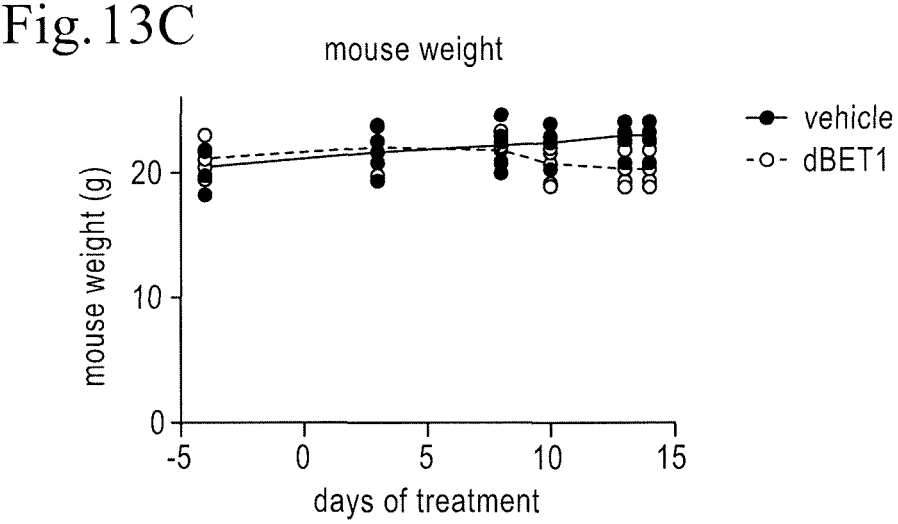
Figure 13D:
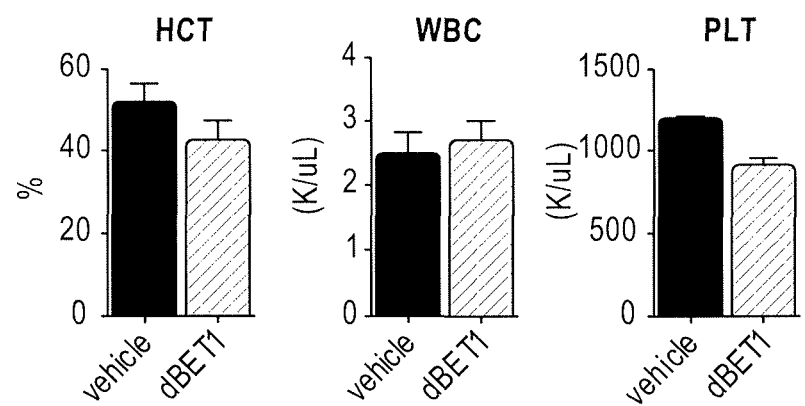

The therapeutic effect of BRD4 degradation was assessed in vivo by evaluating the tolerability and anti-tumor efficacy of repeat-dose dBET1 in an established murine xenograft model of human MV4-11 leukemia cells. Tumor-bearing mice were treated with dBET1 administered by intraperitoneal injection (50 mg/kg daily) or vehicle control. After 14 days of therapy a first tumor reached institutional limits for tumor size, and the study was terminated for comparative assessment of efficacy and modulation of BRD4 stability and function. Administration of dBET1 attenuated tumor progression as determined by serial volumetric measurement (FIG. 12A), and decreased tumor weight assessed post-mortem (FIG. 12B). Acute pharmacodynamic degradation of BRD4 was observed four hours after a first or second daily treatment with dBET1 (50 mg/kg IP) by immunoblot, accompanied by downregulation of MYC (FIG. 12C). The results were confirmed by quantitative immunohistochemistry for BRD4 and MYC following repeat-dose exposure to dBET1 for 14 days (FIG. 12D). A statistically significant destabilization of BRD4, downregulation of MYC and inhibition of proliferation (Ki67 staining) was observed with dBET1 compared to vehicle control in excised tumors (FIGS. 12D and 12E). Pharmacokinetic studies of dBET1 (50 mg/kg IP) corroborated adequate drug exposure in vivo (Cmax=392 nM; FIG. 13B), above the $EC_{50}$ for BRD4 knock-down observed in vitro (<100 nM). Notably, two weeks of dBET1 was well tolerated by mice without a meaningful effect on weight, white blood count, hematocrit or platelet count (FIGS. 13C and 13D).

Example 36

Degradation is Specific for dBET1

Figure 3C:
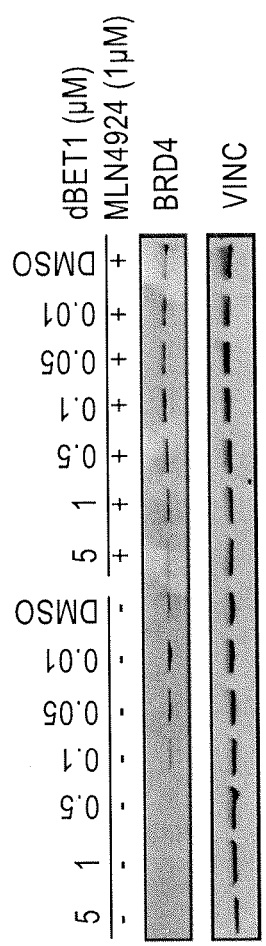
FIGS. 3A-3F (i.e.
Figure 3A:
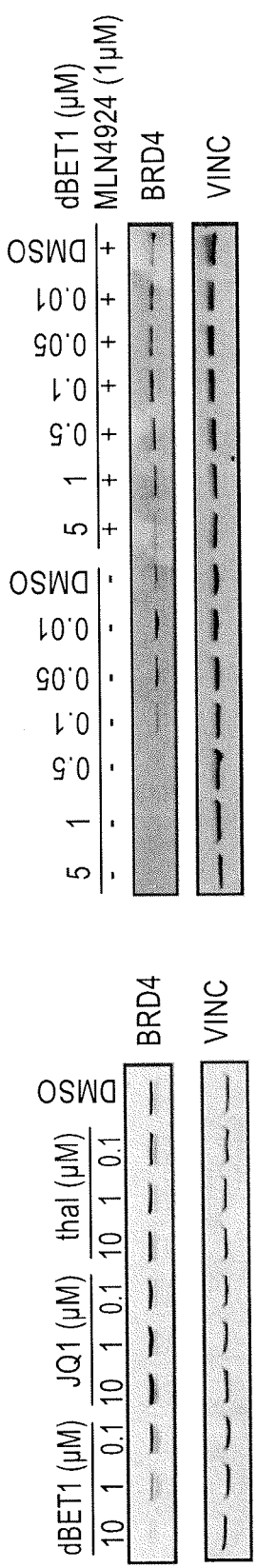
Figure 3D:
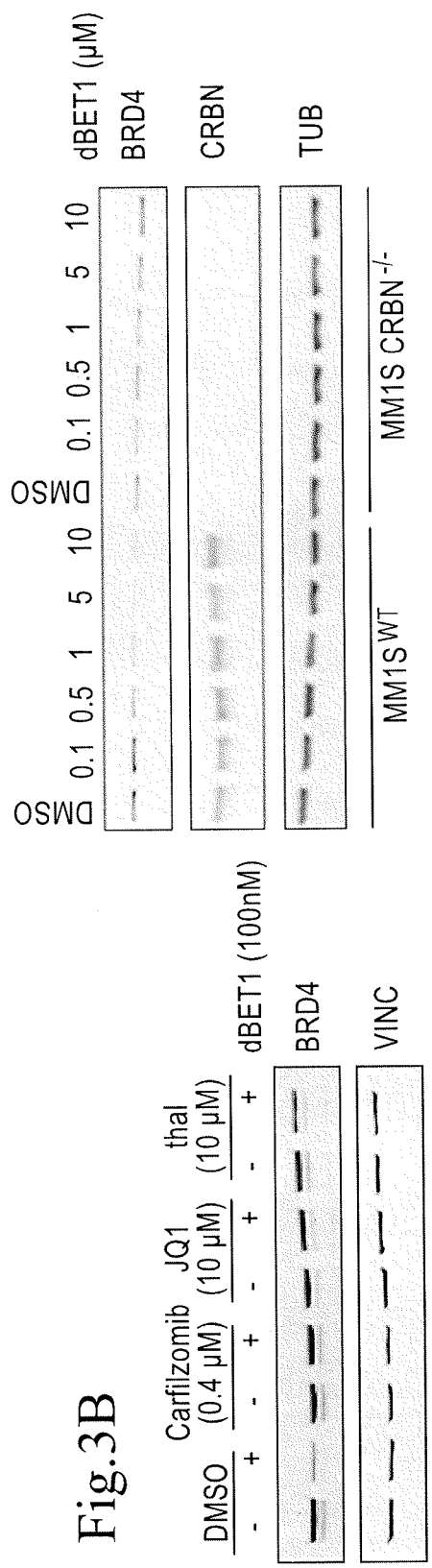
Figure 3B:
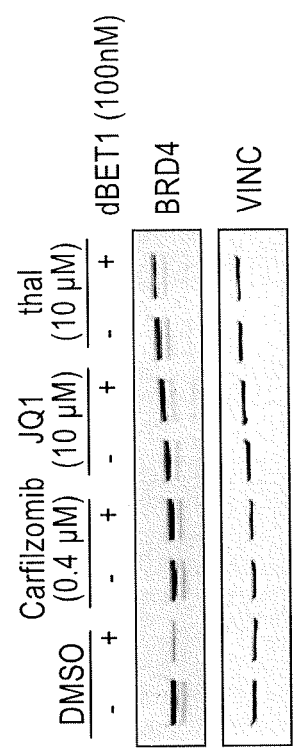
Figure 3E:
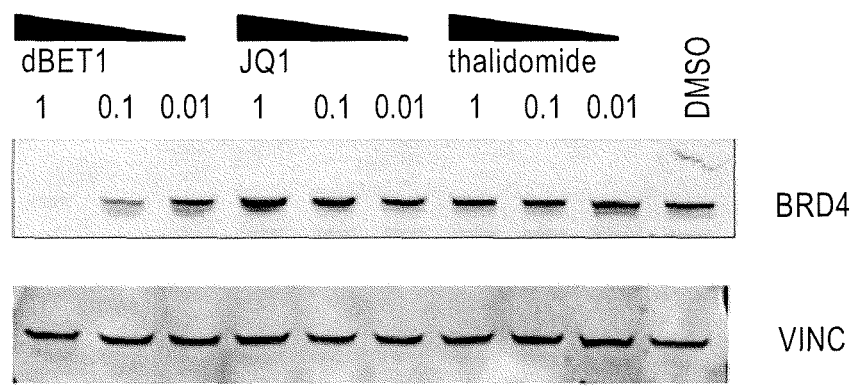
Figure 3F:
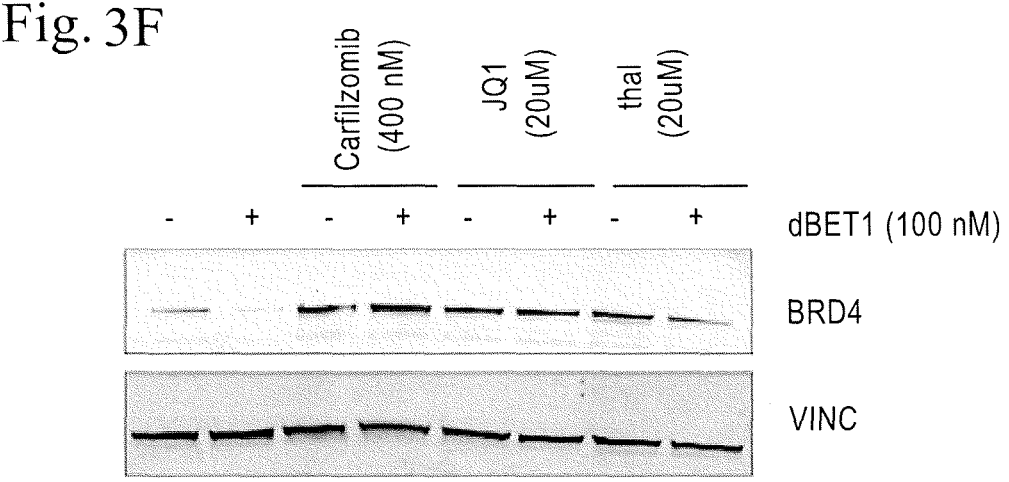

To critically assess the mechanism of dBET1-induced BRD4 degradation, requirements on proteasome function, BRD4 binding, and CRBN binding, were examined using chemical genetic and gene editing approaches. Treatment with either JQ1 or thalidomide alone was insufficient to induce BRD4 degradation in MV4-11 cells (FIGS. 3A and 3E). BRD4 stability was rescued by pre-treatment with the irreversible proteasome inhibitor carfilzomib (0.4 µM), indicating that proteasome function is required in dBET1-mediated BRD4 degradation (FIGS. 3B and 3F). Pre-treatment with excess JQ1 or thalidomide abolished dBET1-induced BRD4 degradation, further confirming the requirement for both BRD4 and CRBN (FIGS. 3B and 3F). Cullin-based ubiquitin ligases require neddylation of the cullin subunit for processive E3 ligase activity and target polyubiquitination (G. Lu, et al., Science 343, 305-309 (2014); R. I. Sufan, M. Ohh, Neoplasia 8, 956-963 (2006)). Pre-treatment with the selective NAE1 inhibitor MLN4924 (29) rescued BRD4 stability from dBET1 exposure, further supporting dependence on active RING E3 ligase activity (FIG. 3C). Moreover, using a recently published human MM cell line (MM1.S-CRBN$^{-/-}$) that features an engineered knockout of CRBN by CRISPR/Cas9 technology (G. Lu, et al., Science 343, 305-309 (2014)) confirmed the cellular requirement for CRBN (FIG. 3D). These data showed CRBN-dependent proteasomal degradation of BRD4 by dBET1.

Example 37

Highly Selective BET Bromodomain Degradation by Expression Proteomics

An unbiased, proteome-wide approach was selected to assess the cellular consequences of dBET1 treatment on protein stability. The acute impact of dBET1 treatment (250 nM) was compared to JQ1 (250 nM) and vehicle (DMSO 0.0025%) controls on protein stability in MV4-11 cells. A 2 hour incubation was selected to capture primary, immediate consequences of small-molecule action and to mitigate expected, confounding effects on suppressed transactivation of BRD4 target genes. Three biological sample replicates were prepared for each treatment condition using isobaric tagging that allowed the detection of 7429 proteins using a lower cut-off of at least two identified spectra per protein. Following BET bromodomain inhibition with JQ1, few proteomic changes are observed (FIG. 4A). Only MYC was significantly depleted by more than 2-fold after 2 hours of JQ1 treatment, indicating the reported rapid and selective effect of BET bromodomain inhibition on MYC expression in AML (FIGS. 4A and 4C) (J. Zuber et al., Nature 478, 524-528 (2011)). JQ1 treatment also downregulated the oncoprotein PIM1 (FIGS. 4A and 4C).

Figure 4D:
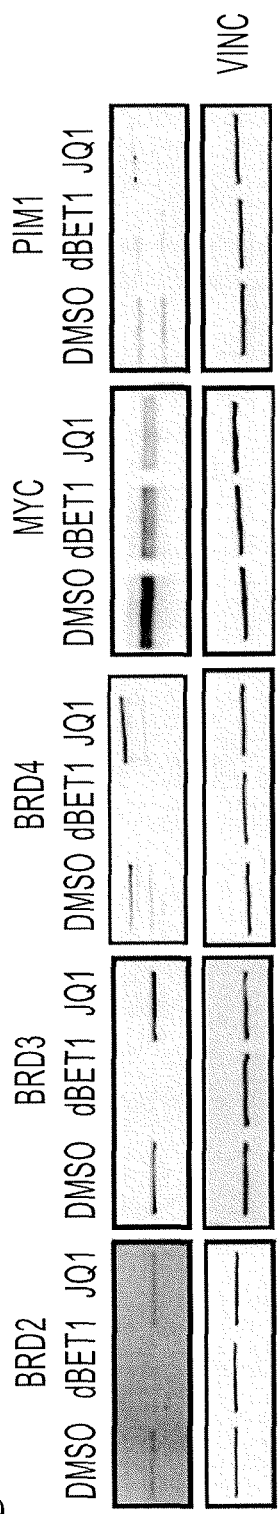
Figure 4E:
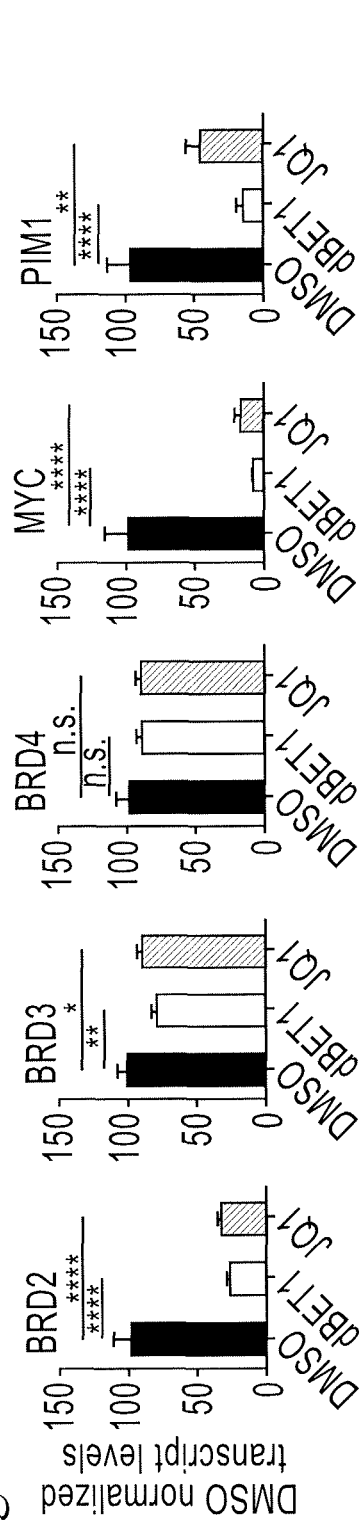
Figure 4F:
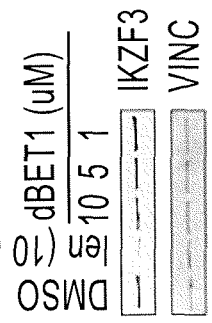

Treatment with dBET1 elicited a comparable, modest effect on MYC and PIM1 expression. Only three additional proteins were identified as significantly ($p<0.001$) and markedly (>5-fold) depleted in dBET1-treated cells: BRD2, BRD3 and BRD4 (FIGS. 4B and 4C). Orthogonal detection of BRD2, BRD3, BRD4, MYC and PIM1 was performed by immunoblot following treatment of MV4-11 leukemia cells with dBET1 or JQ1. BET family members were degraded only by dBET1, whereas MYC and PIM1 abundance was decreased by both dBET1 and JQ1, and to a lesser degree (FIG. 4D). No effect on Ikaros TF expression was observed in either treatment condition (FIG. 4F). Because MYC and PIM1 are often associated with massive adjacent enhancer loci by epigenomic profiling (B. Chapuy et al., Cancer Cell 24, 777-790 (2013); J. Lovén et al., Cell 153, 320-334 (2013)) suggestive of a transcriptional mechanism of downregulation, mRNA transcript abundance was measured for each depleted gene product (FIG. 4E). Treatment with either JQ1 or dBET1 downregulated MYC and PIM1 transcription, suggestive of secondary transcriptional effects. Transcription of BRD4 and BRD3 were unaffected, consistent with post-transcriptional effects. Transcription of BRD2 was affected by JQ1 and dBET1, whereas protein stability of the BRD2 gene product was only influenced by dBET1, indicating transcriptional and post-transcriptional consequences. These data demonstrated a highly selective effect of dBET1 on target protein stability, proteome-wide.

Example 38

Negative SAR JQ1-Rev (JQI-II-079)

Figure 5B:
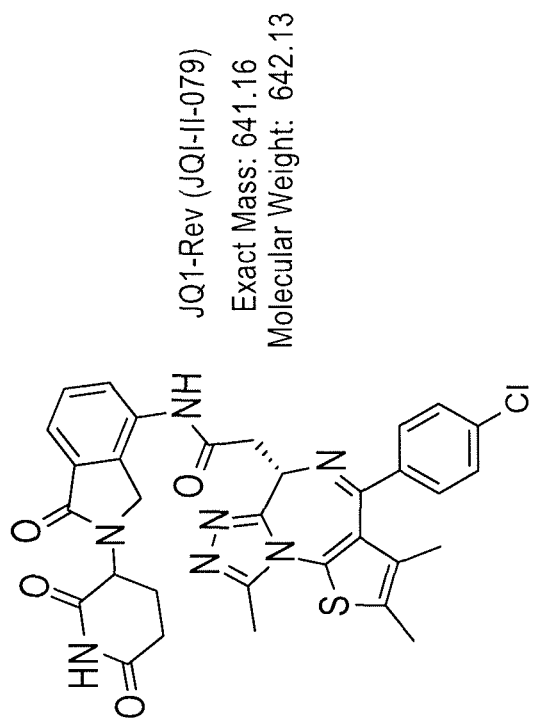
FIGS. 5A and 5B.
Figure 5A:
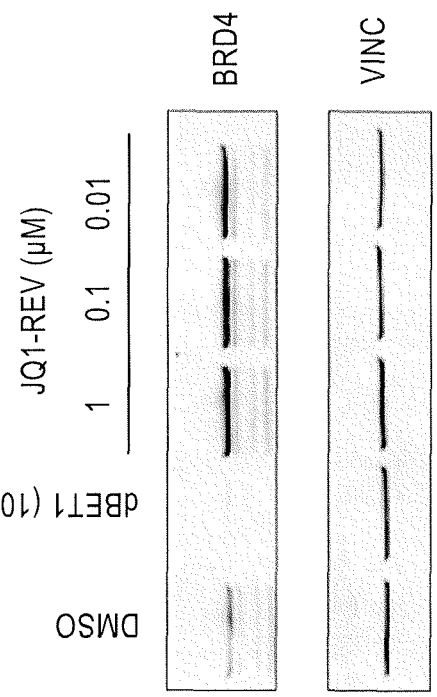

MV4-11 cells were treated for 24 hours with either DMSO, dBET1 (100 nM) or the indicated concentrations of JQ1-REV (JQ-II-079), lysed with RIPA buffer, and immunoblotted for BRD4 and Vinculin as loading control. While BRD4 levels were significantly decreased with dBET 1 treatment, JQ1-Rev treatment did not yield any measureable effect. The results are shown in FIG. 5A.

Example 39

Decrease in BRD4 Protein Levels Proceed Measurable Decrease in BRD4 Transcript Levels MV4-11 cells were treated with dBET1 or JQ1 for 2 and 4 hours at 100 nM or 1 uM each. RNA was isolated using Qiagen RNAeasy kit and converted to cDNA using VILO Superscript reverse transcriptase. BRD4 transcript levels were assayed via qRT-PCR. The results are shown in FIGS. 6A and 6B.

Example 40 dBET1 Mediated Degradation of BRD4 is Dependent on CRBN Availability

Figure 7:
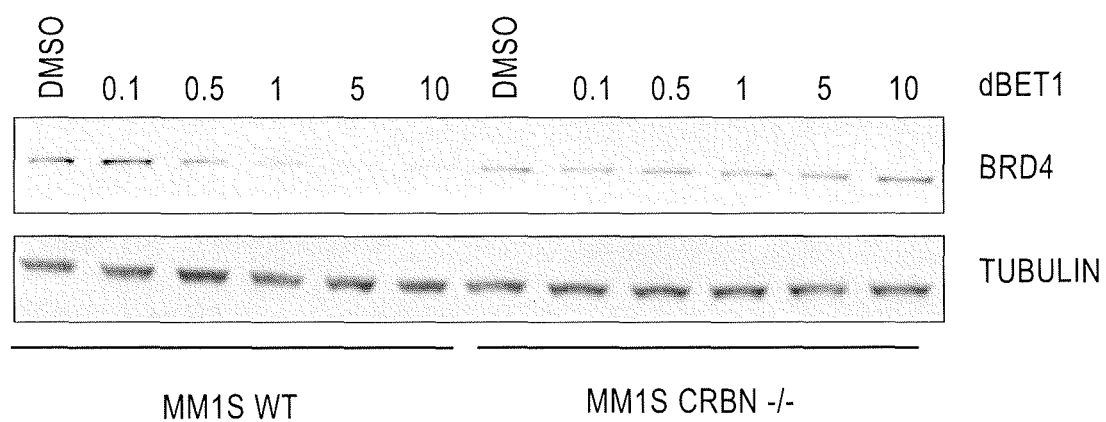
FIG. 7 is a Western blot illustrating the degree of degradation of BRD4 by treatment of a human cell line MM1S and a human cell line MM1S that is deficient in cereblon with increased concentrations of a bifunctional compound of the application, dBET1.

Wild type MM proficient of CBRN expression (MM1S WT) as well as deficient of CRBN expression (MM1S $CRBN^{-/-}$) were treated with dBET1 for 8 hours. CRBN deficient isogenic cell line was reported elsewhere (Lu et al. Science 2014). Cells were lysed with RIPA buffer and immunoblotted for BRD4 and tubulin as loading control. The results are shown in FIG. 7.

Example 41

Effects of dBET2 on BRD4 Expression Levels

Figure 8:
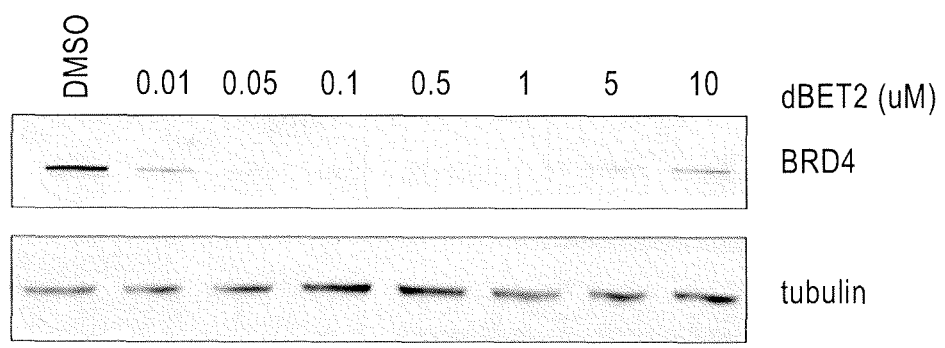
FIG. 8 is a Western blot illustrating the degree of degradation of BRD4 by treatment of cells with increased concentrations of a bifunctional compound of the application, dBET2.

MV4-11 cells were treated with DMSO or increasing concentrations of dBET2 for 8 hours, lysed in RIPA buffer and immunoblotting was performed against BRD4 and tubulin as loading control. The results are shown in FIG. 8.

Example 42

Figure 9B:
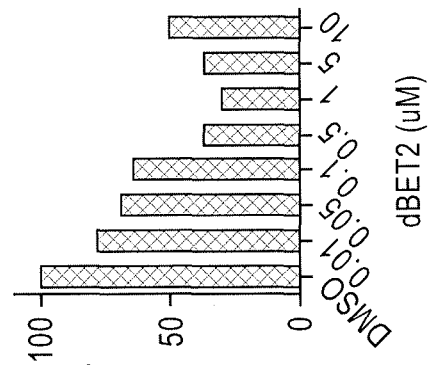
FIGS. 9A and 9B.
Figure 9A:
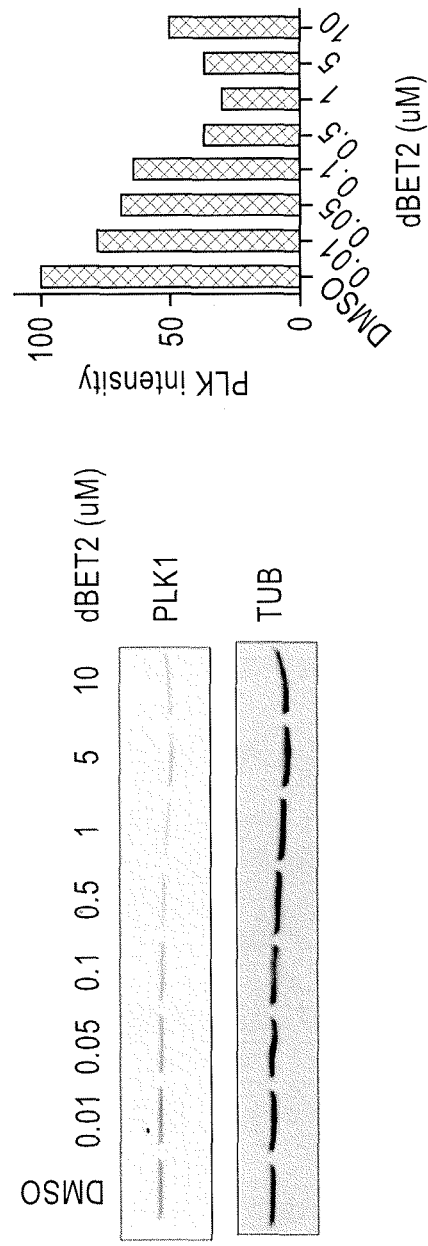

Effects of dBET2 on PLK1 Expression Levels (A) MV4-11 cells were treated with DMSO or increasing concentrations of dBET2 for 8 hours, lysed in RIPA buffer and immunoblotting was performed against PLK1 and tubulin as loading control. (B) Quantification of (A). The intensity of the PLK1 bands was quantified to the respective tubulin loading control bands. The results are shown in FIGS. 9A and 9B.

Example 43 dBET1 Mediated Degradation In Vivo

Short-term treatment studies were conducted with tumor-bearing mice using the human MV4-11 leukemia murine xenograft model. Mice with established tumors were administered dBET1 (50 mg/kg), JQ1 (50 mg/kg) or a vehicle control, once daily for two days. Pharmacodynamic effects on BRD4 stability were determined 4 h after the second drug exposure, by immunoblot. Treatment with dBET1 was associated with unambiguous suppression of BRD4, compared to JQ1 and vehicle controls (FIG. 2O). Corroborating the pharmacologic advantage observed in cell lines and primary patient cells, an increased apoptotic response following dBET1 treatment in vivo was observed as measured by immunoblotting for PARP and caspase cleavage (FIG. 2O).

Example 44 dFKBP-1 and dFKBP-2 Mediated Degradation of FKBP12

Figure 10A:
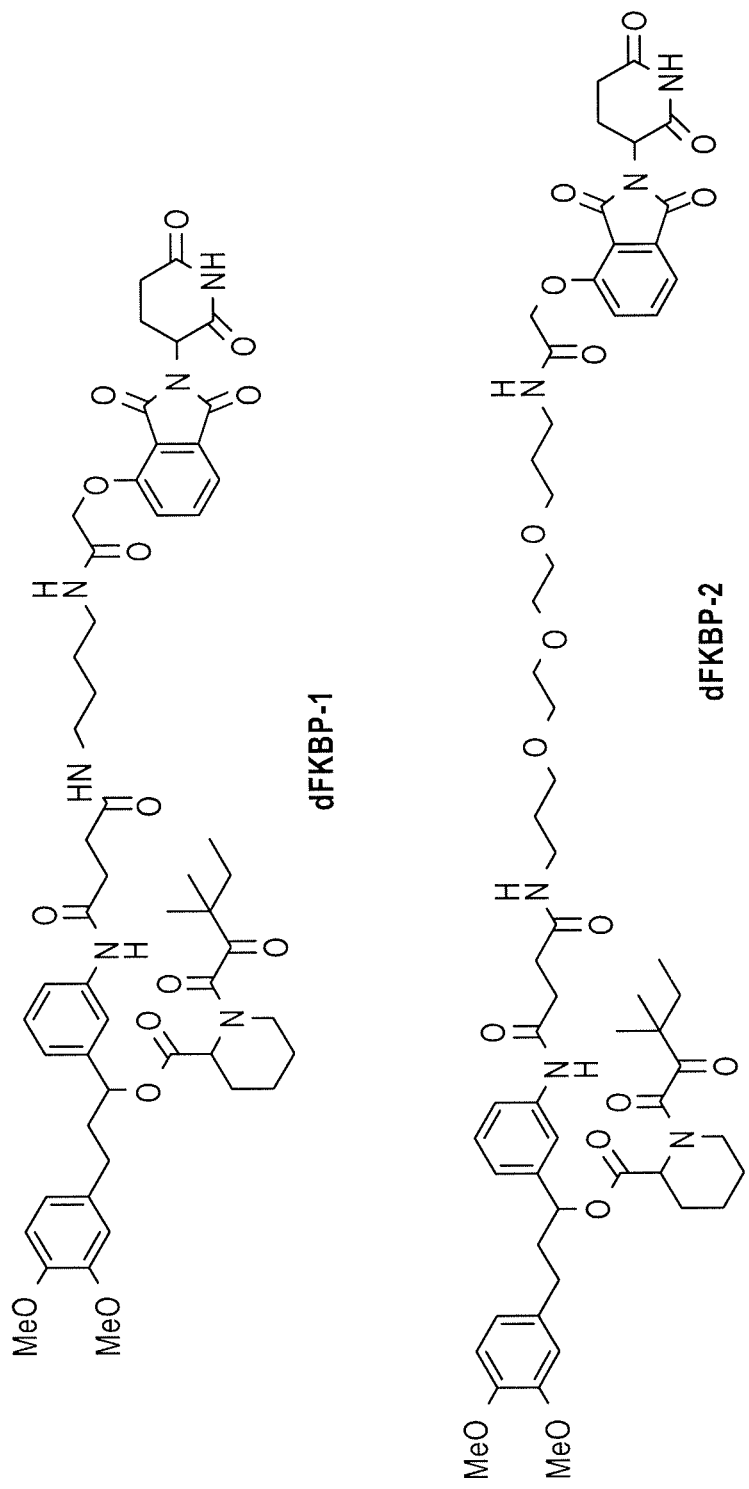
FIGS. 10A-10D (i.e.
Figure 10B:
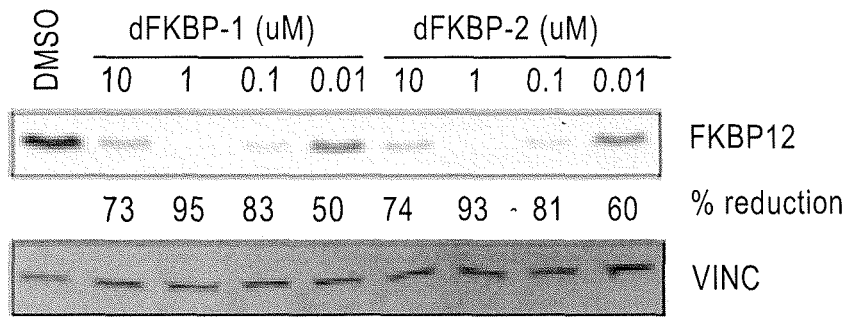
Figure 10C:
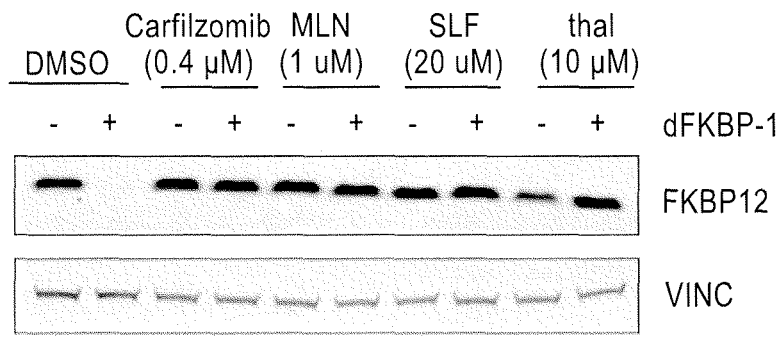
Figure 10D:
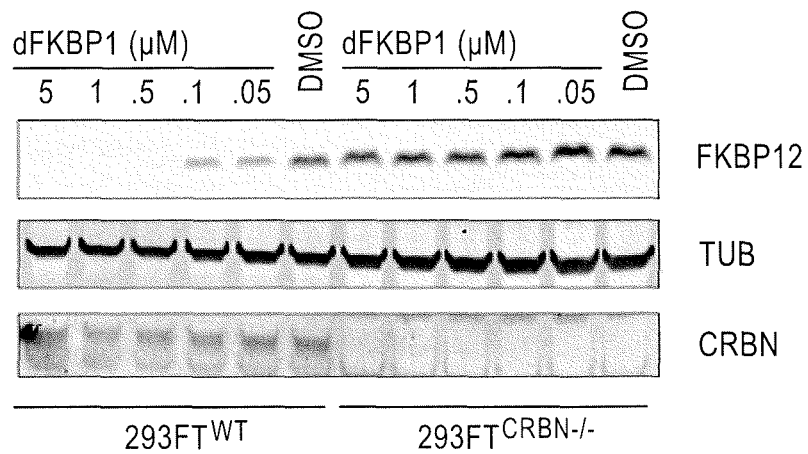

Phthalimide-conjugated ligands to the cytosolic signaling protein, FKBP12, were synthesized. FKBP12 has been identified to play a role in cardiac development, ryanodine receptor function, oncogenic signaling, and other biological phenotypes. At a known permissive site on the FKBP12-directed ligand AP1497, two chemical spacers were placed to create the conjugated phthalimides dFKBP-1 and dFKBP-2 (FIG. 10A). Both potently decreased FKBP12 abundance in MV4-11 cells (FIG. 10B), leading to over 80% reduction of FKBP12 at 0.1 µM and 50% reduction at 0.01 µM, a 1000-fold improvement in potency as compared to conjugated PROTAC ligands which demonstrated activity at 25 µM. As with dBET1, destabilization of FKBP12 by dFKBP-1 was rescued by pre-treatment with carfilzomib, MLN4924, free AP1497 or free thalidomide (FIG. 10C). CRBN-dependent degradation was established using previously published isogenic 293FT cell lines which are wild-type (293FT-WT) or deficient (293FT-CRBN$^{-/-}$) for CRBN (G. Lu, et al., *Science* 343, 305-309 (2014)). Treatment of 293FT-WT cells with dFKBP-1 induced potent, dose-dependent degradation of FKBP12, whereas 293FT-CRBN$^{-/-}$ were unaffected (FIG. 10D).

Example 45

Figure 14A:
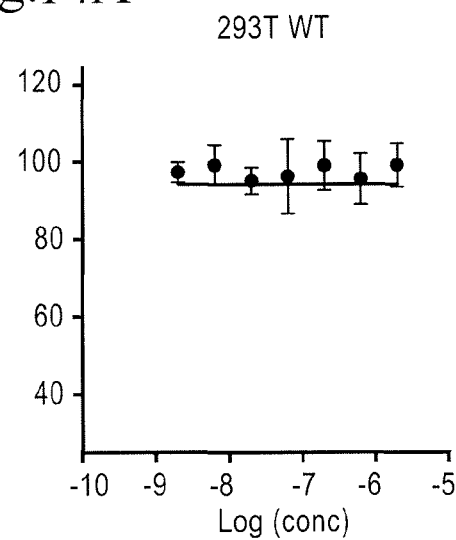
FIGS. 14A-14BB (i.e.
Figure 14B:
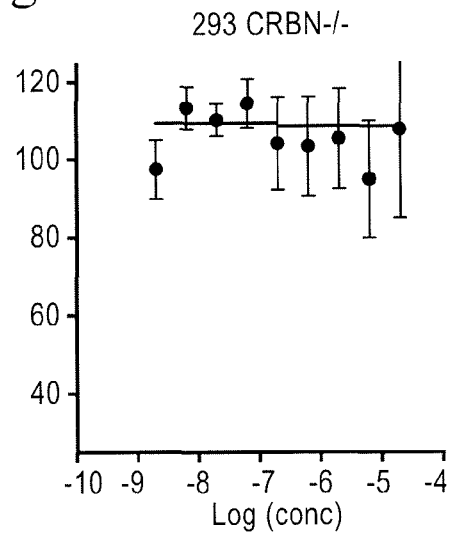
Figure 14C:
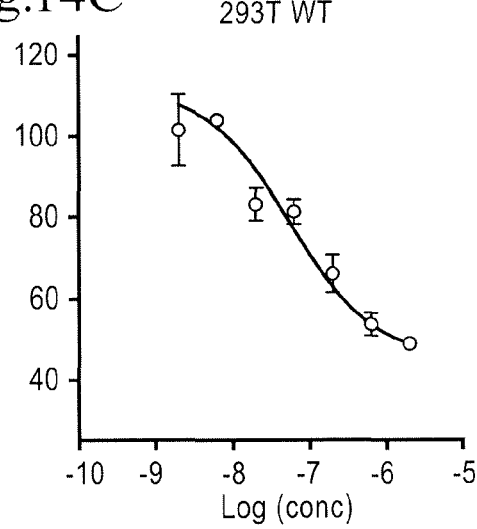
Figure 14D:
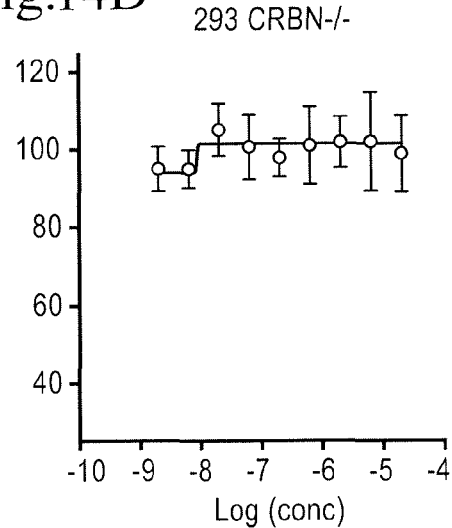
Figure 14E:
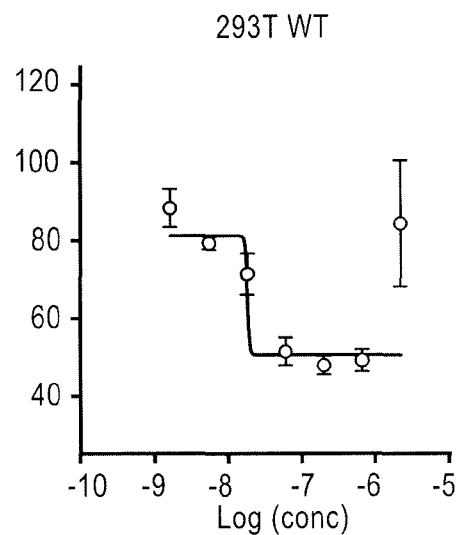
Figure 14F:
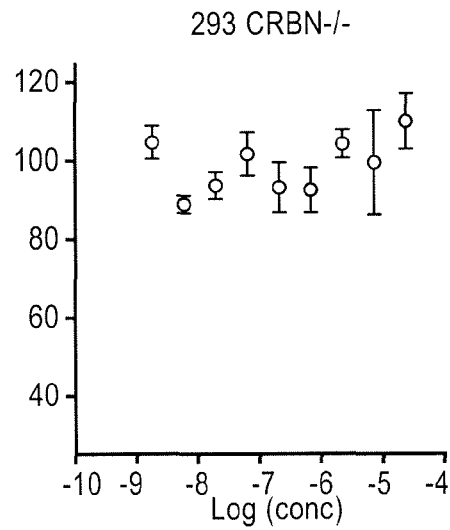
Figure 14G:
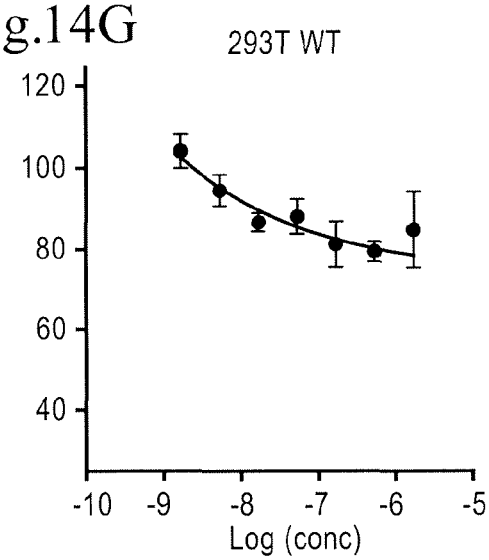
Figure 14H:
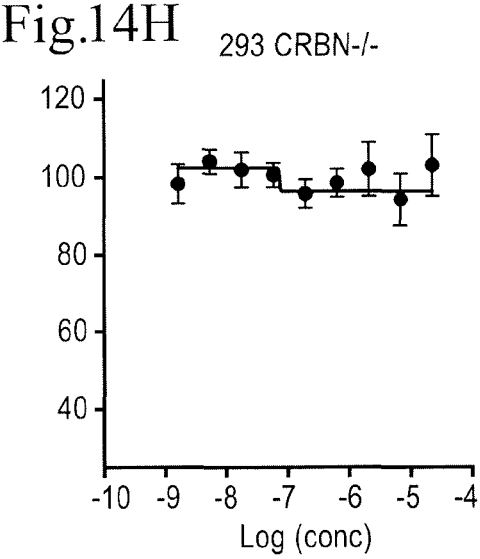
Figure 14I:
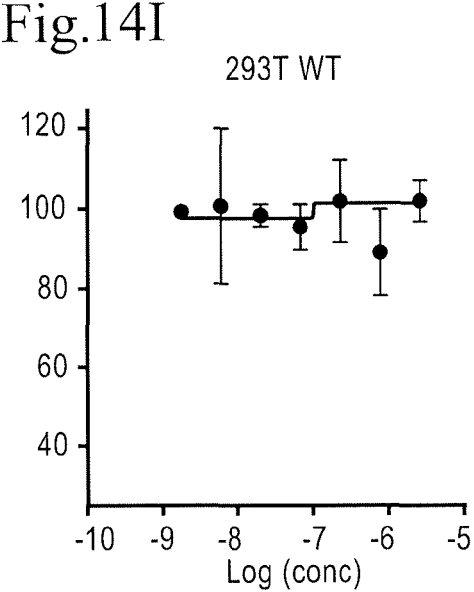
Figure 14J:
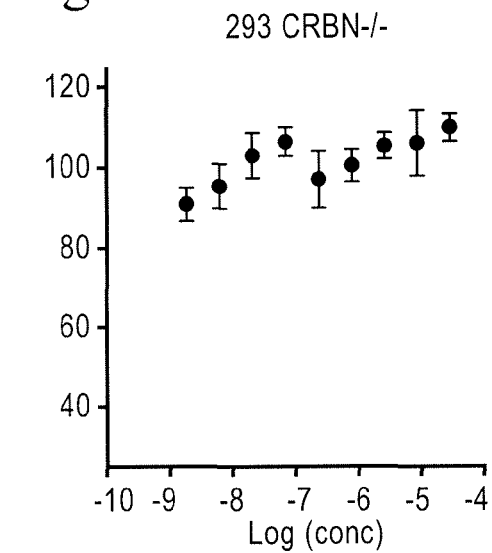
Figure 14K:
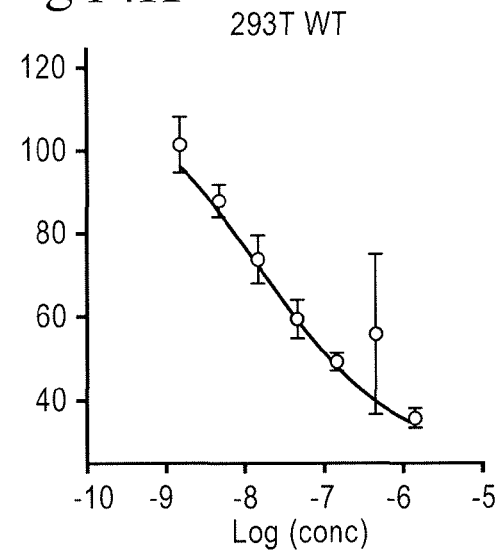
Figure 14L:
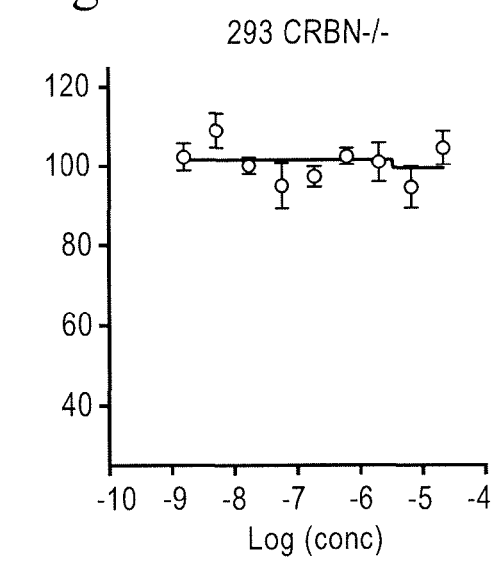
Figure 14M:
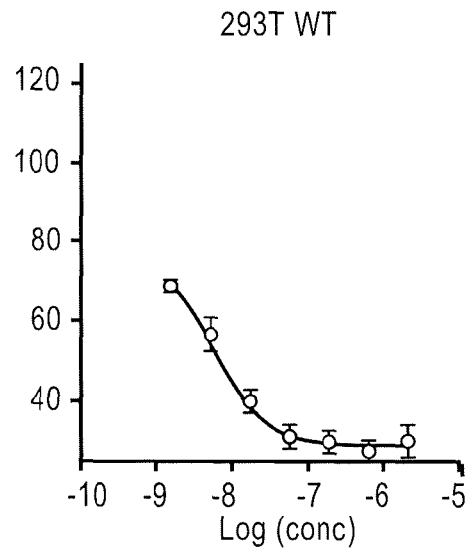
Figure 14N:
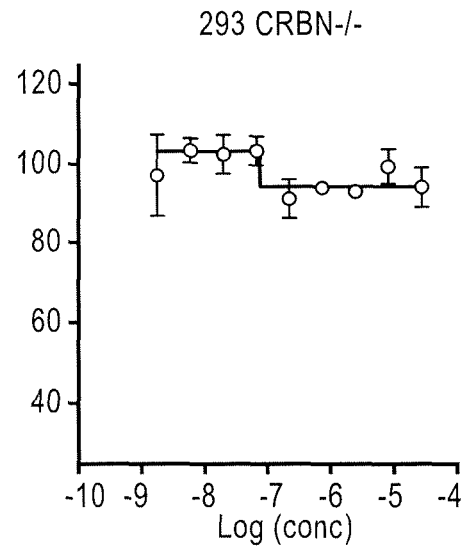
Figure 14O:
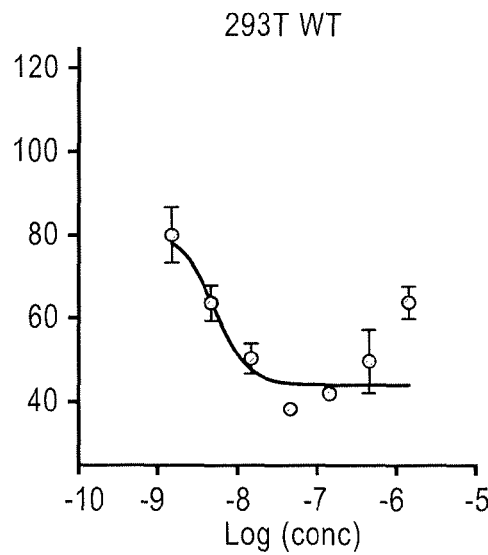
Figure 14P:
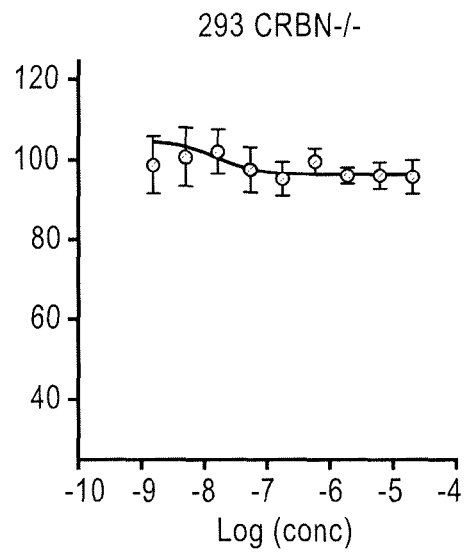
Figure 14Q:
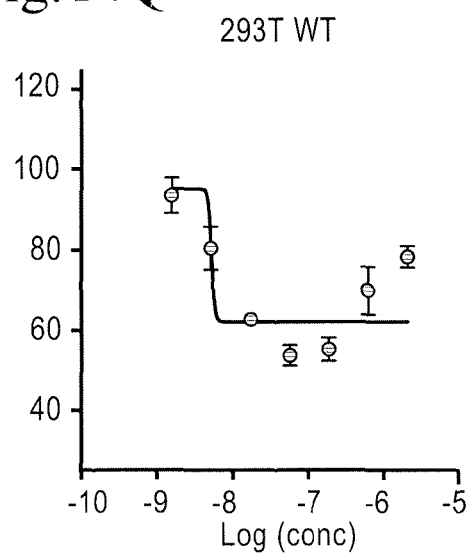
Figure 14R:
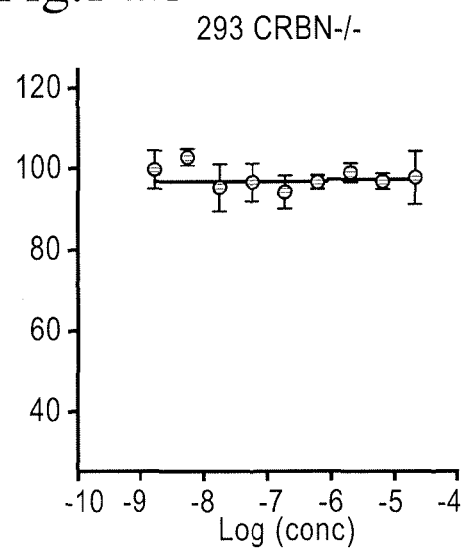
Figure 14S:
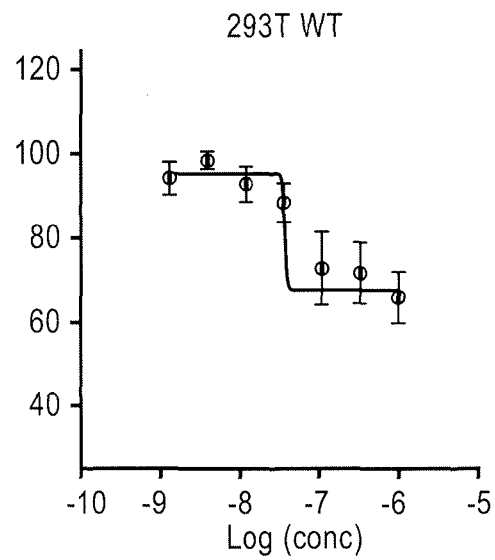
Figure 14T:
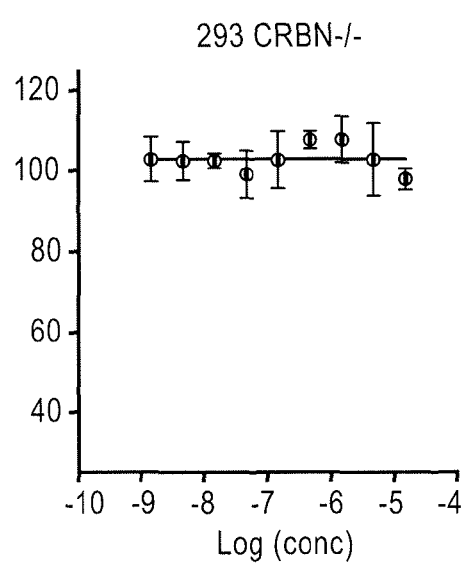
Figure 14U:
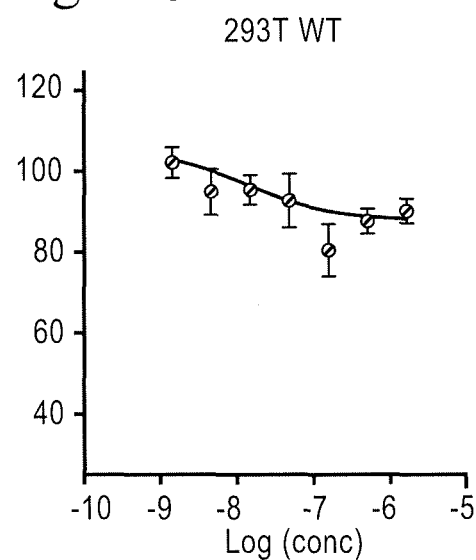
Figure 14V:
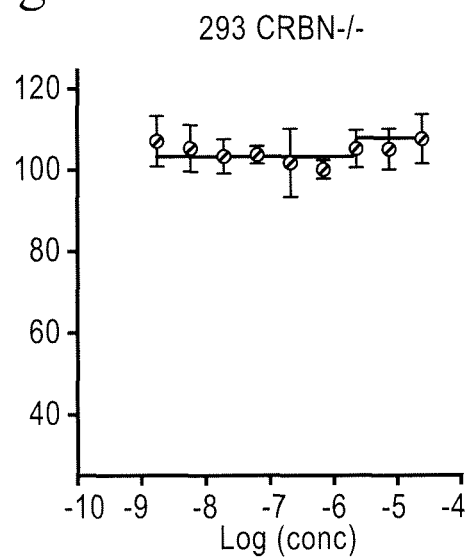
Figure 14W:
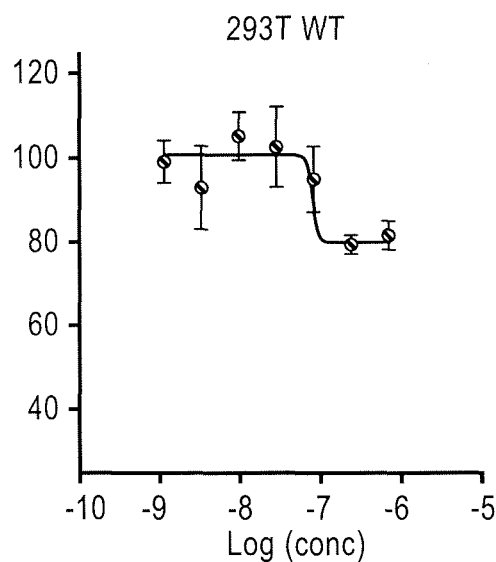
Figure 14X:
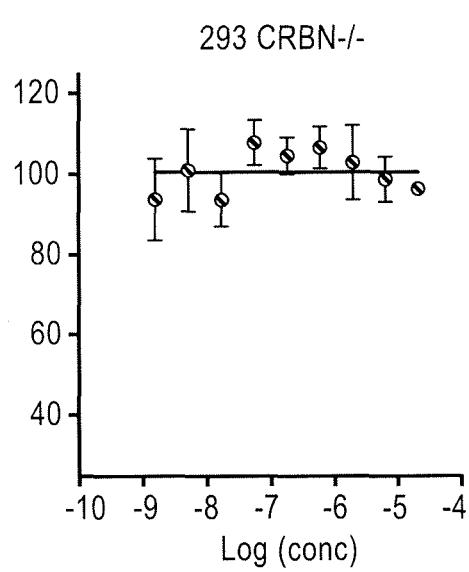
Figure 14Y:
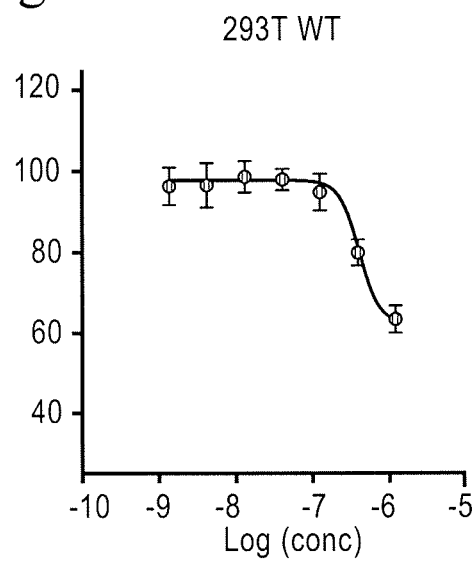
Figure 14Z:
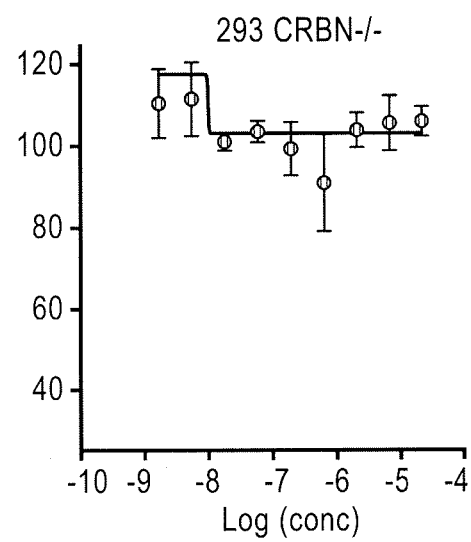
Figure 14A:
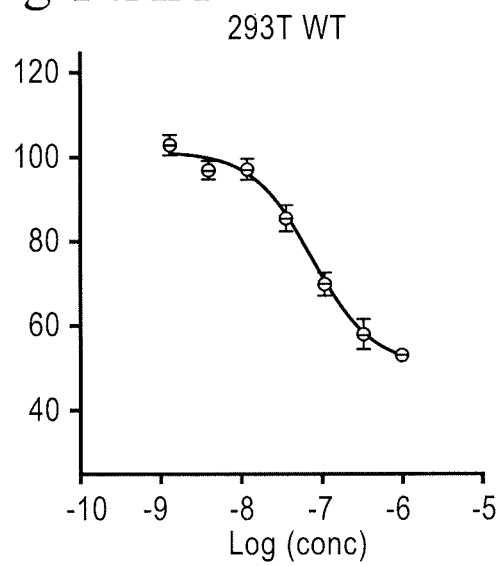
Figure 14B:
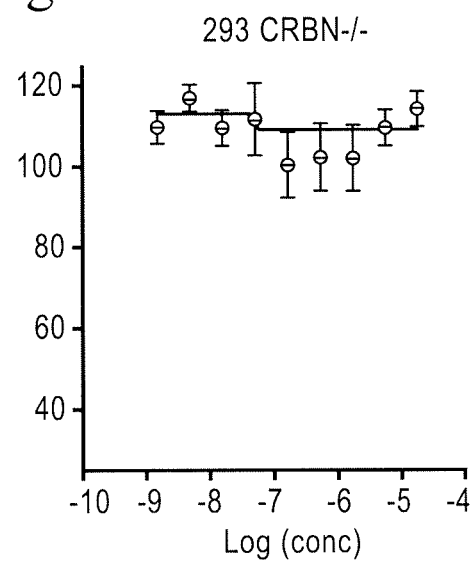

Degradation of BRD Proteins by dBET 10,000 cells (293T WT or 293 CRBN-/-) were seeded per well using 384-well plates. On the following day, dBET compounds were added at various concentrations. After being treated with the dBET compounds for 4 hours, cells were fixed with formaldehyde, permeabilized using 0.1% triton, blocked with LiCor blocking buffer, and incubated with the primary antibody (BRD4, 1:1000) overnight. On the following day, cells were washed (5×TBST) and stained using Odysee Cell Stain (1:500). A secondary antibody recognizing the rabbit BRD4 antibody was added simultaneously (1:800). Images were quantified using LiCOR imager. BRD4 levels in the cells after the dBET treatment were shown in FIGS. 14A-BB.

Various cells (BAF3_K-RAS, SEMK2, Monomac1, MM1S$^{WT}$, MM1S$^{CRBN-/-}$) were treated with increasing concentrations of dBET1 or dBET6 for ~16 hours. Cells were lysed and the lysates were immunoblotted to measure levels of BRD4. The results are shown in FIGS. 15A-15D and 15F.

Figure 15A:
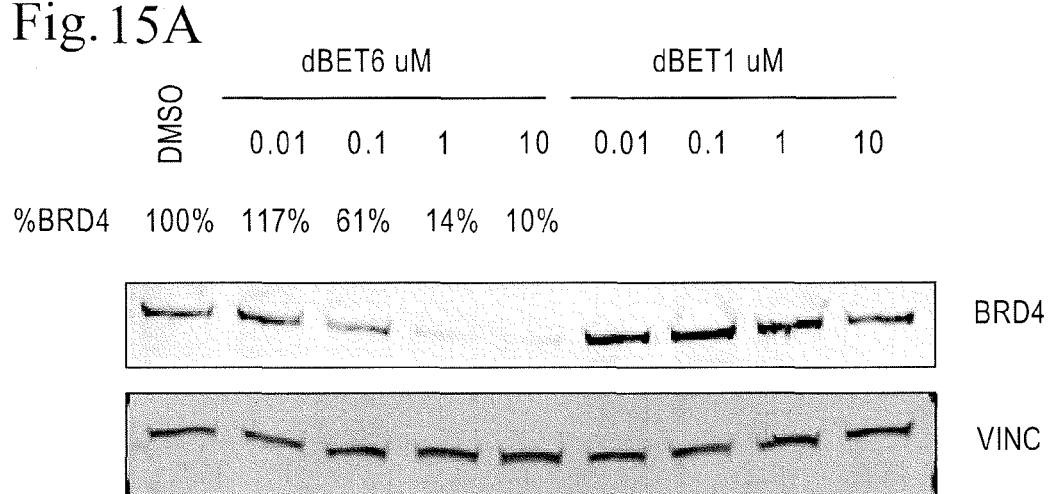
FIGS. 15A-15F (i.e.
Figure 15B:
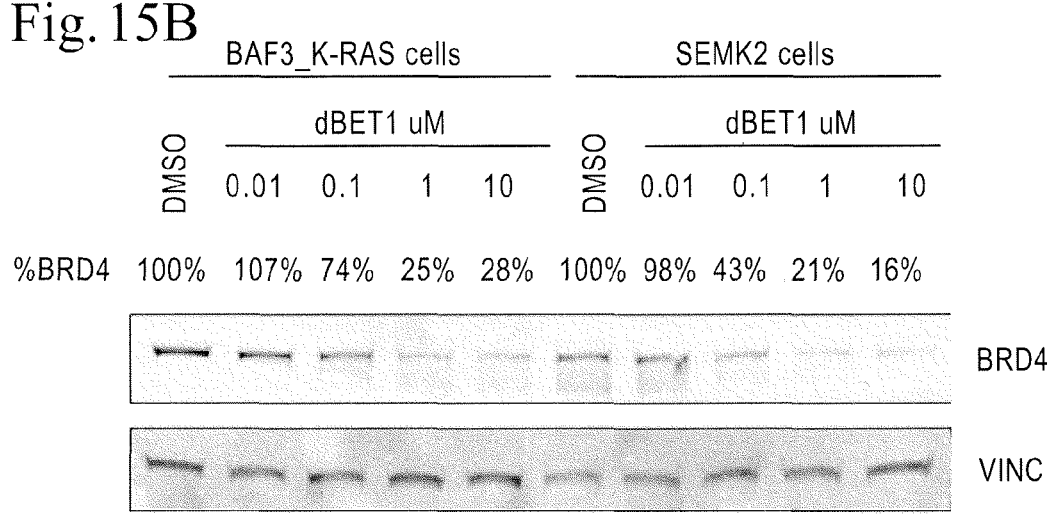
Figure 15C:
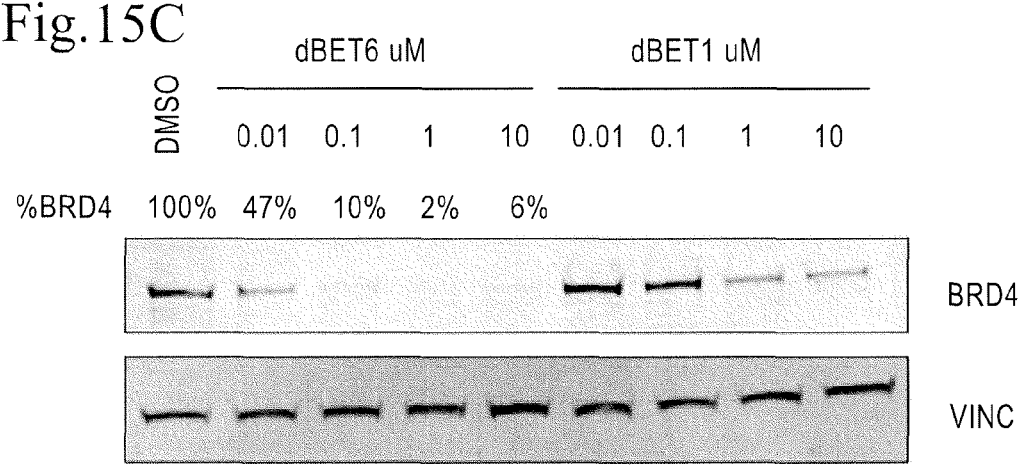
Figure 15D:
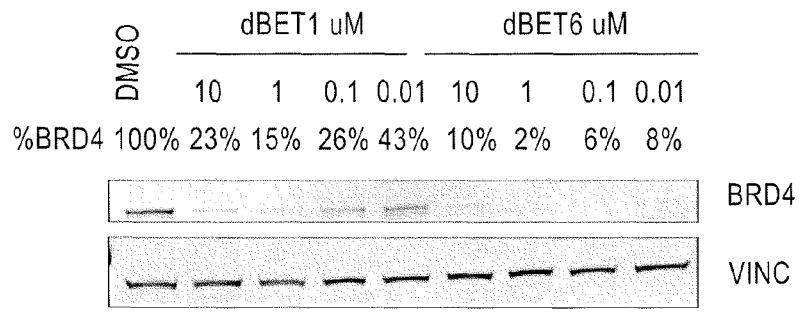
Figure 15E:
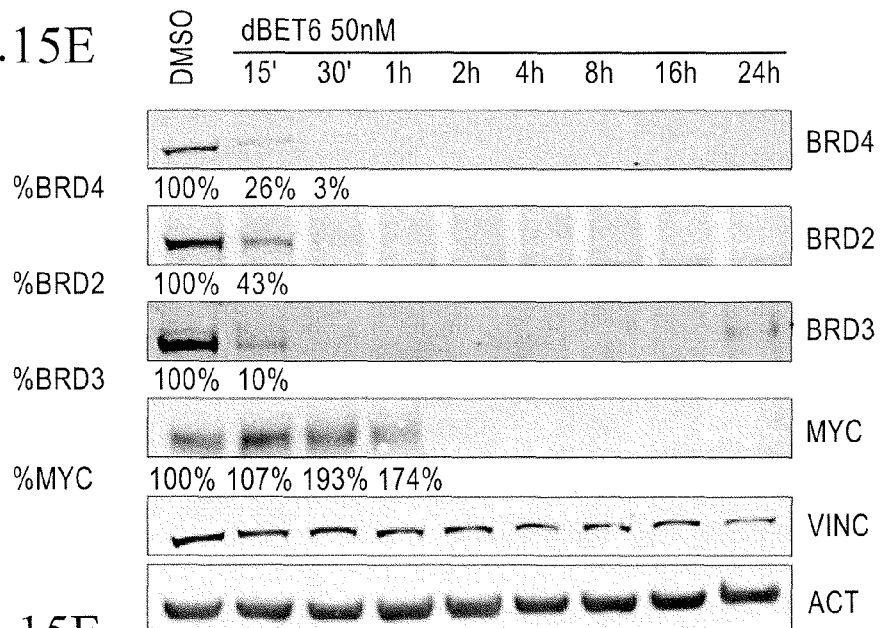
Figure 15F:
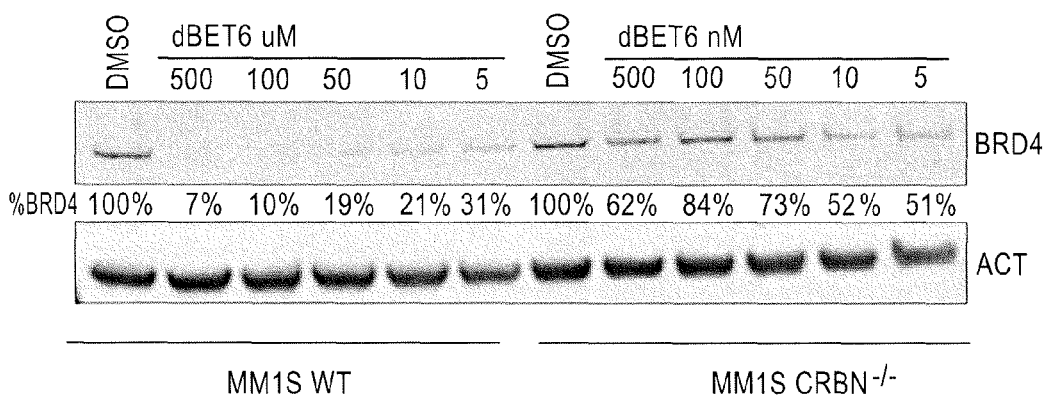
Figure 16A:
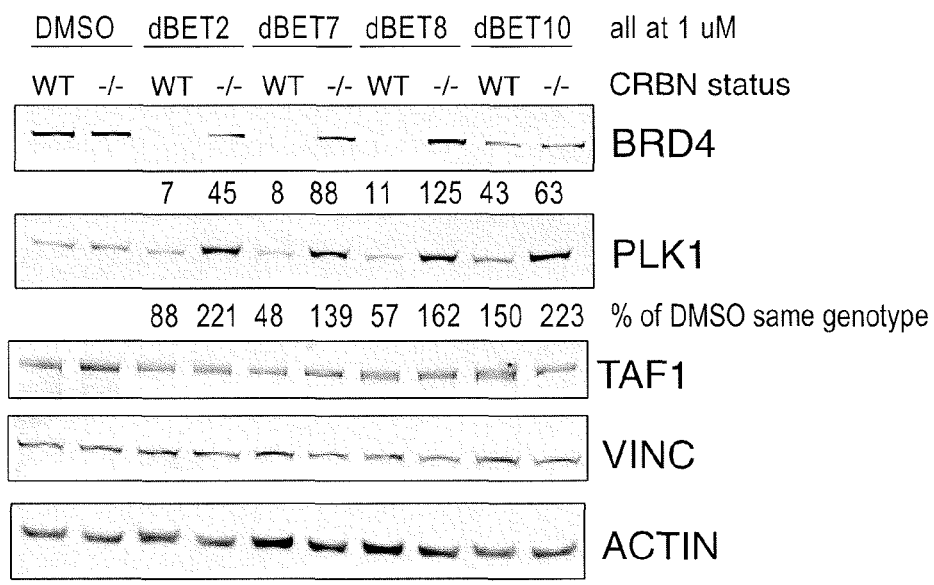
FIGS. 16A and 16B: Immunoblots of protein levels in cells treated with the bifunctional compounds of the present application.
Figure 16B:
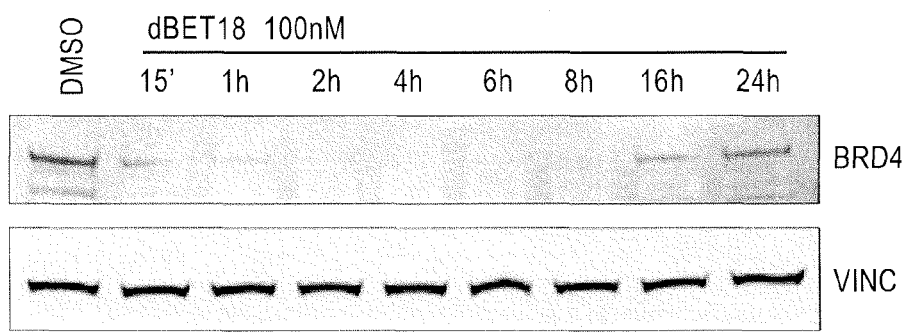
Figure 17B:
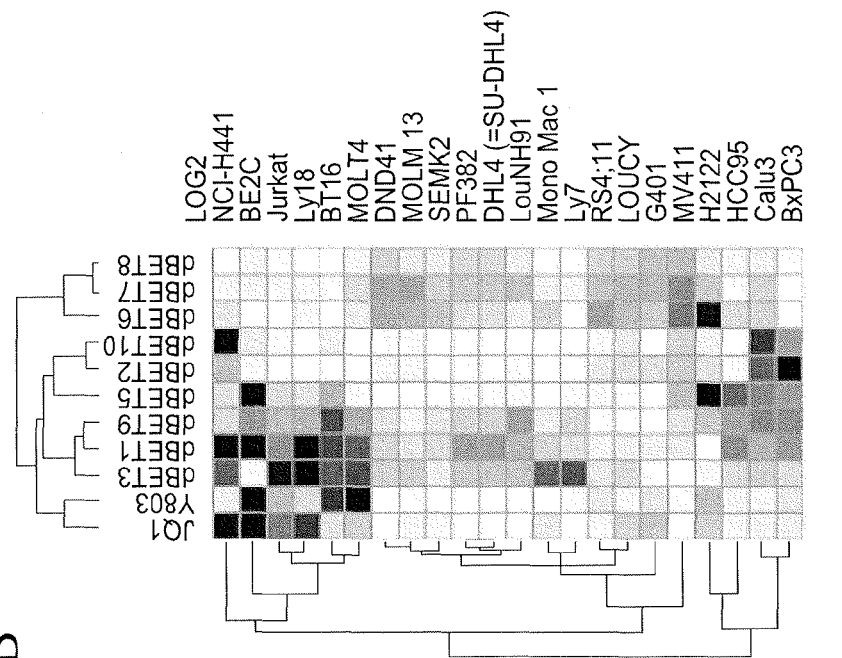
Figure 17A:
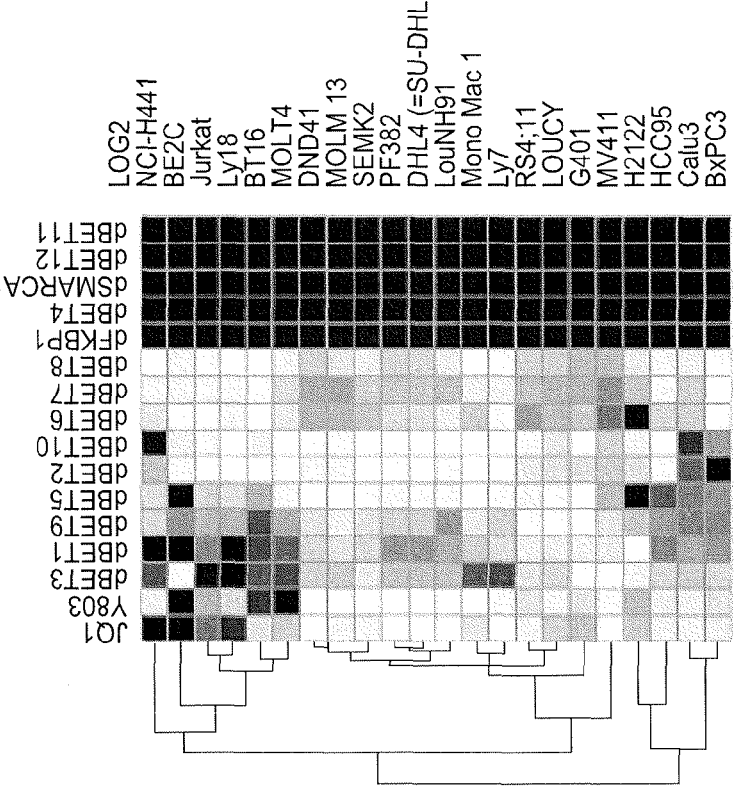
Figure 18A:
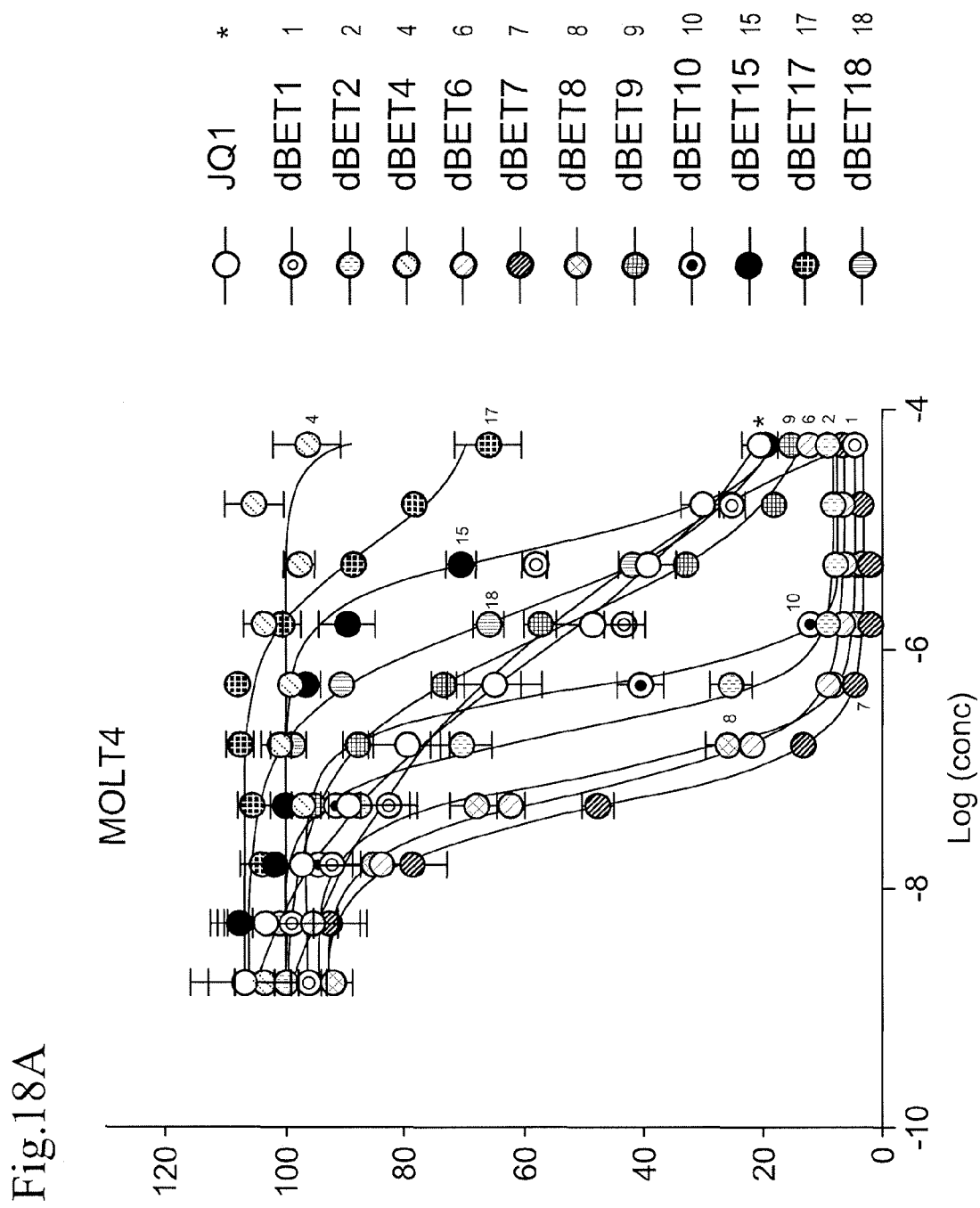
FIGS. 18A-18C (i.e.
Figure 18B:
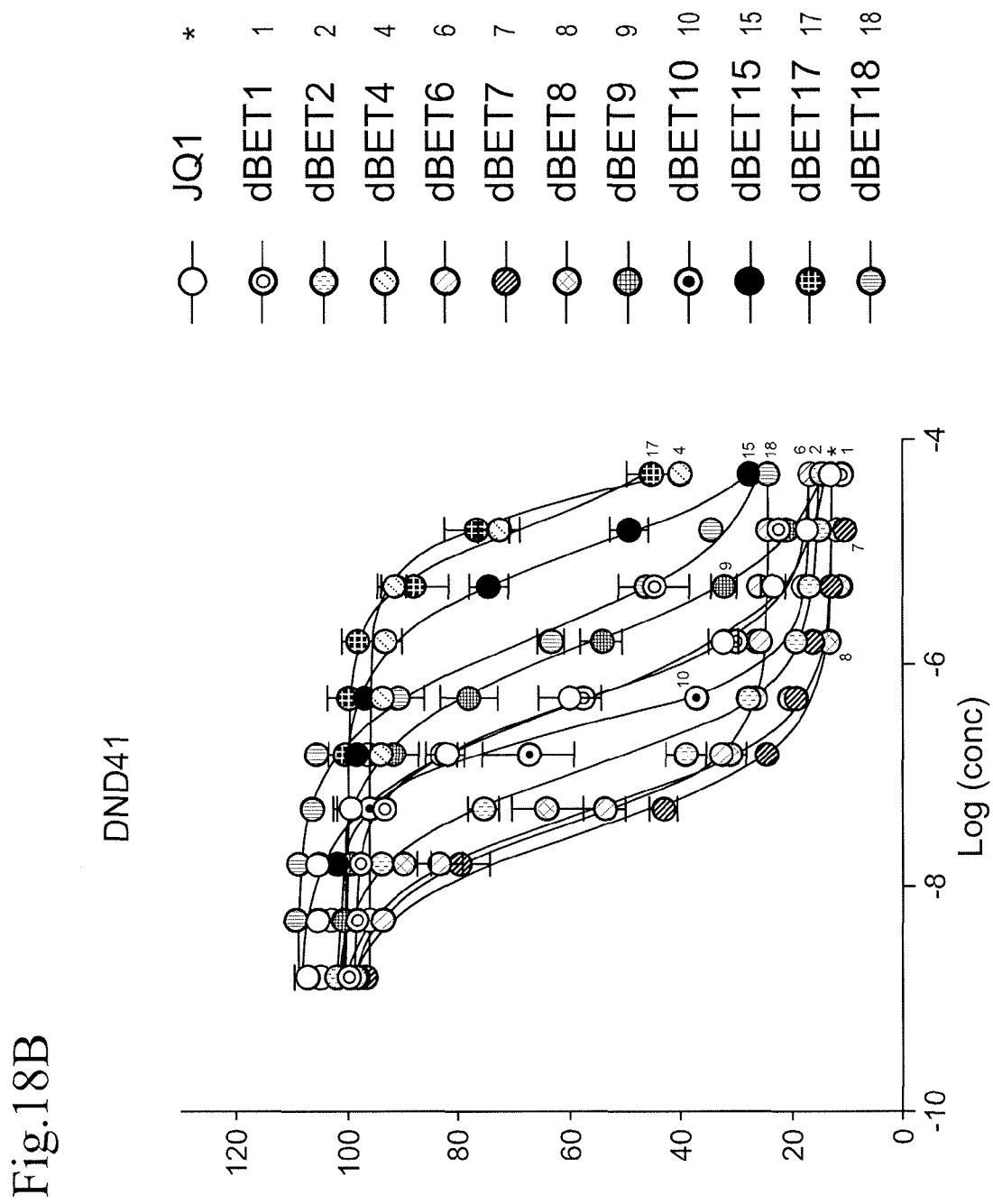
Figure 18C:
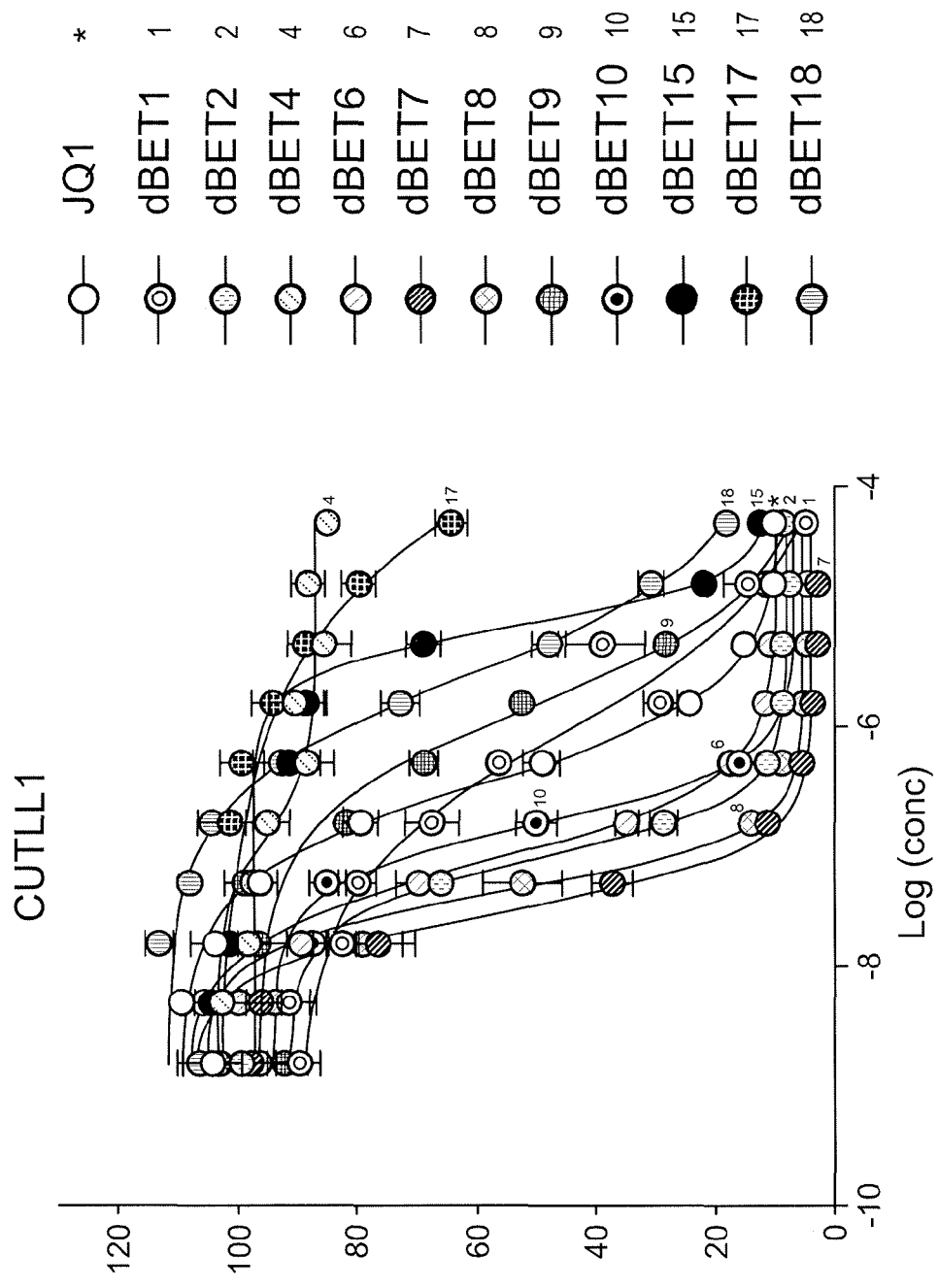

MV4-11 cells were treated with 50 nM dBET6 or 200 nM dBET18. For the following 24 hours, levels of BRD4 or BRD4, BRD2 and BRD3 were detected by immunoblotting at various time points. The results are shown in FIG. 15E and FIG. 16B.

Example 46

Degradation of BRD and Other Proteins by dBET

293T WT or 293 CRBN-/- were treated with dBET2, dBET7, dBET8, or dBET10 at 1 µM for 16 hours. The cells were then lysed and the lysates were immunoblotted to measure levels of BRD4 and PLK1. The results are shown in FIG. 16A.

Example 47

Viability of Cells Treated with dBET Compounds

Various cell lines (T-ALL (MOLT4, DND41, CUTLL1), LOUCY, MV4-11, and RS4-11) were plated in 384 well plates at 1000 cells/well. dBET compounds were then added to the cells and incubated for 48 hours. ATP content was measured as a surrogate for cellular viability using ATPlite (Promega). The results were shown in FIGS. 17A, 17B, 17C, 17D, and 17E and FIGS. 18A, 18B and 18C.

Example 48 dGR Mediated Glucocorticoid Receptor Degradation

Figure 19:
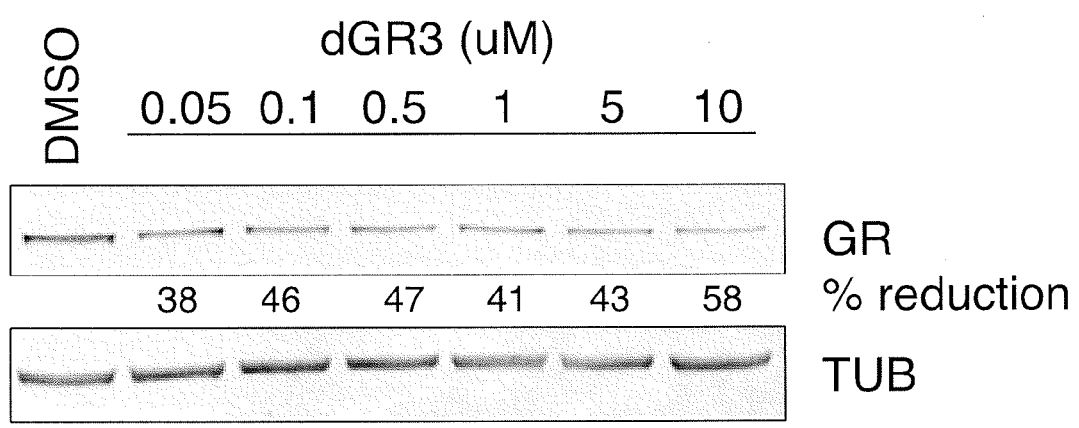
FIG. 19 is an immunoblot showing GR levels in cells treated with indicated concentrations of dGR3.

DND41 cells were grown in culture plates. dGR3 was added at various concentrations and incubated for 16 hours. The cells were then lysed, and the lysates were immunoblotted to measure GR levels. The results are shown in FIG. 19.

Example 49

Experimental Procedures

Protein Purification and Crystal Structure

A construct of human BRD4 covering residues 44-168 in the pNIC28Bsa4 vector (Addgene) was overexpressed in *E. coli* BL21 (DE3) in LB medium in the presence of 50 mg/ml of kanamycin. Cells were grown at 37° C. to an OD of 0.8, induced with 500 µM isopropyl-1-thio-D-galactopyranoside, incubated overnight at 17° C., collected by centrifugation, and stored at −80° C. Cell pellets were sonicated in buffer A (50 mM hepes 7.5+300 mM NaCl+10% glycerol+ 10 mM Imidazole+3 mM BME) and the resulting lysate was centrifuged at 35,000×g for 40 min. Ni-NTA beads (Qiagen) were mixed with lysate supernatant for 30 min and washed with buffer A. Beads were transferred to an FPLC-compatible column and the bound protein was washed with 15% buffer B (50 mM hepes 7.5+300 mM NaCl+10% glycerol+ 300 mM Imidazole+3 mM BME) and eluted with 100% buffer B. TEV was added to the eluted protein and incubated at 4° C. overnight. The sample was then passed through a desalting column (26/10 column) equilibrate with buffer A (without imidazole), and the eluted protein was subjected to a second Ni-NTA step to remove His-tag and TEV. The eluant was concentrated and passed through a Superdex-200 10/300 column in 20 mM hepes 7.5+150 mM NaCl+1 mM DTT. Fractions were pooled, concentrated to 14 mg/ml, and frozen at −80° C.

Crystallization, Data Collection and Structure Determination

A 1.5-fold excess of 10 mM dBET1 (in DMSO) was mixed with 500 µM protein and crystallized by sitting-drop vapor diffusion at 20° C. in the following crystallization buffer: 15% PEG3350, 0.1 M Succinate. Crystals were transferred briefly into crystallization buffer containing 25% glycerol prior to flash-freezing in liquid nitrogen. Diffraction data from complex crystals were collected at beamline 24ID-C of the NE-CAT at the Advanced Photon Source (Argonne National Laboratory), and data-sets were integrated and scaled using XDS (Kabsch, W. *Acta crystallographica Section D, Biological crystallography* 2010, 66, 133). Structures were solved by molecular replacement using the program Phaser (Mccoy et al., *Journal of Applied*

Crystallography 2007, 40, 658) and the search model PDB entry XXXX. The ligand was automatically positioned and refined using Buster (Smart et al. *Acta crystallographica Section D, Biological crystallography* 2012, 68, 368). Iterative model building and refinement using Phenix (Adams et al. *Acta crystallographica Section D, Biological crystallography* 2010, 66, 213) and Coot (Emsley, P.; Cowtan, K. *Acta crystallographica Section D, Biological crystallography* 2004, 60, 2126) led to a model with statistics shown in Table 3.

TABLE 3

Data collection and refinement statistics.

|  | BRD4a/DB-2-190 |
|---|---|
| Wavelength (Å) | 0.9792 |
| Resolution range (Å) | 34.31-0.99 (1.025-0.99) |
| Space group | P 21 21 21 |
| Unit cell | 38.01 43.05 79.7 90 90 90 |
| Total reflections | 440045 (17524) |
| Unique reflections | 67392 (4589) |
| Multiplicity | 6.5 (3.8) |
| Completeness (%) | 91.60 (63.09) |
| Mean I/sigma(I) | 21.20 (2.46) |
| Wilson B-factor | 9.95 |
| R-merge | 0.04633 (0.6184) |
| R-meas | 0.05011 |
| CC1/2 | 0.999 (0.742) |
| cc* | 1 (0.923) |
| Reflections used for R-free |  |
| R-work | 0.1887 (0.2620) |
| R-free | 0.1863 (0.2788) |
| CC(work) |  |
| CC(free) |  |
| Number of non-hydrogen atoms | 1333 |
| macromolecules | 1059 |
| ligands | 55 |
| water | 219 |
| Protein residues | 128 |
| RMS(bonds) | 0.005 |
| RMS(angles) | 1.07 |
| Ramachandran favored (%) | 9.80E+01 |
| Ramachandran allowed (%) |  |
| Ramachandran outliers (%) | 0 |
| Clashscore | 4.63 |
| Average B-factor | 14.5 |
| macromolecules | 12.4 |
| ligands | 22.8 |
| solvent | 22.8 |

Statistics for the highest-resolution shell are shown in parentheses.

BRD4 AlphaScreen

Assays were performed with minimal modifications from the manufacturer's protocol (PerkinElmer, USA). All reagents were diluted in 50 mM HEPES, 150 mM NaCl, 0.1% w/v BSA, 0.01% w/v Tween20, pH 7.5 and allowed to equilibrate to room temperature prior to addition to plates. After addition of Alpha beads to master solutions all subsequent steps were performed under low light conditions. A 2× solution of components with final concentrations of BRD4 (see protein expression section) at 40 nM, Ni-coated Acceptor Bead at 10 µg/mL, and 20 nM biotinylated-JQ1 (Anders et al. *Nature Biotechnology* 2013, 32, 92) was added in 10 µL to 384-well plates (AlphaPlate-384, PerkinElmer, USA). Plates were spun down at 150×g, 100 nL of compound in DMSO from stock plates were added by pin transfer using a Janus Workstation (PerkinElmer, USA). The streptavidin-coated donor beads (10 µg/mL final) were added as with previous the solution in a 2×, 10 µL volume. Following this addition, plates were sealed with foil to prevent light exposure and evaporation. The plates were spun down again at 150×g. Plates were incubated at room temperature for 1 hour and then read on an Envision 2104 (PerkinElmer, USA) using the manufacturer's protocol.

CRBN-DDB1 Expression and Purification

Expression and purification of CRBN-DDB1 were performed as described in Fischer, E. S. et al., *Nature* 512, 49 (2014), using Sf9 cells (Invitrogen). pFastBac vectors encoding human CRBN and DDB1 were used for expression of the proteins.

CRBN-DDB1/BRD4 Dimerization Assay

A bead-based AlphaScreen technology was used to detect CRBN-DDB1/BRD4 dimerization by dBET1. In brief, GST-BRD4[49-170] (Sigma Aldrich) and CRBN-DDB1 were diluted to 125 nM and 250 nM, respectively, in assay buffer (50 mM HEPES pH 7.4, 200 mM NaCl, 1 mM TCEP, and 0.1% BSA), and 20 uL of protein mixture was added to each well of a 384-well AlphaPlate (PerkinElmer). Compounds were then added at 100 nL per well from DMSO stock plates using a CyBi®-Well vario pin tool. After 1 hr incubation at room temperature, Nickel Chelate AlphaLISA® Acceptor and Glutathione AlphaLISA® Donor beads (PerkinElmer) were diluted in assay buffer to a 2× concentration (20 ug/ul) and added at 20 uL per well. Plates were incubated for 1 hr at room temperature prior to luminescence detection on an Envision 2104 plate reader (PerkinElmer).

For competition assays, GST-BRD4[49-170] and CRBN-DDB1 were diluted as above in the presence of 111 nM dBET1. Compound addition and subsequent detection was performed as described above.

Cell Lines

293FT and 293FT$^{CRBN-/-}$ were cultured in DMEM supplemented with 10% FCS and 1% Penicillin/Streptomycin. MV4-11, MOLM13, MM1S and MM1S$^{CRBN-/-}$ were cultured in RPMI supplemented with 10% FCS and 1% Penicillin/Streptomycin. SUM149 cells were cultured in HUMEC medium (cell application, 815-500) with DMEM F12 (corning cellgro, 10-090-CV) (1:1) and final 5% FCS with 1% Penicillin/Streptomycin.

Culture of Primary Patient Material

Cells were freshly thawed and grown for 24 hours in StemSpan SFEM media (Stemcell) supplemented with (all in ng/ml final concentration): IL-3 (20), IL-6 (20), FLT3L (100), SCF (100) and GSCF (20). After that, cells were treated with dBET1 or JQ1 at the indicated concentrations with renewed cytokines for 24 hours. Subsequently, cells were either used for immunoblot analysis or for FACS analysis.

Analysis of Apoptotic Cells by Flow Cytometry

For each sample, cells were washed with 500 µL of PBS and spun down at 400×g for 5 minutes and media aspirated off. Cells were then resuspended in Annexin V binding buffer: 140 mM NaCl, 10 mM HEPES, 2.5 mM CaCl$_2$, pH 7.4 and 500 µL of each sample transferred to 5 mL polystyrene FACS tubes (Falcon Cat. No. 352054). Cells were spun down at 400×g for 5 minutes and buffer aspirated off. To each sample, 400 µL of Annexin V binding buffer with 250 ng/mL FITC-Annexin V and 500 ng/mL propidium iodide were added for staining Cells were then sorted on a BD LSRFortessa and analyzed using FlowJo V10 software (Tree Star, Inc).

Analysis of Apoptotic Cells by Caspase Glo Assay

Caspaseglo assay (Promega) has been conducted following the manufacturer's recommendations. Cells were seeded at a density of 5000 cells/well in a white 384 well plate (Thermo Scientific Nunc, #164610) in a total volume of 40 ul with respective compound or vehicle control treatment. After a 24 h incubation, 30 ul of the Caspaseglo substrate were added per well. Plate was incubated in the dark for 90 minutes and read on Envision plate reader (Perkin Elmer).

BRD4-High Content Assay

SUM149 cells were plated at a density of 3×10$^5$ cells/well using the inner 60 wells of a 96 well plate. 24 hours later, compounds were added in at the respective concentrations. Assays were performed with minimal modifications from the manufacturer's protocol (LICOR In-Cell Western Assay Kit). In brief, cells were fixed in 3.7% formaldehyde in PBS for 20 minutes on room temperature (200 ul per well) and subsequently permeabilized using 1×PBS with 0.1% Triton X-100 (5×200 ul per well). Then, cells were blocked using 100 ul of a 1:1 diluted Odyssey Blocking Buffer (LICOR) for 90 minutes on room temperature. Next, cells were incubated with BRD4 antibody diluted 1:1000 in Odyssey Blocking Buffer (LICOR) (50 ul per well) overnight on 4° C. Next day, plate was washed 5 times with TBST (200 ul per well). Then, plates are stained with a 1:800 dilution of IRDye 800CW goat anti-Rabbit antibody (LICOR) and simultaneously with CellTag 700 Stain (1:500, LICOR) for cell normalization. Plates were incubated for 1 h in the dark on RT, washed 5 times with TBST (200 ul per well) and imaged on the Odyssey CLx Imager (LI-COR).

qRT-PCR

RNA was isolated using RNeasy Plus Mini Kit (Qiagen) and 500 ng of total RNA have been used per sample for reverse transcription using SuperScript Reverse Transcriptase (Life Technologies). cDNA has been diluted 1:9 and 2 ul have been used as template for qRT-PCR using SYBR Select master mix. The following primers have been used:

GAPDH (F):
CCACTCCTCCACCTTTGAC
SEQ ID NO. 1

GAPDH (R):
ACCCTGTTGCTGTAGCCA
SEQ ID NO. 2

BRD2 (F):
GTGGTTCTCGGCGGTAAG
SEQ ID NO. 3

BRD2 (R):
GGTTGACACCCCGGATTAC
SEQ ID NO. 4

BRD3 (F):
TTGGCAAACCTCATCTCAAA
SEQ ID NO. 5

BRD3 (R):
GATGTCCGGCTGATGTTCTC
SEQ ID NO. 6

BRD4 (F):
CTCCGCAGACATGCTAGTGA
SEQ ID NO. 7

BRD4 (R):
GTAGGATGACTGGGCCTCTG
SEQ ID NO. 8 c-MYC (F):
CACCGAGTCGTAGTCGAGGT
SEQ ID NO. 9 c-MYC (R):
GCTGCTTAGACGCTGGATTT
SEQ ID NO. 10

PIM1 (F):
TCATACAGCAGGATCCCCA
SEQ ID NO. 11

PIM1 (R):
CCGTCTACACGGACTTCGAT
SEQ ID NO. 12

Sample Preparation for Quantitative Mass Spectrometry Analysis

Sample were prepared as previously described (Weekes, M. P. et al., *Cell* 157, 1460 (2014)) with the following modification. All solutions are reported as final concentrations. Lysis buffer (8 M Urea, 1% SDS, 50 mM Tris pH 8.5, Protease and Phosphatase inhibitors from Roche) was added to the cell pellets to achieve a cell lysate with a protein concentration between 2-8 mg/mL. A micro-BCA assay (Pierce) was used to determine the final protein concentration in the cell lysate. Proteins were reduced and alkylated as previously described. Proteins were precipitated using methanol/chloroform. In brief, four volumes of methanol was added to the cell lysate, followed by one volume of chloroform, and finally three volumes of water. The mixture was vortexed and centrifuged to separate the chloroform phase from the aqueous phase. The precipitated protein was washed with one volume of ice cold methanol. The washed precipitated protein was allowed to air dry. Precipitated protein was resuspended in 4 M Urea, 50 mM Tris pH 8.5. Proteins were first digested with LysC (1:50; enzyme:protein) for 12 hours at 25° C. The LysC digestion is diluted down to 1 M Urea, 50 mM Tris pH8.5 and then digested with trypsin (1:100; enzyme:protein) for another 8 hours at 25° C. Peptides were desalted using a $C_{18}$ solid phase extraction cartridges. Dried peptides were resuspended in 200 mM EPPS, pH 8.0. Peptide quantification was performed using the micro-BCA assay (Pierce). The same amount of peptide from each condition was labeled with tandem mass tag (TMT) reagent (1:4; peptide:TMT label) (Pierce). The 10-plex labeling reactions were performed for 2 hours at 25° C. Modification of tyrosine residue with TMT was reversed by the addition of 5% hydroxyl amine for 15 minutes at 25° C. The reaction was quenched with 0.5% TFA and samples were combined at a 1:1:1:1:1:1:1:1:1:1 ratio. Combined samples were desalted and offline fractionated into 24 fractions as previously described.

Liquid Chromatography-MS3 Spectrometry (LC-MS/MS)

12 of the 24 peptide fraction from the basic reverse phase step (every other fraction) were analyzed with an LC-MS3 data collection strategy (McAlister, G. C. et al., *Anal. Chem.* 86, 7150 (2014)) on an Orbitrap Fusion mass spectrometer (Thermo Fisher Scientific) equipped with a Proxeon Easy nLC 1000 for online sample handling and peptide separations. Approximately 5 μg of peptide resuspended in 5% formic acid+5% acetonitrile was loaded onto a 100 μm inner diameter fused-silica micro capillary with a needle tip pulled to an internal diameter less than 5 μm. The column was packed in-house to a length of 35 cm with a $C_{18}$ reverse phase resin (GP118 resin 1.8 μm, 120 Å, Sepax Technologies). The peptides were separated using a 120 min linear gradient from 3% to 25% buffer B (100% ACN+0.125% formic acid) equilibrated with buffer A (3% ACN+0.125% formic acid) at a flow rate of 600 nL/min across the column. The scan sequence for the Fusion Orbitrap began with an MS1 spectrum (Orbitrap analysis, resolution 120,000, 400-1400 m/z scan range, AGC target 2×105, maximum injection time 100 ms, dynamic exclusion of 75 seconds). "Top N" (the top 10 precursors) was selected for MS2 analysis, which consisted of CID (quadrupole isolation set at 0.5 Da and ion trap analysis, AGC 4×103, NCE 35, maximum injection time 150 ms). The top ten precursors from each MS2 scan were selected for MS3 analysis (synchronous precursor selection), in which precursors were fragmented by HCD prior to Orbitrap analysis (NCE 55, max AGC 5×104, maximum injection time 150 ms, isolation window 2.5 Da, resolution 60,000.

LC-MS3 Data Analysis

A suite of in-house software tools were used to for RAW file processing and controlling peptide and protein level false discovery rates, assembling proteins from peptides, and protein quantification from peptides as previously described. MS/MS spectra were searched against a Uniprot human database (February 2014) with both the forward and reverse sequences. Database search criteria are as follows: tryptic with two missed cleavages, a precursor mass tolerance of 50 ppm, fragment ion mass tolerance of 1.0 Da, static alkylation of cysteine (57.02146 Da), static TMT labeling of lysine residues and N-termini of peptides (229.162932 Da), and variable oxidation of methionine (15.99491 Da). TMT reporter ion intensities were measured using a 0.003 Da window around the theoretical m/z for each reporter ion in the MS3 scan. Peptide spectral matches with poor quality MS3 spectra were excluded from quantitation (<200 summed signal-to-noise across 10 channels and <0.5 precursor isolation specificity).

MV4-11 Xenograft Experiment

1×10e7 MV4-11 cells were injected subcutaneously in a volume of 200 ul of PBS per mouse (NSG). Successful engraftment was monitored via bioluminescence and caliper measurement. 11 days post injection of MV4-11 cells, tumors were palpable and mice were distributed in either the control (vehicle) or the dBET1 treated groups. Mice were treated once daily with 50 mg/kg dBET1 or vehicle (captisol) via intraperitoneal injection. Tumor volume was recorded via caliper measurement. The study was terminated 14 days post treatment start when the tumor size of a vehicle treated mouse reached institutional limits.

Expression Proteomics $5 \times 10^6$ cells have been treated with DMSO, 250 nM dBET1 or 250 nM JQ1 in triplicate for 2 hours, washed with 3 times with ice-cold PBS and snap-frozen in liquid $N_2$. Next, samples were mechanically homogenized in lysis buffer (8 M Urea, 1% SDS, 50 mM Tris, pH 8.5, protease and phosphatase inhibitors) and protein quantification was performed using the micro-BCA kit (Pierce). After protein quantification lysates were immediately reduced with DTT and alkylated with iodoacetimide. 600 µg protein was precipitated by methanol/chloroform and digestion was performed using LysC and trypsin. 50 µg of each sample was labeled with Tandem Mass Tag (TMT, Thermo Scientific) reagent and fractionated for total proteomic analysis.

Reverse-Phase fractionation was conducted under the following conditions: Buffer A: 5% ACN, 50 mM AmBic pH 8.0, Buffer B: 90% ACN, 50 mM AmBic pH 8.0 (Fraction size—37 seconds (~300 µL))

Proteins were fractionated by bRP and collected into two sets of 12 fractions each. One complete set (12 fractions) from HPRP was analyzed on an Orbitrap Fusion mass spectrometer. Peptides were separated using a gradient of 3 to 25% acetonitrile in 0.125% formic acid over 200 minutes. Peptides were detected (MS1) and quantified (MS3) in the Orbitrap, peptides were sequenced (MS2) in the ion trap.MS2 spectra were searched using the SEQUEST algorithm against a Uniprot composite database derived from the human proteome containing its reversed complement and known contaminants. All peptide spectral matches were filtered to a 1% false discovery rate (FDR) using the target-decoy strategy combined with linear discriminant analysis. Proteins were quantified only from peptides with a summed SN threshold of >=200 and MS2 isolation specificity of 0.5.

Immunoblotting

Cells have been lysed using RIPA buffer supplemented with protease inhibitor cocktail (Roche) and 0.1% benzonase (Novagen) on ice for 15 minutes. The lysates were spun at 16000×g for 15 minutes on 4° C. and protein concentration was determined using BCA assay (Pierce). The following primary antibodies were used in this study: BRD2 (Bethyl labs), BRD3 (abcam), BRD4 (Bethyl labs), MYC, tubulin and vinculin (all Santa Cruz) as well as PIM1 (Cell Signaling Technology) and IKZF3 (Novus Biologicals). Blots were imaged using fluorescence-labeled secondary antibodies (LI-COR) on the OdysseyCLxImager (LI-COR). Quantification of band intensities has been performed using OdysseyCLx software (LI-COR).

Immunohistochemistry

BRD4 staining was performed using the A301-985A antibody (Bethyl labs) following the recommended parameters at a concentration of 1:2000. MYC and Ki67 stainings were performed as described previously. Quantification of positively stained nuclei was conducted using the aperio software (Leica Biosystems).

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A compound selected from:

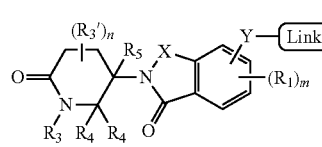
(I)

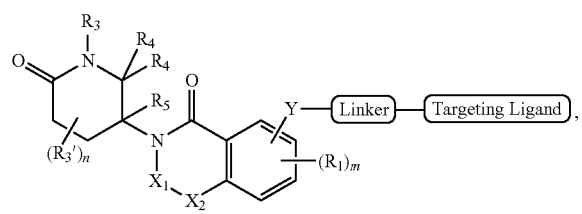
(II)

or an enantiomer, diastereomer, stereoisomer, or a pharmaceutically acceptable salt thereof, wherein:

Y is a bond, $(CH_2)_{1\text{-}6}$, $(CH_2)_{0\text{-}6}$—O, $(CH_2)_{0\text{-}6}$—C(O)NR$_2$', $(CH_2)_{0\text{-}6}$—NR$_2$'C(O), $(CH_2)_{0\text{-}6}$—NH, or $(CH_2)_{0\text{-}6}$—NR$_2$;

X is C(O) or C(R$_3$)$_2$;

X$_1$-X$_2$ is C(R$_3$)=N or C(R$_3$)$_2$—C(R$_3$)$_2$;

each R$_1$ is independently halogen, OH, $C_1$—$C_6$ alkyl, or $C_1$—$C_6$ alkoxy;

R$_2$ is $C_1$—$C_6$ alkyl, C(O)—$C_1$—$C_6$ alkyl, or C(O)—$C_3$-$C_6$ cycloalkyl;

R$_2$' is H or $C_1$-$C_6$ alkyl;

each R$_3$ is independently H or $C_1$—$C_3$ alkyl;

each R$_3$' is independently $C_1$—$C_3$ alkyl;

each R$_4$ is independently H or $C_1$—$C_3$ alkyl and at least one R$_4$ is $C_1$—$C_3$ alkyl; or two R$_4$, together with the carbon atom to which they are attached, form a $C_3$—$C_6$ carbocycle or a 4-, 5-, or 6-membered heterocycle comprising 1 or 2 heteroatoms selected from N and O;

$R_5$ is H, deuterium, $C_1$—$C_3$ alkyl, F, or Cl;
m is 0, 1, 2 or 3;
n is 0, 1 or 2;
the Linker is

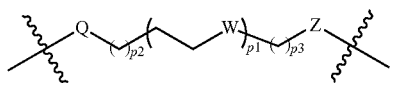

each W is independently absent, $CH_2$, O, S, NH or $NR_5$;
Z is absent, $CH_2$, O, NH or $NR_5$;
Q is absent or —$CH_2C(O)NH$—;
p1 is selected from 0, 1, 2, 3, 4, 5, and 6;
p2 is selected from 0, 1, 2, 3, 4, 5, and 6;
p3 is selected from 1, 2, 3, 4, and 5;
the Targeting Ligand binds to a targeted protein selected from SMARCA2, and Ras;
wherein the Targeting Ligand is selected from:

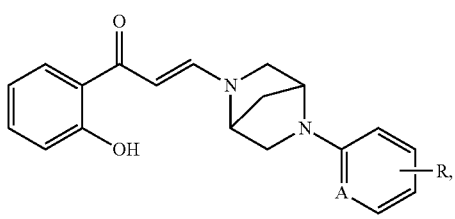

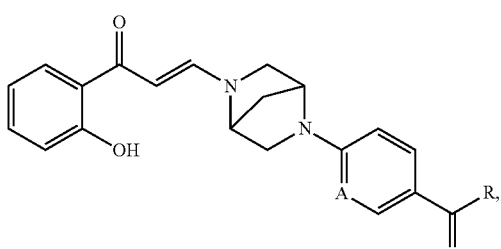

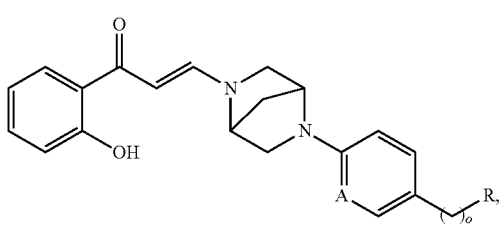

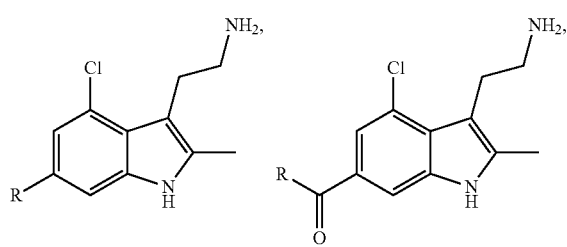

-continued

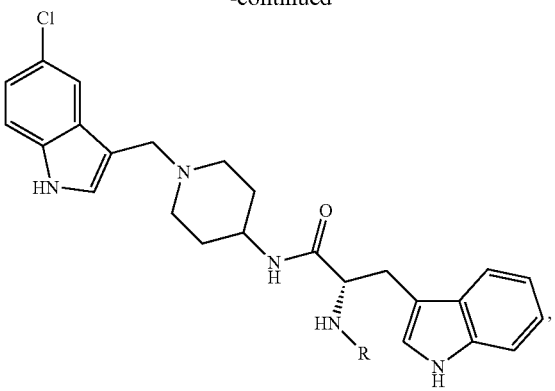

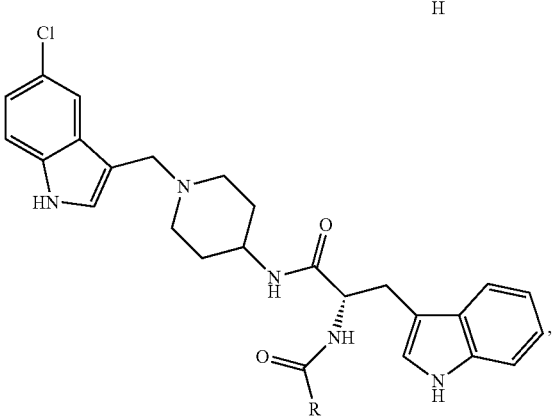

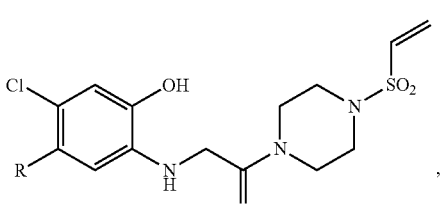

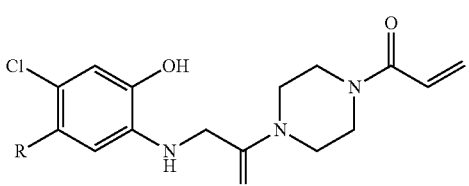

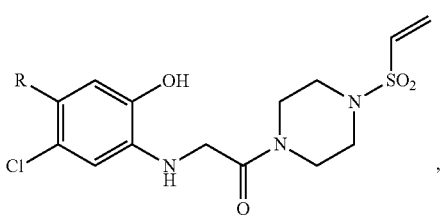

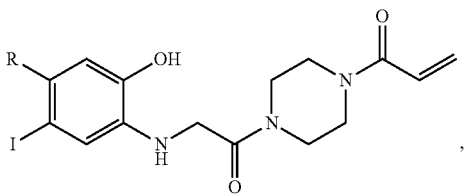

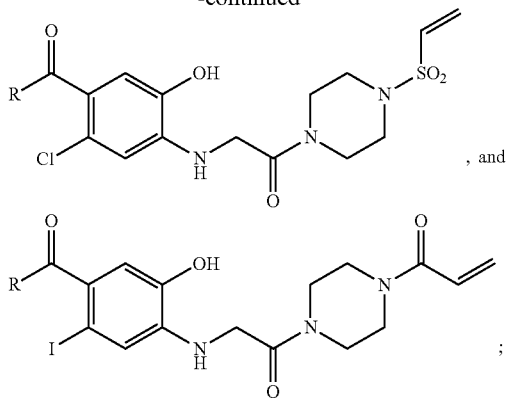

R is the attachment point to the Linker;
o is 0, 1, 2, 3, 4, 5, 6, 7, or 8; and
A is N or CH.

2. The compound of claim 1, wherein the targeted protein is SMARCA2.
3. The compound of claim 1, wherein the targeted protein is Ras.
4. The compound of claim 1, wherein one $R_4$ is $C_1$-$C_3$ alkyl.
5. The compound of claim 4, wherein one $R_4$ is methyl or ethyl.
6. The compound of claim 1, wherein each $R_4$ is independently methyl or ethyl.
7. The compound of claim 1, wherein two $R_4$, together with the carbon to which they are attached, form a cyclopropyl, cyclobutyl, cyclopentyl, or cyclohexyl.
8. The compound of claim 1, wherein two $R_4$, together with the carbon to which they are attached, form a 4-, 5-, or 6-membered heterocycle comprising 1 or 2 heteroatoms selected from N and O.
9. The compound of claim 8, wherein the heterocycle is selected from azetidine, tetrahydrofuran, pyrrolidine, piperidine, piperazine, morpholine, and oxetane.
10. The compound of claim 8, wherein the heterocycle is oxetane.
11. The compound of claim 8, wherein the heterocycle is azetidine.
12. The compound of claim 8, wherein the heterocycle is tetrahydrofuran.
13. The compound of claim 8, wherein the heterocycle is pyrrolidine.
14. The compound of claim 8, wherein the heterocycle is piperidine.
15. The compound of claim 8, wherein the heterocycle is piperazine.
16. The compound of claim 8, wherein the heterocycle is morpholine.
17. The compound of claim 1, wherein the compound is Formula I.
18. The compound of claim 17, wherein X is C(O).
19. The compound of claim 17, wherein X is $C(R_3)_2$.
20. The compound of claim 1, wherein $R_5$ is H or deuterium.
21. The compound of claim 1, wherein $R_3$ is H or methyl.
22. The compound of claim 1, wherein each $R_1$ is independently selected from F, Cl, OH, methyl, ethyl, propyl, methoxy, ethoxy and propoxy.
23. The compound of claim 1, wherein m is 0.
24. The compound of claim 1, wherein m is 1.
25. The compound of claim 1, wherein n is 0.
26. The compound of claim 1, wherein n is 1.
27. The compound of claim 1, wherein n is 2.
28. The compound of claim 1, wherein the compound is Formula II.
29. The compound of claim 1, wherein each $R_1$ is independently methyl, methoxy, ethoxy or propoxy.
30. The compound of claim 1, wherein X is $C(CH_3)_2$.
31. The compound of claim 1, wherein Y is $(CH_2)_{0-6}$—O.
32. The compound of claim 1, wherein Y is $(CH_2)_{0-6}$—NH.
33. The compound of claim 1, wherein Y is $(CH_2)_{0-6}$—C(O)NR$_2$'.
34. The compound of claim 1, wherein Y is $(CH_2)_{0-6}$—NR$_2$'C(O).
35. The compound of claim 1, wherein Y is $(CH_2)_{0-6}$—NR$_2$.
36. The compound of claim 1, wherein the Linker has 5, 6, 7, 8, 9, 10, 11, 12, 13, 14, 15, or 16 chain atoms.
37. The compound of claim 1, wherein W is independently $CH_2$, O, S, NH, or NR$_5$.
38. The compound of claim 1, wherein at least one W is $CH_2$.
39. The compound of claim 1, wherein at least one W is O.
40. The compound of claim 1, wherein at least one W is S.
41. The compound of claim 1, wherein at least one W is NH.
42. The compound of claim 1, wherein at least one W is NR$_5$.
43. The compound of claim 42, wherein $R_5$ is $C_1$-$C_3$ alkyl selected from methyl, ethyl, and propyl.
44. The compound of claim 1, wherein Q is absent.
45. The compound of claim 1, wherein Q is —$CH_2C(O)NH$—.
46. The compound of claim 1, wherein W is absent.
47. The compound of claim 1, wherein at least one of W is $CH_2$ and Z is NH or O.
48. The compound of claim 1, wherein at least one of W is O and Z is NH or O.
49. The compound of claim 1, wherein at least one of W is S and Z is NH or O.
50. The compound of claim 1, wherein at least one of W is NH and Z is NH or O.
51. The compound of claim 1, wherein at least one of W is NR$_5$ and Z is NH or O.
52. The compound of claim 1, wherein Z is $CH_2$.
53. The compound of claim 1, wherein Z is O.
54. The compound of claim 1, wherein at least one of Z is NH.
55. The compound of claim 1, wherein at least one of Z is NR$_5$.
56. The compound of claim 1, wherein the Linker is of Formula L1 or L2:

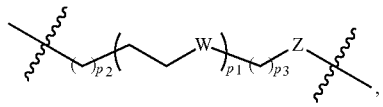

(L1)

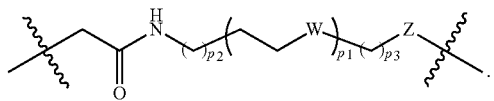

(L2)

57. A compound selected from:

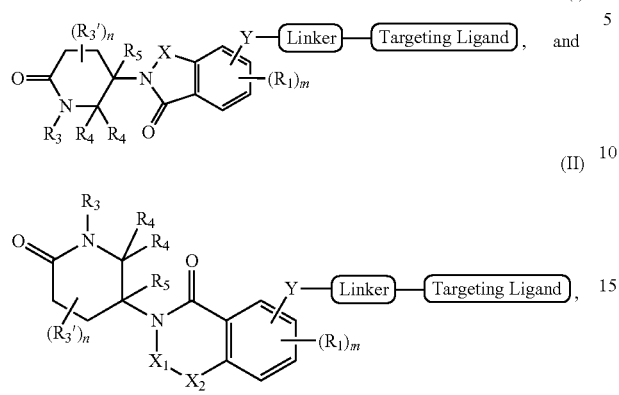

or an enantiomer, diastereomer, stereoisomer, or a pharmaceutically acceptable salt thereof, wherein:

Y is a bond, $(CH_2)_{1-6}$, $(CH_2)_{0-6}$—O, $(CH_2)_{0-6}$—C(O)NR$_2$', $(CH_2)_{0-6}$—NR$_2$'C(O), $(CH_2)_{0-6}$—NH, or $(CH_2)_{0-6}$—NR$_2$;

X is C(O) or C(R$_3$)$_2$;

X$_1$-X$_2$ is C(R$_3$)=N or C(R$_3$)$_2$—C(R$_3$)$_2$;

each R$_1$ is independently halogen, OH, $C_1$—$C_6$ alkyl, or $C_1$—$C_6$ alkoxy;

R$_2$ is $C_1$—$C_6$ alkyl, C(O)—$C_1$—$C_6$ alkyl, or C(O)—$C_3$—$C_6$ cycloalkyl;

R$_2$' is H or $C_1C_6$ alkyl;

each R$_3$ is independently H or $C_1$—$C_3$ alkyl;

each R$_3$' is independently $C_1$—$C_3$ alkyl;

each R$_4$ is independently H or $C_1$—$C_3$ alkyl; or two R$_4$, together with the carbon atom to which they are attached, form a C(O), $C_3$—$C_6$ carbocycle, or a 4-, 5-, or 6-membered heterocycle comprising 1 or 2 heteroatoms selected from N and O;

R$_5$ is H, deuterium, $C_1$—$C_3$ alkyl, F, or Cl;

m is 0, 1, 2 or 3;

n is 1 or 2;

the Linker is

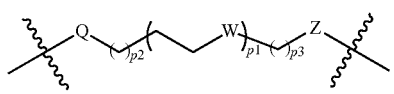

each W is independently absent, CH$_2$, O, S, NH or NR$_5$;

Z is absent, CH$_2$, O, NH or NR$_5$;

Q is absent or —CH$_2$C(O)NH—;

p1 is selected from 0, 1, 2, 3, 4, 5, and 6;

p2 is selected from 0, 1, 2, 3, 4, 5, and 6;

p3 is selected from 1, 2, 3, 4, and 5;

the Targeting Ligand binds to a targeted protein selected from SMARCA2, and Ras;

wherein the Targeting Ligand is selected from:

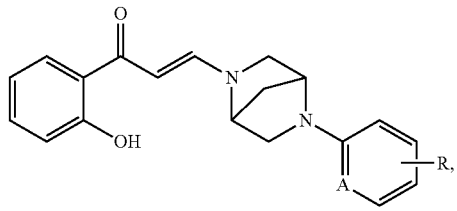

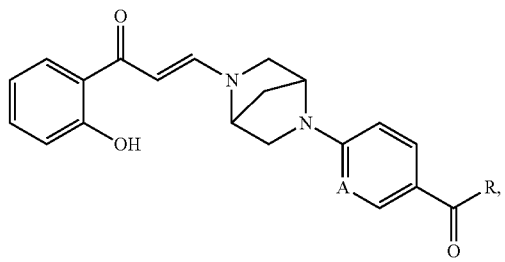

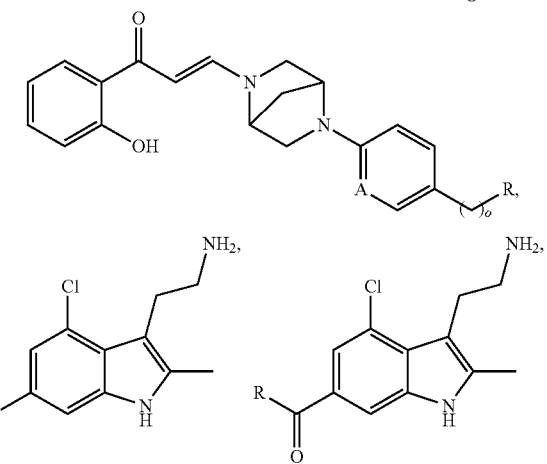

-continued

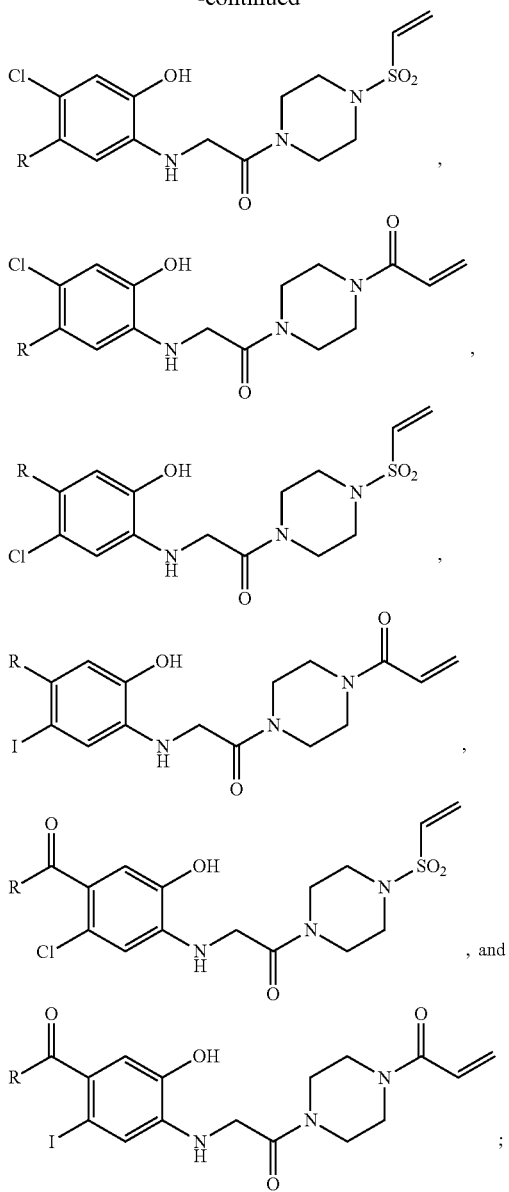

R is the attachment point to the Linker;
o is 0, 1, 2, 3, 4, 5, 6, 7, or 8; and
A is N or CH.

58. The compound of claim 57, wherein the targeted protein is SMARCA2.

59. The compound of claim 57, wherein the targeted protein is Ras.

60. The compound of claim 57, wherein one $R_4$ is $C_1$—$C_3$ alkyl.

61. The compound of claim 57, wherein one $R_4$ is methyl, ethyl, or propyl.

62. The compound of claim 57, wherein $R_4$ is hydrogen.

63. The compound of claim 57, wherein two $R_4$, together with the carbon to which they are attached, form a cyclopropyl, cyclobutyl, cyclopentyl, or cyclohexyl.

64. The compound of claim 57, wherein two $R_4$, together with the carbon to which they are attached, form a 4-, p5-, or 6-membered heterocycle comprising 1 or 2 heteroatoms selected from N and O.

65. The compound of claim 64, wherein the heterocycle is selected from azetidine, tetrahydrofuran, pyrrolidine, piperidine, piperazine, morpholine, and oxetane.

66. The compound of claim 57, wherein the compound is Formula I.

67. The compound of claim 66, wherein Xis C(O).

68. The compound of claim 66, wherein X is $C(R_3)_2$.

69. The compound of claim 57, wherein $R_5$ is H or deuterium.

70. The compound of claim 57, wherein $R_3$ is H or methyl.

71. The compound of claim 57, wherein each $R_1$ is independently selected from F, Cl, OH, methyl, ethyl, propyl, methoxy, ethoxy and propoxy.

72. The compound of claim 57, wherein m is 0.

73. The compound of claim 57, wherein m is 1.

74. The compound of claim 57, wherein n is 1.

75. The compound of claim 57, wherein n is 2.

76. The compound of claim 57, wherein the compound is Formula II.

77. The compound of claim 57, wherein each $R^1$ is independently methyl, methoxy, ethoxy or propoxy.

78. The compound of claim 57, wherein Xis $C(CH_3)_2$.

79. The compound of claim 1, wherein the Targeting Ligand is a SMARCA2 Targeting Ligand selected from:

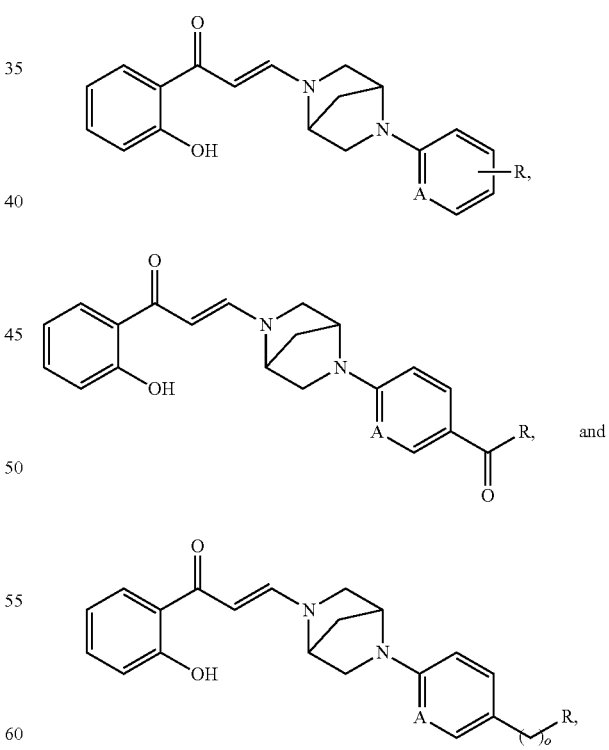

wherein:
R is the attachment point to the Linker;
o is 0, 1, 2, 3, 4, 5, 6, 7, or 8; and
A is N or CH.

80. The compound of claim 1, wherein the Targeting Ligand is a Ras Targeting Ligand selected from:

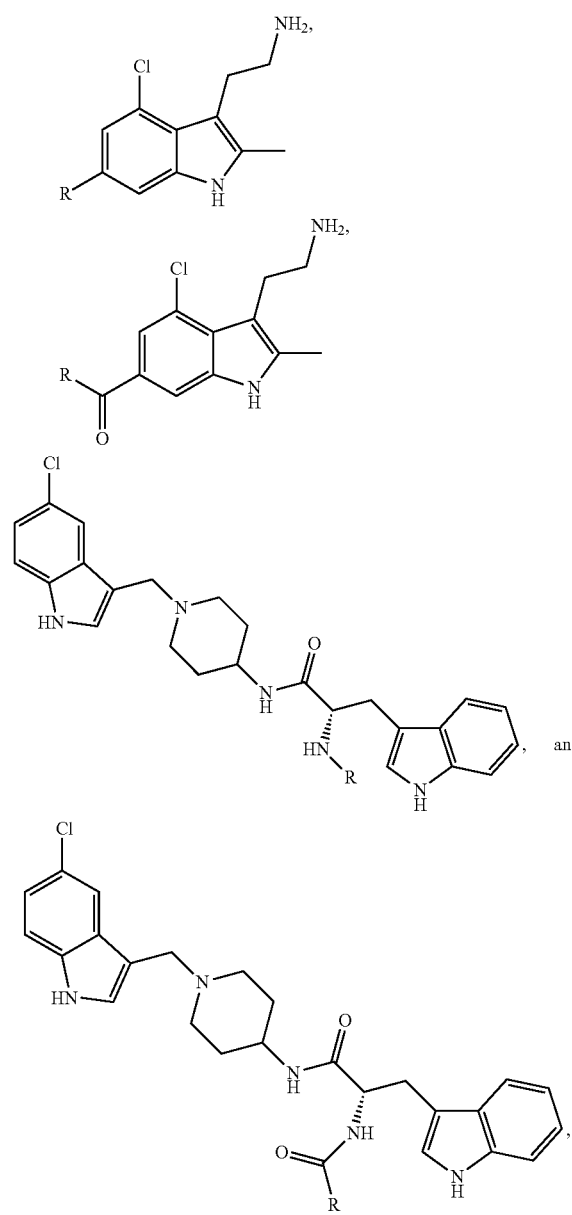

wherein:

R is the attachment point to the Linker.

81. The compound of claim 1, wherein the Targeting Ligand is a RasG12C Targeting Ligand selected from:

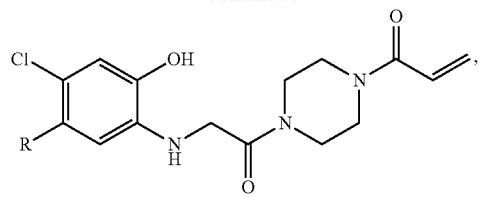

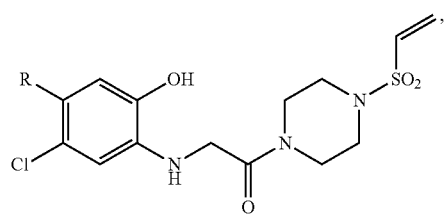

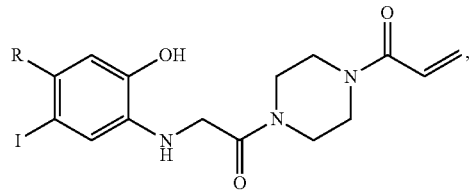

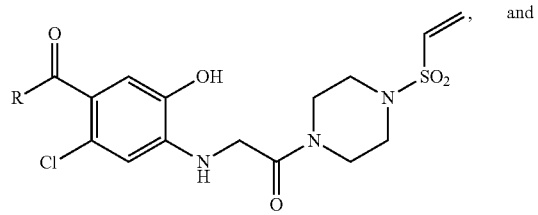

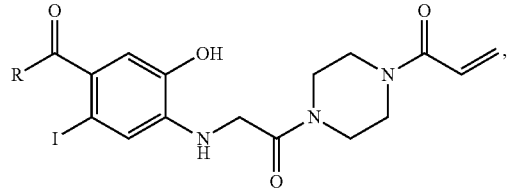

wherein:

R is the attachment point to the Linker.

82. The compound of claim 57, wherein the Targeting Ligand is a SMARCA2 Targeting Ligand selected from:

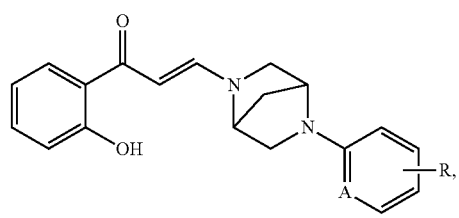

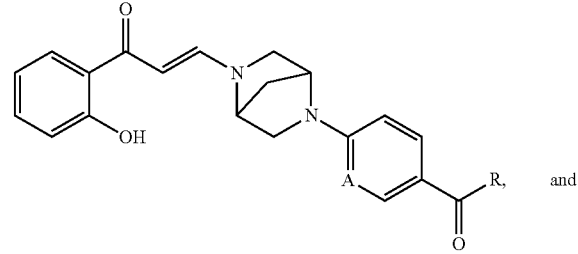

-continued
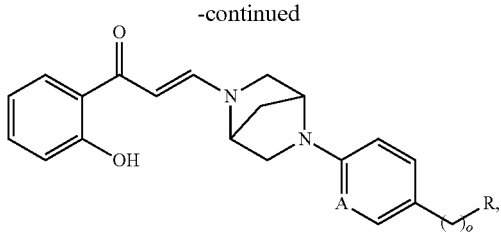
wherein:
R is the attachment point to the Linker;
o is 0, 1, 2, 3, 4, 5, 6, 7, or 8; and
A is N or CH.
83. The compound of claim 57, wherein the Targeting Ligand is a Ras Targeting Ligand selected from:
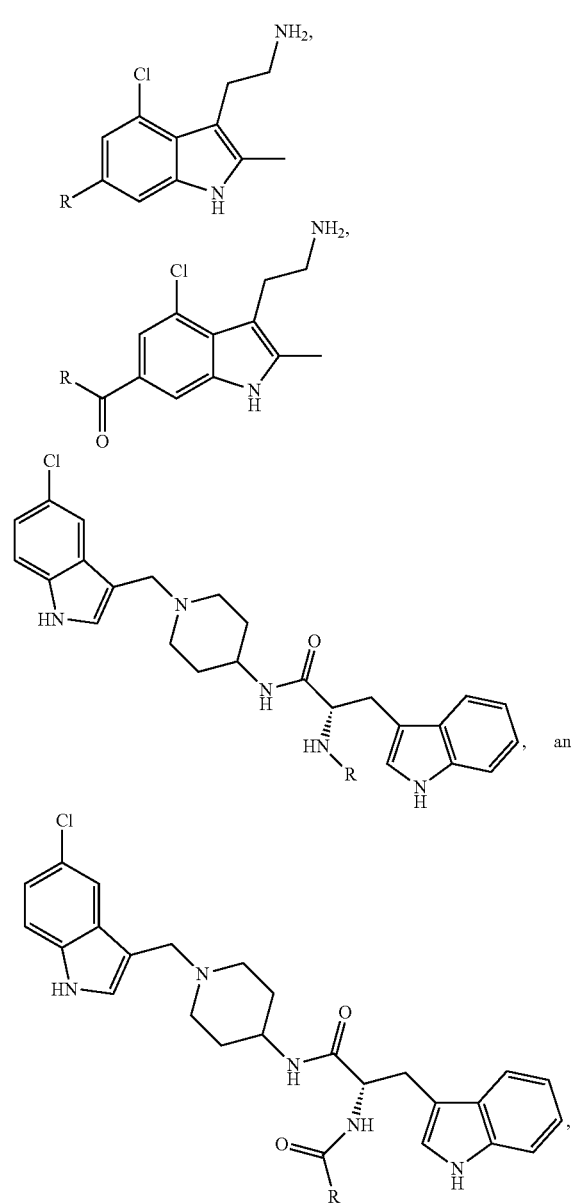
wherein:
R is the attachment point to the Linker.
84. The compound of claim 57, wherein the Targeting Ligand is a RasG12C Targeting Ligand selected from:
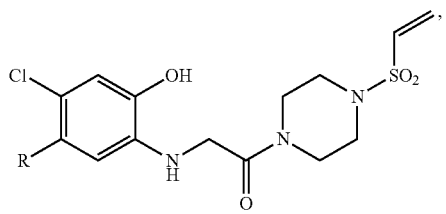
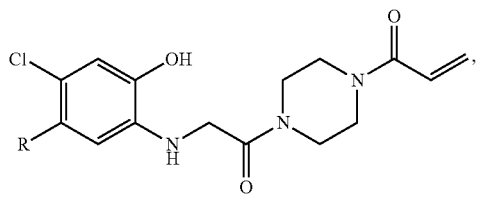
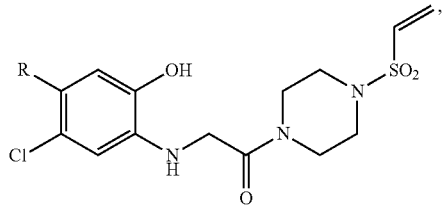
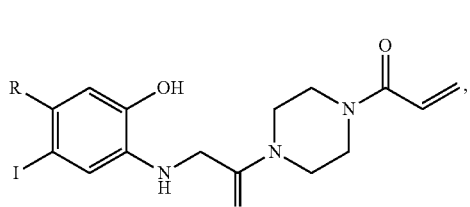
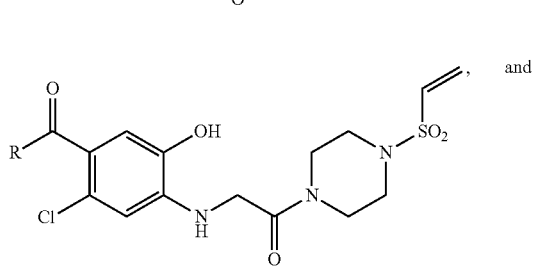
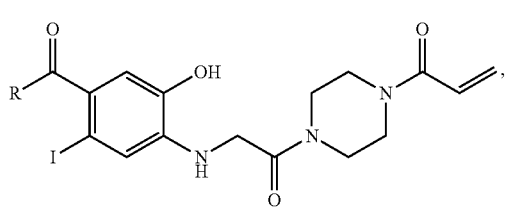
wherein:
R is the attachment point to the Linker.
* * * * *

UNITED STATES PATENT AND TRADEMARK OFFICE
CERTIFICATE OF CORRECTION

PATENT NO. : 9,694,084 B2
APPLICATION NO. : 14/707930
DATED : July 4, 2017
INVENTOR(S) : James Bradner, Dennis Buckley and Georg Winter Page 1 of 1

It is certified that error appears in the above-identified patent and that said Letters Patent is hereby corrected as shown below:

In the Specification

Amend to include the following statement after the Related Applications section and before the Background section on Column 1 Line 13:

STATEMENT OF GOVERNMENT SUPPORT
This invention was made with government support under grant numbers PO1 CA066996 and CA176745 awarded by The National Institutes of Health. The government has certain rights in the invention.

Signed and Sealed this
Twenty-fourth Day of September, 2019

Andrei Iancu
*Director of the United States Patent and Trademark Office*

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
ccactcctcc acctttgac          19

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 2
accctgttgc tgtagcca          18

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 3
gtggttctcg gcggtaag          18

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
ggttgacacc ccggattac          19

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
ttggcaaacc tcatctcaaa          20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
gatgtccggc tgatgttctc          20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ctccgcagac atgctagtga          20

<210> SEQ ID NO 8
<211> LENGTH: 20
<212> TYPE: DNA
<213> ORGANISM: Artificial Sequence -continued

```
<220> FEATURE:
<223> OTHER INFORMATION: Synthetic Oligonucleotide

<400> SEQUENCE: 8
gtaggatgac tgggcctctg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
caccgagtcg tagtcgaggt                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
gctgcttaga cgctggattt                                               20

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
tcatacagca ggatcccca                                                19

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ccgtctacac ggacttcgat                                               20
```